(12) United States Patent
Scott et al.

(10) Patent No.: US 8,895,561 B2
(45) Date of Patent: Nov. 25, 2014

(54) COMPOUNDS AND METHODS FOR TREATING CANDIDIASIS AND ASPERGILLUS INFECTIONS

(71) Applicants: Cellceutix Corporation, Beverly, MA (US); Rutgers, the State University of New Jersey, New Brunswick, NJ (US)

(72) Inventors: Richard W. Scott, Radnor, PA (US); Katie Freeman, Radnor, PA (US); Haizhong Tang, Radnor, PA (US); Gill Diamond, Newark, NJ (US)

(73) Assignees: Cellceutix Corporation, Beverly, MA (US); Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/744,517

(22) Filed: Jan. 18, 2013

(65) Prior Publication Data

US 2013/0252964 A1    Sep. 26, 2013

Related U.S. Application Data

(60) Provisional application No. 61/587,865, filed on Jan. 18, 2012, provisional application No. 61/604,583, filed on Feb. 29, 2012, provisional application No. 61/698,782, filed on Sep. 10, 2012.

(51) Int. Cl.

| | | |
|---|---|---|
| *A61K 31/496* | (2006.01) |
| *C07D 277/28* | (2006.01) |
| *C07D 239/28* | (2006.01) |
| *C07D 209/86* | (2006.01) |
| *C07C 211/28* | (2006.01) |
| *A01N 25/00* | (2006.01) |
| *C07C 279/08* | (2006.01) |
| *C07D 307/91* | (2006.01) |
| *C07D 409/14* | (2006.01) |
| *C07C 217/20* | (2006.01) |
| *C07D 239/26* | (2006.01) |
| *C07D 333/20* | (2006.01) |
| *C07C 211/27* | (2006.01) |
| *C07D 307/52* | (2006.01) |
| *C07D 239/38* | (2006.01) |
| *C07C 237/08* | (2006.01) |
| *C07D 249/06* | (2006.01) |
| *C07D 333/76* | (2006.01) |
| *C07C 279/12* | (2006.01) |

(52) U.S. Cl.
CPC ............ *C07D 409/14* (2013.01); *C07D 277/28* (2013.01); *C07D 239/28* (2013.01); *C07D 209/86* (2013.01); *C07C 211/28* (2013.01); *A01N 25/00* (2013.01); *C07C 279/08* (2013.01); *C07D 307/91* (2013.01); *C07C 217/20* (2013.01); *C07D 239/26* (2013.01); *C07D 333/20* (2013.01); *C07C 211/27* (2013.01); *C07D 307/52* (2013.01); *C07D 239/38* (2013.01); *C07C 237/08* (2013.01); *C07D 249/06* (2013.01); *C07D 333/76* (2013.01); *C07C 279/12* (2013.01)
USPC ...................................................... 514/252.14

(58) Field of Classification Search
USPC .................................................... 514/252.14
See application file for complete search history.

(56) References Cited

PUBLICATIONS

Wilson et al., The interaction with DNA of unfused aromatic systems containing terminal piperazino substituents. Intercalation and groove-binding, 1990, Biophysical Chemistry, 35(2-3), 227-243.*

* cited by examiner

*Primary Examiner* — Kristin Vajda
(74) *Attorney, Agent, or Firm* — Pepper Hamilton LLP

(57) ABSTRACT

The present disclosure provides compounds, or pharmaceutically acceptable salts thereof, for killing or inhibiting the growth of a *Candida* or *Aspergillus* species or preventing or treating a mammal having *candidiasis* (oral and/or disseminated) or an *Aspergillus* infection.

4 Claims, 9 Drawing Sheets

COMPOUNDS AND METHODS FOR TREATING CANDIDIASIS AND ASPERGILLUS INFECTIONS

REFERENCE TO GOVERNMENT GRANTS

The present disclosure was supported by funds from the U.S. Government (NIH/NIDCR Grant No. 2R44DE018371-02) and the U.S. Government may therefore have certain rights in the disclosure.

FIELD

The present disclosure is directed, in part, to compounds, or pharmaceutically acceptable salts thereof, and pharmaceutical compositions comprising the same, and methods for treating a mammal having candidiasis, such as oral candidiasis and/or disseminated candidiasis, and/or an *aspergillus* infection.

BACKGROUND

Candidiasis encompasses fungal infections caused by a variety of species of the genus *Candida*, in particular mostly by *Candida albicans*, which is a yeast-like fungus. *Candida* spp. are normally present in the mouth, vagina, and intestines of healthy individuals; normal bacteria in these areas keep the amount of *Candida* spp. in check. Infection by candidal fungi normally depends on a weakened immune status of an individual to invade tissue that normally would be resistant to infection and the opportunity to gain access to the circulatory system. *Candida* infections that develop in immunocompromised individuals can affect the entire body (e.g., disseminated or systemic candidiasis) and may become life threatening. The most common condition is topical candidiasis (fungus growing on the surface of the body). An example of this is a common form of "diaper rash" in infants. Topical candidiasis can affect the skin, the vagina, the mouth (e.g., oral candidiasis) and the esophagus, and in immunocompromised individuals (e.g., HIV patients).

*Candida* infections are opportunistic and generally begin with increased colonization of the junction of mucous membranes and skin surfaces of vulnerable parts of the body such as, for example, oral, nasal, vaginal, and anal orifices, and the lining of the respiratory tract. Under some abnormal conditions, including the reduction of normal bacteria in a particular part of the body or skin defects such as wounds, ulcerations, and burns, the fungi can overgrow and cause infection of the outer layers of the skin and mucous membranes. This may occur in the mouth (oral thrush), in the vagina or penis (genital candidiasis), between folds and surfaces of skin (intertrigo), and in and around the nails (paronychia and onychomycosis).

In some instances, the fungus enters the bloodstream and causes disseminated disease affecting internal body organs such as the kidneys, spleen, lungs, liver, eyes, meninges, brain, and heart valves. This condition is called systemic or disseminated candidiasis; it can result in a range of diseases such as superficial mucocutaneous disease, candidiasis of the liver and spleen (hepatosplenic candidiasis), and peritonitis. This is usually seen in patients who are seriously ill with other diseases who have been receiving potent antibiotics that treat bacterial infection.

Oral candidiasis (sometimes referred to as "thrush") is an infection in which the fungus of the genus *Candida* (a yeast) accumulates on the mucous membranes of the mouth. It is most often caused by *Candida albicans*, or less commonly by *Candida glabrata* or *Candida tropicalis*. If occurring in the mouth of a baby, the candidiasis is commonly referred to as oral thrush, whereas if occurring in the mouth or throat of an adult, it may also be termed candidosis or moniliasis.

Oral infection by *Candida* species may not be immediately noticeable but can develop suddenly and may persist for a long time. The infection usually appears as thick white or cream-colored deposits on mucosal membranes such as the tongue, inner cheeks, gums, tonsils, and palate. The infected mucosa may appear inflamed (red and possibly slightly raised) and sometimes have a cottage cheese-like appearance. The lesions can be painful and may become tender and often bleed if rubbed or scraped. Cracking at the corners of the mouth, a cottony-like sensation inside the mouth, and even temporary loss of taste can occur. In more severe cases, the infection can spread down the esophagus and cause difficulty swallowing, which is sometimes referred to as esophageal candidiasis. Thrush does not usually cause a fever unless the infection has spread beyond the esophagus to other body parts, such as the lungs (i.e., systemic candidiasis).

Although oral thrush can affect anyone, it is more likely to occur in babies and in people who wear dentures, use inhaled corticosteroids, or have compromised immune systems. Oral thrush and other *Candida* infections can occur when the immune system is weakened by disease or drugs such as prednisone, or when antibiotics disturb the natural balance of microorganisms in the body. Normally, the immune system repels harmful invading organisms, such as fungi, while maintaining a balance between "good" and "bad" microbes that normally inhabit the body. When these protective mechanisms fail, however, an oral thrush infection may take hold.

The following diseases or conditions may make one more susceptible to oral thrush infection:

1) HIV/AIDS. The human immunodeficiency virus (HIV) damages or destroys cells of the immune system, making one more susceptible to opportunistic infections. Repeated bouts of oral thrush may be the first sign of an HIV infection.

2) Cancer. The immune system is likely to be weakened from the disease and from treatments, such as chemotherapy and radiation. Both the disease and treatments can increase the risk of *Candida* infections such as oral thrush.

3) Diabetes mellitus. In untreated or under-treated diabetes, the saliva may contain large amounts of sugar, which encourages the growth of *Candida*.

4) Vaginal yeast infections. Vaginal yeast infections are caused by the same fungus that causes oral thrush. Although a yeast infection is not typically dangerous, a pregnant female can pass the fungus to the baby during delivery.

Oral candidiasis can be treated with topical anti-fungal drugs, such as nystatin, miconazole, Gentian violet, or amphotericin B. Topical therapy is normally provided as an oral suspension which is washed around the mouth and then swallowed by the patient. Patients who are immunocompromised, either with HIV/AIDS or as a result of chemotherapy, may require systemic treatment with oral or intravenous administered anti-fungals. Some anti-fungal medications, however, may cause liver damage. For this reason, a physician will likely perform blood tests to monitor liver function, especially if prolonged treatment is required or there is a history of liver disease.

Some *Aspergillus* species cause serious disease in humans and animals. The most common pathogenic species include *Aspergillus fumigatus* and *Aspergillus flavus*. *Aspergillus flavus* produces aflatoxin which is both a toxin and a carcinogen, and which can contaminate foods. The most common causing allergic disease are *Aspergillus fumigatus* and *Aspergillus clavatus*. Other species, *Aspergillus* spp., are important agricultural pathogens.

SUMMARY

The present disclosure provides compounds of Formula I:

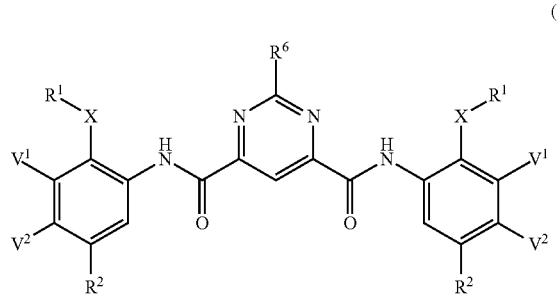

(I)

wherein: each X is, independently, O, S, or S(=O)$_2$; each R$^1$ is, independently, —CH$_3$, —(CH$_2$)$_n$—NH$_2$, —(CH$_2$)$_n$—NH—C(=NH)NH$_2$, or —(CH$_2$)$_n$—NH—C(=O)—R$^4$, where each n is, independently, 1 to 4, and each R$^4$ is, independently, H, —C$_1$-C$_3$alkyl, or —(CH$_2$)$_p$—NH$_2$, where each p is, independently, 1 or 2; each R$^2$ is, independently, H, halo, —CF$_3$, or —C(CH$_3$)$_3$; each V$^2$ is H, and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 1 to 4; or each V$^1$ is H and each V$^2$ is, independently, —S—R$^5$, where each R$^5$ is, independently, —(CH$_2$)$_n$—NH$_2$ or —(CH$_2$)$_n$—NH—C(=NH)NH$_2$, where each n is, independently, 1 to 4; and each R$^6$ is H, —S—(CH$_2$)$_m$—NH$_2$, —S—(CH$_2$)$_m$—NH—C(=NH)NH$_2$, —O—(CH$_2$)$_m$—NH$_2$, or —O—(CH$_2$)$_m$—NH—C(=NH)NH$_2$, where each m is, independently, 1 to 4; or a pharmaceutically acceptable salt thereof.

The present disclosure also provides compounds of Formula II:

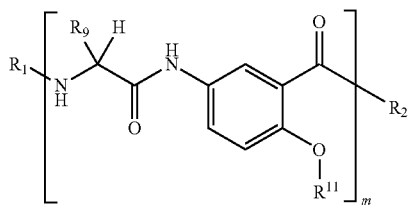

(II)

wherein: R$_1$ is H; R$_2$ is —NH$_2$; each R$^{11}$ is, independently, —(CH$_2$)$_{0-4}$—R$^4$ where R$^4$ is chosen from hydrogen, —C$_1$-C$_4$alkyl, —C$_3$-C$_{12}$branched alkyl, —C$_3$-C$_8$cycloalkyl, phenyl optionally substituted with one or more —C$_1$-C$_4$alkyl groups, —C$_1$-C$_4$alkoxy groups, or halo groups, and heteroaryl optionally substituted with one or more —C$_1$-C$_4$alkyl groups, —C$_1$-C$_4$alkoxy groups, or halo groups; each R$_9$ is, independently, hydroxyethoxymethyl, methoxyethoxymethyl, polyoxyethylene, or —(CH$_2$)$_q$—V where q is from 1 to 5, and each V is, independently, chosen from amino, hydroxyl, —C$_1$-C$_6$alkylamino, —C$_1$-C$_6$dialkylamino, —C$_1$-C$_6$alkylurea, —NH(CH$_2$)$_{1-4}$NH$_2$, —N(CH$_2$CH$_2$NH$_2$)$_2$, amidine, guanidine, semicarbazone, imidazole, piperidine, piperazine, 4-alkylpiperazine, phenyl optionally substituted with an amino, —C$_1$-C$_6$alkylamino, or —C$_1$-C$_6$dialkylamino, and lower acylamino optionally substituted with one or more amino, lower alkylamino, or lower dialkylamino, where the alkylene chain is optionally substituted with an amino or hydroxyl group; and m is 2 to at least about 30; or a pharmaceutically acceptable salt thereof.

The present disclosure also provides compounds of Formula III:

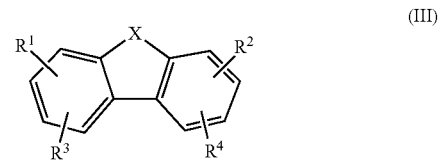

(III)

wherein:
X is —C(R$^7$)C(R), —C(=O), N(R$^9$), O, S, S(=O), or S(=O)$_2$;
R$^7$, R$^8$, and R$^9$ are, independently, H, —C$_1$-C$_8$alkyl, —C$_1$-C$_8$alkoxy, halo, —OH, —CF$_3$, aromatic group, —(CH$_2$)$_q$NH$_2$, or —(CH$_2$)$_q$NHC(=NH)NH$_2$, where q is 0 to 4;
R$^1$ and R$^2$ are, independently, H, —C$_1$-C$_8$alkyl, —C$_1$-C$_8$alkoxy, halo, OH, -haloC$_1$-C$_8$alkyl, —CN, or —CF$_3$;
R$^3$ and R$^4$ are, independently, H or -carbocycle(R$^5$)(R$^6$);
each R$^5$ and each R$^6$ are, independently, H, —C$_1$-C$_8$alkyl, —C$_1$-C$_8$alkoxy, halo, amino, —OH, —CF$_3$, —O—(CH$_2$)$_p$—NH$_2$, —O—(CH$_2$)$_p$NHC(=NH)NH$_2$, —S—(CH$_2$)—NH$_2$, —N((CH$_2$)$_p$NH$_2$)$_2$, —S—(CH$_2$)$_p$NHC(=NH)NH$_2$, —C(=O)NH(CH$_2$)$_p$NH$_2$, —(CH$_2$)$_p$N((CH$_2$)$_p$NH$_2$)$_2$, where each p is, independently, 1 to 5, aromatic group, heterocycle, or the free base or salt form of —(CH$_2$)$_n$—NH$_2$, —(CH$_2$)$_n$—NH—(CH$_2$)$_n$—NH$_2$, or —(CH$_2$)$_n$—NH—C(=NH)NH$_2$, where each n is, independently, 1 to 8;
provided that the compound is not Compound 116-134; or a pharmaceutically acceptable salt thereof.

The present disclosure also provides compounds of Formula IV:

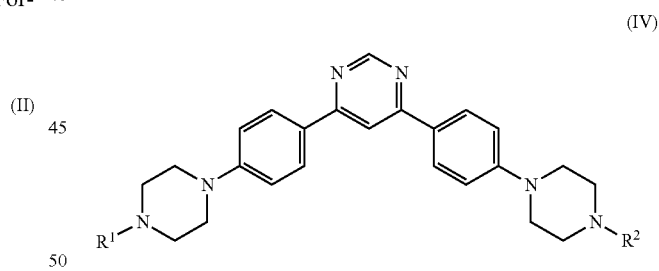

(IV)

wherein:
R$^1$ and R$^2$ are, independently, —C(=NH)NH$_2$, —(CH$_2$)$_n$NH$_2$, or —(CH$_2$)$_n$NC(=NH)NH$_2$, where n is 2, 3, or 4; or a pharmaceutically acceptable salt thereof.

The present disclosure also provides compounds of Formula V:

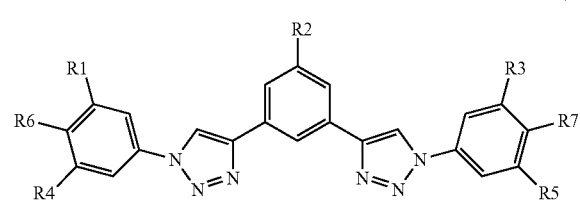

(V)

wherein:

$R^1$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^2$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^3$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4; and $R^7$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

or a pharmaceutically acceptable salt thereof.

The present disclosure also provides compounds of Formula VI:

(VI)

wherein:

$R^1$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^2$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^3$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4; and $R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

or a pharmaceutically acceptable salt thereof.

The present disclosure also provides compounds of Formula VII:

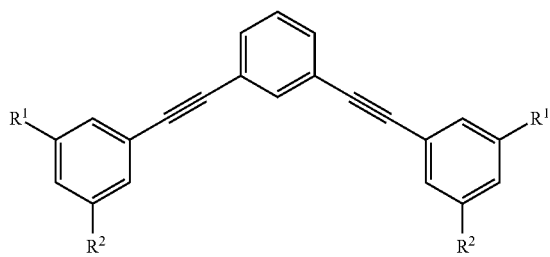

(VII)

wherein:
each $R^1$ is, independently, H, —$C_1$-$C_8$alkyl, —$C_1$-$C_8$alkoxy, halo, —OH, —$CF_3$, or —CN; and
each $R^2$ is, independently, —$(CH_2)_n$—$NH_2$ or —$(CH_2)_n$—NH—C(=NH)$NH_2$, where each n is, independently, 1 to 4; or a pharmaceutically acceptable salt thereof.

The present disclosure also provides compounds of Formula VIII:

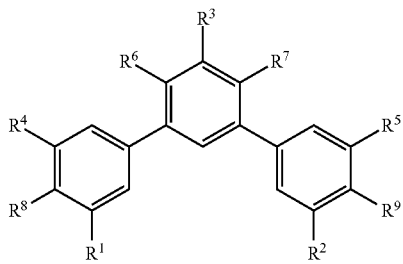

(VIII)

wherein:
$R^1$ is H, halo, haloalkyl, —$NH_2$, —$C_{1-3}$alkyl, —NH$(CH_2)_n$$NH_2$, —NH$(CH_2)_n$NC(=N)$NH_2$, —$(CH_2)_n$$NH_2$, —$(CH_2)_n$NC(=N)$NH_2$, —O—$(CH_2)_n$$NH_2$, —O—$(CH_2)_n$NC(=N)$NH_2$, —C≡C—$CH_2NH_2$, —CH=CH—$CH_2NH_2$, —CH=CH—$CH_2$NC(=N)$NH_2$, —CH=CH—$(CH_2)_2$$NH_2$, —C≡C—$(CH_2)_2$$NH_2$, —CH=CH—$(CH_2)_2$NC(=N)$NH_2$, —C≡C—$CH_2$NC(=N)$NH_2$, or —C≡C—$(CH_2)_2$—NC(=N)$NH_2$, where n is 2, 3, or 4;

$R^2$ is H, halo, haloalkyl, —$NH_2$, —$C_{1-3}$alkyl, —NH$(CH_2)_n$$NH_2$, —$(CH_2)_n$$NH_2$, —O—$(CH_2)_n$$NH_2$, —NH$(CH_2)_n$NC(=N)$NH_2$, —$(CH_2)_n$NC(=N)$NH_2$, —O—$(CH_2)_n$NC(=N)$NH_2$, —CH=CH—$CH_2NH_2$, —CH=CH—$CH_2$NC(=N)$NH_2$, —C≡C—$CH_2NH_2$, —CH=CH—$(CH_2)_2NH_2$, —CH=CH—$(CH_2)_2$NC(=N)$NH_2$, —C≡C—$CH_2$NC(=N)$NH_2$, —C≡C—$(CH_2)_2$$NH_2$, or —C≡C—$(CH_2)_2$—NC(=N)$NH_2$, where n is 2, 3, or 4;

$R^3$ is H, halo, haloalkyl, —$NH_2$, —$C_{1-3}$alkyl, —NH$(CH_2)_n$$NH_2$, —NH$(CH_2)_n$NC(=N)$NH_2$, —$(CH_2)_n$$NH_2$, —$(CH_2)_n$NC(=N)$NH_2$, —O—$(CH_2)_n$$NH_2$, —O—$(CH_2)_n$NC(=N)$NH_2$, —CH=CH—$CH_2NH_2$, —CH=CH—$CH_2$NC(=N)$NH_2$, —C≡C—$CH_2NH_2$, —CH=CH—$(CH_2)_2$$NH_2$, —CH=CH—$(CH_2)_2$NC(=N)$NH_2$, —C≡C—$CH_2$NC(=N)$NH_2$, —C≡C—$(CH_2)_2$$NH_2$, or —C≡C—$(CH_2)_2$—NC(=N)$NH_2$, where n is 2, 3, or 4;

$R^4$ is H, halo, haloalkyl, —$NH_2$, —$C_{1-3}$alkyl, —NH$(CH_2)_n$$NH_2$, —NH$(CH_2)_n$NC(=N)$NH_2$, —$(CH_2)_n$$NH_2$, —$(CH_2)_n$NC(=N)$NH_2$, —O—$(CH_2)_n$$NH_2$, —O—$(CH_2)_n$NC(=N)$NH_2$, —CH=CH—$CH_2NH_2$, —CH=CH—$CH_2$NC(=N)$NH_2$, —C≡C—$CH_2NH_2$, —C≡C—$CH_2$NC(=N)$NH_2$, —C≡C—$(CH_2)_2NH_2$, or —C≡C—$(CH_2)_2$—NC(=N)$NH_2$, where n is 2, 3, or 4;

$R^5$ is H, halo, haloalkyl, —$NH_2$, —$C_{1-3}$alkyl, —NH$(CH_2)_n$$NH_2$, —NH$(CH_2)_n$NC(=N)$NH_2$, —$(CH_2)_n$$NH_2$, —$(CH_2)_n$NC(=N)$NH_2$, —O—$(CH_2)_n$$NH_2$, —C≡C—$CH_2NH_2$, —O—$(CH_2)_n$NC(=N)$NH_2$, —CH=CH—$CH_2NH_2$, —CH=CH—$CH_2$NC(=N)$NH_2$, —C≡C—$(CH_2)_2$$NH_2$, —CH=CH—$(CH_2)_2$$NH_2$, —CH=CH—$(CH_2)_2$NC(=N)$NH_2$, —C≡C—$CH_2$NC(=N)$NH_2$, or —C≡C—$(CH_2)_2$—NC(=N)$NH_2$, where n is 2, 3, or 4;

$R^6$ is H, halo, haloalkyl, —$NH_2$, —$C_{1-3}$alkyl, —NH$(CH_2)_n$$NH_2$, —$(CH_2)_n$$NH_2$, —NH$(CH_2)_n$NC(=N)$NH_2$, —$(CH_2)_n$NC(=N)$NH_2$, —O—$(CH_2)_n$$NH_2$, —O—$(CH_2)_n$NC(=N)$NH_2$, —CH=CH—$CH_2NH_2$, —CH=CH—$CH_2$NC(=N)$NH_2$, —C≡C—$CH_2NH_2$, —CH=CH—$(CH_2)_2$$NH_2$, —CH=CH—$(CH_2)_2$NC(=N)$NH_2$, —C≡C—$CH_2$NC(=N)$NH_2$, —C≡C—$(CH_2)_2$$NH_2$, or —C≡C—$(CH_2)_2$—NC(=N)$NH_2$, where n is 2, 3, or 4;

$R^7$ is H, halo, haloalkyl, —$NH_2$, —$C_{1-3}$alkyl, —NH$(CH_2)_n$$NH_2$, —NH$(CH_2)_n$NC(=N)$NH_2$, —$(CH_2)_n$$NH_2$, —$(CH_2)_n$NC(=N)$NH_2$, —O—$(CH_2)_n$$NH_2$, —O—$(CH_2)_n$NC(=N)$NH_2$, —CH=CH—$CH_2NH_2$, —CH=CH—$CH_2$NC(=N)$NH_2$, —C≡C—$CH_2NH_2$, —CH=CH—$(CH_2)_2$$NH_2$, —C≡C—$(CH_2)_2$$NH_2$, —CH=CH—$(CH_2)_2$NC(=N)$NH_2$, —C≡C—$CH_2$NC(=N)$NH_2$, or —C≡C—$(CH_2)_2$—NC(=N)$NH_2$, where n is 2, 3, or 4;

$R^8$ is H, halo, haloalkyl, —$NH_2$, —$C_{1-3}$alkyl, —NH$(CH_2)_n$$NH_2$, —$(CH_2)_n$$NH_2$, —NH$(CH_2)_n$NC(=N)$NH_2$, —$(CH_2)_n$NC(=N)$NH_2$, —O—$(CH_2)_n$$NH_2$, —O—$(CH_2)_n$NC(=N)$NH_2$, —CH=CH—$CH_2NH_2$, —CH=CH—$CH_2$NC(=N)$NH_2$, —CH=CH—$(CH_2)_2$$NH_2$, —C≡C—$CH_2NH_2$, —CH=CH—$(CH_2)_2$NC(=N)$NH_2$, —C≡C—$CH_2$NC(=N)$NH_2$, —C≡C—$(CH_2)_2$$NH_2$, or —C≡C—$(CH_2)_2$—NC(=N)$NH_2$, where n is 2, 3, or 4; and $R^9$ is H, halo, haloalkyl, —$NH_2$, —$C_{1-3}$alkyl, —NH$(CH_2)_n$$NH_2$, —NH$(CH_2)_n$NC(=N)$NH_2$, —$(CH_2)_n$$NH_2$, —$(CH_2)_n$NC(=N)$NH_2$, —O—$(CH_2)_n$$NH_2$, —O—$(CH_2)_n$NC(=N)$NH_2$, —CH=CH—$CH_2NH_2$, —CH=CH—$CH_2$NC(=N)$NH_2$, —C≡C—$CH_2NH_2$, —CH=CH—$(CH_2)_2$$NH_2$, —CH=CH—$(CH_2)_2$NC(=N)$NH_2$, —C≡C—$(CH_2)_2$$NH_2$, —C≡C—$CH_2$NC(=N)$NH_2$, or —C≡C—$(CH_2)_2$—NC(=N)$NH_2$, where n is 2, 3, or 4;

or a pharmaceutically acceptable salt thereof.

The present disclosure also provides compounds of Formula IX:

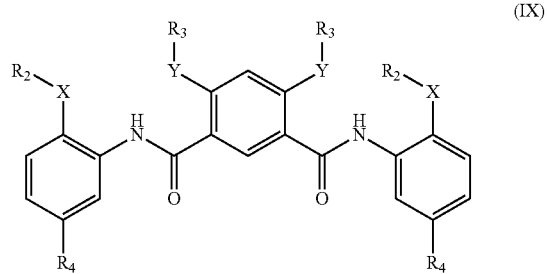

(IX)

wherein:
each X is, independently, O or S;
each Y is, independently, O or S;
each $R_2$ is, independently, —$C_1$-$C_9$ straight or branched alkyl optionally substituted with one or more —$NH_2$, —N$(CH_3)_2$ or —NH—C(=NH)$NH_2$;

each $R_3$ is, independently, —$C_1$-$C_9$ straight or branched alkyl optionally substituted with one or more —$NH_2$, —$N(CH_3)_2$ or —NH—C(=NH)$NH_2$; and each $R_4$ is, independently, —$(CH_2)_n$—$NH_2$ or —$(CH_2)_n$—NH—C(=NH)$NH_2$, where n is an integer from 1 to 4;

or a pharmaceutically acceptable salt thereof.

The present disclosure also provides compounds of Formula X:

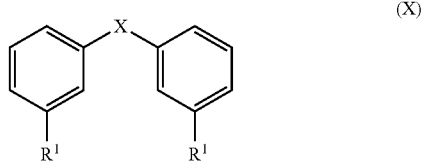

(X)

wherein:
X is

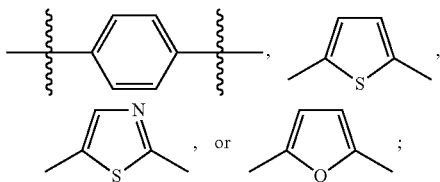

, or and each $R^1$ is, independently, —$(CH_2)_n$—$NH_2$ or —$(CH_2)_n$—NH—C(=NH)$NH_2$, where n is an integer from 1 to 4;

or a pharmaceutically acceptable salt thereof.

The present disclosure also provides pharmaceutical compositions comprising any one or more of the foregoing compounds, or a pharmaceutically acceptable salt thereof, and a pharmaceutically acceptable carrier.

The present disclosure also provides methods of killing or inhibiting the growth of a *Candida* or *Aspergillus* species comprising contacting the *Candida* or *Aspergillus* species with any one or more of the foregoing compounds, or pharmaceutically acceptable salt thereof.

The present disclosure also provides methods of preventing or treating a mammal having candidiasis (oral and/or disseminated) and/or an *aspergillus* infection comprising administering to the mammal in need thereof an effective amount of any one or more of the foregoing compounds, or pharmaceutically acceptable salt thereof.

The present disclosure also provides any one or more of the foregoing compounds, or pharmaceutically acceptable salts thereof, for killing or inhibiting the growth of a *Candida* or *Aspergillus* species or preventing or treating a mammal having candidiasis (oral and/or disseminated) and/or an *aspergillus* infection.

The present disclosure also provides any one or more of the foregoing compounds, or pharmaceutically acceptable salts thereof, for use in the manufacture of a medicament for killing or inhibiting the growth of a *Candida* or *Aspergillus* species or preventing or treating a mammal having candidiasis (oral and/or disseminated) and/or an *aspergillus* infection.

The present disclosure also provides uses of any one or more of the foregoing compounds, or pharmaceutically acceptable salts thereof, for killing or inhibiting the growth of a *Candida* or *Aspergillus* species or preventing or treating a mammal having candidiasis (oral and/or disseminated) and/or an *aspergillus* infection.

The present disclosure also provides uses of any one or more of the foregoing compounds, or pharmaceutically acceptable salts thereof, in the manufacture of a medicament for killing or inhibiting the growth of a *Candida* or *Aspergillus* species or preventing or treating a mammal having candidiasis (oral and/or disseminated) and/or an *aspergillus* infection.

DESCRIPTION OF EMBODIMENTS

Figure 1:
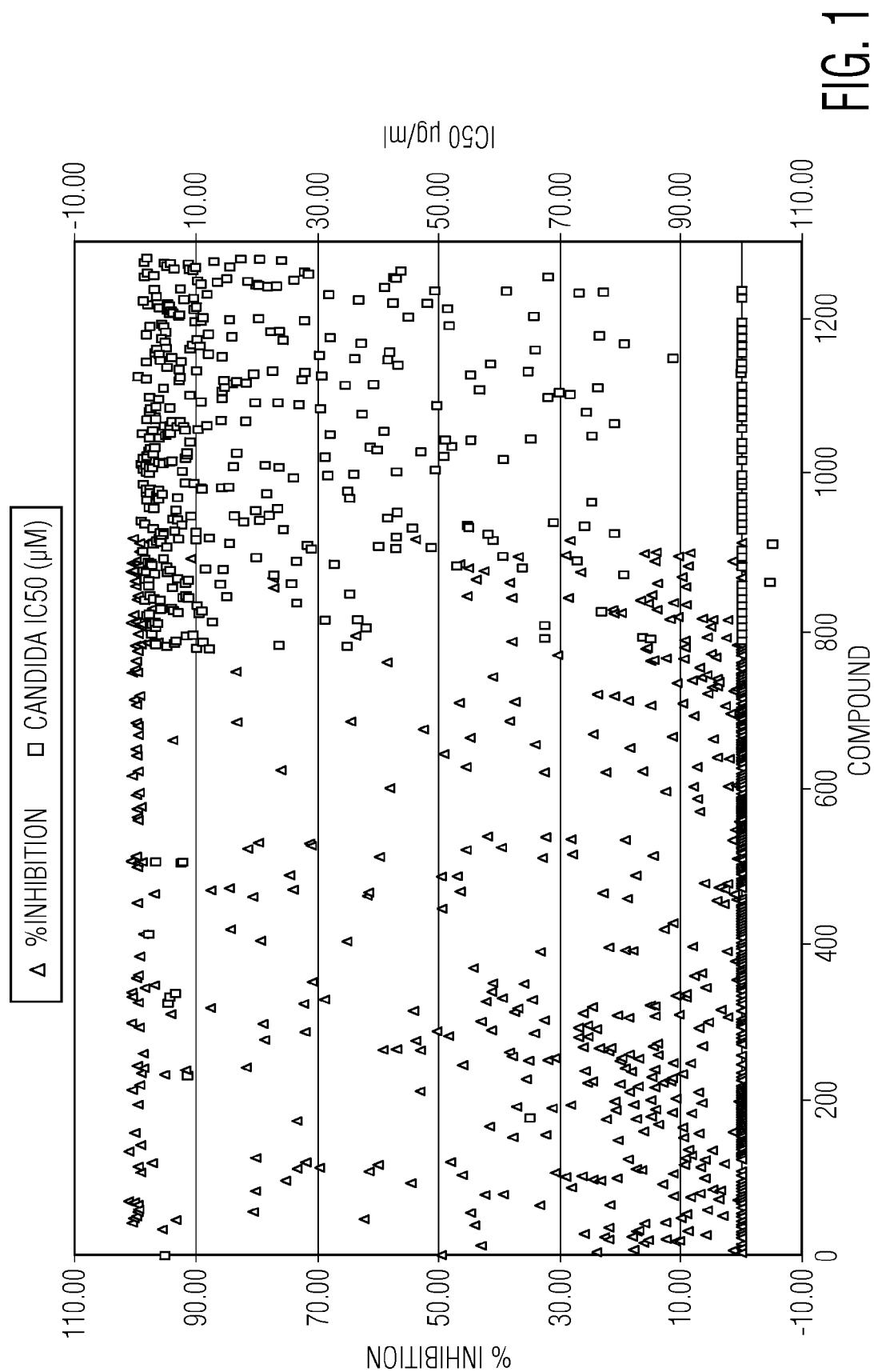
FIG. 1 shows results of screening over 800 compounds at a single concentration of 10 μM against a clinical isolate of *C. albicans* GDH2346 (triangles), and an additional 400 compounds with 11 concentrations to give an $IC_{50}$ (see, green squares).

The identification of a potent HDP mimetic (Compound 100), inter alia, that exhibits rapid membrane-disrupting activity against *Candida albicans* at low concentrations, using propidium iodide uptake is demonstrated here. In contrast to Histatin 5, Compound 100 treatment resulted in rapid efflux of ATP, and killing occurred even in the presence of sodium azide, which prevents membrane transport. Fluorescence microscopy, however, showed incorporation of the compound into the cells, suggesting a mechanism of self-promoted uptake. The compound also demonstrated a significant reduction of metabolic activity in mature biofilms of *C. albicans* grown at an air-liquid interface. To examine the activity of Compound 100 in vivo, an oral model of *Candida* infection was established in C57B1/6 mice. Animals were first treated for 5 days with oral tetracycline to reduce normal oral flora. An infection was initiated in the mice by inoculating a 50 μL suspension of *C. albicans* onto lightly scored tongues. This led to colonization of the tongues by days 2 to 4 after inoculation as measured by histological analysis and by recovery of viable colonies upon homogenization. Topical treatment of the infections on day 3 with a single 50 μL dose of a 1 mg/mL compound solution in a neutral hydrogel was sufficient to reduce the total colony counts by greater than 10-fold, equivalent to a similar treatment with an equivalent concentration of Nystatin suspension. These results, as well as those presented herein, suggest that the compounds described herein represent a strong potential source of fungicidal drugs.

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "acylamino" means an amino group substituted by an acyl group (e.g., —O—C(=O)—H or —O—C(=O)-alkyl). An example of an acylamino is —NHC(=O)H or —NHC(=O)CH$_3$. The term "lower acylamino" refers to an amino group substituted by a loweracyl group (e.g., —O—C(=O)—H or —O—C(=O)—C$_{1-6}$alkyl). An example of a lower acylamino is —NHC(=O)H or —NHC(=O)CH$_3$.

As used herein, the term "alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like.

In some embodiments, the alkenyl chain is from 2 to 10 carbon atoms in length, from 2 to 8 carbon atoms in length, from 2 to 6 carbon atoms in length, or from 2 to 4 carbon atoms in length.

As used herein, the term "alkoxy" means a straight or branched —O-alkyl group of 1 to 20 carbon atoms, including, but not limited to, methoxy, ethoxy, n-propoxy, isopropoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "alkylamino" means an amino group substituted by an alkyl group having from 1 to 6 carbon atoms. An example of an alkylamino is —NHCH$_2$CH$_3$.

As used herein, the term "alkylene" or "alkylenyl" means a divalent alkyl linking group. An example of an alkylene (or alkylenyl) is methylene or methylenyl (—CH$_2$—).

As used herein, the term "alkylthio" means an —S-alkyl group having from 1 to 6 carbon atoms. An example of an alkylthio group is —SCH$_2$CH$_3$.

As used herein, the term "alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

As used herein, the term "amidino" means —C(=NH)NH$_2$.

As used herein, the term "amino" means —NH$_2$.

As used herein, the term "aminoalkoxy" means an alkoxy group substituted by an amino group. An example of an aminoalkoxy is —OCH$_2$CH$_2$NH$_2$.

As used herein, the term "aminoalkyl" means an alkyl group substituted by an amino group. An example of an aminoalkyl is —CH$_2$CH$_2$NH$_2$.

As used herein, the term "aminosulfonyl" means —S(=O)$_2$NH$_2$.

As used herein, the term "aminoalkylthio" means an alkylthio group substituted by an amino group. An example of an aminoalkylthio is —SCH$_2$CH$_2$NH$_2$.

As used herein, the term "amphiphilic" means a three-dimensional structure having discrete hydrophobic and hydrophilic regions. An amphiphilic compound suitably has the presence of both hydrophobic and hydrophilic elements.

As used herein, the term "animal" includes, but is not limited to, humans and non-human vertebrates such as wild, domestic, and farm animals.

As used herein, the phrase "an effective amount" of a compound can be measured by the effectiveness of the compound. In some embodiments, an effective amount inhibits growth of a particular *Candida* or *Aspergillus* species by at least 10%, by at least 20%, by at least 30%, by at least 40%, by at least 50%, by at least 60%, by at least 70%, by at least 80%, by at least 90%, or by at least 95%. In some embodiments, "an effective amount" is also a "therapeutically effective amount" whereby the compound reduces or eliminates at least one harmful effect of a *Candida* or *Aspergillus* species on a mammal.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, and the like.

As used herein, the term "arylalkyl" means a C$_{1-6}$alkyl substituted by aryl.

As used herein, the term "arylamino" means an amino group substituted by an aryl group. An example of an arylamino is —NH(phenyl).

As used herein, the term "arylene" means an aryl linking group, i.e., an aryl group that links one group to another group in a molecule.

As used herein, the term "candidiasis" means a yeast infection of a *Candida* species. Types of candidiasis include, local infections such as, for example, oral thrush or oral candidiasis, genital candidiasis, intertrigo, paronychia, and onychomycosis, as well as disseminated candidiasis.

As used herein, the term "carbocycle" means a 5- or 6-membered, saturated or unsaturated cyclic ring, optionally containing O, S, or N atoms as part of the ring. Examples of carbocycles include, but are not limited to, cyclopentyl, cyclohexyl, cyclopenta-1,3-diene, phenyl, and any of the heterocycles recited above.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term "chemically nonequivalent termini" means a functional group such as an ester, amide, sulfonamide, or N-hydroxyoxime that, when reversing the orientation of the functional group (e.g., —(C=O)O—) produces different chemical entities (e.g., —$R^1C(=O)OR^2$— vs. —$R^1OC(=O)R^2$—).

As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "cyano" means —CN.

As used herein, the term "cycloalkyl" means non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein, the term "dialkylamino" means an amino group substituted by two alkyl groups, each having from 1 to 6 carbon atoms.

As used herein, the term "facially amphiphilic" or "facial amphiphilicity" means compounds with polar (hydrophilic) and nonpolar (hydrophobic) side chains that adopt conformation(s) leading to segregation of polar and nonpolar side chains to opposite faces or separate regions of the structure or molecule.

As used herein, the phrase "groups with chemically nonequivalent termini" means functional groups such as esters amides, sulfonamides and N-hydroxyoximes where reversing the orientation of the substituents, e.g. $R^1C(=O)OR^2$ vs. $R^{10}(O=)CR^2$, produces unique chemical entities.

As used herein, the term "guanidino" means —NH(=NH)NH$_2$.

As used herein, the term "halo" means halogen groups including, but not limited to fluoro, chloro, bromo, and iodo.

As used herein, the term "haloalkoxy" means an —O-haloalkyl group. An example of an haloalkoxy group is OCF$_3$.

As used herein, the term "haloalkyl" means a $C_{1-6}$alkyl group having one or more halogen substituents. Examples of haloalkyl groups include, but are not limited to, —CF$_3$, —C$_2$F$_5$, —CHF$_2$, —CCl$_3$, —CHCl$_2$, —C$_2$Cl$_5$, —CH$_2$CF$_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heteroarylalkyl" means a $C_{1-6}$alkyl group substituted by a heteroaryl group.

As used herein, the term "heteroarylamino" means an amino group substituted by a heteroaryl group. An example of a heteroarylamino is —NH-(2-pyridyl).

As used herein, the term "heteroarylene" means a heteroaryl linking group, i.e., a heteroaryl group that links one group to another group in a molecule.

As used herein, the term "heterocycle" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" means nonaromatic heterocycles having up to 20 ring-forming atoms including cyclized alkyl, alkenyl, and alkynyl groups, where one or more of the ring-forming carbon atoms is replaced by a heteroatom such as an O, N, or S atom. Heterocycloalkyl groups can be mono or polycyclic (e.g., fused, bridged, or spiro systems). In some embodiments, the heterocycloalkyl group has from 1 to 20 carbon atoms, or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or S(O)$_2$). For another example, a ring-forming C atom can be substituted by oxo (form carbonyl). Also included in the definition of heterocycloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, 5,6-dihydrothieno[2,3-c]pyridin-7(4H)-one-5-yl, isoindolin-1-one-3-yl, and 3,4-dihydroisoquinolin-1(2H)-one-3-yl groups. Ring-forming carbon atoms and heteroatoms of the heterocycloalkyl group can be optionally substituted by oxo or sulfido.

As used herein, the term "hydroxy" or "hydroxyl" means an —OH group.

As used herein, the term "hydroxyalkyl" or "hydroxylalkyl" means an alkyl group substituted by a hydroxyl group. Examples of a hydroxyalkyl include, but are not limited to, —CH$_2$OH and —CH$_2$CH$_2$OH.

As used herein, the term "individual" or "patient," used interchangeably, means any animal, including mammals, such as mice, rats, other rodents, rabbits, dogs, cats, swine, cattle, sheep, horses, or primates, such as humans.

As used herein, the phrase "inhibiting the growth" means reducing by any measurable amount the growth of one or more yeast or mold, such as a *Candida* or *Aspergillus* species.

In some embodiments, the inhibition of growth may result in cell death of the yeast or mold.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevelant.

As used herein, the phrase "integer from 1 to 5" means 1, 2, 3, 4, or 5.

As used herein, the term "isolated" means that the compounds described herein are separated from other components of either (a) a natural source, such as a plant or cell, such as a bacterial culture, or (b) a synthetic organic chemical reaction mixture, such as by conventional techniques.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "nitro" means —NO$_2$.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present disclosure also includes quaternary ammonium salts of the compounds described herein, where the compounds have one or more tertiary amine moiety.

As used herein, the term "phenyl" means —$C_6H_5$. A phenyl group can be unsubstituted or substituted with one, two, or three suitable substituents.

As used herein, the terms "prevention" or "preventing" mean a reduction of the risk of acquiring a particular disease, condition, or disorder.

As used herein, the term "prodrug" means a derivative of a known direct acting drug, which derivative has enhanced delivery characteristics and therapeutic value as compared to the drug, and is transformed into the active drug by an enzymatic or chemical process.

As used herein, the term "purified" means that when isolated, the isolate contains at least 90%, at least 95%, at least 98%, or at least 99% of a compound described herein by weight of the isolate.

As used herein, the phrase "quaternary ammonium salts" means derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $Cl^-$, $CH_3COO^-$, and $CF_3COO^-$), for example methylation or ethylation.

As used herein, the term "semicarbazone" means =$NNHC(=O)NH_2$.

As used herein, the phrase "solubilizing agent" means agents that result in formation of a micellar solution or a true solution of the drug.

As used herein, the term "solution/suspension" means a liquid composition wherein a first portion of the active agent is present in solution and a second portion of the active agent is present in particulate form, in suspension in a liquid matrix.

As used herein, the phrase "substantially isolated" means a compound that is at least partially or substantially separated from the environment in which it is formed or detected.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: —$C_1$-$C_6$alkyl, —$C_1$-$C_6$alkenyl, —$C_1$-$C_6$alkynyl, —$C_5$-$C_6$aryl, —$C_1$-$C_6$alkoxy, —$C_3$-$C_8$heteroaryl, —$C_3$-$C_6$cycloalkyl, —$C_5$-$C_6$aryloxy, —CN, —OH, oxo, halo, haloalkyl, —$NO_2$, —C(=O)OH, —$NH_2$, —NH($C_1$-$C_8$alkyl), —N($C_1$-$C_8$alkyl)$_2$, —NH($C_6$aryl), —N($C_5$-$C_6$aryl)$_2$, —C(=O)H, —C(=O)($C_1$-$C_6$alkyl), —C(=O)($C_5$-$C_6$aryl), —C(=O)—O—(($C_1$-$C_6$)alkyl), and —C(=O)—O—(($C_5$-$C_6$)aryl). Any of the compounds herein may be further substituted at, for example, open positions (such as on a ring structure) by any of these substituents as desired by one skilled in the art. One of skill in art can readily choose a suitable substituent based on the stability and pharmacological and synthetic activity of the compounds described herein.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" mean both therapeutic treatment and prophylactic or preventative measures wherein the object is to prevent or slow down (lessen) an undesired physiological condition, disorder or disease, or obtain beneficial or desired clinical results. For purposes herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment.

At various places in the present specification, substituents of compounds may be disclosed in groups or in ranges. It is specifically intended that the disclosure include each and every individual subcombination of the members of such groups and ranges. For example, the term "$C_{1-6}$alkyl" is specifically intended to individually disclose methyl, ethyl, propyl, $C_4$alkyl, $C_5$alkyl, and $C_6$alkyl.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

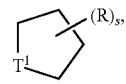

then it is understood that substituent R can occur s number of times on the ring, and R can be a different moiety at each occurrence. Further, in the above example, where the variable $T^1$ is defined to include hydrogens, such as when $T^1$ is $CH_2$, NH, etc., any H can be replaced with a suitable substituent.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

It is understood that the present disclosure encompasses the use, where applicable, of stereoisomers, diastereomers and optical stereoisomers of the compounds described herein, as well as mixtures thereof. Additionally, it is understood that stereoisomers, diastereomers, and optical stereoisomers of the compounds described herein, and mixtures thereof, are within the scope of the present disclosure. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the present disclosure unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds are also included within the scope of the disclosure and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallizaion using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as (3-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound described herein. Substantial separation can include compositions containing at least about 50%, at least about 60%, at least about 70%, at least about 80%, at least about 90%, at least about 95%, at least about 97%, or at least about 99% by weight of the compound, or salt thereof. Methods for isolating compounds and their salts are routine in the art.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds also include derivatives referred to as prodrugs, which can be prepared by modifying functional groups present in the compounds in such a way that the modifications are cleaved, either in routine manipulation or in vivo, to the parent compounds. Examples of prodrugs include compounds as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds described herein. Preparation and use of prodrugs is discussed in T. Higuchi et al., "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference in their entireties.

Some of the compounds may be capable of adopting amphiphilic conformations that allow for the segregation of polar and nonpolar regions of the molecule into different spatial regions and provide the basis for a number of uses.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

The structures depicted herein may omit one or more necessary hydrogen atoms to complete the appropriate valency. Thus, in some instances a carbon atom or nitrogen atom, for example, may appear to have an open valency (i.e., a carbon atom with only two bonds showing would implicitly also be bonded to two hydrogen atoms; in addition, a nitrogen atom with a single bond depicted would implicitly also be bonded to two hydrogen atoms). For example, "—N" would be considered by one skilled in the art to be "—NH$_2$." Thus, in any structure depicted herein wherein a valency is open, one or more hydrogen atoms is implicit, and is only omitted for brevity.

The present disclosure provides compounds of Formula I:

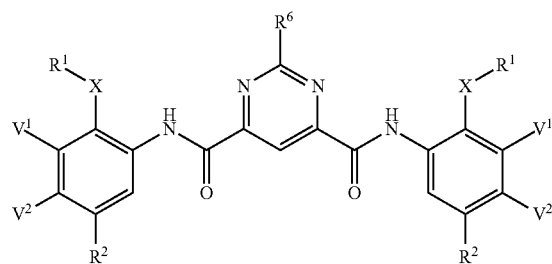

(I)

wherein:

each X is, independently, O, S, or S(=O)$_2$;

each $R^1$ is, independently, —CH$_3$, —(CH$_2$)$_n$—NH$_2$, —(CH$_2$)$_n$—NH—C(=NH)NH$_2$, or —(CH$_2$)$_n$—NH—C(=O)—R$^4$, where each n is, independently, 1 to 4, and each $R^4$ is, independently, H, —C$_1$-C$_3$alkyl, or —(CH$_2$)$_p$—NH$_2$, where each p is, independently, 1 or 2;

each $R^2$ is, independently, H, halo, —CF$_3$, or —C(CH$_3$)$_3$;

each $V^2$ is H, and each $V^1$ is, independently, —N—C(=O)—R$^3$, where each $R^3$ is, independently, —(CH$_2$)$_n$—NH$_2$ or —(CH$_2$)$_n$—NH—C(=NH)NH$_2$, where each n is, independently, 1 to 4; or each $V^1$ is H and each $V^2$ is, independently, —S—R$^5$, where each $R^5$ is, independently, —(CH$_2$)$_n$—NH$_2$ or —(CH$_2$)$_n$—NH—C(=NH)NH$_2$, where each n is, independently, 1 to 4; and each $R^6$ is H, —S—(CH$_2$)$_m$—NH$_2$, —S—(CH$_2$)$_m$—NH—C(=NH)NH$_2$, —O—(CH$_2$)$_m$—NH$_2$, or —O—(CH$_2$)$_m$—NH—C(=NH)NH$_2$, where each m is, independently, 1 to 4; r a pharmaceutically acceptable salt thereof, provided that the compound is not:

a)

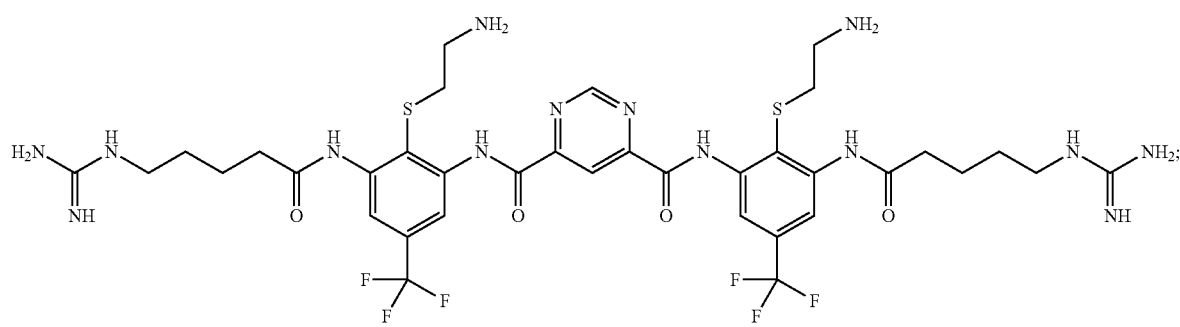

b)

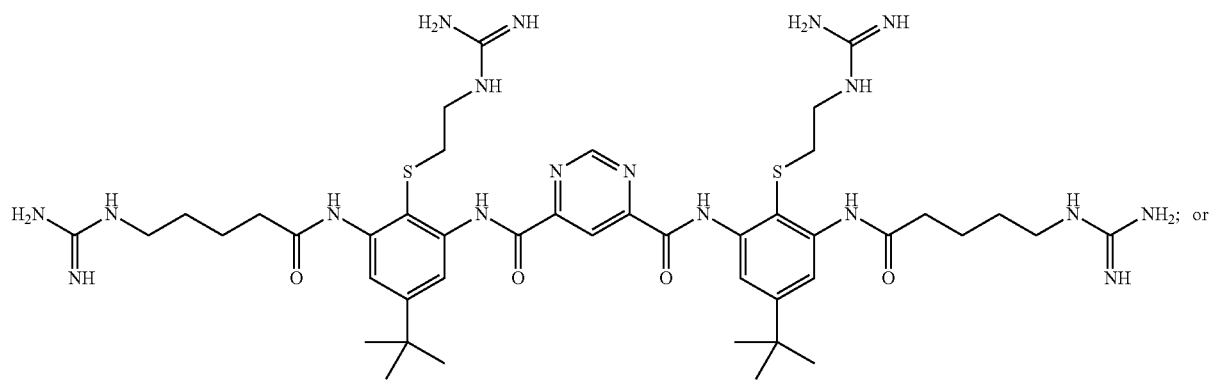

; or c)

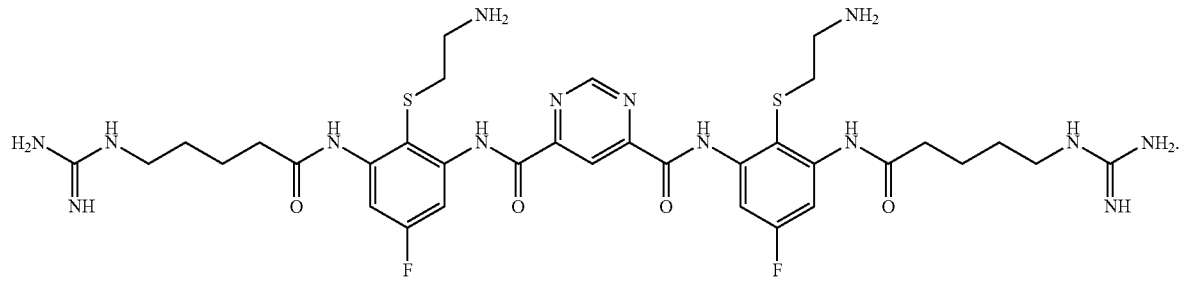

In some embodiments, each X is S.

In any of the above embodiments, each $R^1$ is, independently, —$CH_3$, —$(CH_2)_n$—$NH_2$, —$(CH_2)_n$—NH—C(=NH)$NH_2$, or —$(CH_2)_n$—NH—C(=O)—$R^4$, where each n is, independently, 1 or 2, and each $R^4$ is, independently, H or methyl; or each $R^1$ is, independently, —$CH_3$, —$(CH_2)_n$—$NH_2$, —$(CH_2)_n$—NH—C(=NH)$NH_2$, or —$(CH_2)_n$—NH—C(=O)—$R^4$, where each n is 2 and each $R^4$ is H; or each $R^1$ is, independently, —$CH_3$, —$(CH_2)_n$—$NH_2$ or —$(CH_2)_n$—NH—C(=NH)$NH_2$, where each n is 2; or each $R^1$ is —$CH_3$, —$(CH_2)_n$—$NH_2$, or —$(CH_2)_n$—NH—C(=NH)$NH_2$, where each n is 2; or each $R^1$ is —$CH_3$ or —$(CH_2)_n$—$NH_2$ where each n is 2.

In any of the above embodiments, each $R^2$ is, independently, H, Br, F, Cl, —$CF_3$, or —$C(CH_3)_3$; or each $R^2$ is, independently, Br, F, Cl, —$CF_3$, or —$C(CH_3)_3$; or each $R^2$ is —$CF_3$.

In any of the above embodiments, each $V^2$ is H and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4; or each $V^2$ is H and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 or 2; or each $V^2$ is H and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is 2; or each $V^2$ is H and each $V^1$ is —N—C(=O)—$R^3$, where each $R^3$ is —$(CH_2)_n$—$NH_2$ or —$(CH_2)_n$—NH—C(=NH)$NH_2$, where n is 2.

In any of the above embodiments, each $V^1$ is H and each $V^2$ is, independently, —S—$R^5$, where each $R^5$ is, independently, —$(CH_2)_n$—$NH_2$ or —$(CH_2)_n$—NH—C(=NH)$NH_2$, where each n is, independently, 1 to 4; or each $V^1$ is H and each $V^2$ is, independently, —S—$R^5$, where each $R^5$ is, independently, —$(CH_2)_n$—$NH_2$ or —$(CH_2)_n$—NH—C(=NH)$NH_2$, where each n is 1 or 2; or each $V^1$ is H and each $V^2$ is, independently, —S—$R^5$, where each $R^5$ is, independently, —$(CH_2)_n$—$NH_2$ or —$(CH_2)_n$—NH—C(=NH)$NH_2$, where each n is 2; or each $V^1$ is H and each $V^2$ is —S—$R^5$, where each $R^5$ is —$(CH_2)_n$—$NH_2$ or —$(CH_2)_n$—NH—C(=NH)$NH_2$, where each n is 2; or each $V^1$ is H and each $V^2$ is —S—$R^5$, where each $R^5$ is —$(CH_2)_n$—$NH_2$ where each n is 2.

In any of the above embodiments, each $R^6$ is H, —S—$(CH_2)_m$—$NH_2$, or —S—$(CH_2)_m$—NH—C(=NH)$NH_2$, where each m is, independently, 1 to 4; or each $R^6$ is H, —S—$(CH_2)_m$—$NH_2$, or —S—$(CH_2)_m$—NH—C(=NH)$NH_2$, where each m is, independently, 1 or 2; or each $R^6$ is H or —S—$(CH_2)_m$—NH—C(=NH)$NH_2$, where each m is, independently, 1 or 2; or each $R^6$ is H or —S—$(CH_2)_m$—NH—C(=NH)$NH_2$, where each m is 2.

In some embodiments, each X is S; each $R^1$ is, independently, —$(CH_2)_n$—$NH_2$ or —$(CH_2)_n$—NH—C(=NH)$NH_2$, where each n is, independently, 1 to 4; each $R^2$ is, independently, halo, —$CF_3$, or —$C(CH_3)_3$; and each $V^1$ is H and each $V^2$ is, independently, —S—$R^5$, where each $R^5$ is, independently, —$(CH_2)_n$—$NH_2$, where each n is, independently, 1 to 4.

In some embodiments, each X is S; each $R^1$ is, independently, —$(CH_2)_n$—$NH_2$, where each n is, independently, 1 or 2; each $R^2$ is, independently, —$CF_3$ or —$C(CH_3)_3$; and each $V^1$ is H and each $V^2$ is, independently, —S—$R^5$, where each $R^5$ is, independently, —$(CH_2)_n$—$NH_2$, where each n is, independently, 1 or 2.

In some embodiments, each X is S; each $R^1$ is —$(CH_2)_n$—$NH_2$, where each n is 1 or 2; each $R^2$ is, independently, —$CF_3$ or —$C(CH_3)_3$; and each $V^1$ is H and each $V^2$ is —S—$R^5$, where each $R^5$ is —$(CH_2)_n$—$NH_2$, where each n is 1 or 2.

In some embodiments, each X is O or S; each $R^1$ is, independently, —$(CH_2)_n$—$NH_2$, or —$(CH_2)_n$—NH—C(=NH)$NH_2$, or —$(CH_2)_n$—NH—C(=O)—$R^4$, where each n is, independently, 1 to 4, and each $R^4$ is, independently, H or methyl; each $R^2$ is, independently, halo, —$CF_3$, or —$C(CH_3)_3$; and each $V^2$ is H, and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4.

In some embodiments, each X is S; each $R^1$ is, independently, —$(CH_2)_n$—NH—C(=O)—$R^4$, where each n is, independently, 1 or 2, and each $R^4$ is, independently, H or methyl; each $R^2$ is, independently, halo; and each $V^2$ is H, and each $V^1$ is —N—C(=O)—$R^3$, where each $R^3$ is —$(CH_2)_n$—$NH_2$ or —$(CH_2)_n$—NH—C(=NH)$NH_2$, where each n is 4.

In some embodiments, each X is O or S; each $R^1$ is, independently, —$(CH_2)_n$—$NH_2$ or —$(CH_2)_n$—NH—C(=NH)$NH_2$, where each n is, independently, 1 to 4; each $R^2$ is, independently, halo, —$CF_3$, or —$C(CH_3)_3$; and each $V^2$ is H, and each $V^1$ is, independently, —N—C(=O)—$R^3$, where each $R^3$ is, independently, —$(CH_2)_n$—$NH_2$ or —$(CH_2)_n$—NH—C(=NH)$NH_2$, where each n is, independently, 1 to 4.

In some embodiments, each X is O or S; each $R^1$ is —$(CH_2)_n$—$NH_2$ or —$(CH_2)_n$—NH—C(=NH)$NH_2$, where each n is 1 or 2; each $R^2$ is halo, —$CF_3$, or —$C(CH_3)_3$; and each $V^2$ is H, and each $V^1$ is —N—C(=O)—$R^3$, where each $R^3$ is —$(CH_2)_n$—$NH_2$ or —$(CH_2)_n$—NH—C(=NH)$NH_2$, where each n is 3 or 4.

In some embodiments, each X is, independently, S or S(=O)$_2$; each $R^1$ is, independently, —$(CH_2)_n$—$NH_2$ or —$(CH_2)_n$—NH—C(=O)—$R^4$, where each n is, independently, 1 or 2, and each $R^4$ is, independently, —$(CH_2)_p$—$NH_2$, where each p is, independently, 1 or 2; each $R^2$ is, independently, halo or —$CF_3$; and each $V^2$ is H, and each $V^1$ is, independently, —N—C(=O)—R³, where each R³ is, independently, —(CH₂)ₙ—NH₂ or —(CH₂)ₙ—NH—C(=NH)NH₂, where each n is, independently, 3 or 4.

In some embodiments, each X is O or S; each R¹ is —CH₃; each R² is —CF₃; each V¹ is H and each V² is, independently, —S—R⁵, where each R⁵ is, independently, —(CH₂)ₙ—NH₂ or —(CH₂)ₙ—NH—C(=NH)NH₂, where each n is, independently, 1 to 4; and each R⁶ is —S—(CH₂)ₘ—NH₂ or —S—(CH₂)ₘ—NH—C(=NH)NH₂, where each m is, independently, 1 or 2.

In some embodiments, the compound is chosen from:

Compound 100

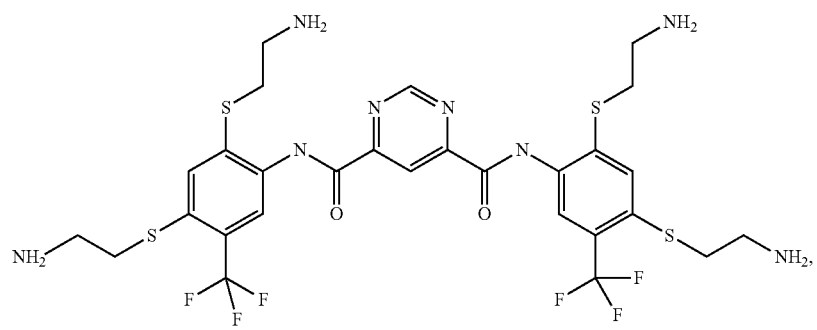

Compound 101

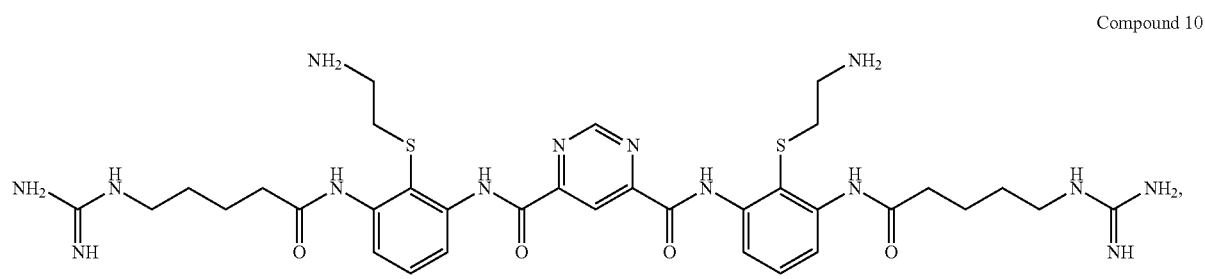

Compound 102

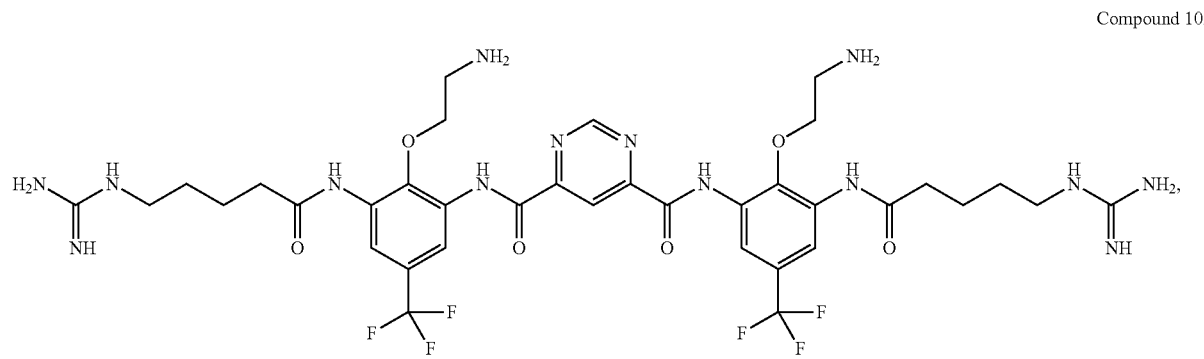

Compound 103

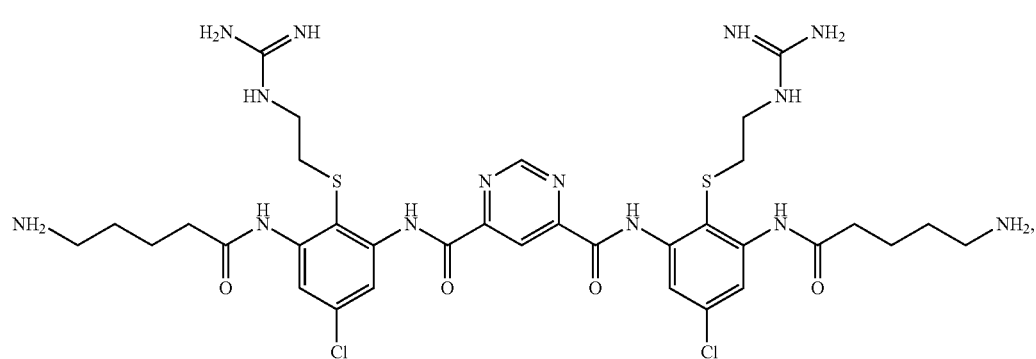

-continued
Compound 104
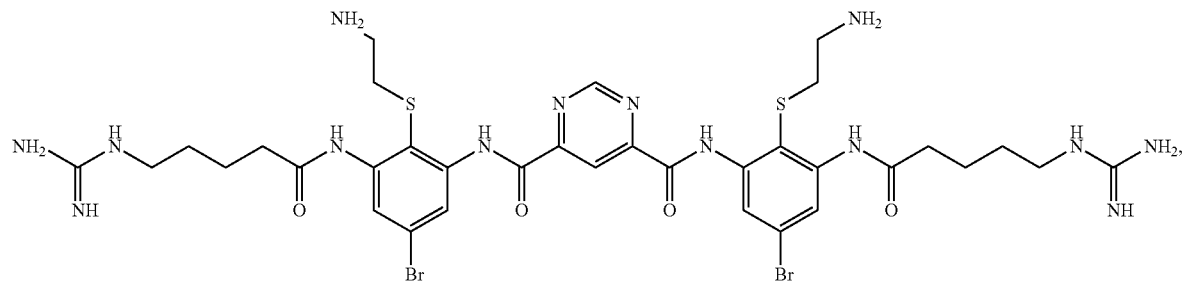
Compound 105
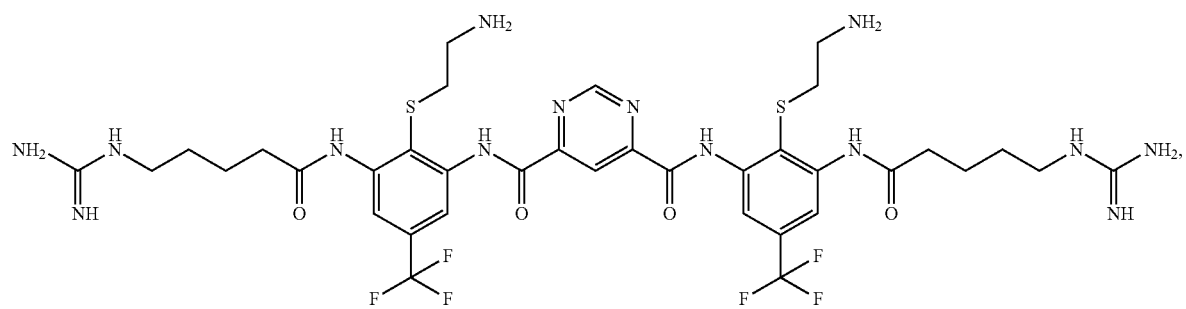
Compound 106
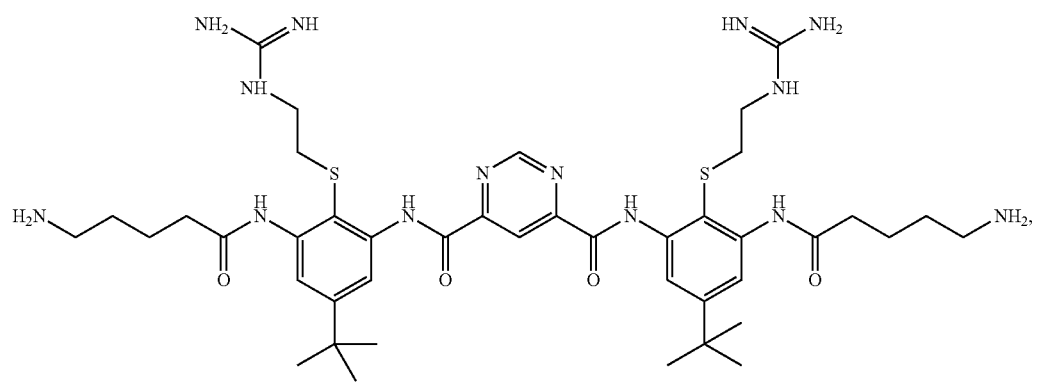
Compound 107
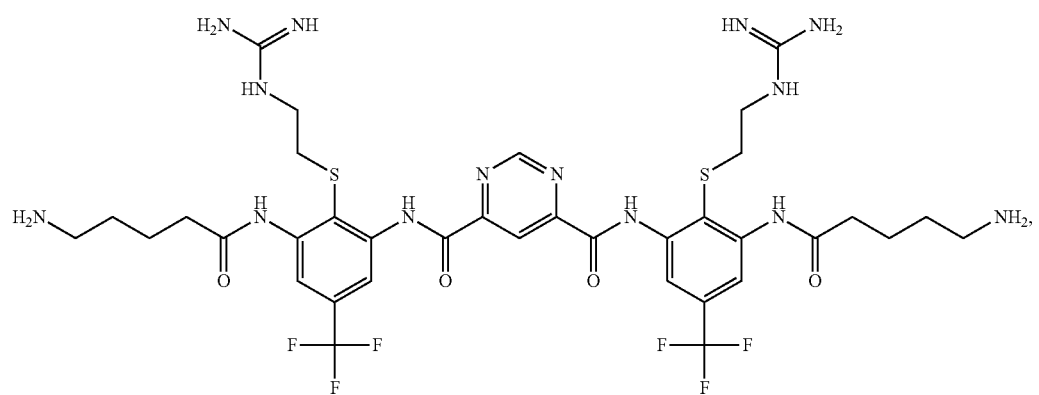

-continued
Compound 108
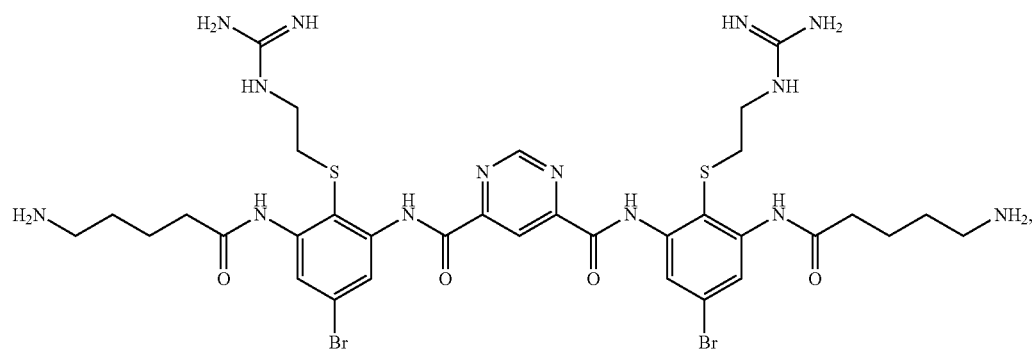
Compound 109
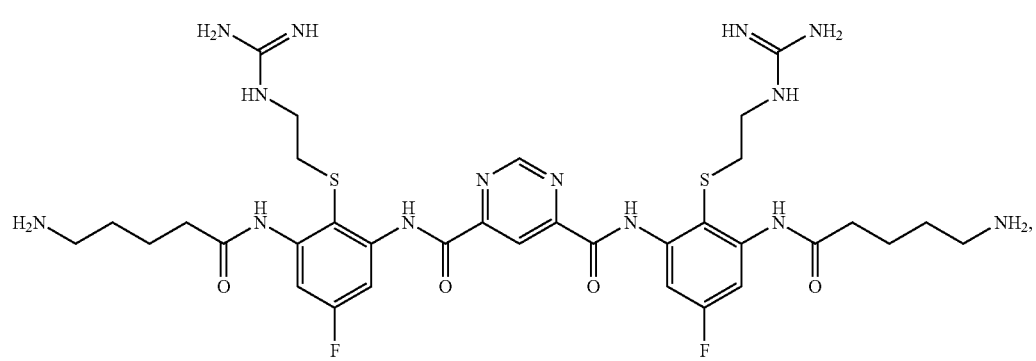
Compound 110
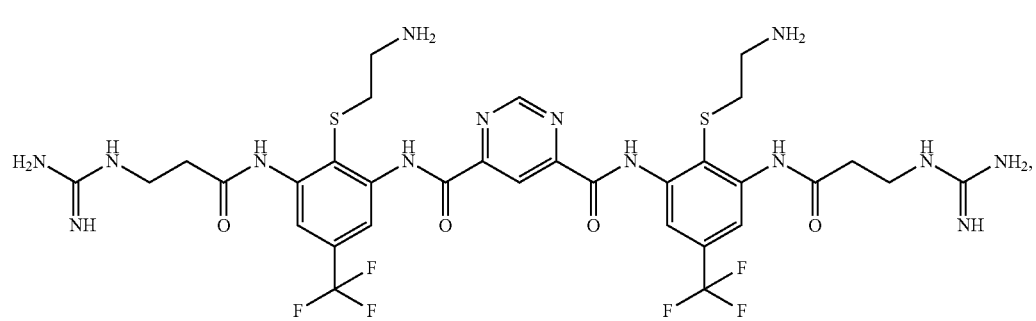
Compound 111
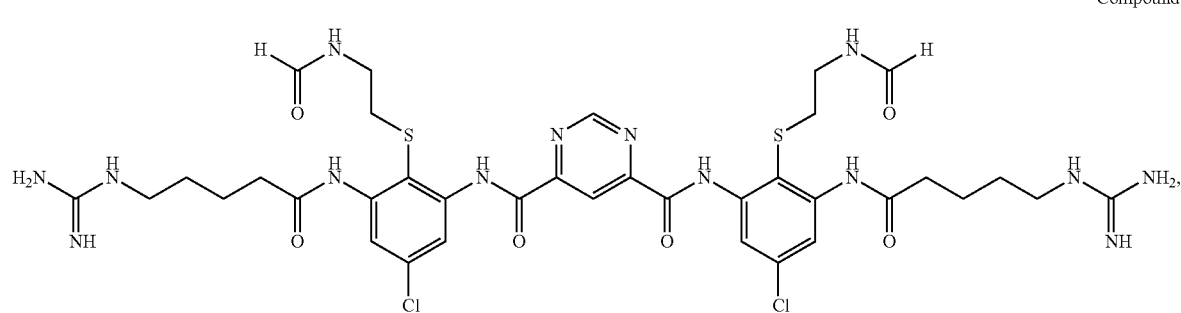
Compound 112
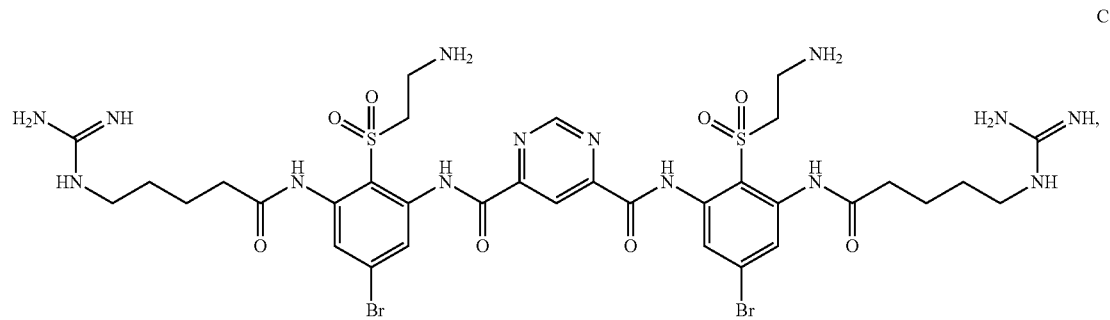

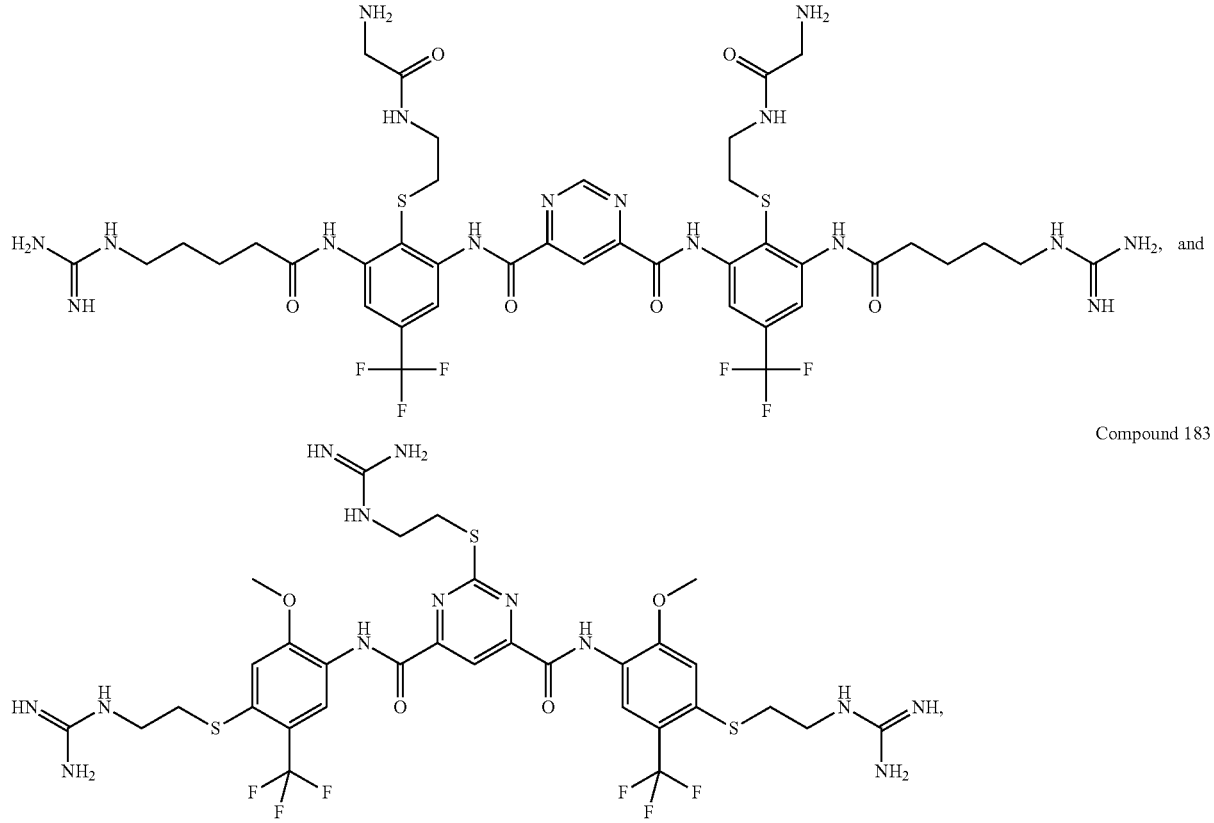

Compound 113

Compound 183 or a pharmaceutically acceptable salt thereof.

In some embodiments, any one or more of the above compounds may be excluded from any of the genus of compounds described above.

The present disclosure also provides compositions comprising one or more of the compounds or salts described above and a pharmaceutically acceptable carrier.

The present disclosure also provides methods of preventing or treating candidiasis (oral and/or disseminated) or an *aspergillus* infection in a mammal comprising administering to the mammal in need thereof an effective amount of a compound of Formula I:

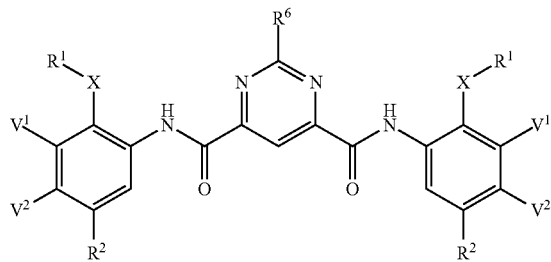

(I)

wherein:
each X is, independently, O, S, or S($=$O)$_2$;
each $R^1$ is, independently, —CH$_3$, —(CH$_2$)$_n$—NH$_2$, —(CH$_2$)$_n$—NH—C($=$NH)NH$_2$, or —(CH$_2$)$_n$—NH—C($=$O)—R$^4$, where each n is, independently, 1 to 4, and each $R^4$ is, independently, H, —C$_1$-C$_3$alkyl, or —(CH$_2$)$_p$—NH$_2$, where each p is, independently, 1 or 2;
each $R^2$ is, independently, H, halo, —CF$_3$, or —C(CH$_3$)$_3$;
each $V^2$ is H, and each $V^1$ is, independently, —N—C($=$O)—R$^3$, where each $R^3$ is, independently, —(CH$_2$)$_n$—NH$_2$ or —(CH$_2$)$_n$—NH—C($=$NH)NH$_2$, where each n is, independently, 1 to 4; or each $V^1$ is H and each $V^2$ is, independently, —S—R$^5$, where each $R^5$ is, independently, —(CH$_2$)$_n$—NH$_2$ or —(CH$_2$)$_n$—NH—C($=$NH)NH$_2$, where each n is, independently, 1 to 4; and
each $R^6$ is H, —S—(CH$_2$)$_m$—NH$_2$, —S—(CH$_2$)$_m$—NH—C($=$NH)NH$_2$, —O—(CH$_2$)$_m$—NH$_2$, or —O—(CH$_2$)$_m$—NH—C($=$NH)NH$_2$, where each m is, independently, 1 to 4; or a pharmaceutically acceptable salt thereof.

In some embodiments, each X is S.

In any of the above embodiments, each $R^1$ is, independently, —CH$_3$, —(CH$_2$)$_n$—NH$_2$, —(CH$_2$)$_n$—NH—C($=$NH)NH$_2$, or —(CH$_2$)$_n$—NH—C($=$O)—R$^4$, where each n is, independently, 1 or 2, and each $R^4$ is, independently, H or methyl; or each $R^1$ is, independently, —CH$_3$, —(CH$_2$)$_n$—NH$_2$, —(CH$_2$)$_n$—NH—C($=$NH)NH$_2$, or —(CH$_2$)$_n$—NH—C($=$O)—R$^4$, where each n is 2 and each $R^4$ is H; or each $R^1$ is, independently, —CH$_3$, —(CH$_2$)$_n$—NH$_2$ or —(CH$_2$)$_n$—NH—C($=$NH)NH$_2$, where each n is 2; or each $R^1$ is —CH$_3$, —(CH$_2$)$_n$—NH$_2$, or —(CH$_2$)$_n$—NH—C($=$NH)NH$_2$, where each n is 2; or each $R^1$ is —CH$_3$ or —(CH$_2$)$_n$—NH$_2$ where each n is 2.

In any of the above embodiments, each $R^2$ is, independently, H, Br, F, Cl, —CF$_3$, or —C(CH$_3$)$_3$; or each $R^2$ is, independently, Br, F, Cl, —CF$_3$, or —C(CH$_3$)$_3$; or each $R^2$ is —CF$_3$.

In any of the above embodiments, each $V^2$ is H and each $V^1$ is, independently, —N—C(=O)—$R^3$, where each $R^3$ is, independently, —(CH$_2$)$_n$—NH$_2$ or —(CH$_2$)$_n$—NH—C(=NH)NH$_2$, where each n is, independently, 1 to 4; or each $V^2$ is H and each $V^1$ is, independently, —N—C(=O)—$R^3$, where each $R^3$ is, independently, —(CH$_2$)$_n$—NH$_2$ or —(CH$_2$)$_n$—NH—C(=NH)NH$_2$, where each n is, independently, 1 or 2; or each $V^2$ is H and each $V^1$ is, independently, —N—C(=O)—$R^3$, where each $R^3$ is, independently, —(CH$_2$)$_n$—NH$_2$ or —(CH$_2$)$_n$—NH—C(=NH)NH$_2$, where each n is 2; or each $V^2$ is H and each $V^1$ is —N—C(=O)—$R^3$, where each $R^3$ is —(CH$_2$)$_n$—NH$_2$ or —(CH$_2$)$_n$—NH—C(=NH)NH$_2$, where n is 2.

In any of the above embodiments, each $V^1$ is H and each $V^2$ is, independently, —S—$R^5$, where each $R^5$ is, independently, —(CH$_2$)$_n$—NH$_2$ or —(CH$_2$)$_n$—NH—C(=NH)NH$_2$, where each n is, independently, 1 to 4; or each $V^1$ is H and each $V^2$ is, independently, —S—$R^5$, where each $R^5$ is, independently, —(CH$_2$)$_n$—NH$_2$ or —(CH$_2$)$_n$—NH—C(=NH)NH$_2$, where each n is 1 or 2; or each $V^1$ is H and each $V^2$ is, independently, —S—$R^5$, where each $R^5$ is, independently, —(CH$_2$)$_n$—NH$_2$ or —(CH$_2$)$_n$—NH—C(=NH)NH$_2$, where each n is 2; or each $V^1$ is H and each $V^2$ is —S—$R^5$, where each $R^5$ is —(CH$_2$)$_n$—NH$_2$ or —(CH$_2$)$_n$—NH—C(=NH)NH$_2$, where each n is 2; or each $V^1$ is H and each $V^2$ is —S—$R^5$, where each $R^5$ is —(CH$_2$)$_n$—NH$_2$ where each n is 2.

In any of the above embodiments, each $R^6$ is H, —S—(CH$_2$)$_m$—NH$_2$, or —S—(CH$_2$)$_m$—NH—C(=NH)NH$_2$, where each m is, independently, 1 to 4; or each $R^6$ is H, —S—(CH$_2$)$_m$—NH$_2$, or —S—(CH$_2$)$_m$—NH—C(=NH)NH$_2$, where each m is, independently, 1 or 2; or each $R^6$ is H or —S—(CH$_2$)$_m$—NH—C(=NH)NH$_2$, where each m is, independently, 1 or 2; or each $R^6$ is H or —S—(CH$_2$)$_m$—NH—C(=NH)NH$_2$, where each m is 2.

In some embodiments, each X is S; each $R^1$ is, independently, —(CH$_2$)$_n$—NH$_2$ or —(CH$_2$)$_n$—NH—C(=NH)NH$_2$, where each n is, independently, 1 to 4; each $R^2$ is, independently, halo, —CF$_3$, or —C(CH$_3$)$_3$; and each $V^1$ is H and each $V^2$ is, independently, —S—$R^5$, where each $R^5$ is, independently, —(CH$_2$)$_n$—NH$_2$, where each n is, independently, 1 to 4.

In some embodiments, each X is S; each $R^1$ is, independently, —(CH$_2$)$_n$—NH$_2$, where each n is, independently, 1 or 2; each $R^2$ is, independently, —CF$_3$ or —C(CH$_3$)$_3$; and each $V^1$ is —H and each $V^2$ is, independently, —S—$R^5$, where each $R^5$ is, independently, —(CH$_2$)$_n$—NH$_2$, where each n is, independently, 1 or 2.

In some embodiments, each X is S; each $R^1$ is —(CH$_2$)$_n$—NH$_2$, where each n is 1 or 2; each $R^2$ is, independently, —CF$_3$ or —C(CH$_3$)$_3$; and each $V^1$ is H and each $V^2$ is —S—$R^5$, where each $R^5$ is —(CH$_2$)$_n$—NH$_2$, where each n is 1 or 2.

In some embodiments, each X is O or S; each $R^1$ is, independently, —(CH$_2$)$_n$—NH$_2$, or —(CH$_2$)$_n$—NH—C(=NH)NH$_2$, or —(CH$_2$)$_n$—NH—C(=O)—$R^4$, where each n is, independently, 1 to 4, and each $R^4$ is, independently, H or methyl; each $R^2$ is, independently, halo, —CF$_3$, or —C(CH$_3$)$_3$; and each $V^2$ is H, and each $V^1$ is, independently, —N—C(=O)—$R^3$, where each $R^3$ is, independently, —(CH$_2$)$_n$—NH$_2$ or —(CH$_2$)$_n$—NH—C(=NH)NH$_2$, where each n is, independently, 1 to 4.

In some embodiments, each X is S; each $R^1$ is, independently, —(CH$_2$)$_n$—NH—C(=O)—$R^4$, where each n is, independently, 1 or 2, and each $R^4$ is, independently, H or methyl; each $R^2$ is, independently, halo; and each $V^2$ is H, and each $V^1$ is —N—C(=O)—$R^3$, where each $R^3$ is —(CH$_2$)$_n$—NH$_2$ or —(CH$_2$)$_n$—NH—C(=NH)NH$_2$, where each n is 4.

In some embodiments, each X is O or S; each $R^1$ is, independently, —(CH$_2$)$_n$—NH$_2$ or —(CH$_2$)$_n$—NH—C(=NH)NH$_2$, where each n is, independently, 1 to 4; each $R^2$ is, independently, halo, —CF$_3$, or —C(CH$_3$)$_3$; and each $V^2$ is H, and each $V^1$ is, independently, —N—C(=O)—$R^3$, where each $R^3$ is, independently, —(CH$_2$)$_n$—NH$_2$ or —(CH$_2$)$_n$—NH—C(=NH)NH$_2$, where each n is, independently, 1 to 4.

In some embodiments, each X is O or S; each $R^1$ is —(CH$_2$)$_n$—NH$_2$ or —(CH$_2$)$_n$—NH—C(=NH)NH$_2$, where each n is 1 or 2; each $R^2$ is halo, —CF$_3$, or —C(CH$_3$)$_3$; and each $V^2$ is H, and each $V^1$ is —N—C(=O)—$R^3$, where each $R^3$ is —(CH$_2$)$_n$—NH$_2$ or —(CH$_2$)$_n$—NH—C(=NH)NH$_2$, where each n is 3 or 4.

In some embodiments, each X is, independently, S or S(=O)$_2$; each $R^1$ is, independently, —(CH$_2$)$_n$—NH$_2$ or —(CH$_2$)$_n$—NH—C(=O)—$R^4$, where each n is, independently, 1 or 2, and each $R^4$ is, independently, —(CH$_2$)$_p$—NH$_2$, where each p is, independently, 1 or 2; each $R^2$ is, independently, halo or —CF$_3$; and each $V^2$ is H, and each $V^1$ is, independently, —N—C(=O)—$R^3$, where each $R^3$ is, independently, —(CH$_2$)$_n$—NH$_2$ or —(CH$_2$)$_n$—NH—C(=NH)NH$_2$, where each n is, independently, 3 or 4.

In some embodiments, each X is O or S; each $R^1$ is —CH$_3$; each $R^2$ is —CF$_3$; each $V^1$ is H and each $V^2$ is, independently, —S—$R^5$, where each $R^5$ is, independently, —(CH$_2$)$_n$—NH$_2$ or —(CH$_2$)$_n$—NH—C(=NH)NH$_2$, where each n is, independently, 1 to 4; and each $R^6$ is —S—(CH$_2$)$_m$—NH$_2$ or —S—(CH$_2$)$_m$—NH—C(=NH)NH$_2$, where each m is, independently, 1 or 2.

In some embodiments, the compound is chosen from:

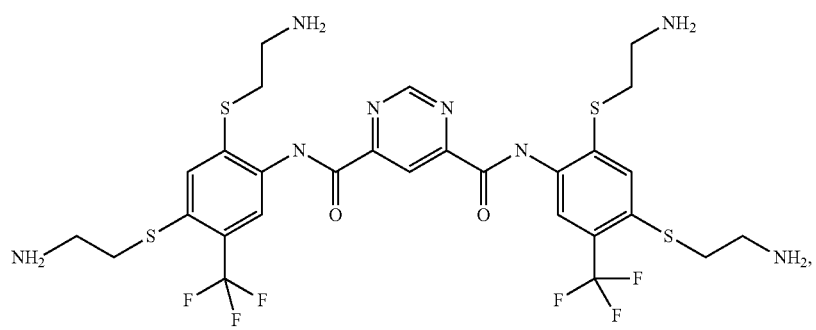

Compound 100

Compound 101
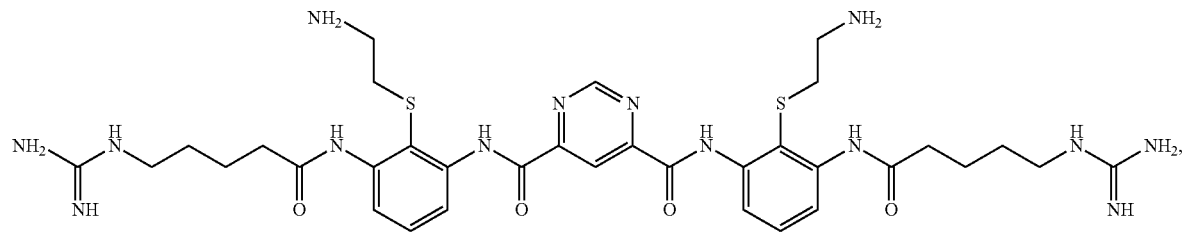
Compound 102
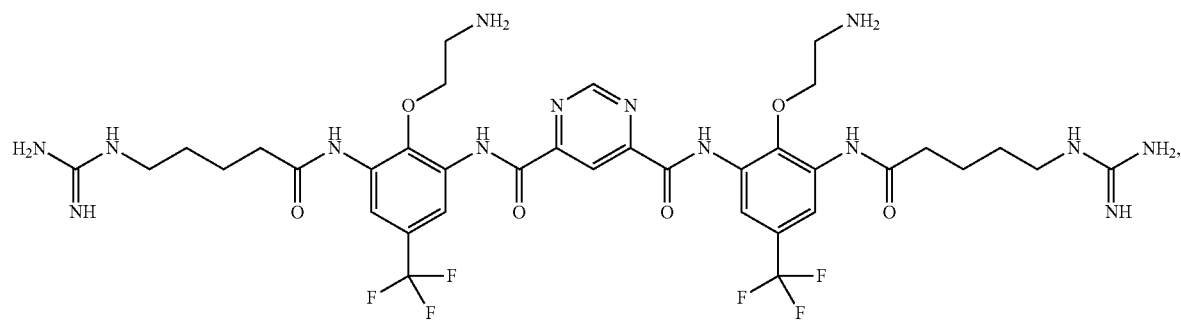
Compound 103
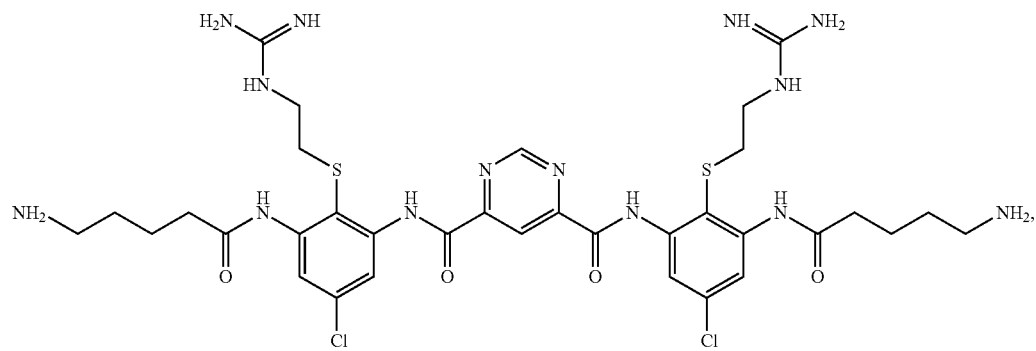
Compound 104
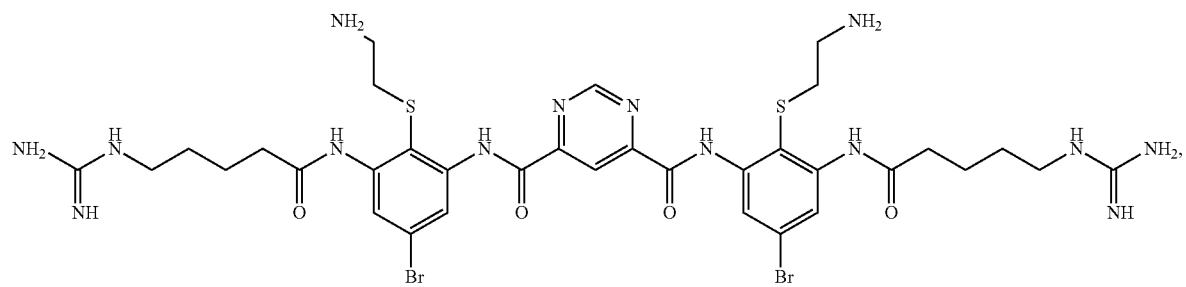
Compound 105
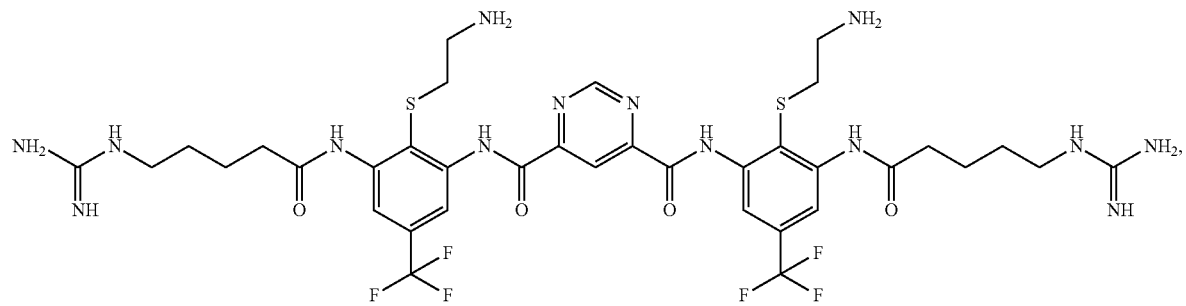

-continued
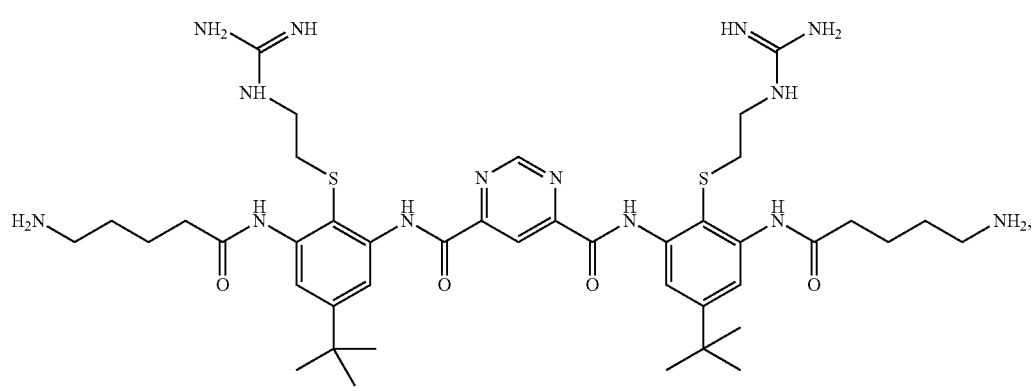
Compound 106
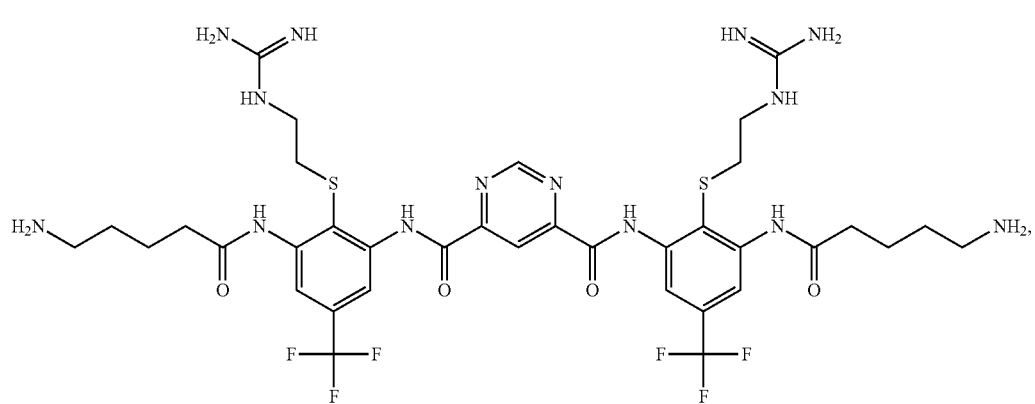
Compound 107
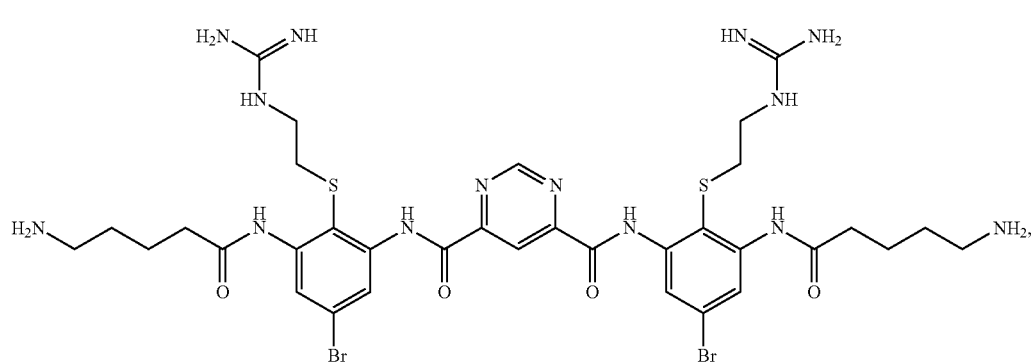
Compound 108
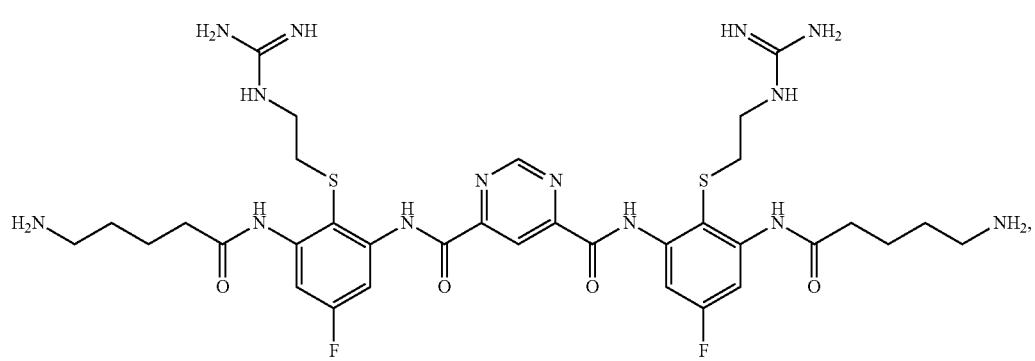
Compound 109

-continued
Compound 110
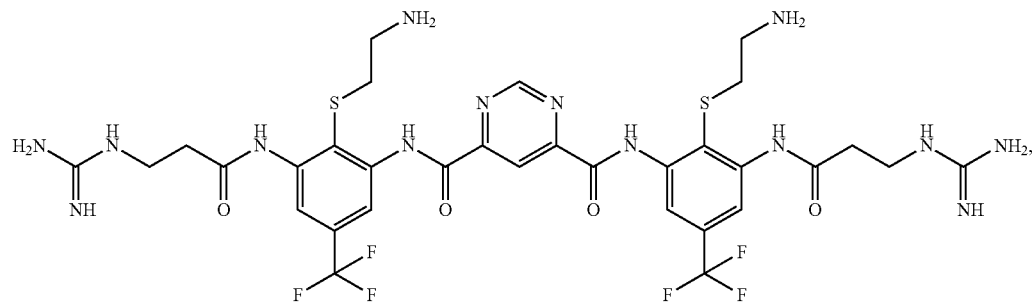
Compound 111
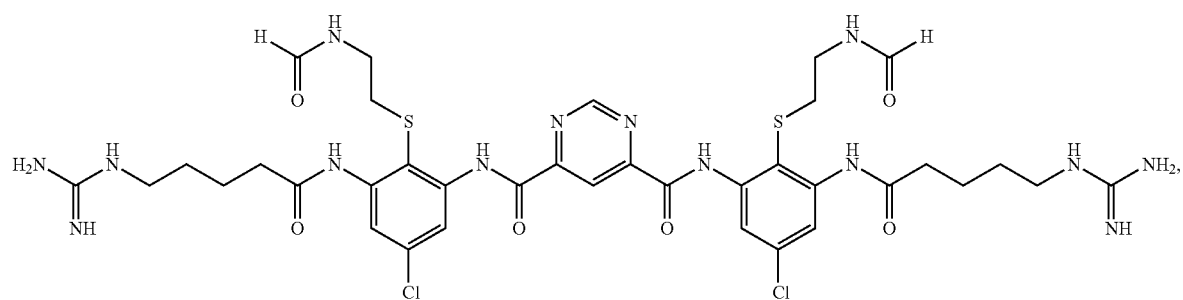
Compound 112
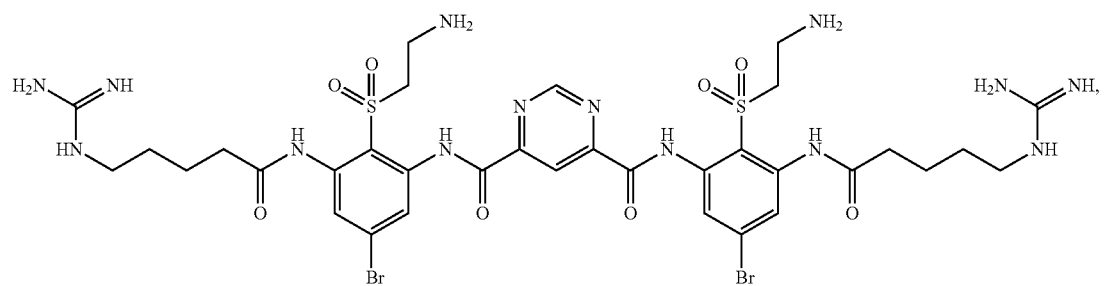
Compound 113
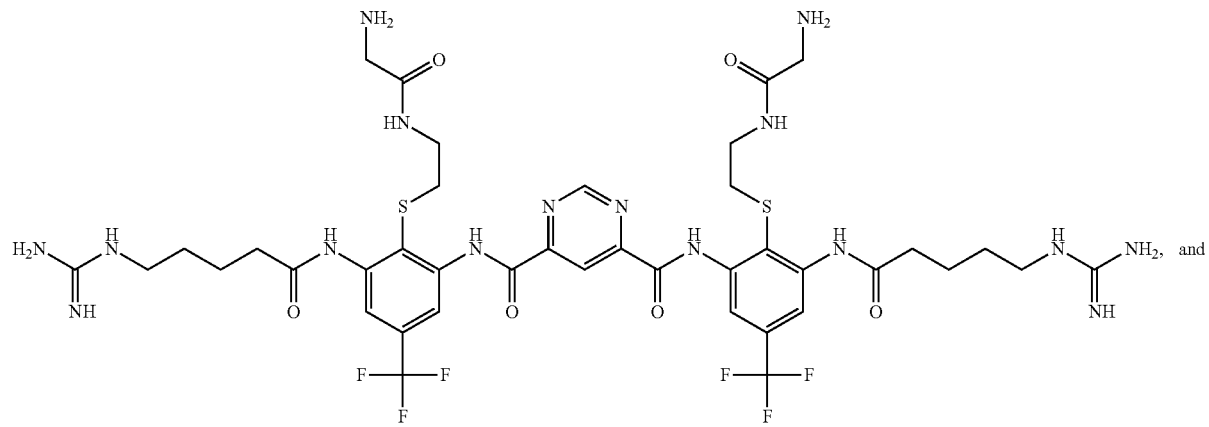
and -continued

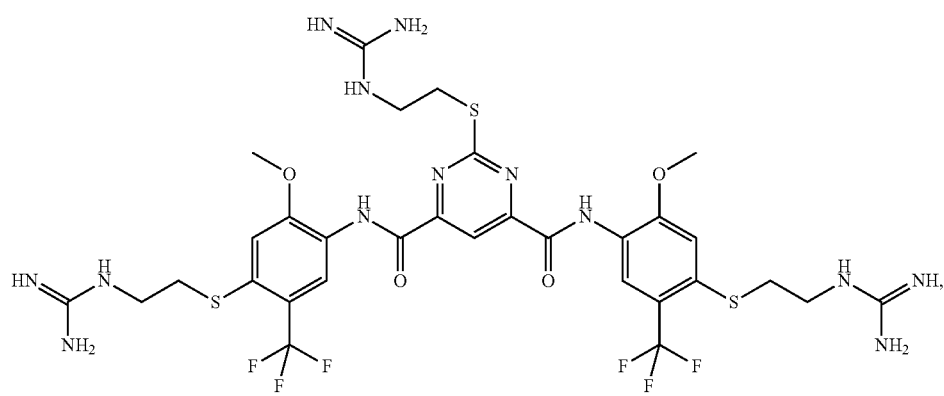

Compound 183 or a pharmaceutically acceptable salt thereof.

The present disclosure also provides methods of killing or inhibiting the growth of a *Candida* or *Aspergillus* species comprising contacting the *Candida* or *Aspergillus* species with an effective amount of a compound of Formula I:

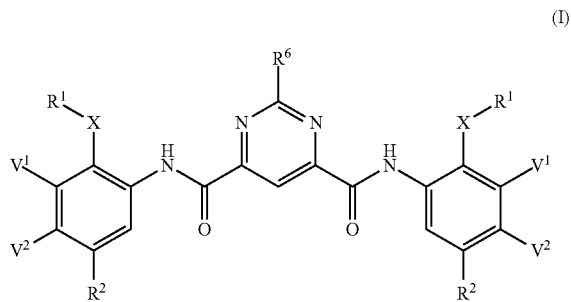

(I)

wherein:
each X is, independently, O, S, or S(=O)$_2$;
each R$^1$ is, independently, —CH$_3$, —(CH$_2$)$_n$—NH$_2$, —(CH$_2$)$_n$—NH—C(=NH)NH$_2$, or —(CH$_2$)$_n$—NH—C(=O)—R$^4$, where each n is, independently, 1 to 4, and each R$^4$ is, independently, H, —C$_1$-C$_3$alkyl, or —(CH$_2$)$_p$—NH$_2$, where each p is, independently, 1 or 2;
each R$^2$ is, independently, H, halo, —CF$_3$, or —C(CH$_3$)$_3$;
each V$^2$ is H, and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 1 to 4; or each V$^1$ is H and each V$^2$ is, independently, —S—R$^5$, where each R$^5$ is, independently, —(CH$_2$)$_n$—NH$_2$ or —(CH$_2$)$_n$—NH—C(=NH)NH$_2$, where each n is, independently, 1 to 4; and
each R$^6$ is H, —S—(CH$_2$)$_m$—NH$_2$, —S—(CH$_2$)$_m$—NH—C(=NH)NH$_2$, —O—(CH$_2$)$_m$—NH$_2$, or —O—(CH$_2$)$_m$—NH—C(=NH)NH$_2$, where each m is, independently, 1 to 4; or a pharmaceutically acceptable salt thereof.

In some embodiments, each X is S.

In any of the above embodiments, each R$^1$ is, independently, —CH$_3$, —(CH$_2$)$_n$—NH$_2$, —(CH$_2$)$_n$—NH—C(=NH)NH$_2$, or —(CH$_2$)$_n$—NH—C(=O)—R$^4$, where each n is, independently, 1 or 2, and each R$^4$ is, independently, H or methyl; or each R$^1$ is, independently, —CH$_3$, —(CH$_2$)$_n$—NH$_2$, —(CH$_2$)$_n$—NH—C(=NH)NH$_2$, or —(CH$_2$)$_n$—NH—C(=O)—R$^4$, where each n is 2 and each R$^4$ is H; or each R$^1$ is, independently, —CH$_3$, —(CH$_2$)$_n$—NH$_2$ or —(CH$_2$)$_n$—NH—C(=NH)NH$_2$, where each n is 2; or each R$^1$ is —CH$_3$, —(CH$_2$)$_n$—NH$_2$, or —(CH$_2$)$_n$—NH—C(=NH)NH$_2$, where each n is 2; or each R$^1$ is —CH$_3$ or —(CH$_2$)$_n$—NH$_2$ where each n is 2.

In any of the above embodiments, each R$^2$ is, independently, H, Br, F, Cl, —CF$_3$, or —C(CH$_3$)$_3$; or each R$^2$ is, independently, Br, F, Cl, —CF$_3$, or —C(CH$_3$)$_3$; or each R$^2$ is —CF$_3$.

In any of the above embodiments, each V$^2$ is H and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 1 to 4; or each V$^2$ is H and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is, independently, 1 or 2; or each V$^2$ is H and each V$^1$ is, independently, —N—C(=O)—R$^3$, where each R$^3$ is, independently, —(CH$_2$)$_n$—NH$_2$ or —(CH$_2$)$_n$—NH—C(=NH)NH$_2$, where each n is 2; or each V$^2$ is H and each V$^1$ is —N—C(=O)—R$^3$, where each R$^3$ is —(CH$_2$)$_n$—NH$_2$ or —(CH$_2$)$_n$—NH—C(=NH)NH$_2$, where n is 2.

In any of the above embodiments, each V$^1$ is H and each V$^2$ is, independently, —S—R$^5$, where each R$^5$ is, independently, —(CH$_2$)$_n$—NH$_2$ or —(CH$_2$)$_n$—NH—C(=NH)NH$_2$, where each n is, independently, 1 to 4; or each V$^1$ is H and each V$^2$ is, independently, —S—R$^5$, where each R$^5$ is, independently, —(CH$_2$)$_n$—NH$_2$ or —(CH$_2$)$_n$—NH—C(=NH)NH$_2$, where each n is 1 or 2; or each V$^1$ is H and each V$^2$ is, independently, —S—R$^5$, where each R$^5$ is, independently, —(CH$_2$)$_n$—NH$_2$ or —(CH$_2$)$_n$—NH—C(=NH)NH$_2$, where each n is 2; or each V$^1$ is H and each V$^2$ is —S—R$^5$, where each R$^5$ is —(CH$_2$)$_n$—NH$_2$ or —(CH$_2$)$_n$—NH—C(=NH)NH$_2$, where each n is 2; or each V$^1$ is H and each V$^2$ is —S—R$^5$, where each R$^5$ is —(CH$_2$)$_n$—NH$_2$ where each n is 2.

In any of the above embodiments, each R$^6$ is H, —S—(CH$_2$)$_m$—NH$_2$, or —S—(CH$_2$)$_m$—NH—C(=NH)NH$_2$, where each m is, independently, 1 to 4; or each R$^6$ is H, —S—(CH$_2$)$_m$—NH$_2$, or —S—(CH$_2$)$_m$—NH—C(=NH)NH$_2$, where each m is, independently, 1 or 2; or each R$^6$ is H or —S—(CH$_2$)$_m$—NH—C(=NH)NH$_2$, where each m is, independently, 1 or 2; or each R$^6$ is H or —S—(CH$_2$)$_m$—NH—C(=NH)NH$_2$, where each m is 2.

In some embodiments, each X is S; each R$^1$ is, independently, —(CH$_2$)$_n$—NH$_2$ or —(CH$_2$)$_n$—NH—C(=NH)NH$_2$, where each n is, independently, 1 to 4; each R$^2$ is, independently, halo, CF$_3$, or C(CH$_3$)$_3$; and each V$^1$ is H and each V$^2$ is, independently, —S—R$^5$, where each R$^5$ is, independently, —(CH$_2$)$_n$—NH$_2$, where each n is, independently, 1 to 4.

In some embodiments, each X is S; each $R^1$ is, independently, —$(CH_2)_n$—$NH_2$, where each n is, independently, 1 or 2; each $R^2$ is, independently, —$CF_3$ or —$C(CH_3)_3$; and each $V^1$ is H and each $V^2$ is, independently, —S—$R^5$, where each $R^5$ is, independently, —$(CH_2)_n$—$NH_2$, where each n is, independently, 1 or 2.

In some embodiments, each X is S; each $R^1$ is —$(CH_2)_n$—$NH_2$, where each n is 1 or 2; each $R^2$ is, independently, —$CF_3$ or —$C(CH_3)_3$; and each $V^1$ is H and each $V^2$ is —S—$R^5$, where each $R^5$ is —$(CH_2)_n$—$NH_2$, where each n is 1 or 2.

In some embodiments, each X is O or S; each $R^1$ is, independently, —$(CH_2)_n$—$NH_2$, or —$(CH_2)_n$—$NH$—$C(=NH)NH_2$, or —$(CH_2)_n$—$NH$—$C(=O)$—$R^4$, where each n is, independently, 1 to 4, and each $R^4$ is, independently, H or methyl; each $R^2$ is, independently, halo, —$CF_3$, or —$C(CH_3)_3$; and each $V^2$ is H, and each $V^1$ is, independently, —N—$C(=O)$—$R^3$, where each $R^3$ is, independently, —$(CH_2)_n$—$NH_2$ or —$(CH_2)_n$—$NH$—$C(=NH)NH_2$, where each n is, independently, 1 to 4.

In some embodiments, each X is S; each $R^1$ is, independently, —$(CH_2)_n$—$NH$—$C(=O)$—$R^4$, where each n is, independently, 1 or 2, and each $R^4$ is, independently, H or methyl; each $R^2$ is, independently, halo; and each $V^2$ is H, and each $V^1$ is —N—$C(=O)$—$R^3$, where each $R^3$ is —$(CH_2)_n$—$NH_2$ or —$(CH_2)_n$—$NH$—$C(=NH)NH_2$, where each n is 4.

In some embodiments, each X is O or S; each $R^1$ is, independently, —$(CH_2)_n$—$NH_2$ or —$(CH_2)_n$—$NH$—$C(=NH)NH_2$, where each n is, independently, 1 to 4; each $R^2$ is, independently, halo, —$CF_3$, or —$C(CH_3)_3$; and each $V^2$ is H, and each $V^1$ is, independently, —N—$C(=O)$—$R^3$, where each $R^3$ is, independently, —$(CH_2)_n$—$NH_2$ or —$(CH_2)_n$—$NH$—$C(=NH)NH_2$, where each n is, independently, 1 to 4.

In some embodiments, each X is O or S; each $R^1$ is —$(CH_2)_n$—$NH_2$ or —$(CH_2)_n$—$NH$—$C(=NH)NH_2$, where each n is 1 or 2; each $R^2$ is halo, —$CF_3$, or —$C(CH_3)_3$; and each $V^2$ is H, and each $V^1$ is —N—$C(=O)$—$R^3$, where each $R^3$ is —$(CH_2)_n$—$NH_2$ or —$(CH_2)_n$—$NH$—$C(=NH)NH_2$, where each n is 3 or 4.

In some embodiments, each X is, independently, S or $S(=O)_2$; each $R^1$ is, independently, —$(CH_2)_n$—$NH_2$ or —$(CH_2)_n$—$NH$—$C(=O)$—$R^4$, where each n is, independently, 1 or 2, and each $R^4$ is, independently, —$(CH_2)_p$—$NH_2$, where each p is, independently, 1 or 2; each $R^2$ is, independently, halo or —$CF_3$; and each $V^2$ is H, and each $V^1$ is, independently, —N—$C(=O)$—$R^3$, where each $R^3$ is, independently, —$(CH_2)_n$—$NH_2$ or —$(CH_2)_n$—$NH$—$C(=NH)NH_2$, where each n is, independently, 3 or 4.

In some embodiments, each X is O or S; each $R^1$ is —$CH_3$; each $R^2$ is —$CF_3$; each $V^1$ is H and each $V^2$ is, independently, —S—$R^5$, where each $R^5$ is, independently, —$(CH_2)_n$—$NH_2$ or —$(CH_2)_n$—$NH$—$C(=NH)NH_2$, where each n is, independently, 1 to 4; and each $R^6$ is —S—$(CH_2)_m$—$NH_2$ or —S—$(CH_2)_m$—$NH$—$C(=NH)NH_2$, where each m is, independently, 1 or 2.

In some embodiments, the compound is chosen from:

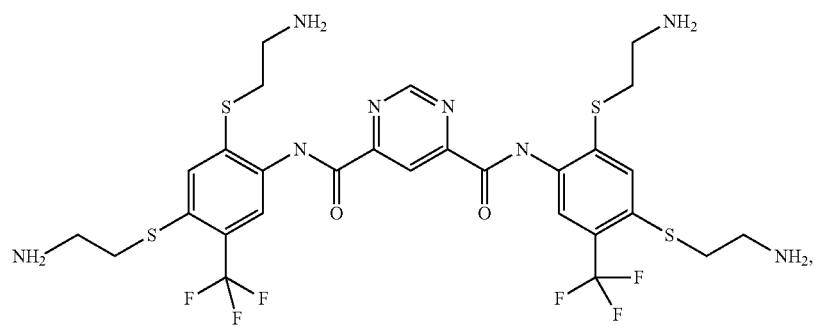

Compound 100

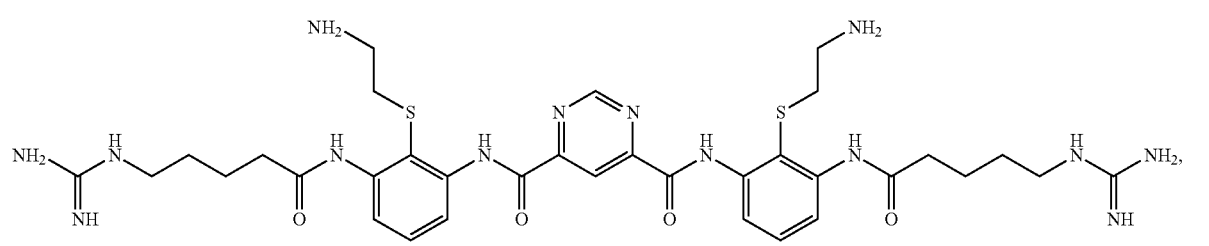

Compound 101

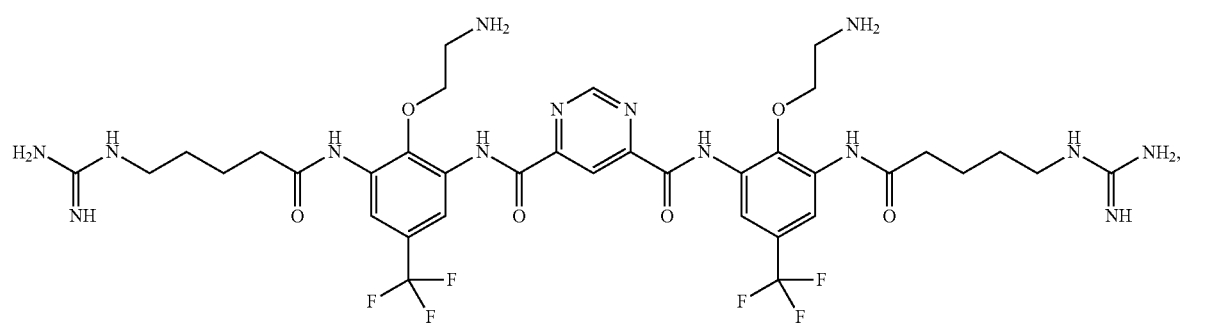

Compound 102

Compound 103
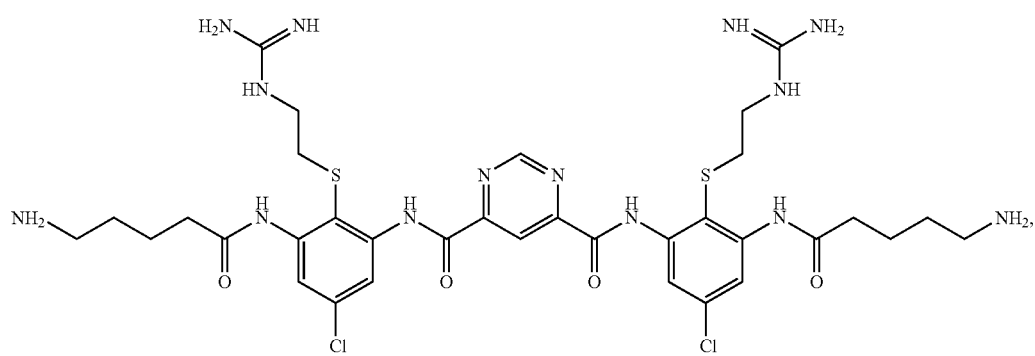
Compound 104
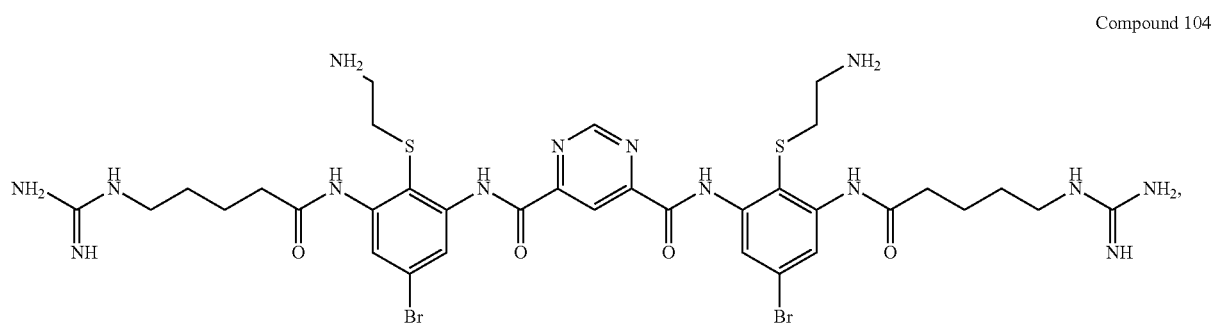
Compound 105
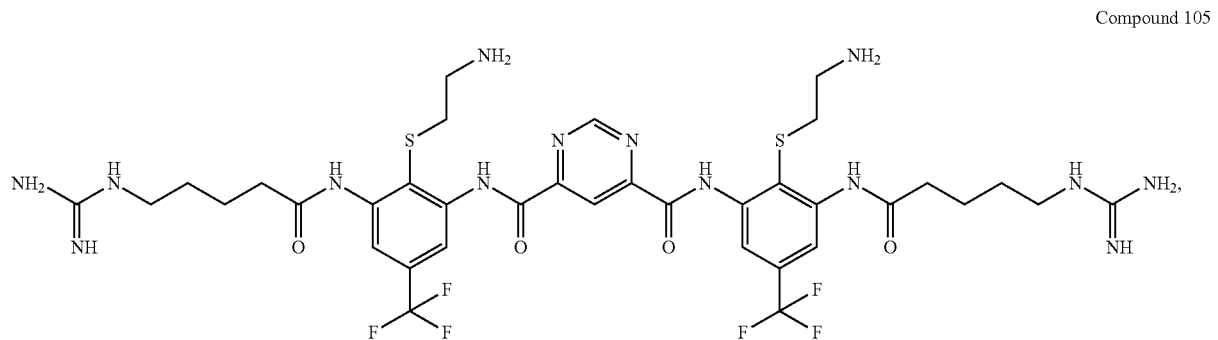
Compound 106
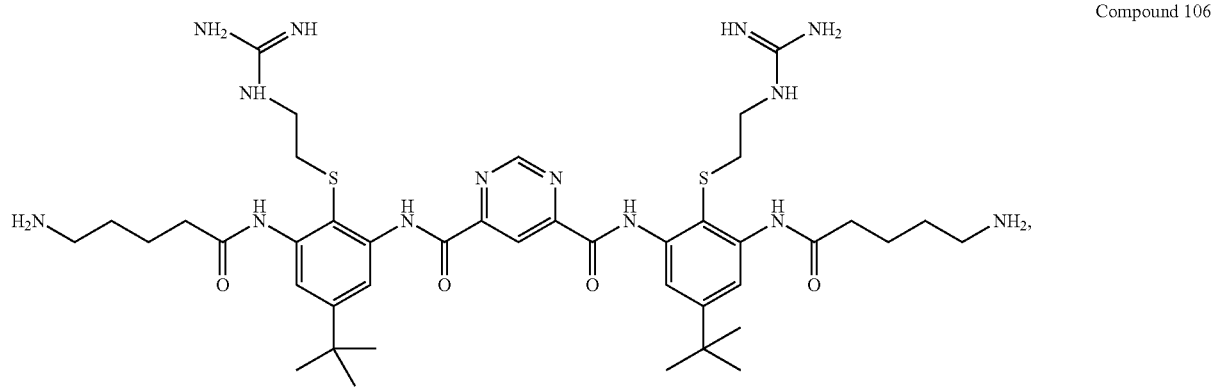

-continued
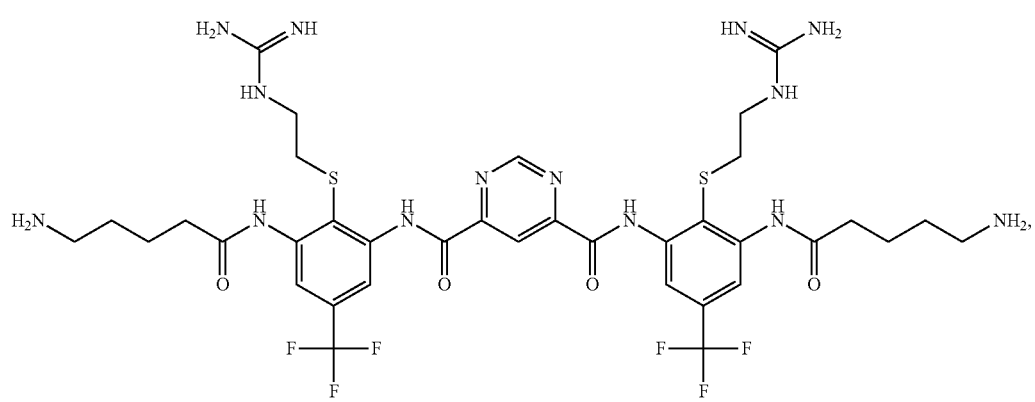
Compound 107
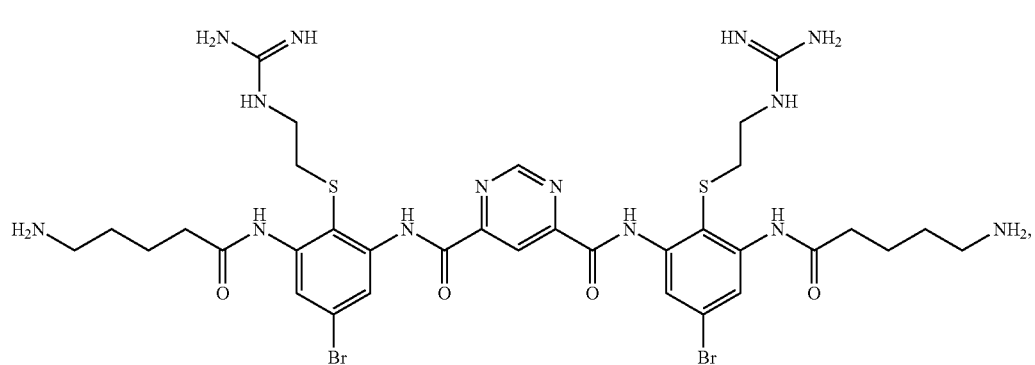
Compound 108
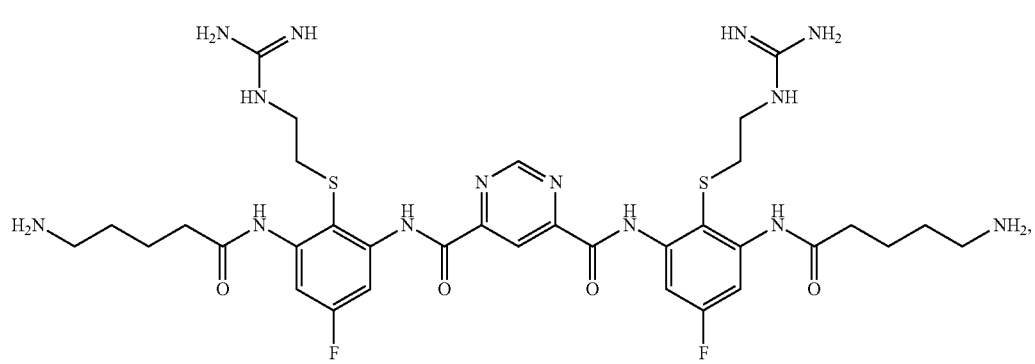
Compound 109
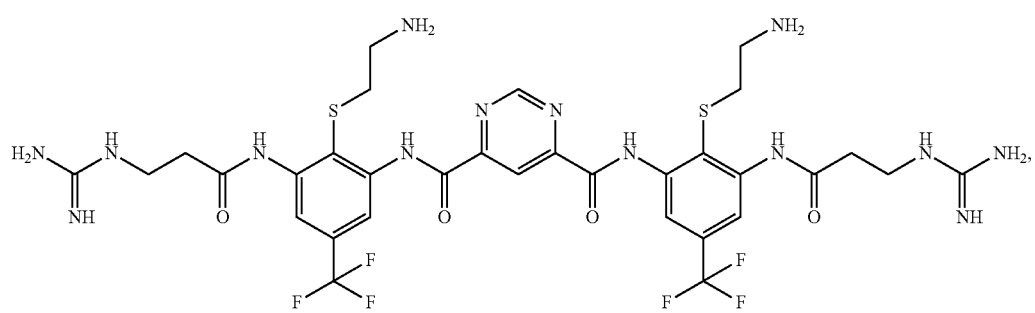
Compound 110

-continued
Compound 111
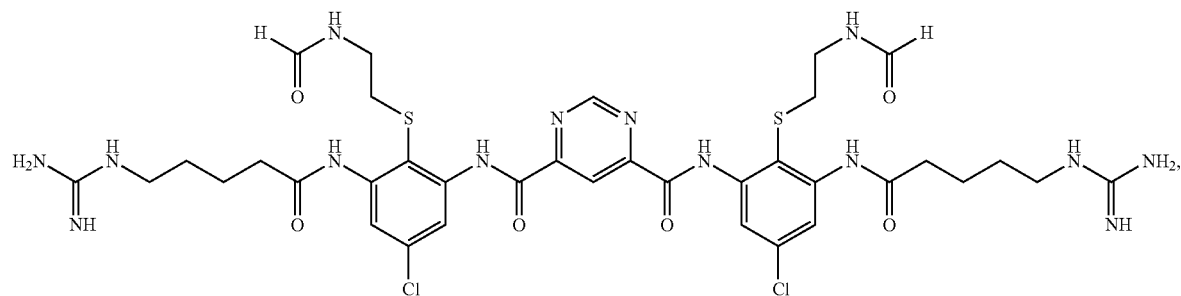
Compound 112
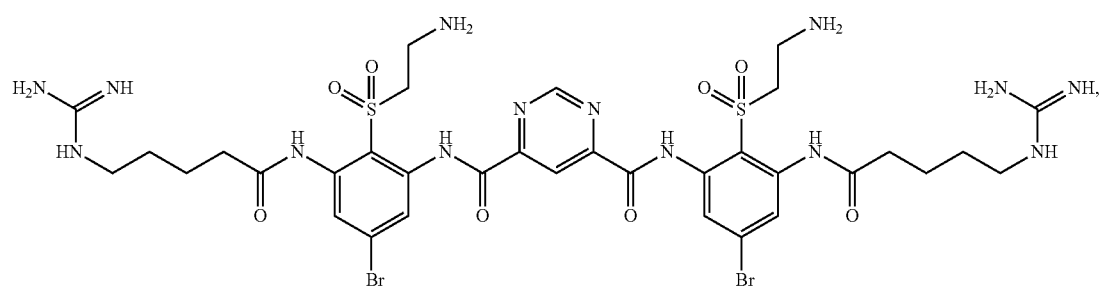
Compound 113
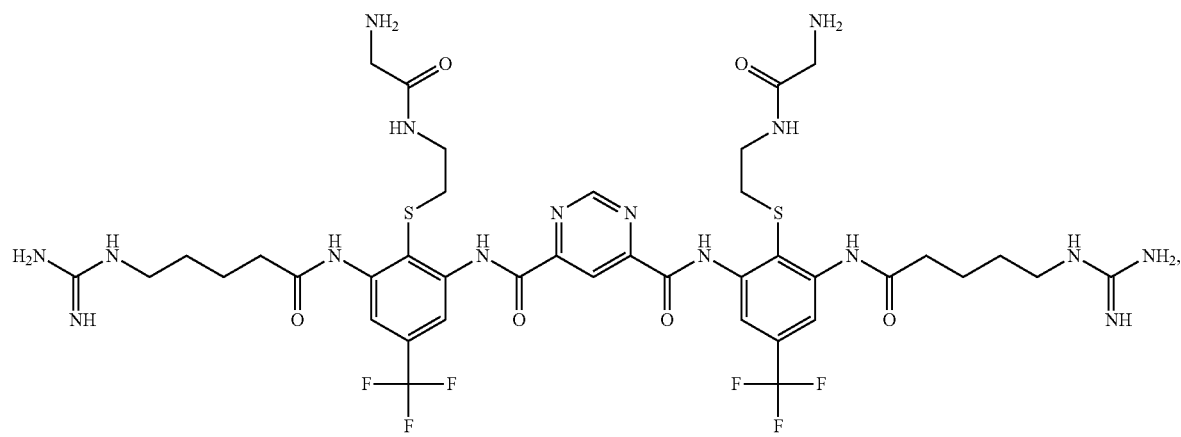
Compound 183
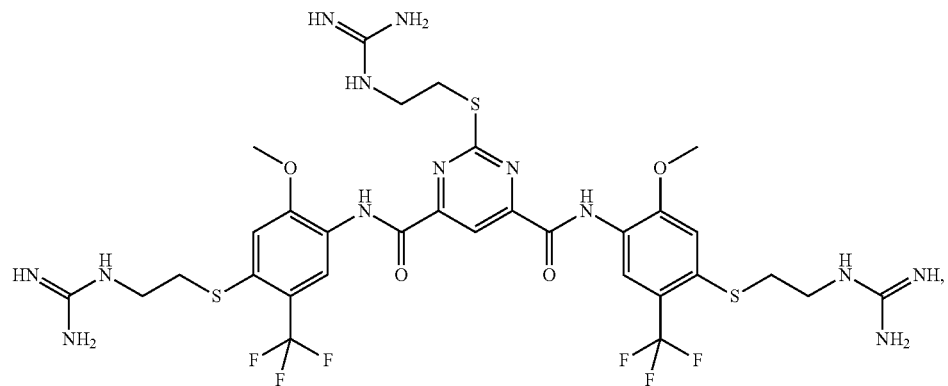

or a pharmaceutically acceptable salt thereof.

The present disclosure also provides compounds of Formula II:

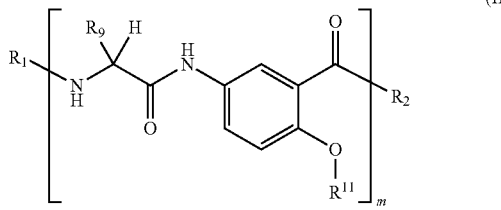

wherein:
$R^1$ is H;
$R_2$ is —$NH_2$;
each $R^{11}$ is, independently, —$(CH_2)_{0-4}$—$R^4$ where $R^4$ is chosen from hydrogen, —$C_1$-$C_4$alkyl, —$C_3$-$C_{12}$branched alkyl, —$C_3$-$C_8$cycloalkyl, phenyl optionally substituted with one or more —$C_1$-$C_4$alkyl groups, —$C_1$-$C_4$alkoxy groups, or halo groups, and heteroaryl optionally substituted with one or more —$C_1$-$C_4$alkyl groups, —$C_1$-$C_4$alkoxy groups, or halo groups;
each $R_9$ is, independently, hydroxyethoxymethyl, methoxyethoxymethyl, polyoxyethylene, or —$(CH_2)_q$—V where q is from 1 to 5, and each V is, independently, chosen from amino, hydroxyl, —$C_1$-$C_6$alkylurea, —$C_1$-$C_6$alkylamino, —$C_1$-$C_6$dialkylamino, —$NH(CH_2)_{1-4}NH_2$, —$N(CH_2CH_2NH_2)_2$, amidine, guanidine, semicarbazone, imidazole, piperidine, piperazine, 4-alkylpiperazine, phenyl optionally substituted with an amino, —$C_1$-$C_6$alkylamino, or —$C_1$-$C_6$dialkylamino, and lower acylamino optionally substituted with one or more amino, lower alkylamino, or lower dialkylamino, where the alkylene chain is optionally substituted with an amino or hydroxyl group; and
m is 2 to at least about 30;
or a pharmaceutically acceptable salt thereof.

In some embodiments, each $R^{11}$ is, independently, —$(CH_2)_{0-4}$—$R^4$ where $R^4$ is chosen from hydrogen, —$C_1$-$C_4$alkyl, —$C_3$-$C_{12}$branched alkyl, and —$C_3$-$C_8$cycloalkyl; or each $R^{11}$ is, independently, —$(CH_2)_{1-3}$—$R^4$ where $R^4$ is chosen from hydrogen, —$C_1$-$C_4$alkyl, —$C_3$-$C_{12}$branched alkyl, and —$C_3$-$C_8$cycloalkyl; or each $R^{11}$ is, independently, —$(CH_2)_{1-2}$—$R^4$ where $R^4$ is chosen from hydrogen or —$C_1$-$C_4$alkyl; or each $R^{11}$ is chosen from methyl, ethyl, n-propyl, iso-propyl, n-butyl iso-butyl, sec-butyl, tert-butyl, n-pentyl, iso-pentyl, sec-pentyl, and benzyl.

In any of the above embodiments, each $R_9$ is, independently, —$(CH_2)_q$—V where q is from 1 to 5, and each V is, independently, chosen from amino, hydroxyl, —$C_1$-$C_6$alkylamino, —$C_1$-$C_6$dialkylamino, —$C_1$-$C_3$alkylurea, —$NH(CH_2)_{1-4}NH_2$, —$N(CH_2CH_2NH_2)_2$, amidine, guanidine, semicarbazone, imidazole, piperidine, piperazine, 4-alkylpiperazine; or each $R_9$ is, independently, —$(CH_2)_q$—V where q is from 1 to 4, and each V is, independently, chosen from amino, hydroxyl, —$C_1$-$C_6$alkylamino, —$C_1$-$C_6$dialkylamino, —$C_1$-$C_2$alkylurea, —$NH(CH_2)_{1-4}NH_2$, —$N(CH_2CH_2NH_2)_2$, amidine, and guanidine; or each $R_9$ is, independently, —$(CH_2)_q$—V where q is from 1 to 4, and each V is, independently, chosen from amino, —$C_1$-$C_6$alkylamino, —$C_1$-$C_6$dialkylamino, —$C_1$-$C_2$alkylurea, amidine, and guanidine; or each $R_9$ is, independently, —$(CH_2)_q$—V where q is from 1 to 4, and each V is, independently, chosen from amino, amidine, —$C_1$-$C_2$alkylurea, and guanidine.

In any of the above embodiments, m is 2 to at least about 20; or m is 2 to at least about 10; or m is 2 to at least about 8; or m is 3 to at least about 6; or m is 4 to at least about 5; or m is 5.

In some embodiments, $R_1$ is H; $R_2$ is —$NH_2$; each $R^{11}$ is, independently, —$(CH_2)_{0-4}$—$R^4$ where $R^4$ is chosen from hydrogen, —$C_1$-$C_4$alkyl, —$C_3$-$C_{12}$branched alkyl, and —$C_3$-$C_8$cycloalkyl; each $R_9$ is, independently, —$(CH_2)_q$—V where q is from 1 to 5, and each V is, independently, chosen from amino, hydroxyl, —$C_1$-$C_6$alkylamino, —$C_1$-$C_6$dialkylamino, —$C_1$-$C_3$alkylurea, —$NH(CH_2)_{1-4}NH_2$, —$N(CH_2CH_2NH_2)_2$, amidine, guanidine, semicarbazone, imidazole, piperidine, piperazine, 4-alkylpiperazine; and m is 2 to at least about 20.

In some embodiments, $R_1$ is H; $R_2$ is —$NH_2$; each $R^{11}$ is, independently, —$(CH_2)_{1-3}$—$R^4$ where $R^4$ is chosen from hydrogen, —$C_1$-$C_4$alkyl, —$C_3$-$C_{12}$branched alkyl, and —$C_3$-$C_8$cycloalkyl; each $R_9$ is, independently, —$(CH_2)_q$—V where q is from 1 to 4, and each V is, independently, chosen from amino, hydroxyl, —$C_1$-$C_6$alkylamino, —$C_1$-$C_6$dialkylamino, —$NH(CH_2)_{1-4}NH_2$, —$N(CH_2CH_2NH_2)_2$, amidine, —$C_1$-$C_2$alkylurea, and guanidine; and m is 2 to at least about 10.

In some embodiments, $R_1$ is H; $R_2$ is —$NH_2$; each $R^{11}$ is, independently, —$(CH_2)_{1-2}$—$R^4$ where $R^4$ is chosen from hydrogen or —$C_1$-$C_4$alkyl; each $R_9$ is, independently, —$(CH_2)_q$—V where q is from 1 to 4, and each V is, independently, chosen from amino, —$C_1$-$C_6$alkylamino, —$C_1$-$C_6$dialkylamino, amidine, and —$C_1$-$C_2$alkylurea, guanidine; and m is 3 to at least about 6.

In some embodiments, $R_1$ is H; $R_2$ is —$NH_2$; each $R^{11}$ is chosen from methyl, ethyl, n-propyl, iso-propyl, n-butyl iso-butyl, sec-butyl, tert-butyl, n-pentyl, iso-pentyl, sec-pentyl, and benzyl; each $R_9$ is, independently, —$(CH_2)_q$—V where q is from 1 to 4, and each V is, independently, chosen from amino, amidine, —$C_1$-$C_2$alkylurea, and guanidine; and m is 4 to 5.

In some embodiments, the compound is chosen from:

Compound 114

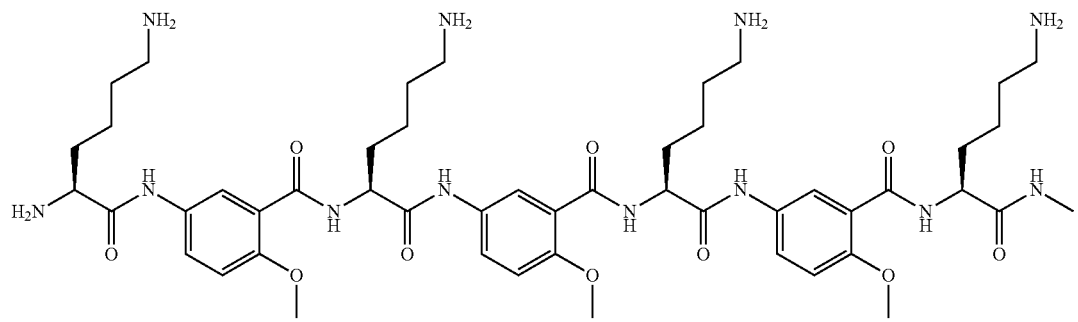

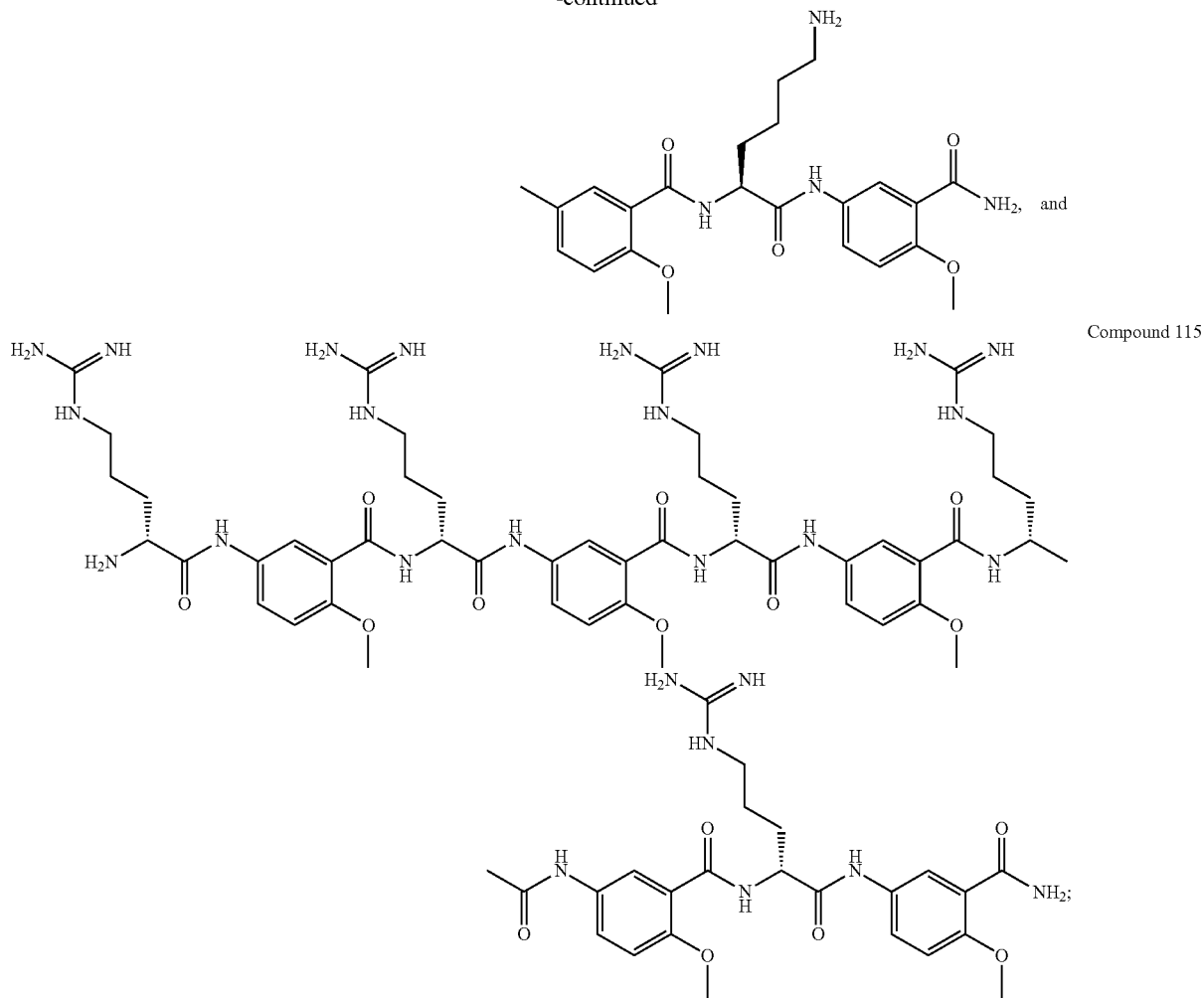

Compound 115 or a pharmaceutically acceptable salt thereof.

In some embodiments, any one or more of the above compounds may be excluded from any of the genus of compounds described above.

The present disclosure also provides compositions comprising one or more of the compounds or salts described above and a pharmaceutically acceptable carrier.

The present disclosure also provides methods of preventing or treating candidiasis (oral and/or disseminated) or an *aspergillus* infection in a mammal comprising administering to the mammal in need thereof an effective amount of a compound of Formula II:

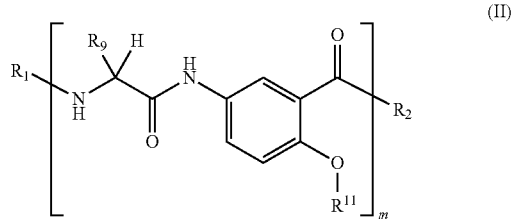

wherein:
$R_1$ is H;
$R_2$ is —$NH_2$;

each $R^{11}$ is, independently, —$(CH_2)_{0-4}$—$R^4$ where $R^4$ is chosen from hydrogen, —$C_1$-$C_4$alkyl, —$C_3$-$C_{12}$branched alkyl, —$C_3$-$C_8$cycloalkyl, phenyl optionally substituted with one or more —$C_1$-$C_4$alkyl groups, —$C_1$-$C_4$alkoxy groups, or halo groups, and heteroaryl optionally substituted with one or more —$C_1$-$C_4$alkyl groups, —$C_1$-$C_4$alkoxy groups, or halo groups;

each $R_9$ is, independently, hydroxyethoxymethyl, methoxyethoxymethyl, polyoxyethylene, or —$(CH_2)_q$—V where q is from 1 to 5, and each V is, independently, chosen from amino, hydroxyl, —$C_1$-$C_6$alkylurea, —$C_1$-$C_6$alkylamino, —$C_1$-$C_6$dialkylamino, —$NH(CH_2)_{1-4}NH_2$, —$N(CH_2CH_2NH_2)_2$, amidine, guanidine, semicarbazone, imidazole, piperidine, piperazine, 4-alkylpiperazine, phenyl optionally substituted with an amino, —$C_1$-$C_6$alkylamino, or —$C_1$-$C_6$dialkylamino, and lower acylamino optionally substituted with one or more amino, lower alkylamino, or lower dialkylamino, where the alkylene chain is optionally substituted with an amino or hydroxyl group; and m is 2 to at least about 30;

or a pharmaceutically acceptable salt thereof.

In some embodiments, each $R^{11}$ is, independently, —$(CH_2)_{0-4}$—$R^4$ where $R^4$ is chosen from hydrogen, —$C_1$-$C_4$alkyl, —$C_3$-$C_{12}$branched alkyl, and —$C_3$-$C_8$cycloalkyl; or each $R^{11}$ is, independently, —(CH$_2$)$_{1-3}$—R$^4$ where R$^4$ is chosen from hydrogen, —C$_1$-C$_4$alkyl, —C$_3$-C$_{12}$branched alkyl, and —C$_3$-C$_8$cycloalkyl; or each $R^{11}$ is, independently, —(CH$_2$)$_{1-2}$—R$^4$ where R$^4$ is chosen from hydrogen or —C$_1$-C$_4$alkyl; or each $R^{11}$ is chosen from methyl, ethyl, n-propyl, iso-propyl, n-butyl iso-butyl, sec-butyl, tert-butyl, n-pentyl, iso-pentyl, sec-pentyl, and benzyl.

In any of the above embodiments, each $R_9$ is, independently, —(CH$_2$)$_q$—V where q is from 1 to 5, and each V is, independently, chosen from amino, hydroxyl, —C$_1$-C$_6$alkylamino, —C$_1$-C$_6$dialkylamino, —C$_1$-C$_3$alkylurea, —NH(CH$_2$)$_{1-4}$NH$_2$, —N(CH$_2$CH$_2$NH$_2$)$_2$, amidine, guanidine, semicarbazone, imidazole, piperidine, piperazine, 4-alkylpiperazine; or each $R_9$ is, independently, —(CH$_2$)$_q$—V where q is from 1 to 4, and each V is, independently, chosen from amino, hydroxyl, —C$_1$-C$_6$alkylamino, —C$_1$-C$_6$dialkylamino, —C$_1$-C$_2$alkylurea, —NH(CH$_2$)$_{1-4}$NH$_2$, —N(CH$_2$CH$_2$NH$_2$)$_2$, amidine, and guanidine; or each $R_9$ is, independently, —(CH$_2$)$_q$—V where q is from 1 to 4, and each V is, independently, chosen from amino, —C$_1$-C$_6$alkylamino, —C$_1$-C$_6$dialkylamino, —C$_1$-C$_2$alkylurea, amidine, and guanidine; or each $R_9$ is, independently, —(CH$_2$)$_q$—V where q is from 1 to 4, and each V is, independently, chosen from amino, amidine, —C$_1$-C$_2$alkylurea, and guanidine.

In any of the above embodiments, m is 2 to at least about 20; or m is 2 to at least about 10; or m is 2 to at least about 8; or m is 3 to at least about 6; or m is 4 to at least about 5; or m is 5.

In some embodiments, $R_1$ is H; $R_2$ is —NH$_2$; each $R^{11}$ is, independently, —(CH$_2$)$_{0-4}$—R$^4$ where R$^4$ is chosen from hydrogen, —C$_1$-C$_4$alkyl, —C$_3$-C$_{12}$branched alkyl, and —C$_3$-C$_8$cycloalkyl; each $R_9$ is, independently, —(CH$_2$)$_q$—V where q is from 1 to 5, and each V is, independently, chosen from amino, hydroxyl, —C$_1$-C$_6$alkylamino, —C$_1$-C$_6$dialkylamino, —C$_1$-C$_3$alkylurea, —NH(CH$_2$)$_{1-4}$NH$_2$, —N(CH$_2$CH$_2$NH$_2$)$_2$, amidine, guanidine, semicarbazone, imidazole, piperidine, piperazine, 4-alkylpiperazine; and m is 2 to at least about 20.

In some embodiments, $R_1$ is H; $R_2$ is —NH$_2$; each $R^{11}$ is, independently, —(CH$_2$)$_{1-3}$—R$^4$ where R$^4$ is chosen from hydrogen, —C$_1$-C$_4$alkyl, —C$_3$-C$_{12}$branched alkyl, and —C$_3$-C$_8$cycloalkyl; each $R_9$ is, independently, —(CH$_2$)$_q$—V where q is from 1 to 4, and each V is, independently, chosen from amino, hydroxyl, —C$_1$-C$_6$alkylamino, —C$_1$-C$_6$dialkylamino, —NH(CH$_2$)$_{1-4}$NH$_2$, —N(CH$_2$CH$_2$NH$_2$)$_2$, amidine, —C$_1$-C$_2$alkylurea, and guanidine; and m is 2 to at least about 10.

In some embodiments, $R_1$ is H; $R_2$ is —NH$_2$; each $R^{11}$ is, independently, —(CH$_2$)$_{1-2}$—R$^4$ where R$^4$ is chosen from hydrogen or —C$_1$-C$_4$alkyl; each $R_9$ is, independently, —(CH$_2$)$_q$—V where q is from 1 to 4, and each V is, independently, chosen from amino, —C$_1$-C$_6$alkylamino, —C$_1$-C$_6$dialkylamino, amidine, and —C$_1$-C$_2$alkylurea, guanidine; and m is 3 to at least about 6.

In some embodiments, $R_1$ is H; $R_2$ is —NH$_2$; each $R^{11}$ is chosen from methyl, ethyl, n-propyl, iso-propyl, n-butyl iso-butyl, sec-butyl, tert-butyl, n-pentyl, iso-pentyl, sec-pentyl, and benzyl; each $R_9$ is, independently, —(CH$_2$)$_q$—V where q is from 1 to 4, and each V is, independently, chosen from amino, amidine, —C$_1$-C$_2$alkylurea, and guanidine; and m is 4 to 5.

In some embodiments, the compound is chosen from:

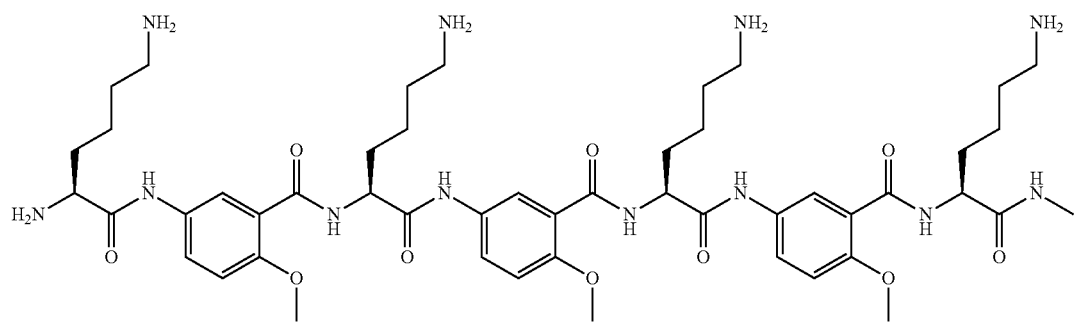

Compound 114

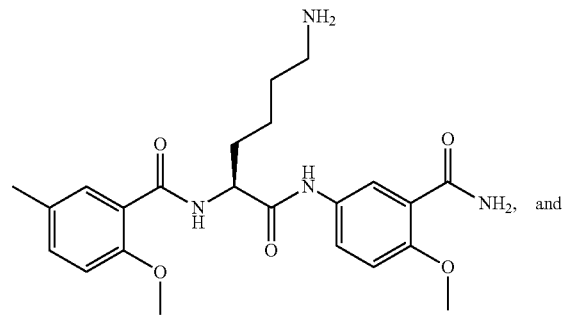

and

-continued

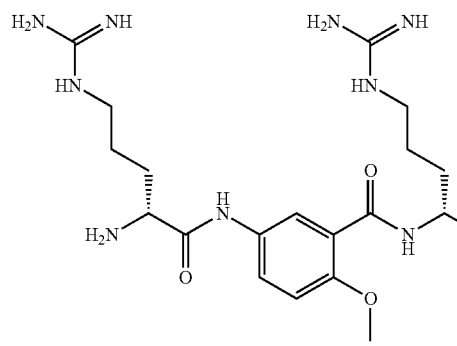
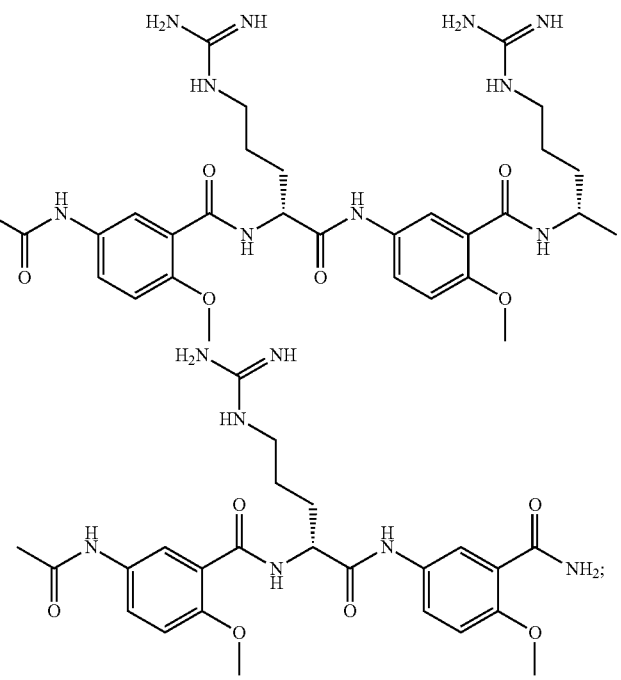

Compound 115 or a pharmaceutically acceptable salt thereof.

The present disclosure also provides methods of killing or inhibiting the growth of a *Candida* or *Aspergillus* species comprising contacting the *Candida* or *Aspergillus* species with an effective amount of a compound of Formula II:

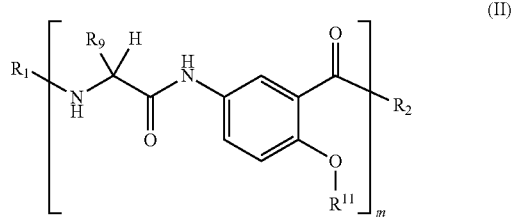

(II)

wherein:
$R_1$ is H;
$R_2$ is —$NH_2$;
each $R^{11}$ is, independently, —$(CH_2)_{0-4}$—$R^4$ where $R^4$ is chosen from hydrogen, —$C_1$-$C_4$alkyl, —$C_3$-$C_{12}$branched alkyl, —$C_3$-$C_8$cycloalkyl, phenyl optionally substituted with one or more —$C_1$-$C_4$alkyl groups, —$C_1$-$C_4$alkoxy groups, or halo groups, and heteroaryl optionally substituted with one or more —$C_1$-$C_4$alkyl groups, —$C_1$-$C_4$alkoxy groups, or halo groups;
each $R_9$ is, independently, hydroxyethoxymethyl, methoxyethoxymethyl, polyoxyethylene, or —$(CH_2)_q$—V where q is from 1 to 5, and each V is, independently, chosen from amino, hydroxyl, —$C_1$-$C_6$alkylurea, —$C_1$-$C_6$alkylamino, —$C_1$-$C_6$dialkylamino, —$NH(CH_2)_{1-4}NH_2$, —$N(CH_2CH_2NH_2)_2$, amidine, guanidine, semicarbazone, imidazole, piperidine, piperazine, 4-alkylpiperazine, phenyl optionally substituted with an amino, —$C_1$-$C_6$alkylamino, or —$C_1$-$C_6$dialkylamino, and lower acylamino optionally substituted with one or more amino, lower alkylamino, or lower dialkylamino, where the alkylene chain is optionally substituted with an amino or hydroxyl group; and
m is 2 to at least about 30;
or a pharmaceutically acceptable salt thereof.

In some embodiments, each $R^{11}$ is, independently, —$(CH_2)_{0-4}$—$R^4$ where $R^4$ is chosen from hydrogen, —$C_1$-$C_4$alkyl, —$C_3$-$C_{12}$branched alkyl, and —$C_3$-$C_8$cycloalkyl; or each $R^{11}$ is, independently, —$(CH_2)_{1-3}$—$R^4$ where $R^4$ is chosen from hydrogen, —$C_1$-$C_4$alkyl, —$C_3$-$C_{12}$branched alkyl, and —$C_3$-$C_8$cycloalkyl; or each $R^{11}$ is, independently, —$(CH_2)_{1-2}$—$R^4$ where $R^4$ is chosen from hydrogen or —$C_1$-$C_4$alkyl; or each $R^{11}$ is chosen from methyl, ethyl, n-propyl, iso-propyl, n-butyl iso-butyl, sec-butyl, tert-butyl, n-pentyl, iso-pentyl, sec-pentyl, and benzyl.

In any of the above embodiments, each $R_9$ is, independently, —$(CH_2)_q$—V where q is from 1 to 5, and each V is, independently, chosen from amino, hydroxyl, —$C_1$-$C_6$alkylamino, —$C_1$-$C_6$dialkylamino, —$C_1$-$C_3$alkylurea, —$NH(CH_2)_{1-4}NH_2$, —$N(CH_2CH_2NH_2)_2$, amidine, guanidine, semicarbazone, imidazole, piperidine, piperazine, 4-alkylpiperazine; or each $R_9$ is, independently, —$(CH_2)_q$—V where q is from 1 to 4, and each V is, independently, chosen from amino, hydroxyl, —$C_1$-$C_6$alkylamino, —$C_1$-$C_6$dialkylamino, —$C_1$-$C_2$alkylurea, —$NH(CH_2)_{1-4}NH_2$, —$N(CH_2CH_2NH_2)_2$, amidine, and guanidine; or each $R_9$ is, independently, —$(CH_2)_q$—V where q is from 1 to 4, and each V is, independently, chosen from amino, —$C_1$-$C_6$alkylamino, —$C_1$-$C_6$dialkylamino, —$C_1$-$C_2$alkylurea, amidine, and guanidine; or each $R_9$ is, independently, —$(CH_2)_q$—V where q is from 1 to 4, and each V is, independently, chosen from amino, amidine, —$C_1$-$C_2$alkylurea, and guanidine.

In any of the above embodiments, m is 2 to at least about 20; or m is 2 to at least about 10; or m is 2 to at least about 8; or m is 3 to at least about 6; or m is 4 to at least about 5; or m is 4 or 5.

In some embodiments, $R_1$ is H; $R_2$ is —$NH_2$; each $R^{11}$ is, independently, —$(CH_2)_{0-4}$—$R^4$ where $R^4$ is chosen from hydrogen, —$C_1$-$C_4$alkyl, —$C_3$-$C_{12}$branched alkyl, and —$C_3$-$C_8$cycloalkyl; each $R_9$ is, independently, —$(CH_2)_q$—V where q is from 1 to 5, and each V is, independently, chosen from amino, hydroxyl, —$C_1$-$C_6$alkylamino, —$C_1$-$C_6$dialkylamino, —$C_1$-$C_3$alkylurea, —$NH(CH_2)_{1-4}NH_2$, —$N(CH_2CH_2NH_2)_2$, amidine, guanidine, semicarbazone, imidazole, piperidine, piperazine, 4-alkylpiperazine; and m is 2 to at least about 20.

In some embodiments, $R_1$ is H; $R_2$ is —$NH_2$; each $R^{11}$ is, independently, —$(CH_2)_{1-3}$—$R^4$ where $R^4$ is chosen from hydrogen, —$C_1$-$C_4$alkyl, —$C_3$-$C_{12}$branched alkyl, and —$C_3$-$C_8$cycloalkyl; each $R_9$ is, independently, —$(CH_2)_q$—V where q is from 1 to 4, and each V is, independently, chosen from amino, hydroxyl, —$C_1$-$C_6$alkylamino, —$C_1$-$C_6$dialkylamino, —$NH(CH_2)_{1-4}NH_2$, —$N(CH_2CH_2NH_2)_2$, amidine, —$C_1$-$C_2$alkylurea, and guanidine; and m is 2 to at least about 10.

In some embodiments, $R_1$ is H; $R_2$ is —$NH_2$; each $R^{11}$ is, independently, —$(CH_2)_{1-2}$—$R^4$ where $R^4$ is chosen from hydrogen or —$C_1$-$C_4$alkyl; each $R_9$ is, independently, —$(CH_2)_q$—V where q is from 1 to 4, and each V is, independently, chosen from amino, —$C_1$-$C_6$alkylamino, —$C_1$-$C_6$dialkylamino, amidine, and —$C_1$-$C_2$alkylurea, guanidine; and m is 3 to at least about 6.

In some embodiments, $R_1$ is H; $R_2$ is —$NH_2$; each $R^{11}$ is chosen from methyl, ethyl, n-propyl, iso-propyl, n-butyl iso-butyl, sec-butyl, tert-butyl, n-pentyl, iso-pentyl, sec-pentyl, and benzyl; each $R_9$ is, independently, —$(CH_2)_q$—V where q is from 1 to 4, and each V is, independently, chosen from amino, amidine, —$C_1$-$C_2$alkylurea, and guanidine; and m is 4 to 5.

In some embodiments, the compound is chosen from:

Compound 114

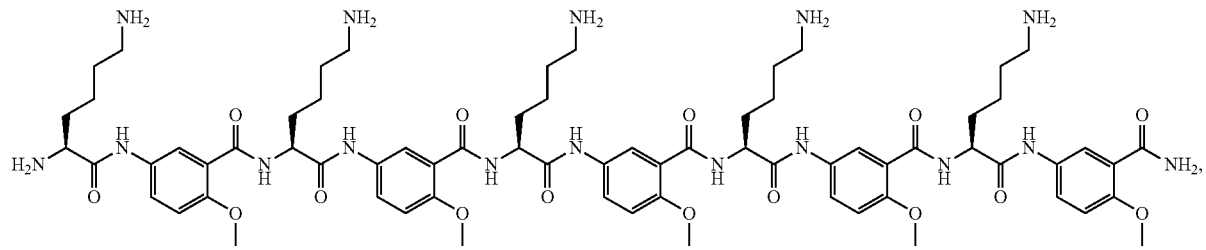

and

Compound 115

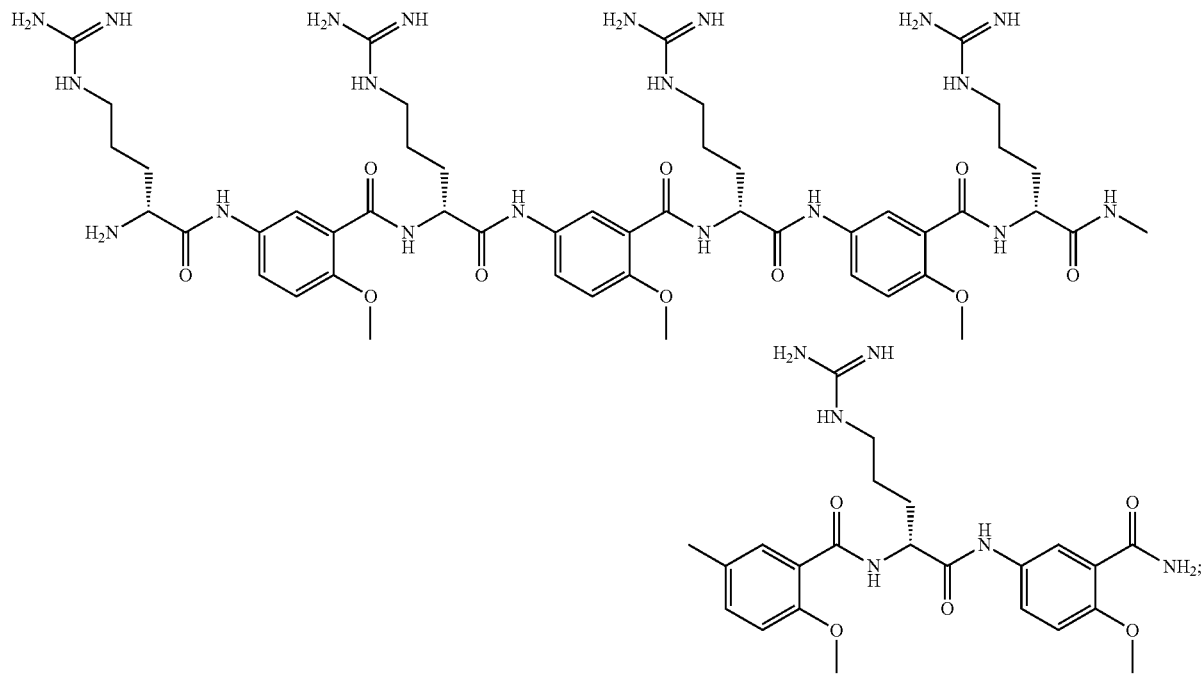

or a pharmaceutically acceptable salt thereof.

The present disclosure also provides compounds of Formula III:

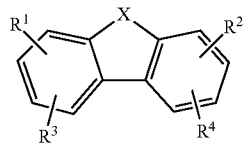

(III)

wherein:

X is —C(R$^7$)C(R$^8$), —C(=O), —N(R$^9$), O, S, S(=O), or S(=O)$_2$;

R$^7$, R$^8$, and R$^9$ are, independently, H, —C$_1$-C$_8$alkyl, —C$_1$-C$_8$alkoxy, halo, —OH, —CF$_3$, aromatic group, —(CH$_2$)$_q$NH$_2$, or —(CH$_2$)$_q$NHC(=NH)NH$_2$, where q is 0 to 4;

R$^1$ and R$^2$ are, independently, H, —C$_1$-C$_8$alkyl, —C$_1$-C$_8$alkoxy, halo, —OH, -haloC$_1$-C$_8$alkyl, —CN, or —CF$_3$;

R$^3$ and R$^4$ are, independently, H or -carbocycle(R$^5$)(R$^6$);

each R$^5$ and each R$^6$ are, independently, H, —C$_1$-C$_8$alkyl, —C$_1$-C$_8$alkoxy, halo, amino, —OH, —CF$_3$, —O—(CH$_2$)$_p$—NH$_2$, —O—(CH$_2$)$_p$NHC(=NH)NH$_2$, —S—(CH$_2$)$_p$—NH$_2$, —N((CH$_2$)$_p$NH$_2$)$_2$, —S—(CH$_2$)$_p$NHC(=NH)NH$_2$, —C(=O)NH(CH$_2$)$_p$NH$_2$, —(CH$_2$)$_p$N((CH$_2$)$_p$NH$_2$)$_2$, where each p is, independently, 1 to 5, aromatic group, heterocycle, or the free base or salt form of —(CH$_2$)$_n$—NH$_2$, —(CH$_2$)$_n$—NH—(CH$_2$)$_n$—NH$_2$, or —(CH$_2$)$_n$—NH—C(=NH)NH$_2$, where each n is, independently, 1 to 8;

provided that the compound is not Compound 116-134; or a pharmaceutically acceptable salt thereof.

In some embodiments, X is —N(R$^9$), O, S, or S(=O)$_2$; or X is —NH, O, S, or —N(CH$_2$)$_q$NH$_2$, where q is 2 or 3; or X is —NH, —N(CH$_2$)$_3$NH$_2$, or S.

In any of the above embodiments, R$^1$ and R$^2$ are, independently, H, —C$_1$-C$_3$alkyl, —C$_1$-C$_3$alkoxy, halo, —OH, -haloC$_1$-C$_3$alkyl, or —CN; or R$^1$ and R$^2$ are, independently, H, —C$_1$-C$_3$alkyl, —C$_1$-C$_3$alkoxy, halo, or —OH; or R$^1$ and R$^2$ are, independently, H, —C$_1$-C$_3$alkyl, or halo; or R$^1$ and R$^2$ are H.

In any of the above embodiments, R$^3$ and R$^4$ are, independently, H or -carbocycle(R$^5$)(R$^6$), where R$^5$ and R$^6$ can be positioned anywhere on the carbocycle. In any of the above embodiments, R$^3$ and R$^4$ are, independently,

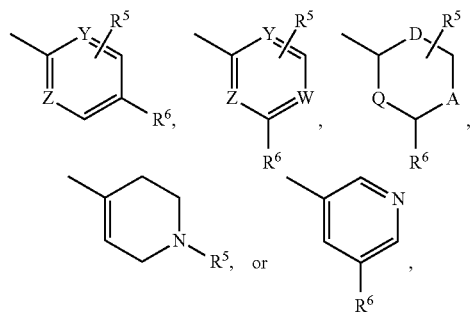

wherein each W, Y, and Z are, independently, C or N, each A, D, and Q are, independently, —C(R$^{10}$)C(R$^{11}$), —C(=O), —N(R$^{12}$), O, or S, and each R$^{10}$, R$^{11}$, and R$^{12}$ are, independently, H, —C$_1$-C$_8$alkyl, —C$_1$-C$_8$alkoxy, halo, —OH, —CF$_3$, or aromatic group.

In any of the above embodiments, R$^3$ and R$^4$ are, independently,

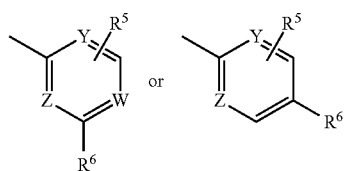

wherein each W, Y, and Z are, independently, C or N; or R$^3$ and R$^4$ are, independently,

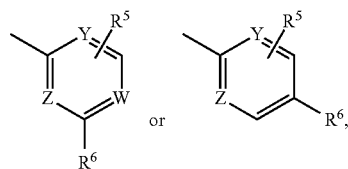

wherein each W, Y, and Z are C, or each Y and Z are C and each W is N.

In any of the above embodiments, each R$^5$ is, independently, H, —C$_1$-C$_8$alkyl, —C$_1$-C$_8$alkoxy, halo, amino, —OH, —CF$_3$, —O—(CH$_2$)$_p$—NH$_2$, —O—(CH$_2$)$_p$NHC(=NH)NH$_2$, —S—(CH$_2$)$_p$—NH$_2$, —S—(CH$_2$)$_p$NHC(=NH)NH$_2$, —C(=O)NH(CH$_2$)$_p$NH$_2$, —N((CH$_2$)$_p$NH$_2$)$_2$, —(CH$_2$)$_p$N((CH$_2$)$_p$NH$_2$)$_2$, where each p is, independently, 1 to 5, or the free base or salt form of —(CH$_2$)$_n$—NH$_2$, —(CH$_2$)$_n$—NH—(CH$_2$)$_n$—NH$_2$, or —(CH$_2$)$_n$—NH—C(=NH)NH$_2$, where each n is, independently, 1 to 8, and each R$^6$ is, independently, amino, heterocycle, —O—(CH$_2$)$_p$—NH$_2$, —O—(CH$_2$)$_p$NHC(=NH)NH$_2$, —S—(CH$_2$)$_p$—NH$_2$, —S—(CH$_2$)$_p$NHC(=NH)NH$_2$, —N((CH$_2$)$_p$NH$_2$)$_2$, —C(=O)NH(CH$_2$)$_p$NH$_2$, —(CH$_2$)$_p$N((CH$_2$)$_p$NH$_2$)$_2$, where each p is, independently, 1 to 5, or the free base or salt form of —(CH$_2$)$_n$—NH$_2$, —(CH$_2$)$_n$—NH—(CH$_2$)$_n$—NH$_2$, or —(CH$_2$)$_n$—NH—C(=NH)NH$_2$, where each n is, independently, 1 to 8; or each R$^5$ is, independently, H, —C$_1$-C$_3$alkyl, —C$_1$-C$_3$alkoxy, halo, —OH, —CF$_3$, or —O—(CH$_2$)—NH$_2$, where each p is, independently, 1 to 5, and each R$^6$ is, independently, heterocycle, —O—(CH$_2$)$_p$—NH$_2$, where each p is, independently, 1 to 5, or the free base or salt form of —(CH$_2$)$_n$—NH$_2$, where each n is, independently, 1 to 8; or each R$^5$ is, independently, H, —C$_1$-C$_3$alkyl, halo, —OH, or —O—(CH$_2$)$_p$—NH$_2$, where each p is, independently, 2 or 3, and each R$^6$ is, independently, heterocycle, —O—(CH$_2$)—NH$_2$, where each p is, independently, 2 or 3, or the free base or salt form of —(CH$_2$)$_n$—NH$_2$, where each n is, independently, 1 to 4; or each R$^5$ is, independently, H, —C$_1$-C$_3$alkyl, halo, —OH, or —O—(CH$_2$)$_3$—NH$_2$, and each R$^6$ is, independently, 6-membered heterocycle, —O—(CH$_2$)$_3$—NH$_2$, or the free base or salt form of —(CH$_2$)$_n$—NH$_2$, where each n is, independently, 1 to 3; or each R$^5$ is, independently, H, halo, or —O—(CH$_2$)$_3$—NH$_2$, and each R$^6$ is piperazinyl, —O—(CH$_2$)$_3$—NH$_2$, or the free base or salt form of —(CH$_2$)$_n$—NH$_2$ where each n is, independently, 1 to 3; or each R$^5$ is —O—(CH$_2$)$_3$—NH$_2$ or piperazinyl, and each R$^6$ is, independently, H, —C$_1$-C$_3$alkyl, —C$_1$-C$_3$alkoxy, halo, —OH, —CF$_3$, or —O—(CH$_2$)$_3$—NH$_2$, or each R$^5$ is piperazinyl or —O—(CH$_2$)$_3$—NH$_2$; and each R$^6$ is H, —C$_1$-C$_3$alkyl, halo, —OH, —CF$_3$, or —O—(CH$_2$)$_3$—NH$_2$.

In some embodiments, X is —NH, O, S, S(=O)$_2$, or —N(CH$_2$)$_{2-3}$NH$_2$; R$^1$ and R$^2$ are H; R$^3$ and R$^4$ are, independently,

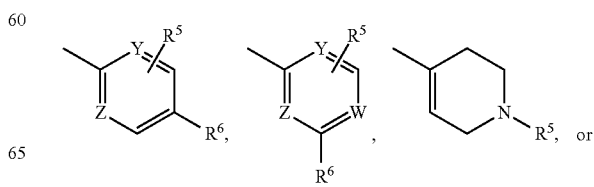

-continued

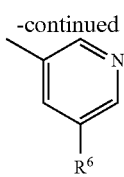

wherein: each W, Y, and Z are, independently, C or N; each R⁵ and each R⁶ are, independently, H, heterocycle, —O—(CH₂)$_p$—NH₂, where each p is, independently, 1 to 3, or the free base or salt form of —(CH₂)$_n$—NH₂, where each n is, independently, 1 to 3.

In some embodiments, X is —NH, O, S, or —N(CH₂)$_{2-3}$NH₂; R¹ and R² are H; R³ and R⁴ are

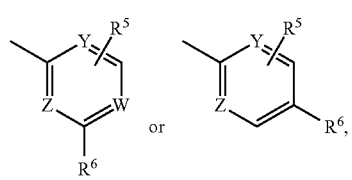

where each Z and Y are C, and each W is N; or each W, Y, and Z are C; each R⁵ is, independently, H, amino, halo, or —O—(CH₂)$_p$—NH₂, —C(=O)NH(CH₂)$_p$NH₂, —N((CH₂)$_p$NH₂)₂, —(CH₂)$_p$N((CH₂)NH₂)₂, where each p is, independently, 2 or 3, and each R⁶ is piperazinyl, amino, —C(=O)NH(CH₂)$_p$NH₂, —N((CH₂)$_p$NH₂)₂, —(CH₂)$_p$N((CH₂)$_p$NH₂)₂, —O—(CH₂)$_p$—NH₂, where each p is, independently, 2 or 3, or the free base or salt form of —(CH₂)$_n$—NH₂, where each n is, independently, 1 to 3; or each R⁵ is piperazinyl or —O—(CH₂)₃—NH₂, and each R⁶ is, independently, H, —C₁-C₃alkyl, —C₁-C₃alkoxy, halo, —OH, —CF₃, or —O—(CH₂)₃—NH₂.

In some embodiments, X is —NH, O, S, or —N(CH₂)$_{2-3}$NH₂; R¹ and R² are H; R³ and R⁴ are or/R⁶

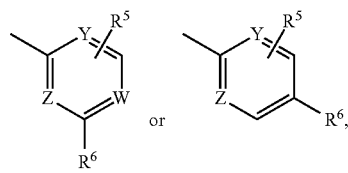

where each Z and Y are C, and each W is N; or each W, Y, and Z are C; each R⁵ is H or —O—(CH₂)₃—NH₂, and each R⁶ is piperazinyl, —O—(CH₂)₃—NH₂, or the free base or salt form of —(CH₂)$_n$—NH₂, where each n is, independently, 1 to 3; or each R⁵ is piperazinyl or —O—(CH₂)₃—NH₂; and each R⁶ is H or —O—(CH₂)₃—NH₂.

In some embodiments, the compound is chosen from:

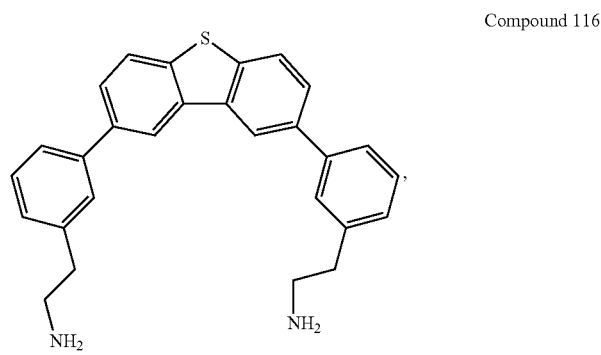

Compound 116

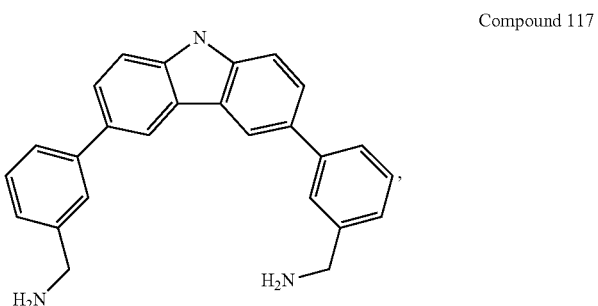

Compound 117

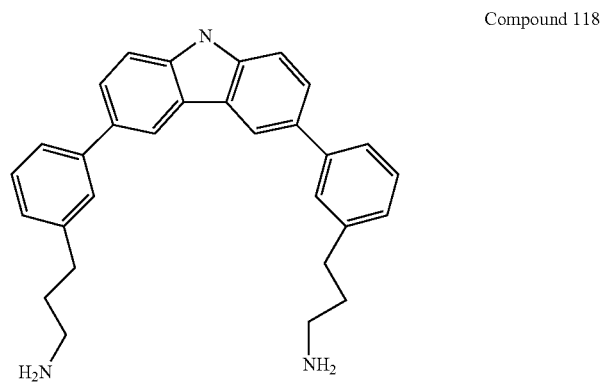

Compound 118

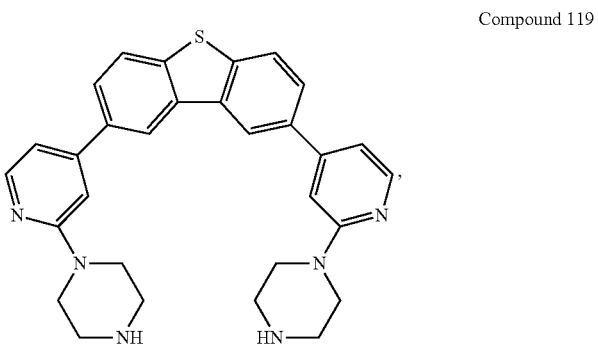

Compound 119

-continued
Compound 120
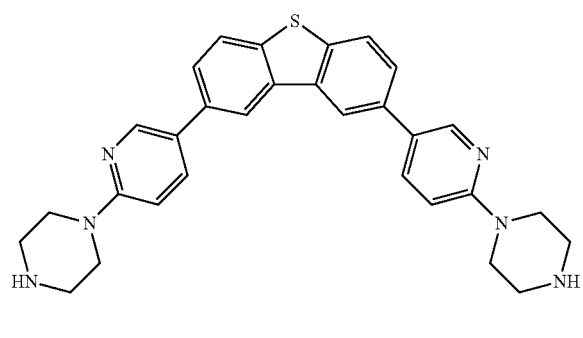
Compound 121
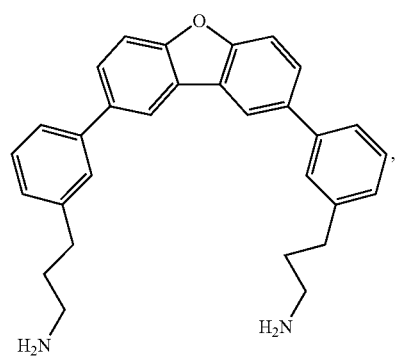
Compound 122
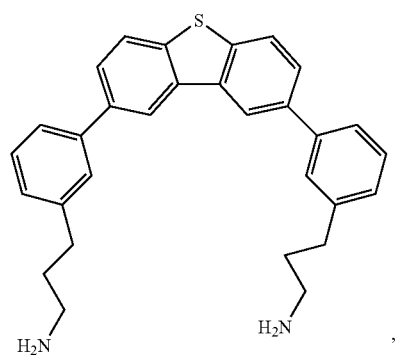
Compound 123
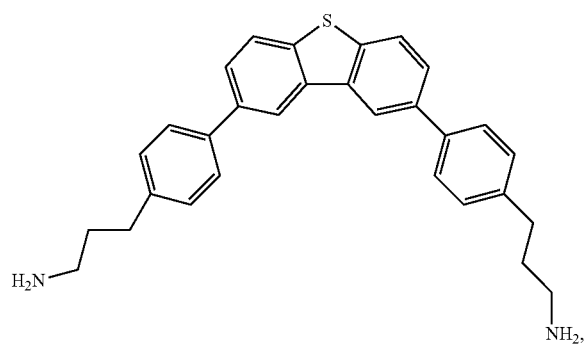
Compound 124
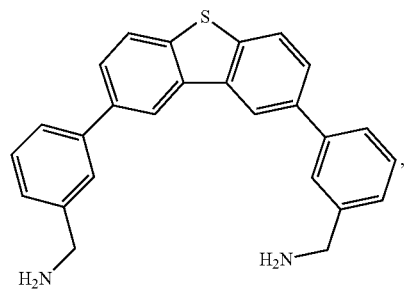
Compound 125
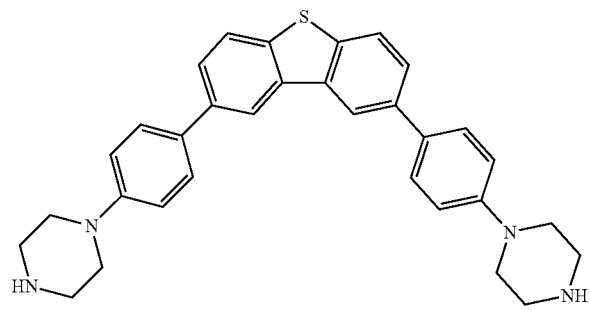
Compound 126
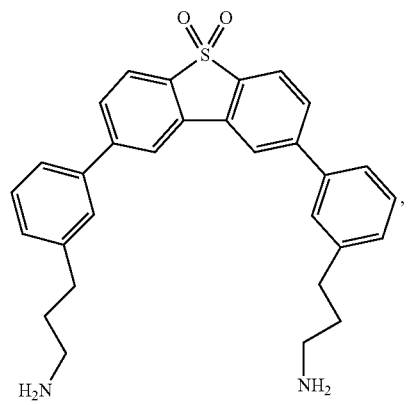
Compound 127
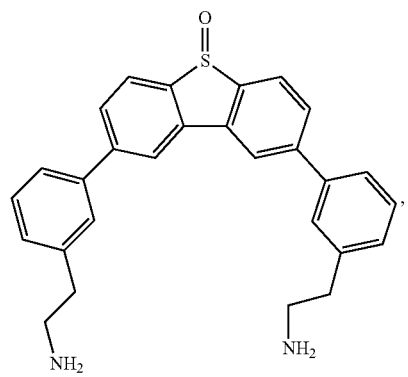

Compound 128
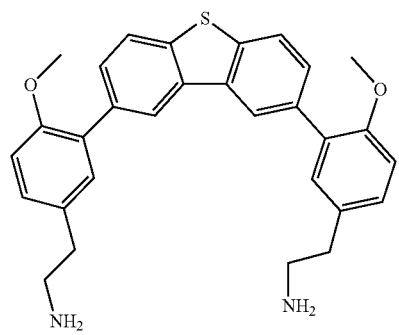
Compound 129
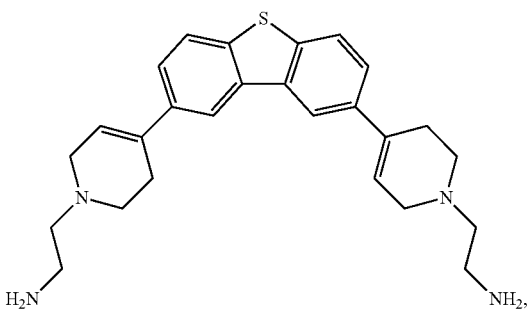
Compound 130
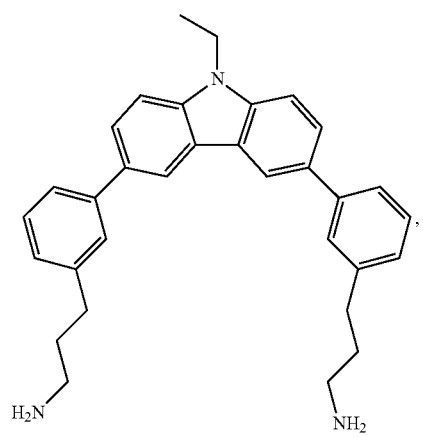
Compound 131
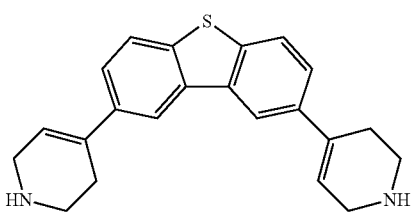
Compound 132
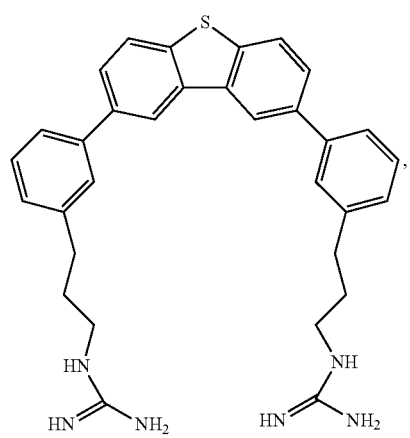
Compound 133
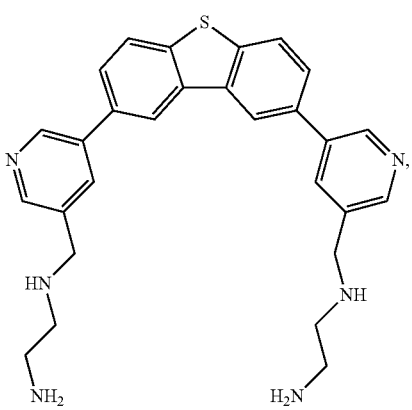
Compound 134
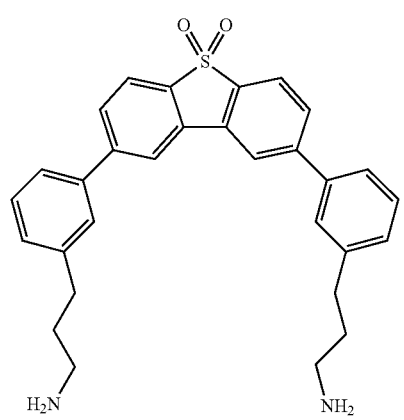

Compound 135
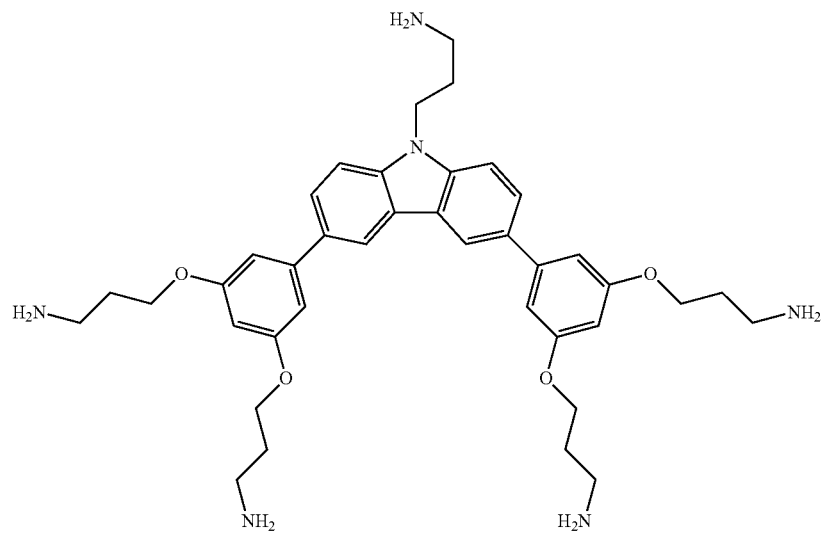
Compound 139
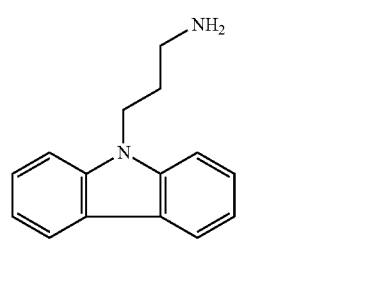
Compound 140
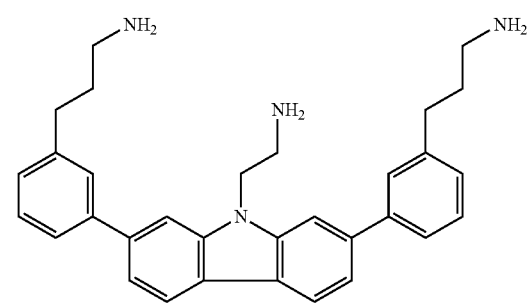
Compound 141
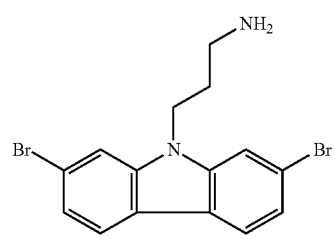
Compound 142
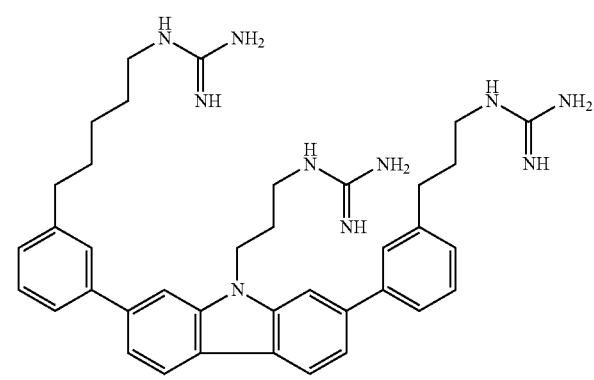
Compound 143
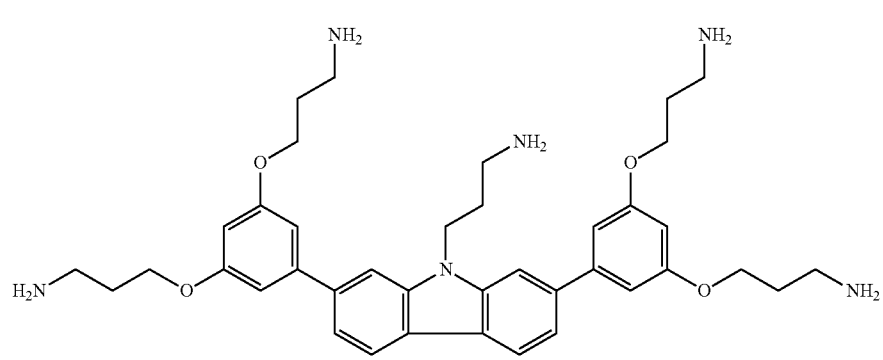

-continued
Compound 144
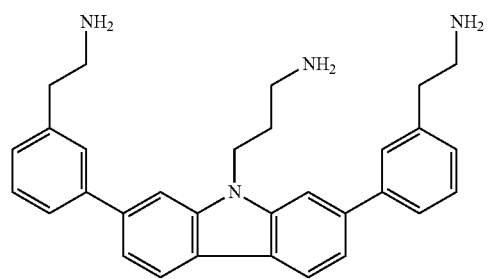
Compound 145
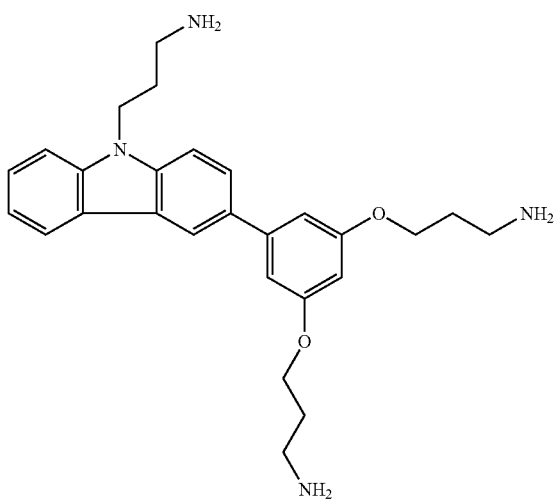
Compound 146
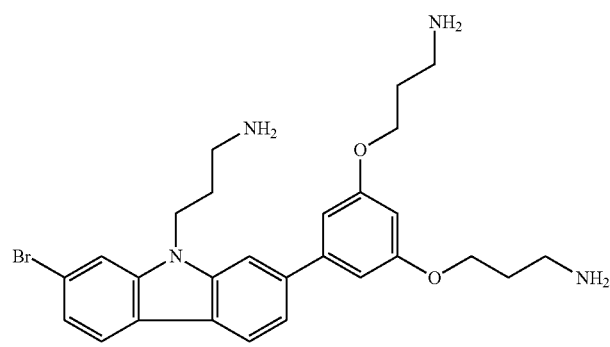
Compound 147
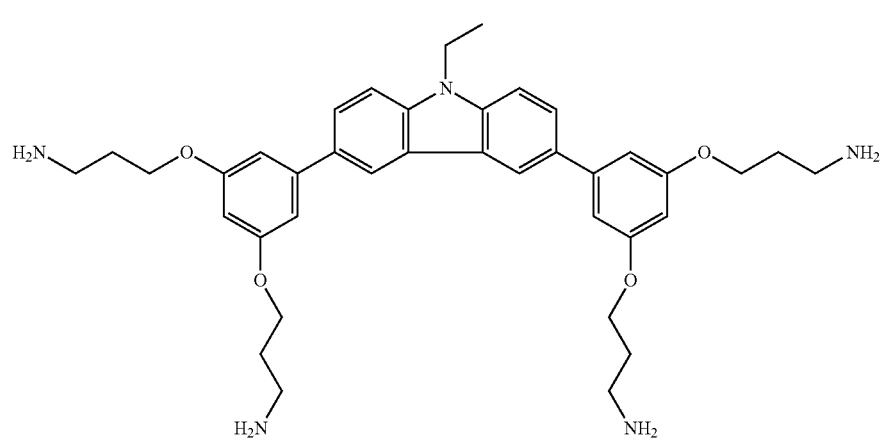

Compound 148
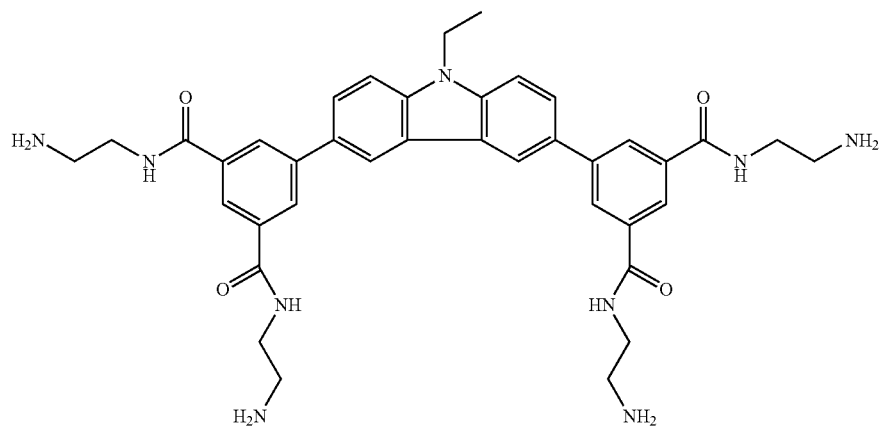
Compound 149
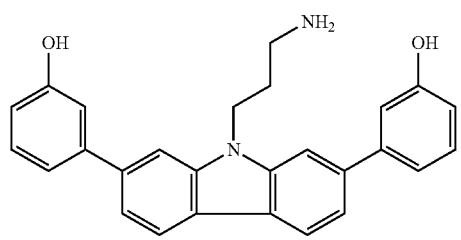
Compound 150
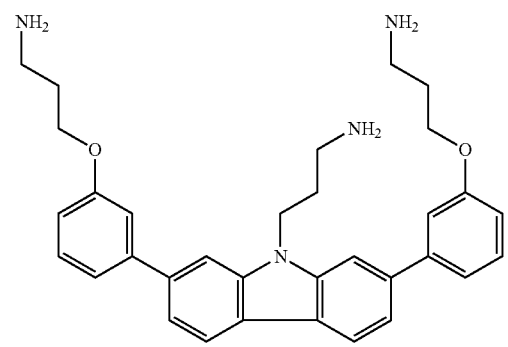
Compound 151
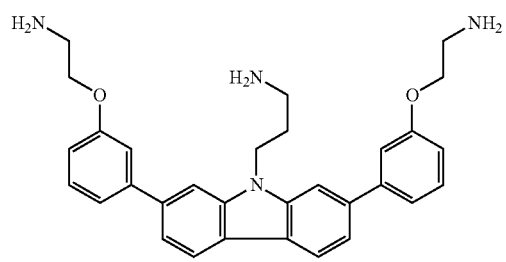
Compound 152
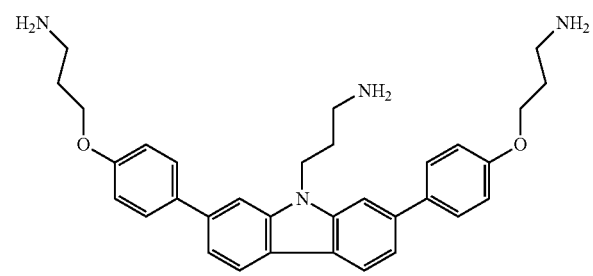
Compound 153
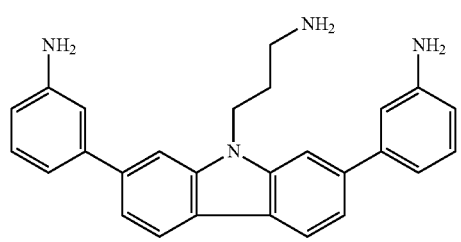
Compound 154
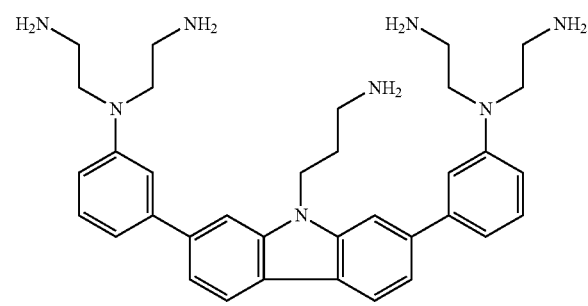

-continued
Compound 155
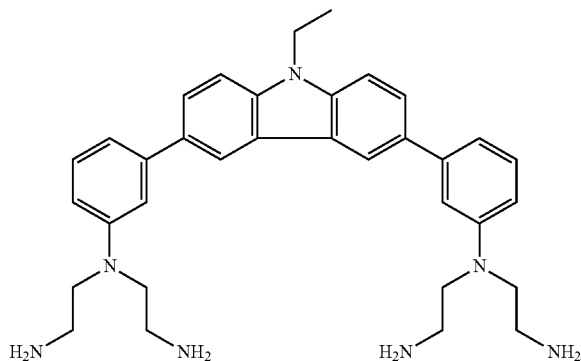
Compound 156
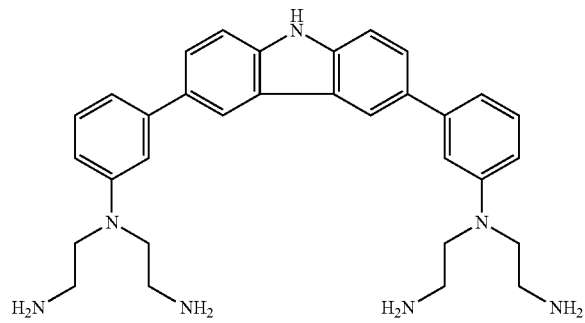
Compound 157
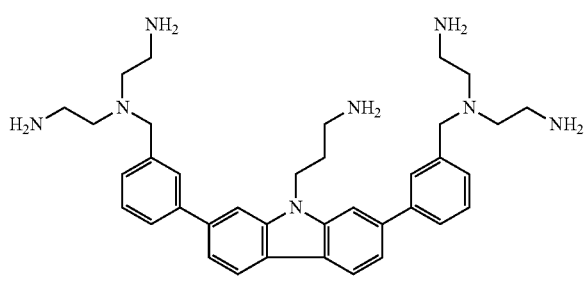
Compound 158
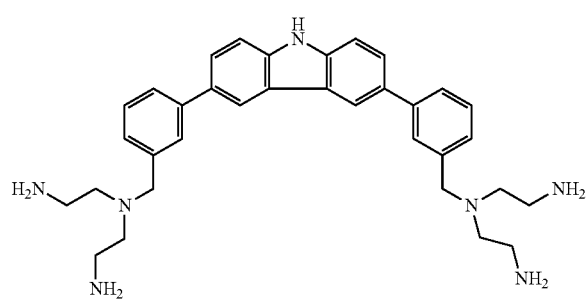
Compound 159
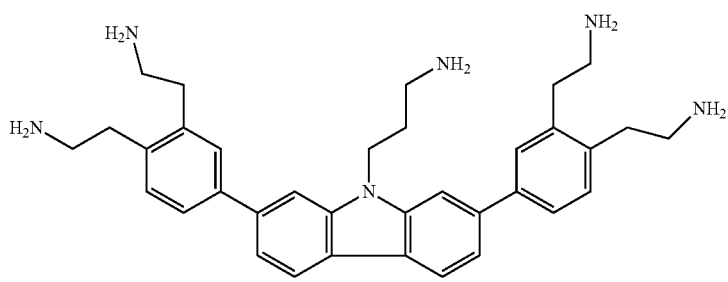
Compound 160
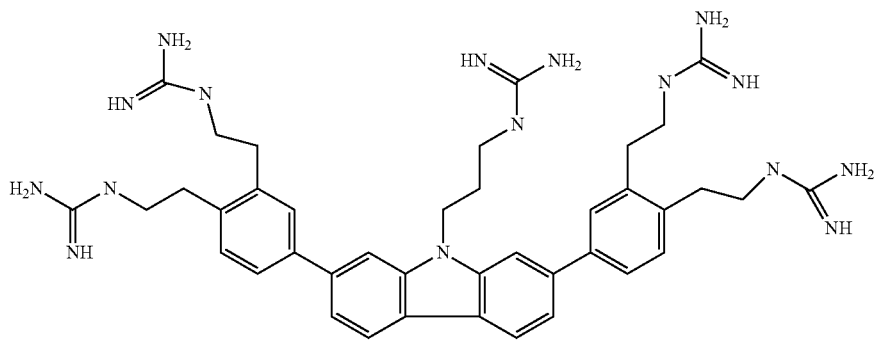
Compound 161
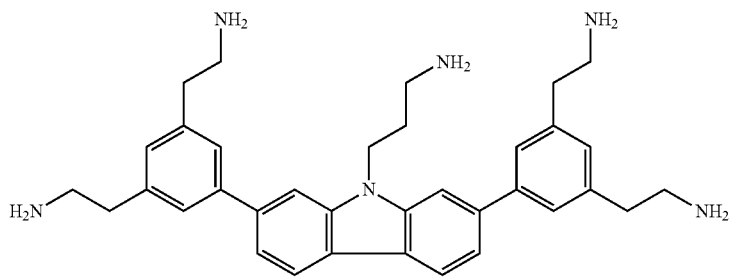

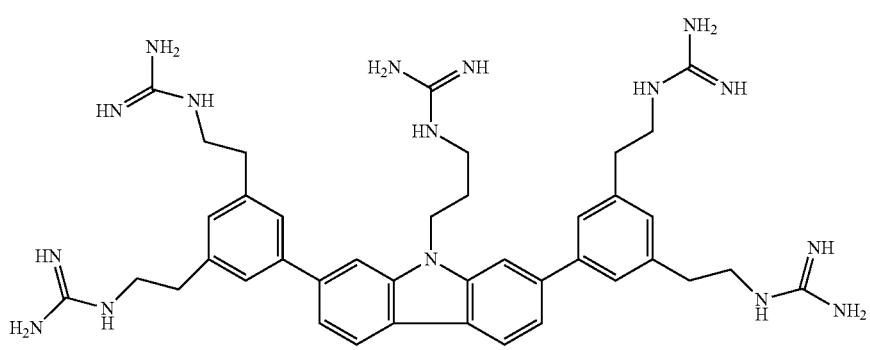

Compound 162

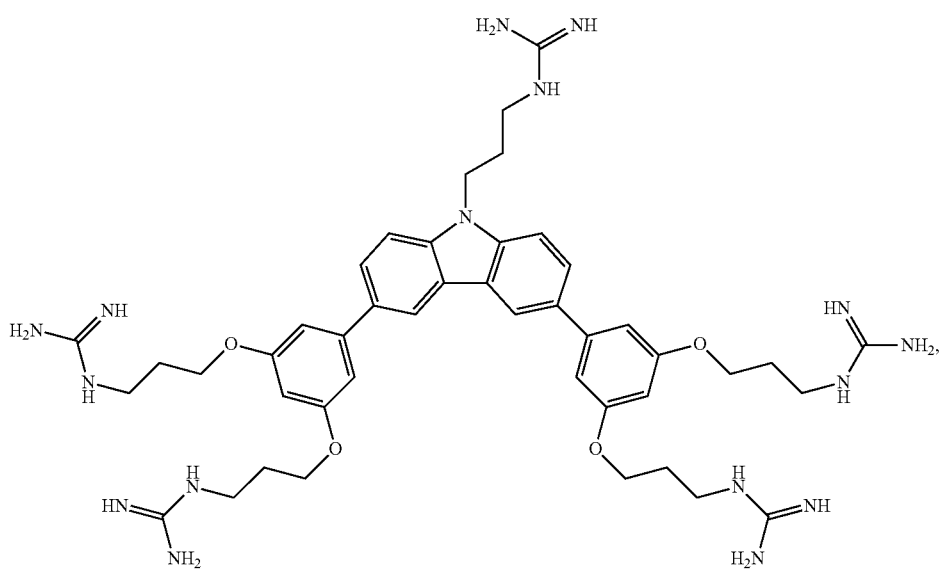

Compound 163 or a pharmaceutically acceptable salt thereof.

In some embodiments, any one or more of the above compounds may be excluded from any of the genus of compounds described above.

The present disclosure also provides compositions comprising one or more of the compounds or salts described above and a pharmaceutically acceptable carrier.

The present disclosure also provides methods of preventing or treating candidiasis (oral and/or disseminated) or an *aspergillus* infection in a mammal comprising administering to the mammal in need thereof an effective amount of a compound of Formula III:

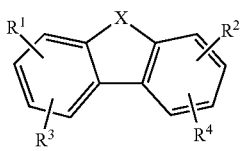

(III)

wherein:

X is —C($R^7$)C(R), —C(=O), N($R^9$), O, S, S(=O), or S(=O)$_2$;

$R^7$, $R^8$, and $R^9$ are, independently, H, —$C_1$-$C_8$alkyl, —$C_1$-$C_8$alkoxy, halo, —OH, —$CF_3$, aromatic group, —$(CH_2)_q$NH$_2$, or —$(CH_2)_q$NHC(=NH)NH$_2$, where q is 0 to 4;

$R^1$ and $R^2$ are, independently, H, —$C_1$-$C_8$alkyl, —$C_1$-$C_8$alkoxy, halo, —OH, -halo$C_1$-$C_8$alkyl, —CN, or —$CF_3$;

$R^3$ and $R^4$ are, independently, H or -carbocycle($R^5$)($R^6$);

each $R^5$ and each $R^6$ are, independently, H, —$C_1$-$C_8$alkyl, —$C_1$-$C_8$alkoxy, halo, amino, —OH, —$CF_3$, —O—$(CH_2)_p$—NH$_2$, —O—$(CH_2)_p$NHC(=NH)NH$_2$, —S—$(CH_2)$—NH$_2$, —N(($CH_2)_p$NH$_2$)$_2$, —S—$(CH_2)_p$NHC(=NH)NH$_2$, —C(=O)NH($CH_2)_p$NH$_2$, —$(CH_2)_p$N(($CH_2)_p$NH$_2$)$_2$, where each p is, independently, 1 to 5, aromatic group, heterocycle, or the free base or salt form of —$(CH_2)_n$—NH$_2$, —$(CH_2)_n$—NH—$(CH_2)_n$—NH$_2$, or —$(CH_2)_n$—NH—C(=NH)NH$_2$, where each n is, independently, 1 to 8;

or a pharmaceutically acceptable salt thereof.

In some embodiments, X is —N($R^9$), O, S, or S(=O)$_2$; or X is —NH, O, S, or —N($CH_2)_q$NH$_2$, where q is 2 or 3; or X is —NH, —N($CH_2)_3$NH$_2$, or S.

In any of the above embodiments, $R^1$ and $R^2$ are, independently, H, —$C_1$-$C_3$alkyl, —$C_1$-$C_3$alkoxy, halo, —OH, -halo$C_1$-$C_3$alkyl, or —CN; or $R^1$ and $R^2$ are, independently, H, —$C_1$-$C_3$alkyl, —$C_1$-$C_3$alkoxy, halo, or —OH; or $R^1$ and $R^2$ are, independently, H, —$C_1$-$C_3$alkyl, or halo; or $R^1$ and $R^2$ are H.

In any of the above embodiments, $R^3$ and $R^4$ are, independently, H or -carbocycle($R^5$)($R^6$), where $R^5$ and $R^6$ can be positioned anywhere on the carbocycle. In any of the above embodiments, $R^3$ and $R^4$ are, independently,

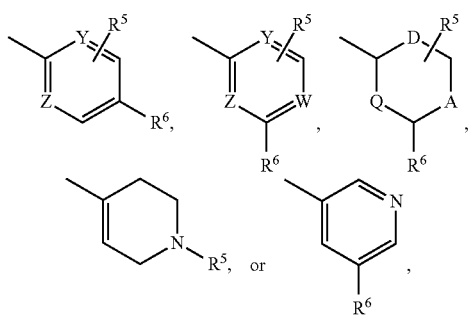

wherein each W, Y, and Z are, independently, C or N, each A, D, and Q are, independently, —C($R^{10}$)C($R^{11}$), —C(=O), —N($R^{12}$), O, or S, and each $R^{10}$, $R^{11}$, and $R^{12}$ are, independently, H, —$C_1$-$C_8$alkyl, —$C_1$-$C_8$alkoxy, halo, —OH, —$CF_3$, or aromatic group.

In any of the above embodiments, $R^3$ and $R^4$ are, independently,

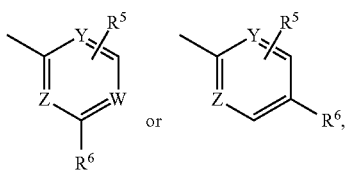

wherein each W, Y, and Z are, independently, C or N; or $R^3$ and $R^4$ are, independently,

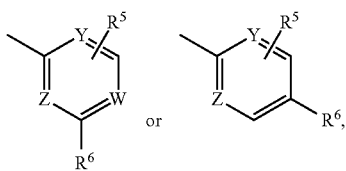

wherein each W, Y, and Z are C, or each Y and Z are C and each W is N.

In any of the above embodiments, each $R^5$ is, independently, H, —$C_1$-$C_8$alkyl, —$C_1$-$C_8$alkoxy, halo, amino, —OH, —$CF_3$, —O—$(CH_2)_p$—$NH_2$, —O—$(CH_2)_p$NHC(=NH)$NH_2$, —S—$(CH_2)_p$—$NH_2$, —S—$(CH_2)_p$NHC(=NH)$NH_2$, —C(=O)NH$(CH_2)_p$$NH_2$, —N($(CH_2)_p$$NH_2$)$_2$, —$(CH_2)_p$N$((CH_2)_p$$NH_2)_2$, where each p is, independently, 1 to 5, or the free base or salt form of —$(CH_2)_n$—$NH_2$, —$(CH_2)_n$—NH—$(CH_2)_n$—$NH_2$, or —$(CH_2)_n$—NH—C(=NH)$NH_2$, where each n is, independently, 1 to 8, and each $R^6$ is, independently, heterocycle, amino, —O—$(CH_2)_p$—$NH_2$, —O—$(CH_2)_p$NHC(=NH)$NH_2$, —S—$(CH_2)_p$—$NH_2$, —S—$(CH_2)_p$NHC(=NH)$NH_2$, —N($(CH_2)_p$$NH_2$)$_2$, —C(=O)NH$(CH_2)_p$$NH_2$, —$(CH_2)_p$N$((CH_2)_p$$NH_2)_2$, where each p is, independently, 1 to 5, or the free base or salt form of —$(CH_2)_n$—$NH_2$, —$(CH_2)_n$—NH—$(CH_2)_n$—$NH_2$, or —$(CH_2)_n$—NH—C(=NH)$NH_2$, where each n is, independently, 1 to 8; or each $R^5$ is, independently, H, —$C_1$-$C_3$alkyl, —$C_1$-$C_3$alkoxy, halo, —OH, —$CF_3$, or —O—$(CH_2)_p$—$NH_2$, where each p is, independently, 1 to 5, and each $R^6$ is, independently, heterocycle, —O—$(CH_2)_p$—$NH_2$, where each p is, independently, 1 to 5, or the free base or salt form of —$(CH_2)_n$—$NH_2$, where each n is, independently, 1 to 8; or each $R^5$ is, independently, H, —$C_1$-$C_3$alkyl, halo, —OH, or —O—$(CH_2)_p$—$NH_2$, where each p is, independently, 2 or 3, and each $R^6$ is, independently, heterocycle, —O—$(CH_2)$—$NH_2$, where each p is, independently, 2 or 3, or the free base or salt form of —$(CH_2)_n$—$NH_2$, where each n is, independently, 1 to 4; or each $R^5$ is, independently, H, —$C_1$-$C_3$alkyl, halo, —OH, or —O—$(CH_2)_3$—$NH_2$, and each $R^6$ is, independently, 6-membered heterocycle, —O—$(CH_2)_3$—$NH_2$, or the free base or salt form of —$(CH_2)_n$—$NH_2$, where each n is, independently, 1 to 3; or each $R^5$ is, independently, H, halo, or —O—$(CH_2)_3$—$NH_2$, and each $R^6$ is piperazinyl, —O—$(CH_2)_3$—$NH_2$, or the free base or salt form of —$(CH_2)_n$—$NH_2$ where each n is, independently, 1 to 3; or each $R^5$ is —O—$(CH_2)_3$—$NH_2$ or piperazinyl, and each $R^6$ is, independently, H, —$C_1$-$C_3$alkyl, —$C_1$-$C_3$alkoxy, halo, —OH, —$CF_3$, or —O—$(CH_2)_3$—$NH_2$, or each $R^5$ is piperazinyl or —O—$(CH_2)_3$—$NH_2$; and each $R^6$ is H, —$C_1$-$C_3$alkyl, halo, —OH, —$CF_3$, or —O—$(CH_2)_3$—$NH_2$.

In some embodiments, X is —NH, O, S, S(=O)$_2$, or —N$(CH_2)_{2-3}$$NH_2$; $R^1$ and $R^2$ are H;

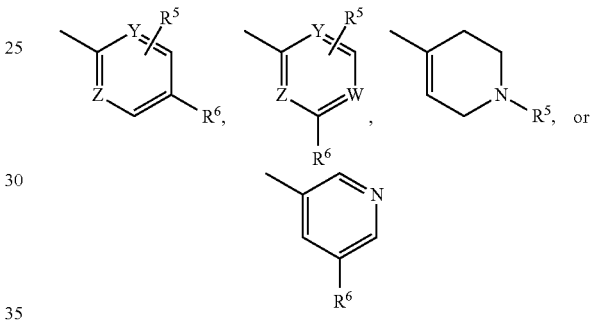

wherein: each W, Y, and Z are, independently, C or N; each $R^5$ and each $R^6$ are, independently, H, heterocycle, —O—$(CH_2)_p$—$NH_2$, where each p is, independently, 1 to 3, or the free base or salt form of —$(CH_2)_n$—$NH_2$, where each n is, independently, 1 to 3.

In some embodiments, X is —NH, O, S, or —N$(CH_2)_{2-3}$$NH_2$; $R^1$ and $R^2$ are H; $R^3$ and

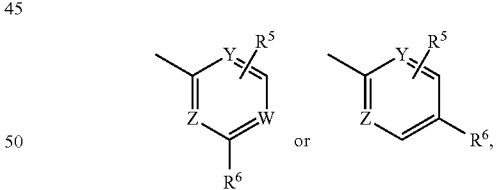

where each Z and Y are C, and each W is N; or each W, Y, and Z are C; each $R^5$ is, independently, H, halo, amino, or —O—$(CH_2)_p$—$NH_2$, —C(=O)NH$(CH_2)_p$$NH_2$, —N($(CH_2)_p$$NH_2$)$_2$, —$(CH_2)_p$N$((CH_2)_p$$NH_2)_2$, where each p is, independently, 2 or 3, and each $R^6$ is piperazinyl, amino, —C(=O)NH$(CH_2)_p$—$NH_2$, —N($(CH_2)_p$$NH_2$)$_2$, —$(CH_2)_p$N$((CH_2)_p$$NH_2)_2$, —O—$(CH_2)_p$—$NH_2$, where each p is, independently, 2 or 3, or the free base or salt form of —$(CH_2)_n$—$NH_2$, where each n is, independently, 1 to 3; or each $R^5$ is piperazinyl or —O—$(CH_2)_3$—$NH_2$, and each $R^6$ is, independently, H, —$C_1$-$C_3$alkyl, —$C_1$-$C_3$alkoxy, halo, —OH, —$CF_3$, or —O—$(CH_2)_3$—$NH_2$.

In some embodiments, X is —NH, O, S, or —N$(CH_2)_{2-3}$$NH_2$; $R^1$ and $R^2$ are H; $R^3$ and $R^4$ are

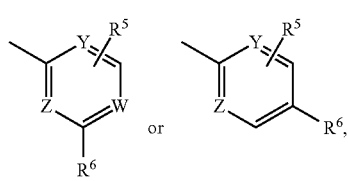

where each Z and Y are C, and each W is N; or each W, Y, and Z are C; each $R^5$ is H or —O—$(CH_2)_3$—$NH_2$, and each $R^6$ is piperazinyl, —O—$(CH_2)_3$—$NH_2$, or the free base or salt form of —$(CH_2)_n$—$NH_2$, where each n is, independently, 1 to 3; or each $R^5$ is piperazinyl or —O—$(CH_2)_3$—$NH_2$; and each $R^6$ is H or —O—$(CH_2)_3$—$NH_2$.

In some embodiments, the compound is chosen from:

Compound 116

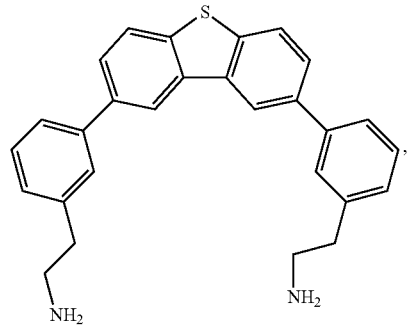

Compound 117

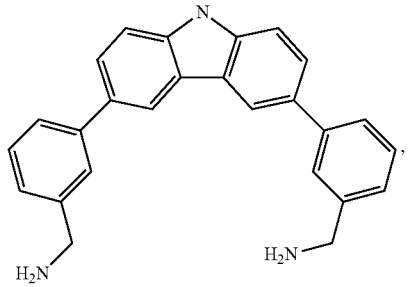

Compound 118

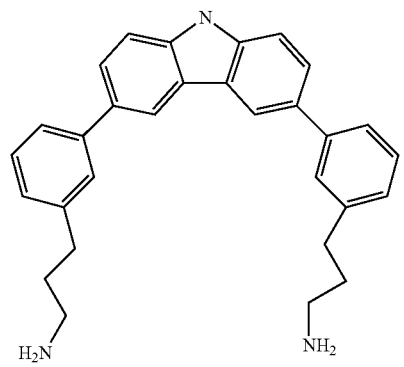

Compound 119

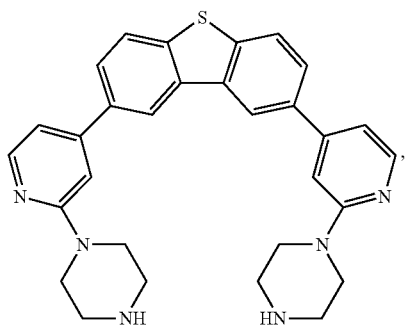

Compound 120

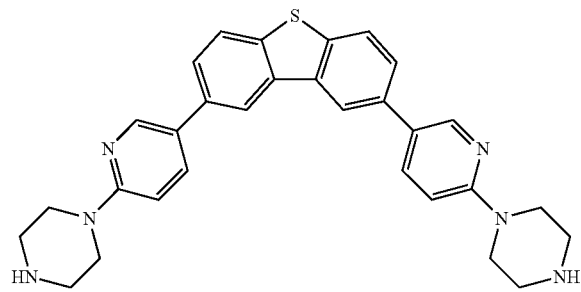

Compound 121

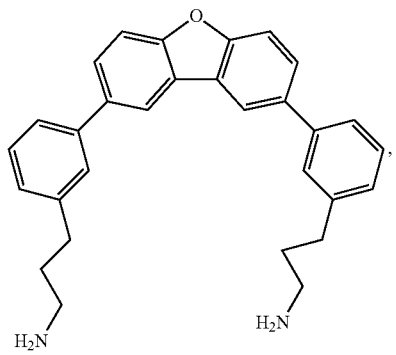

83                                                               84
-continued
Compound 122                                    Compound 123
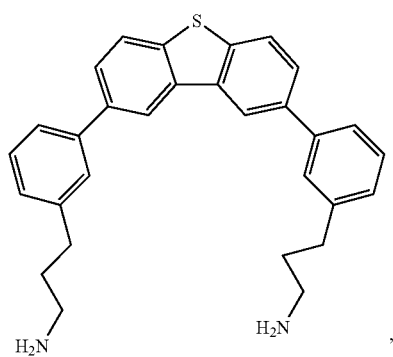                            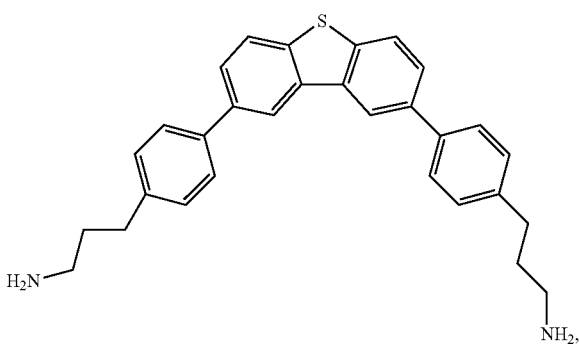
Compound 124                                    Compound 125
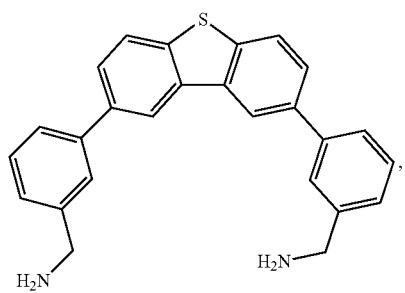                            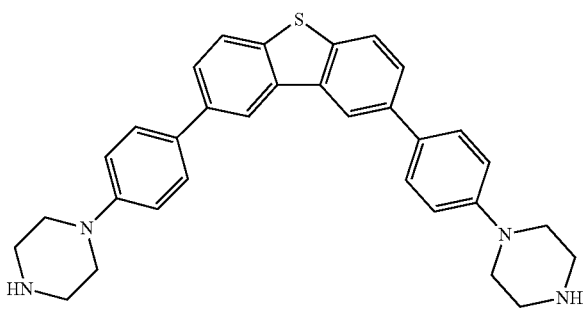
Compound 126                                    Compound 127
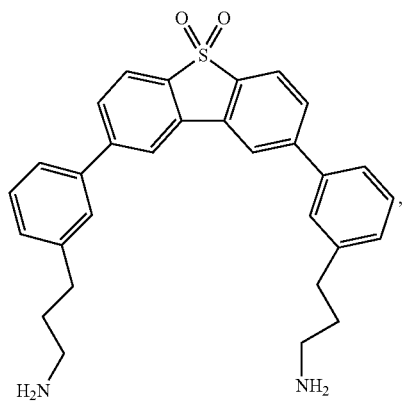                            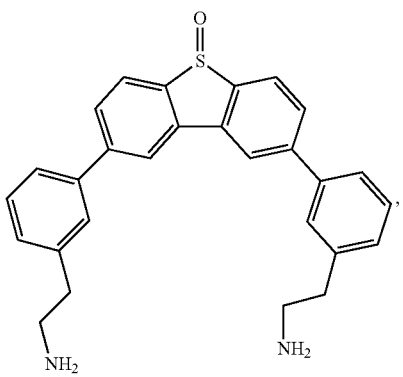
Compound 128                                    Compound 129
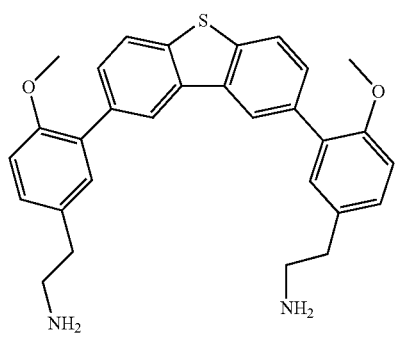                            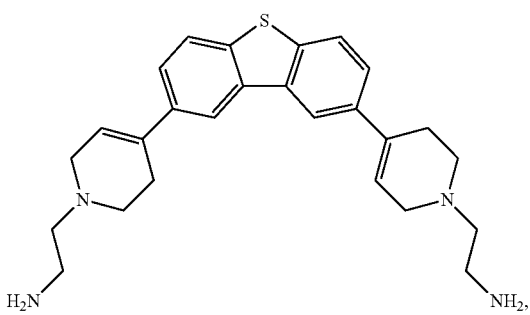

Compound 130
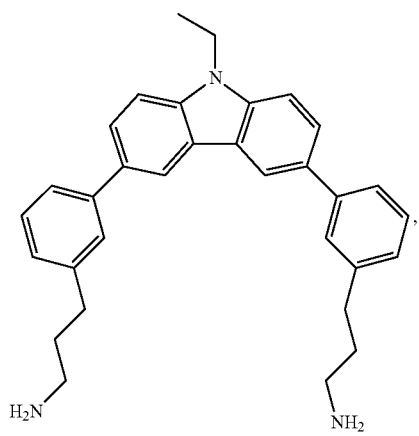
Compound 131
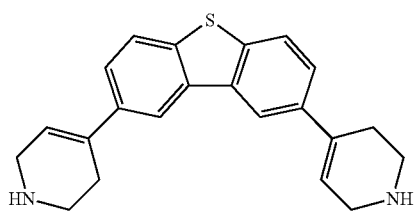
Compound 132
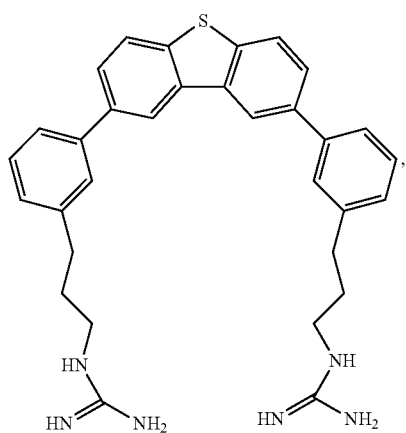
Compound 133
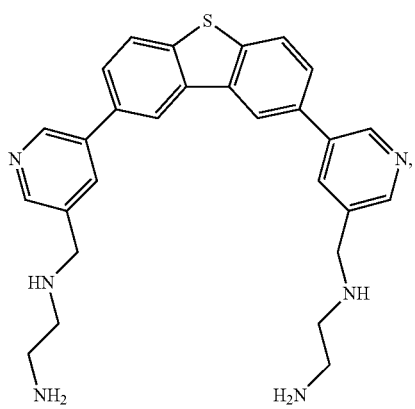
Compound 134
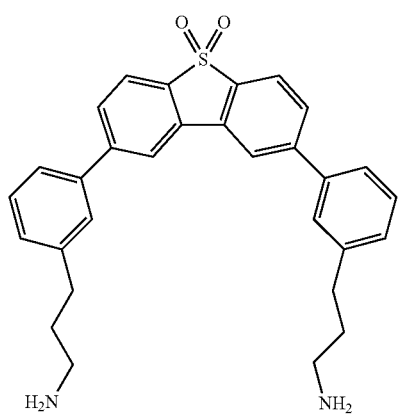

-continued
Compound 135
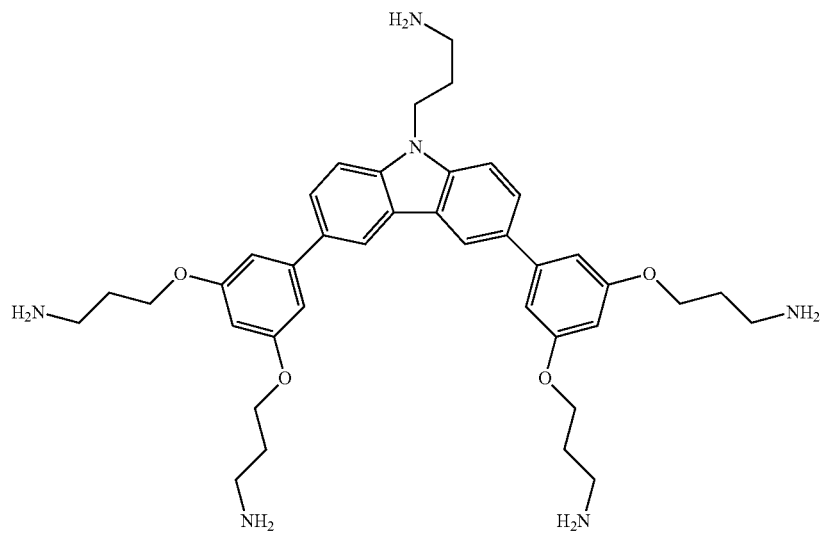
Compound 139
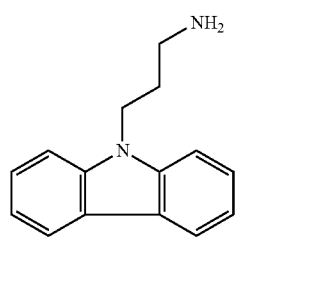
Compound 140
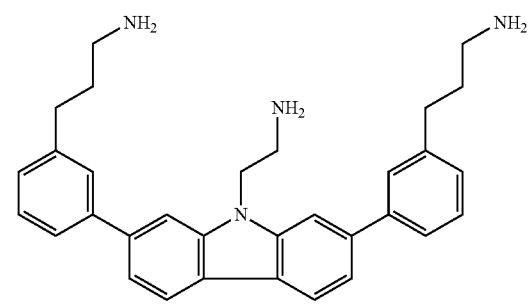
Compound 141
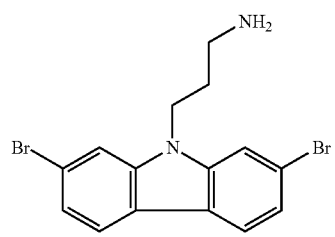
Compound 142
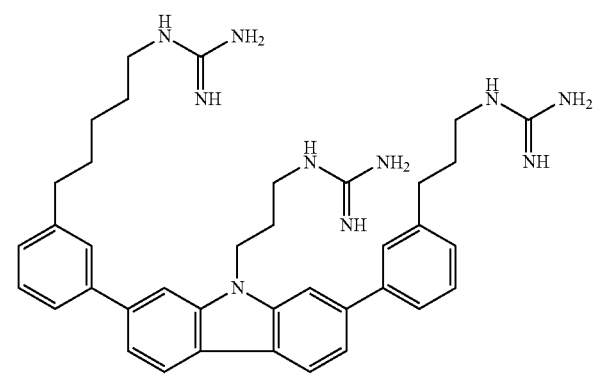
Compound 143
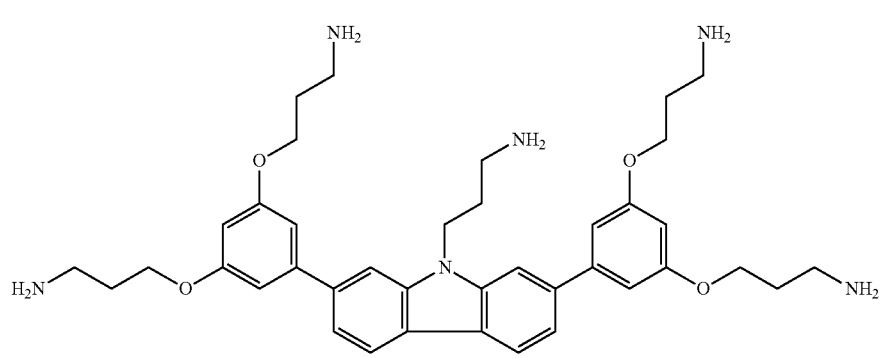

-continued
Compound 144
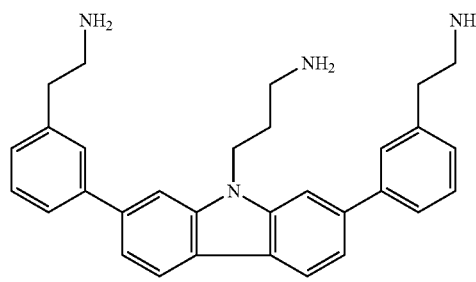
Compound 145
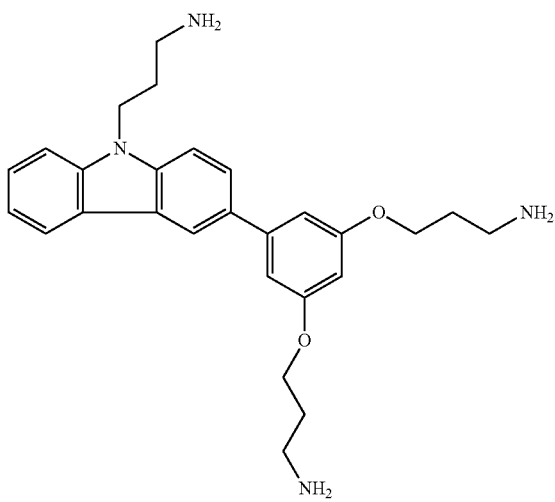
Compound 146
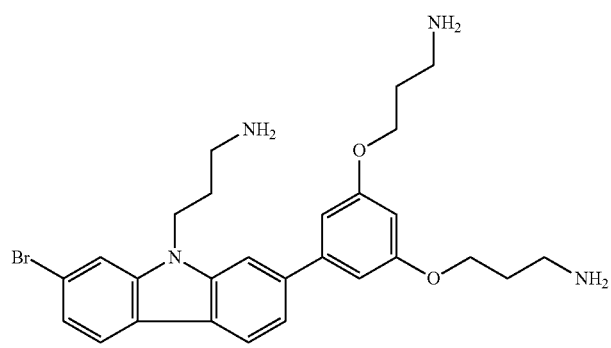
Compound 147
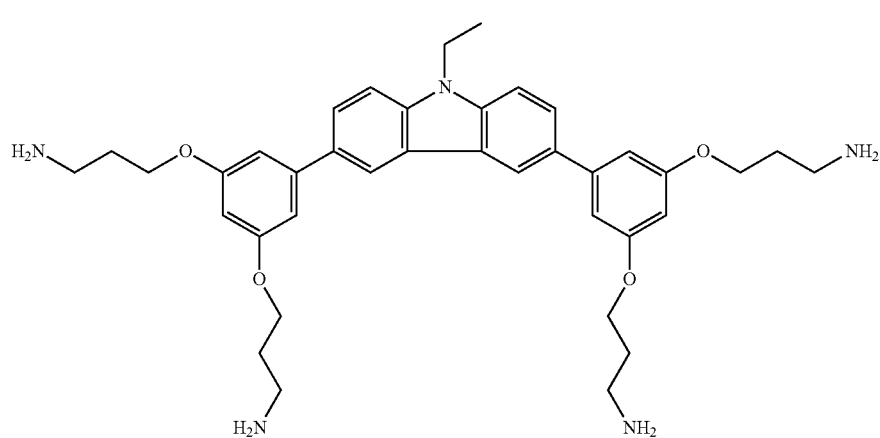

-continued
Compound 148
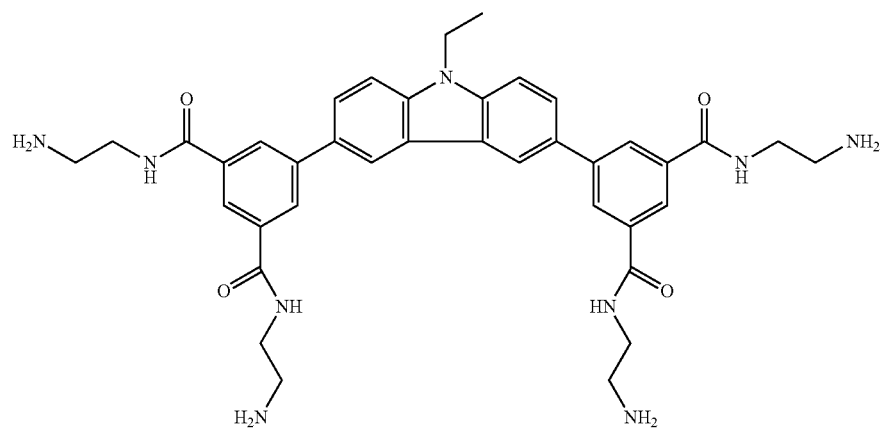
Compound 149
Compound 150
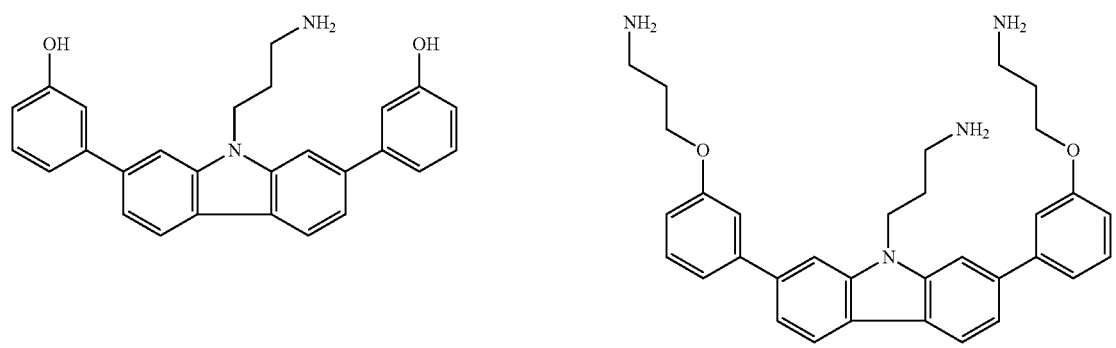
Compound 151
Compound 152
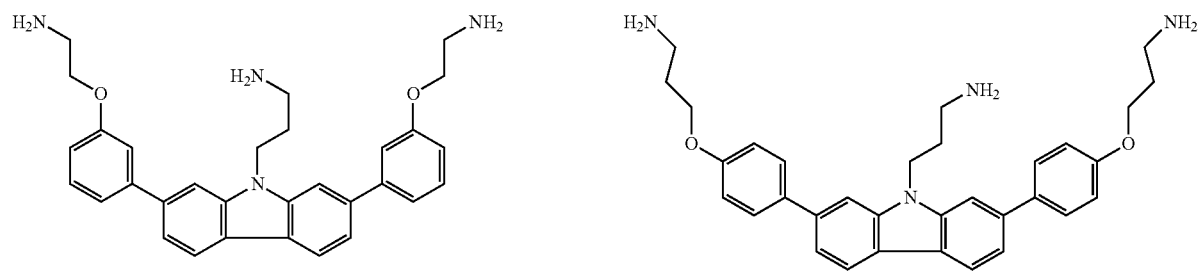
Compound 153
Compound 154
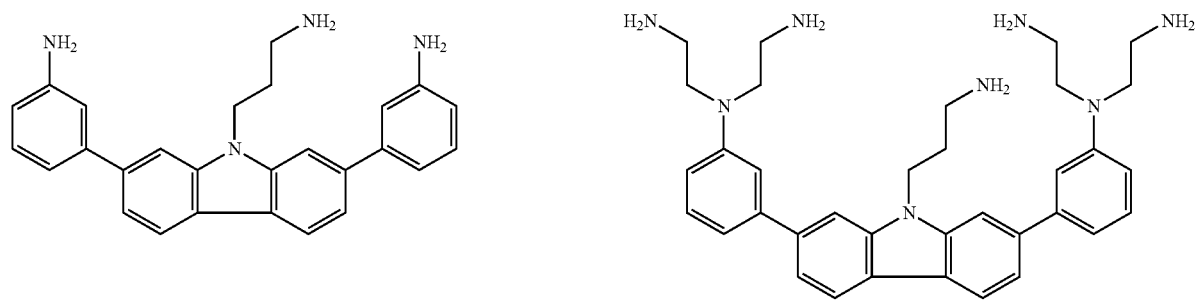

-continued
Compound 155
Compound 156
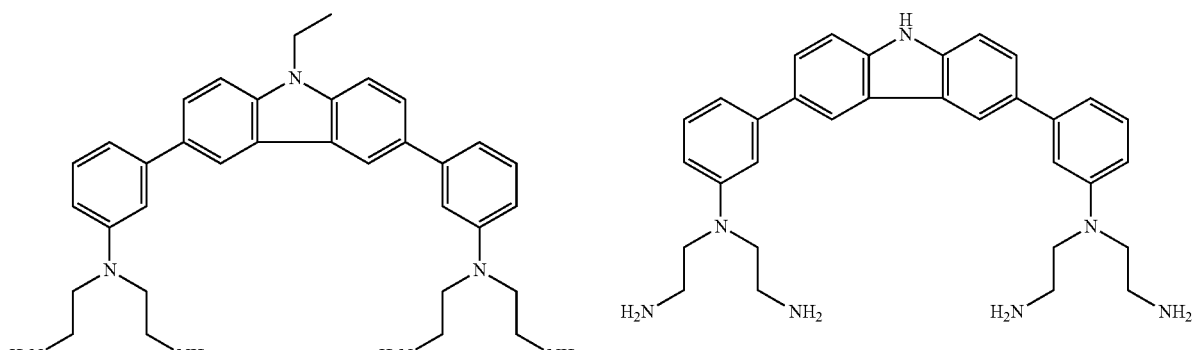
Compound 157
Compound 158
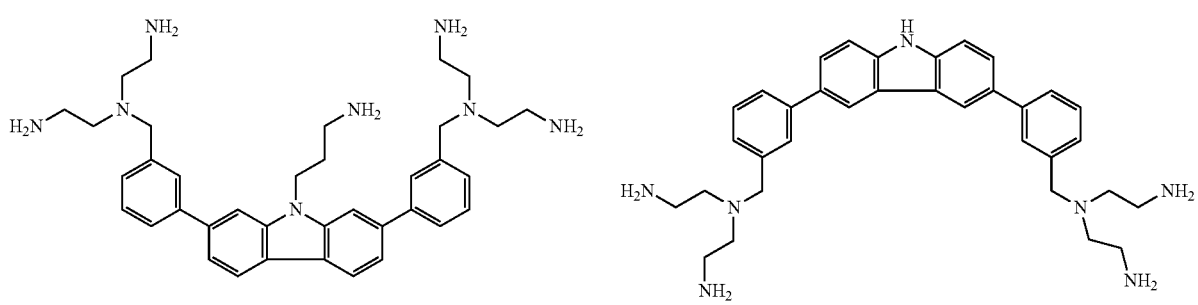
Compound 159
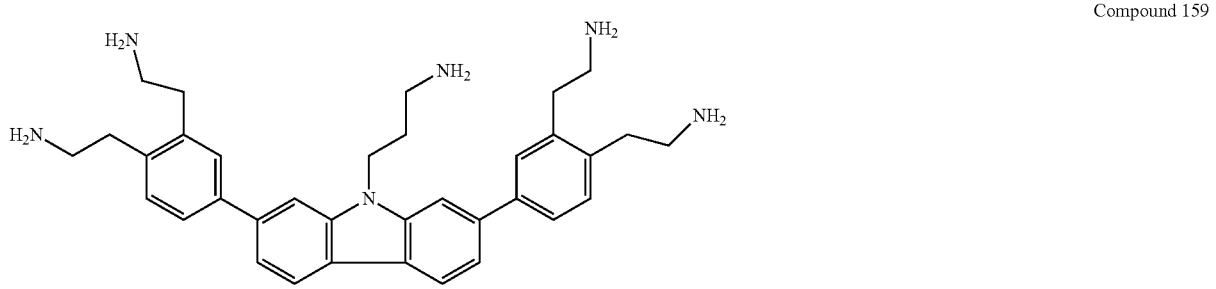
Compound 160
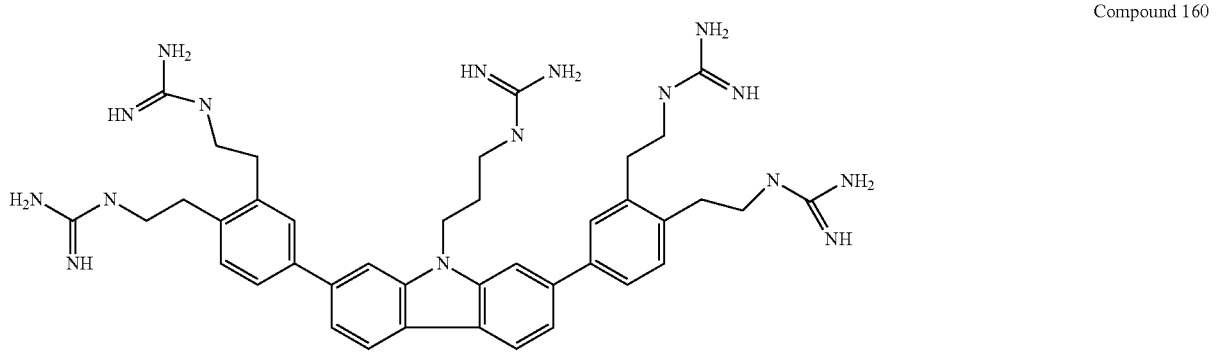
Compound 161
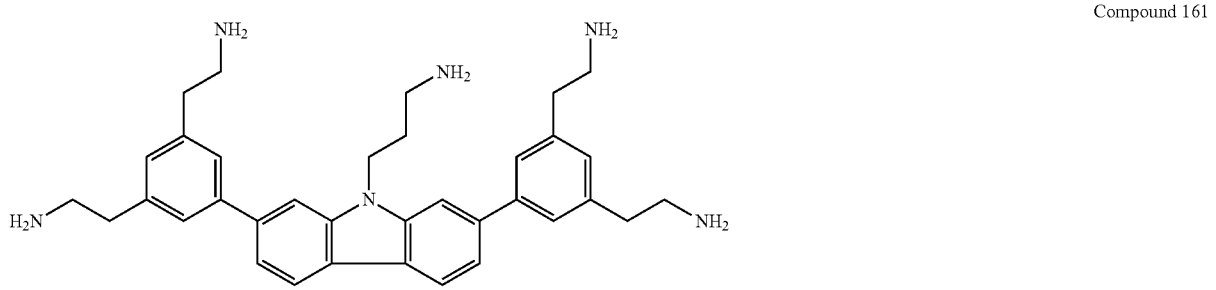

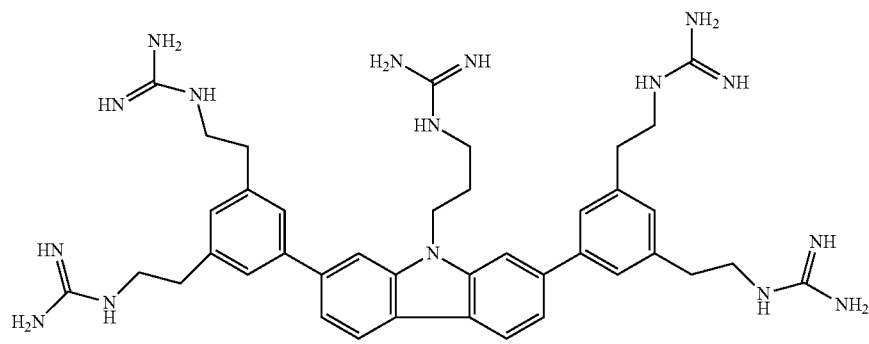

Compound 162

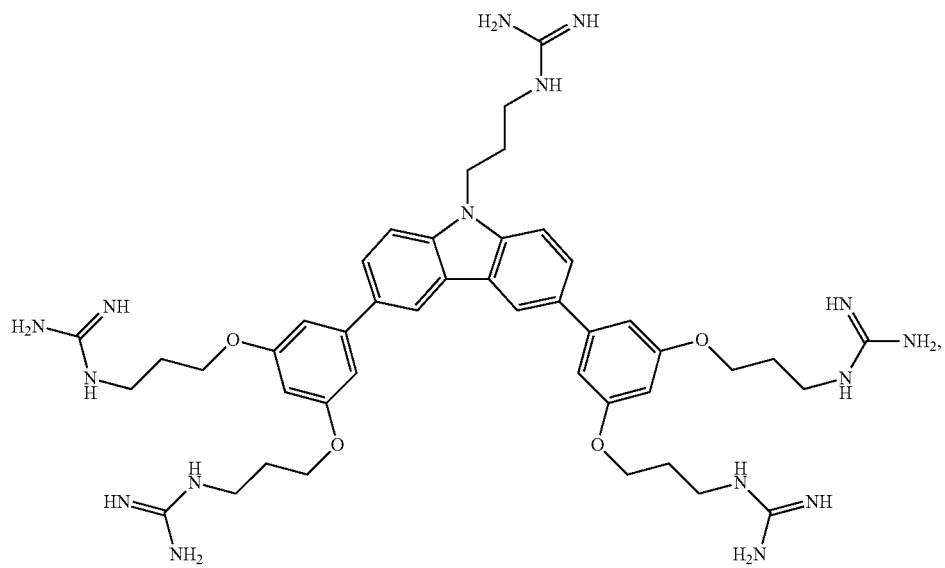

Compound 163 or a pharmaceutically acceptable salt thereof.

The present disclosure also provides methods of killing or inhibiting the growth of a *Candida* or *Aspergillus* species comprising contacting the *Candida* or *Aspergillus* species with an effective amount of a compound of Formula III:

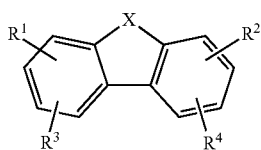
(III)

wherein:

X is —C($R^7$)C(R), —C(=O), —N($R^9$), O, S, S(=O), or S(=O)$_2$;

$R^7$, $R^8$, and $R^9$ are, independently, H, —$C_1$-$C_8$alkyl, —$C_1$-$C_8$alkoxy, halo, —OH, —$CF_3$, aromatic group, —(CH$_2$)$_q$NH$_2$, or —(CH$_2$)$_q$NHC(=NH)NH$_2$, where q is 0 to 4;

$R^1$ and $R^2$ are, independently, H, —$C_1$-$C_8$alkyl, —$C_1$-$C_8$alkoxy, halo, —OH, -halo$C_1$-$C_8$alkyl, —CN, or —$CF_3$;

$R^3$ and $R^4$ are, independently, H or -carbocycle($R^5$)($R^6$);

each $R^5$ and each $R^6$ are, independently, H, —$C_1$-$C_8$alkyl, —$C_1$-$C_8$alkoxy, halo, amino, —OH, —$CF_3$, —O—(CH$_2$)$_p$NH$_2$, —O—(CH$_2$)$_p$NHC(=NH)NH$_2$, —S—(CH$_2$)—NH$_2$, —N((CH$_2$)$_p$NH$_2$)$_2$, —S—(CH$_2$)$_p$NHC(=NH)NH$_2$, —C(=O)NH(CH$_2$)$_p$NH$_2$, —(CH$_2$)$_p$N((CH$_2$)$_p$NH$_2$)$_2$, where each p is, independently, 1 to 5, aromatic group, heterocycle, or the free base or salt form of —(CH$_2$)$_n$—NH$_2$, —(CH$_2$)$_n$—NH—(CH$_2$)$_n$—NH$_2$, or —(CH$_2$)$_n$—NH—C(=NH)NH$_2$, where each n is, independently, 1 to 8;

or a pharmaceutically acceptable salt thereof.

In some embodiments, X is —N($R^9$), O, S, or S(=O)$_2$; or X is —NH, O, S, or —N(CH$_2$)$_q$NH$_2$, where q is 2 or 3; or X is —NH, —N(CH$_2$)$_3$NH$_2$, or S.

In any of the above embodiments, $R^1$ and $R^2$ are, independently, H, —$C_1$-$C_3$alkyl, —$C_1$-$C_3$alkoxy, halo, —OH, -halo$C_1$-$C_3$alkyl, or —CN; or $R^1$ and $R^2$ are, independently, H, —$C_1$-$C_3$alkyl, —$C_1$-$C_3$alkoxy, halo, or —OH; or $R^1$ and $R^2$ are, independently, H, —$C_1$-$C_3$alkyl, or halo; or $R^1$ and $R^2$ are H.

In any of the above embodiments, $R^3$ and $R^4$ are, independently, H or -carbocycle($R^5$)($R^6$), where $R^5$ and $R^6$ can be positioned anywhere on the carbocycle. In any of the above embodiments, $R^3$ and $R^4$ are, independently,

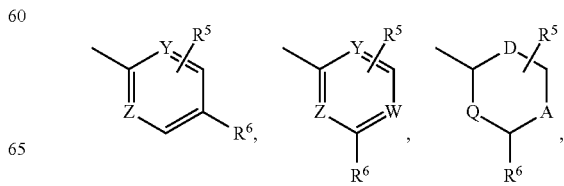

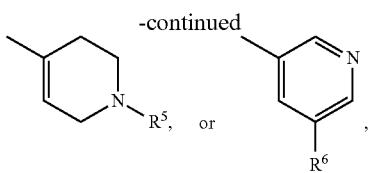

wherein each W, Y, and Z are, independently, C or N, each A, D, and Q are, independently, —C(R$^{10}$)C(R$^{11}$), —C(=O), —N(R$^{12}$), O, or S, and each R$^{10}$, R$^{11}$, and R$^{12}$ are, independently, H, —C$_1$-C$_8$alkyl, —C$_1$-C$_8$alkoxy, halo, —OH, —CF$_3$, or aromatic group.

In any of the above embodiments, R$^3$ and R$^4$ are, independently,

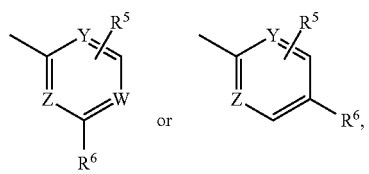

wherein each W, Y, and Z are, independently, C or N; or R$^3$ and R$^4$ are, independently,

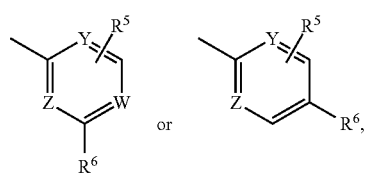

wherein each W, Y, and Z are C, or each Y and Z are C and each W is N.

In any of the above embodiments, each R$^5$ is, independently, H, —C$_1$-C$_8$alkyl, —C$_1$-C$_8$alkoxy, halo, amino, —OH, —CF$_3$, —O—(CH$_2$)$_p$—NH$_2$, —O—(CH$_2$)$_p$NHC(=NH)NH$_2$, —N((CH$_2$)$_p$NH$_2$)$_2$, —S—(CH$_2$)$_p$—NH$_2$, —S—(CH$_2$)$_p$NHC(=NH)NH$_2$, —C(=O)NH(CH$_2$)$_p$NH$_2$, —(CH$_2$)$_p$N((CH$_2$)$_p$NH$_2$)$_2$, where each p is, independently, 1 to 5, or the free base or salt form of —(CH$_2$)$_n$—NH$_2$, —(CH$_2$)$_n$—NH—(CH$_2$)$_n$—NH$_2$, or —(CH$_2$)$_n$—NH—C(=NH)NH$_2$, where each n is, independently, 1 to 8, and each R$^6$ is, independently, heterocycle, amino, —O—(CH$_2$)$_p$—NH$_2$, —O—(CH$_2$)$_p$NHC(=NH)NH$_2$, —S—(CH$_2$)$_p$—NH$_2$, —S—(CH$_2$)$_p$NHC(=NH)NH$_2$, —N((CH$_2$)$_p$NH$_2$)$_2$, —C(=O)NH(CH$_2$)$_p$NH$_2$, —(CH$_2$)$_p$N((CH$_2$)$_p$NH$_2$)$_2$, where each p is, independently, 1 to 5, or the free base or salt form of —(CH$_2$)$_n$—NH$_2$, —(CH$_2$)$_n$—NH—(CH$_2$)$_n$—NH$_2$, or —(CH$_2$)$_n$—NH—C(=NH)NH$_2$, where each n is, independently, 1 to 8; or each R$^5$ is, independently, H, —C$_1$-C$_3$alkyl, —C$_1$-C$_3$alkoxy, halo, —OH, —CF$_3$, or —O—(CH$_2$)—NH$_2$, where each p is, independently, 1 to 5, and each R$^6$ is, independently, heterocycle, —O—(CH$_2$)$_p$—NH$_2$, where each p is, independently, 1 to 5, or the free base or salt form of —(CH$_2$)$_n$—NH$_2$, where each n is, independently, 1 to 8; or each R$^5$ is, independently, H, —C$_1$-C$_3$alkyl, halo, —OH, or —O—(CH$_2$)$_p$—NH$_2$, where each p is, independently, 2 or 3, and each R$^6$ is, independently, heterocycle, —O—(CH$_2$)—NH$_2$, where each p is, independently, 2 or 3, or the free base or salt form of —(CH$_2$)$_n$—NH$_2$, where each n is, independently, 1 to 4; or each R$^5$ is, independently, H, —C$_1$-C$_3$alkyl, halo, —OH, or —O—(CH$_2$)$_3$—NH$_2$, and each R$^6$ is, independently, 6-membered heterocycle, —O—(CH$_2$)$_3$—NH$_2$, or the free base or salt form of —(CH$_2$)$_n$—NH$_2$, where each n is, independently, 1 to 3; or each R$^5$ is, independently, H, halo, or —O—(CH$_2$)$_3$—NH$_2$, and each R$^6$ is piperazinyl, —O—(CH$_2$)$_3$—NH$_2$, or the free base or salt form of —(CH$_2$)$_n$—NH$_2$ where each n is, independently, 1 to 3; or each R$^5$ is —O—(CH$_2$)$_3$—NH$_2$ or piperazinyl, and each R$^6$ is, independently, H, —C$_1$-C$_3$alkyl, —C$_1$-C$_3$alkoxy, halo, —OH, —CF$_3$, or —O—(CH$_2$)$_3$—NH$_2$, or each R$^5$ is piperazinyl or —O—(CH$_2$)$_3$—NH$_2$; and each R$^6$ is H, —C$_1$-C$_3$alkyl, halo, —OH, —CF$_3$, or —O—(CH$_2$)$_3$—NH$_2$.

In some embodiments, X is —NH, O, S, S(=O)$_2$, or —N(CH$_2$)$_{2-3}$NH$_2$; R$^1$ and R$^2$ are H; R$^3$ and R$^4$ are, independently,

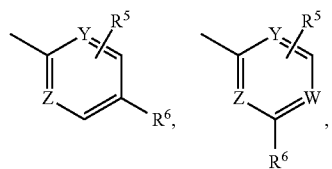

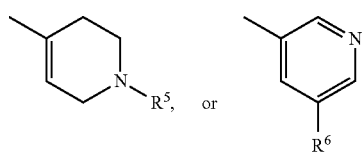

wherein: each W, Y, and Z are, independently, C or N; each R$^5$ and each R$^6$ are, independently, H, heterocycle, —O—(CH$_2$)$_p$—NH$_2$, where each p is, independently, 1 to 3, or the free base or salt form of —(CH$_2$)$_n$—NH$_2$, where each n is, independently, 1 to 3.

In some embodiments, X is —NH, O, S, or —N(CH$_2$)$_{2-3}$NH$_2$; R$^1$ and R$^2$ are H; R$^3$ and

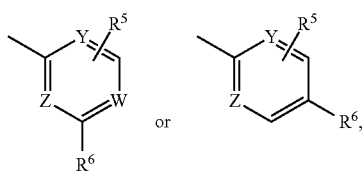

where each Z and Y are C, and each W is N; or each W, Y, and Z are C; each R$^5$ is, independently, H, halo, or amino, —O—(CH$_2$)$_p$—NH$_2$, —C(=O)NH(CH$_2$)$_p$NH$_2$, —N((CH$_2$)$_p$NH$_2$)$_2$, —(CH$_2$)$_p$N((CH$_2$)$_p$NH$_2$)$_2$, where each p is, independently, 2 or 3, and each R$^6$ is piperazinyl, amino, —C(=O)NH(CH$_2$)$_p$NH$_2$, —N((CH$_2$)$_p$NH$_2$)$_2$, —(CH$_2$)$_p$N((CH$_2$)$_p$NH$_2$)$_2$, —O—(CH$_2$)$_p$—NH$_2$, where each p is, independently, 2 or 3, or the free base or salt form of —(CH$_2$)$_n$—NH$_2$, where each n is, independently, 1 to 3; or each R$^5$ is piperazinyl or —O—(CH$_2$)$_3$—NH$_2$, and each R$^6$ is, independently, H, —C$_1$-C$_3$alkyl, —C$_1$-C$_3$alkoxy, halo, —OH, —CF$_3$, or —O—(CH$_2$)$_3$—NH$_2$.

In some embodiments, X is —NH, O, S, or —N(CH$_2$)$_{2-3}$NH$_2$; R$^1$ and R$^2$ are H; R$^3$ and

99

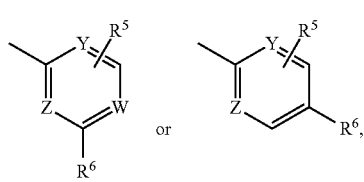 or where each Z and Y are C, and each W is N; or each W, Y, and Z are C; each $R^5$ is H or —O—$(CH_2)_3$—$NH_2$, and each $R^6$ is piperazinyl, —O—$(CH_2)_3$—$NH_2$, or the free base or salt form of —$(CH_2)_n$—$NH_2$, where each n is, independently, 1 to 3; or each $R^5$ is piperazinyl or —O—$(CH_2)_3$—$NH_2$; and each $R^6$ is H or —O—$(CH_2)_3$—$NH_2$.

In some embodiments, the compound is chosen from:

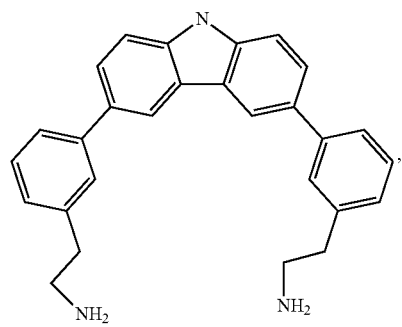

Compound 116

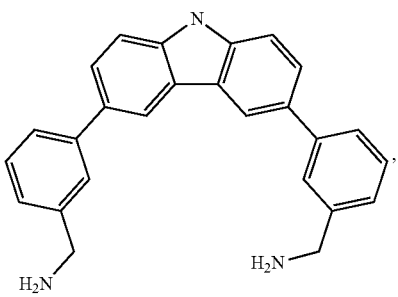

Compound 117

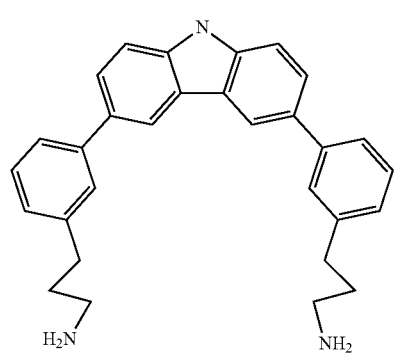

Compound 118

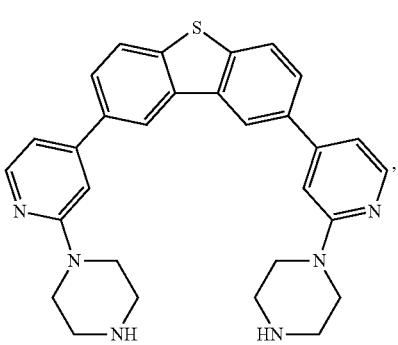

Compound 119

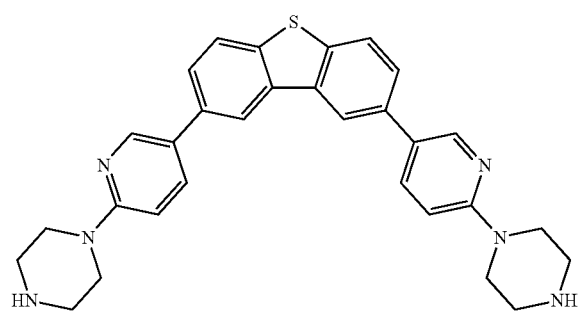

Compound 120

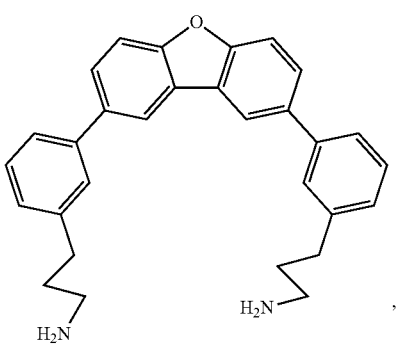

Compound 121

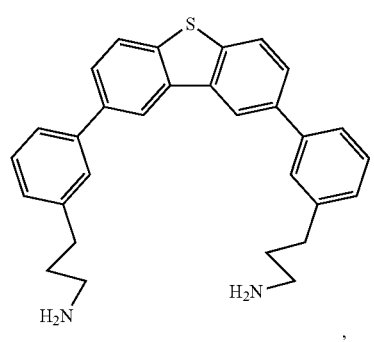

Compound 122

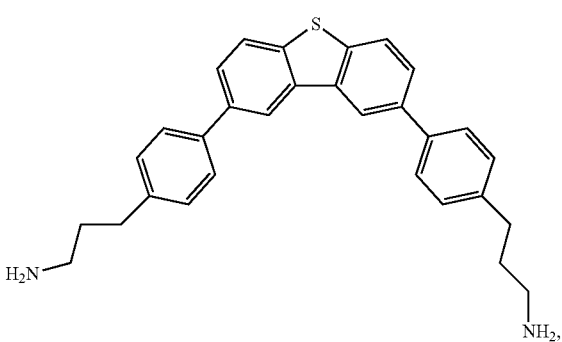

Compound 123

-continued
Compound 124
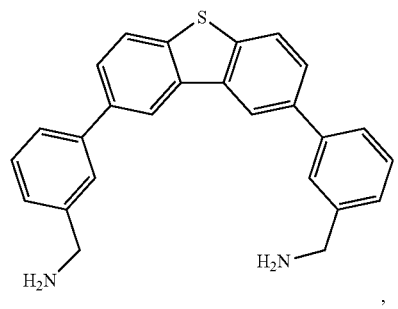
Compound 125
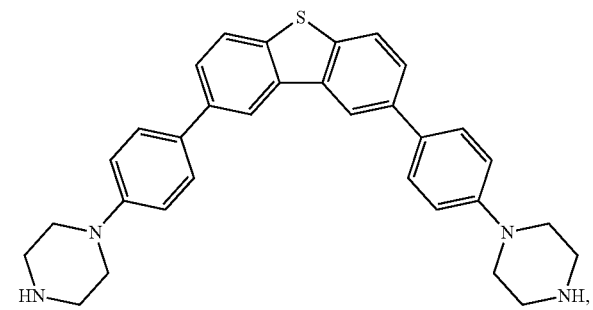
Compound 126
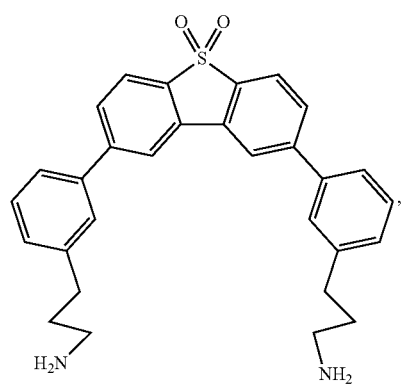
Compound 127
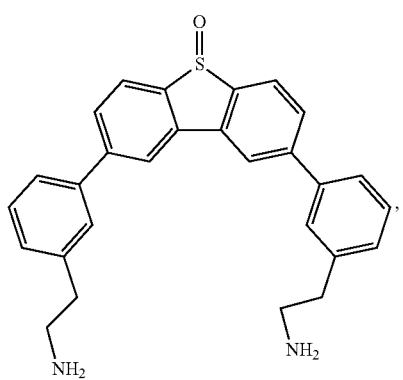
Compound 128
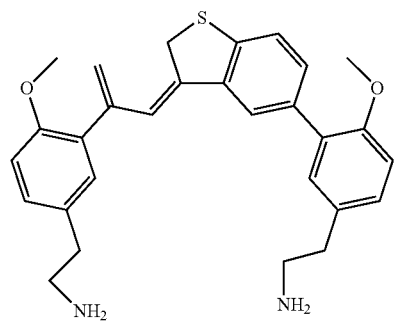
Compound 129
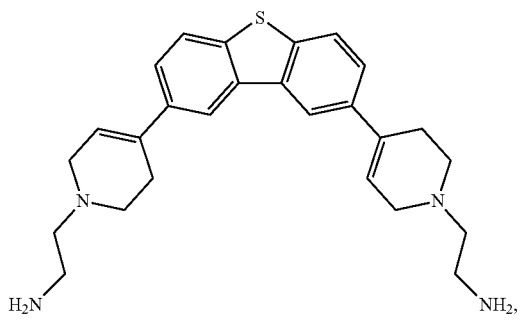
Compound 130
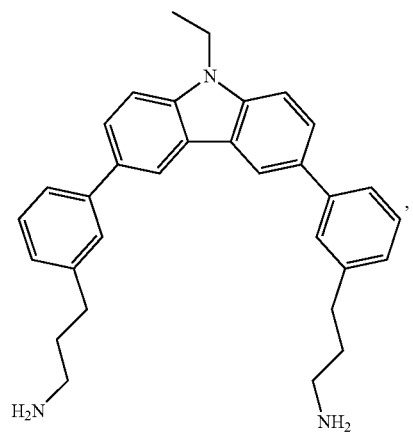
Compound 131
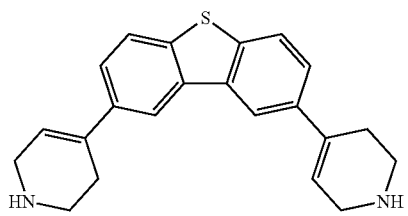

-continued
Compound 132
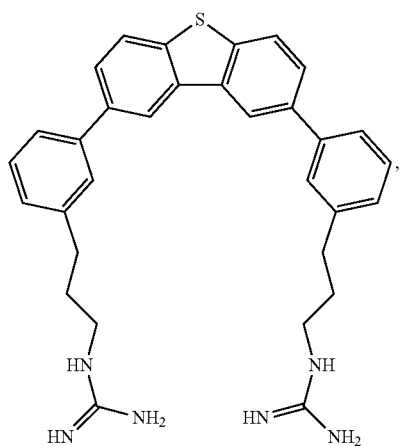
Compound 133
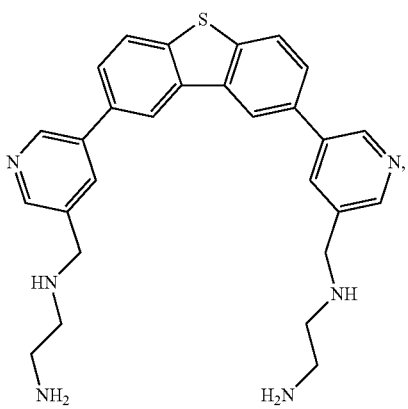
Compound 134
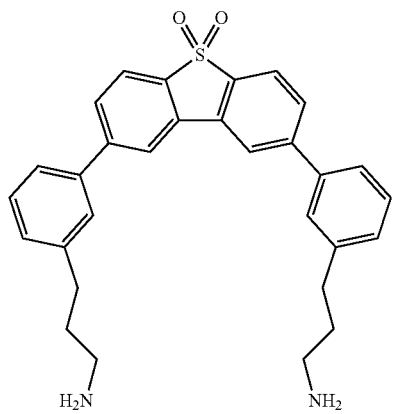
Compound 135
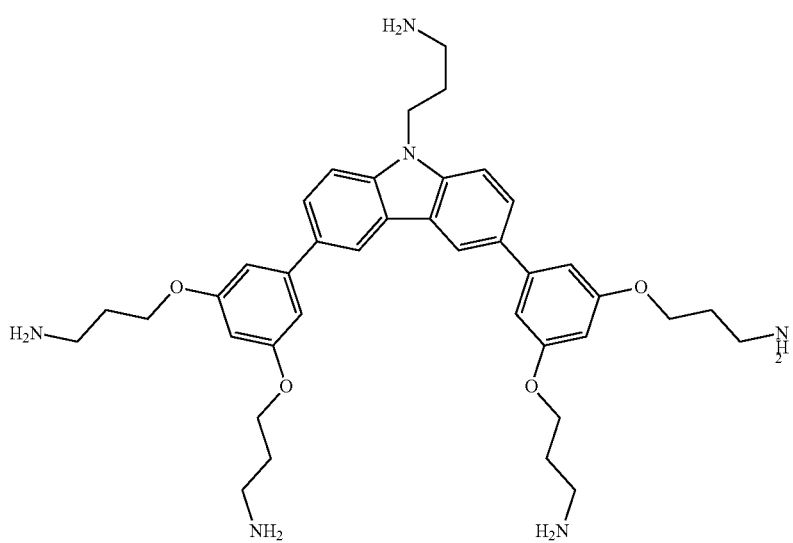

-continued
Compound 139
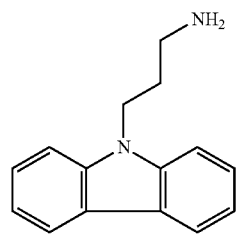
Compound 140
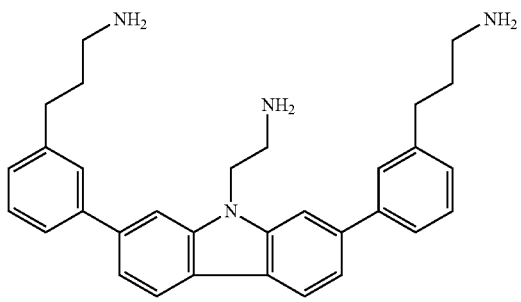
Compound 141
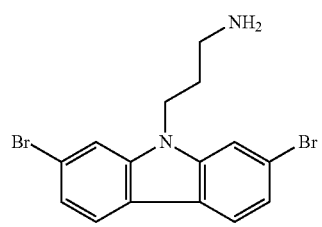
Compound 142
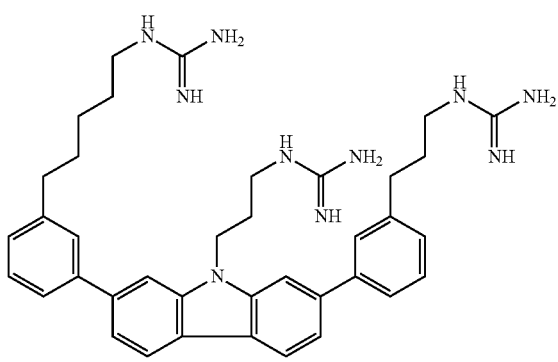
Compound 143
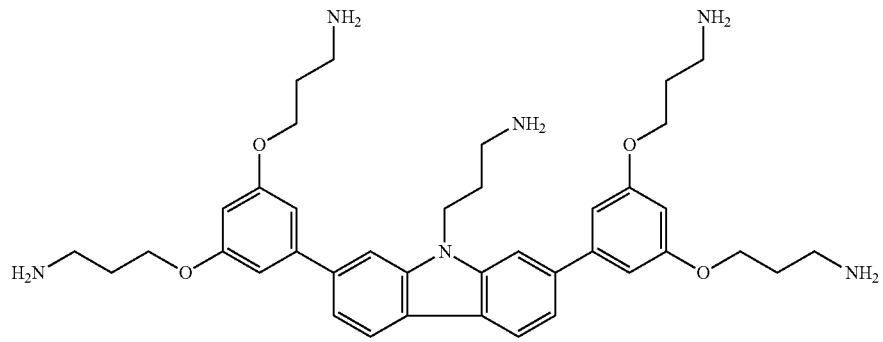
Compound 144
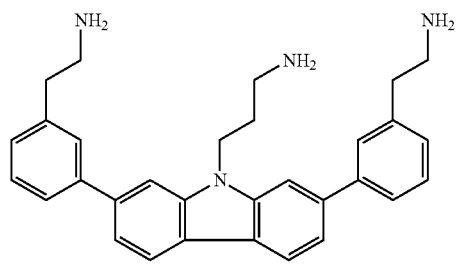
Compound 145
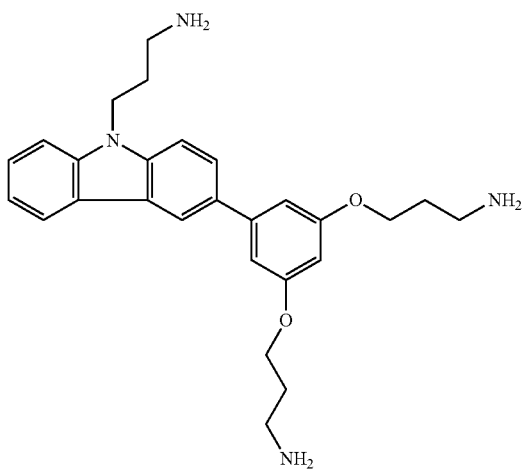

Compound 146
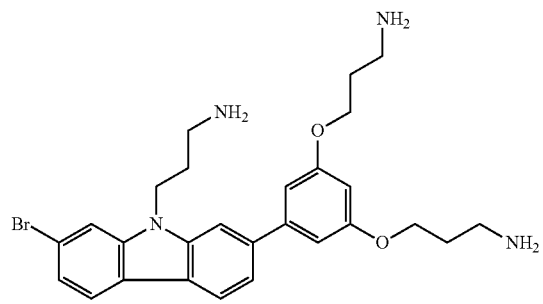
Compound 147
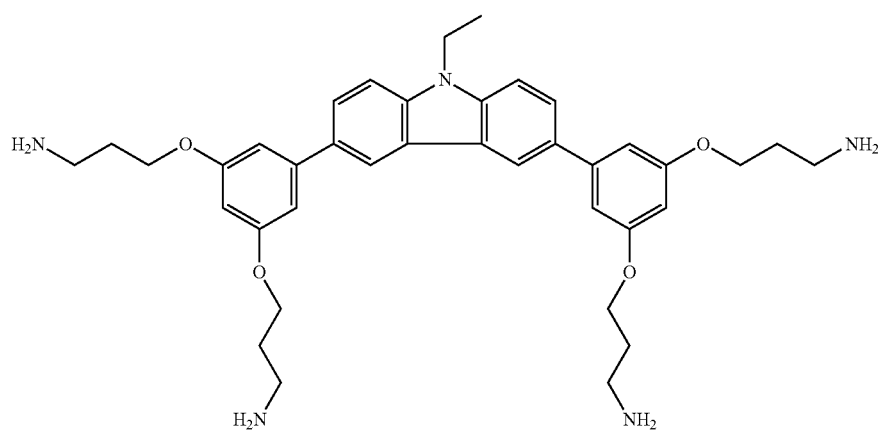
Compound 148
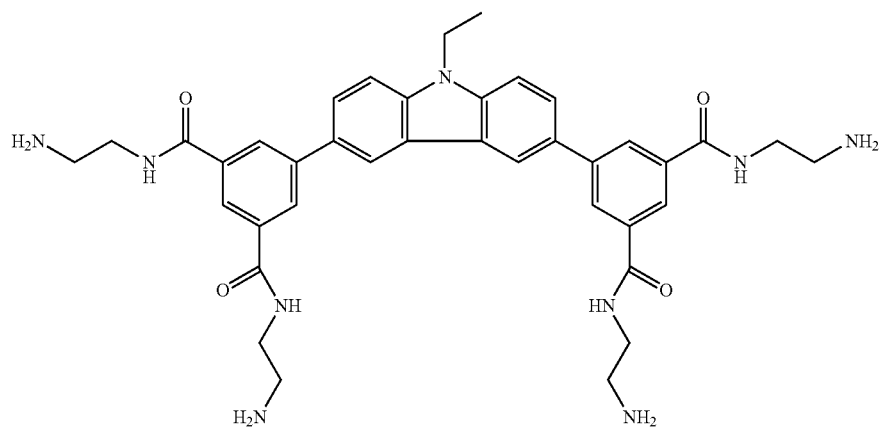
Compound 149
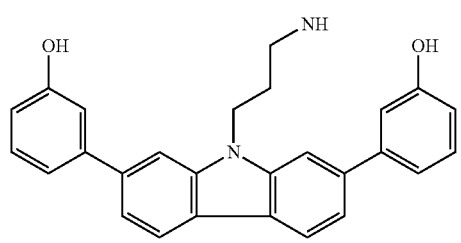
Compound 150
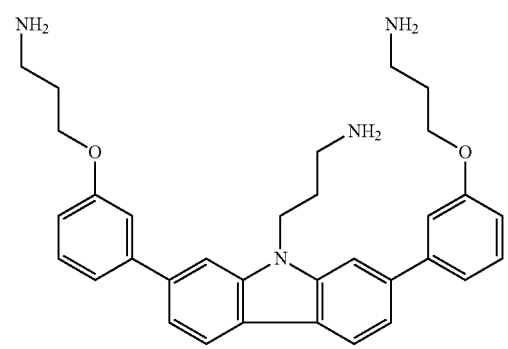

-continued
Compound 151
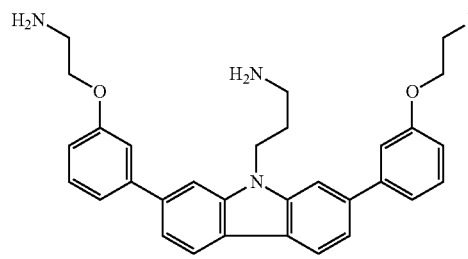
Compound 152
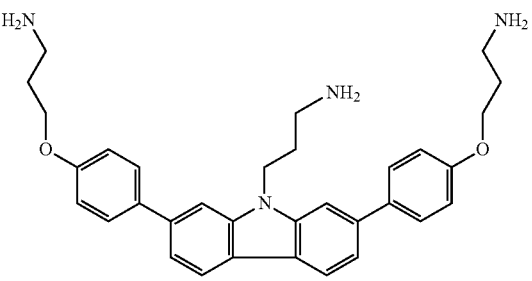
Compound 153
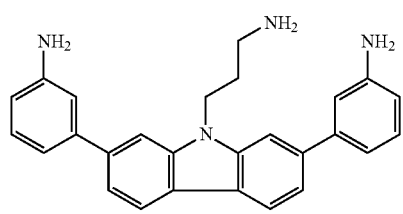
Compound 154
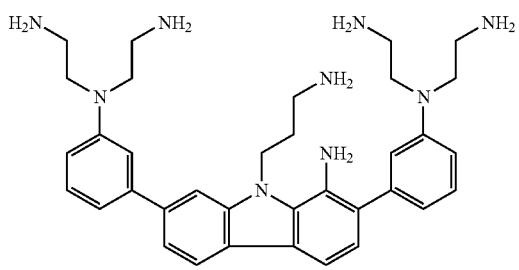
Compound 155
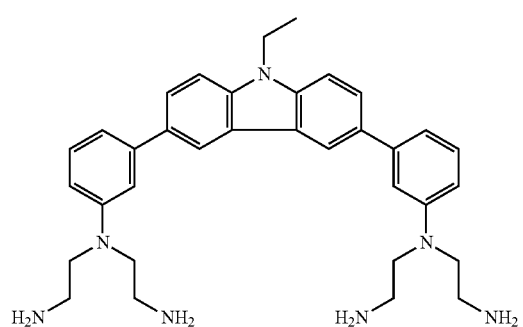
Compound 156
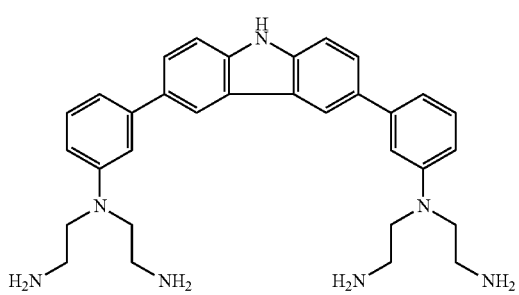
Compound 157
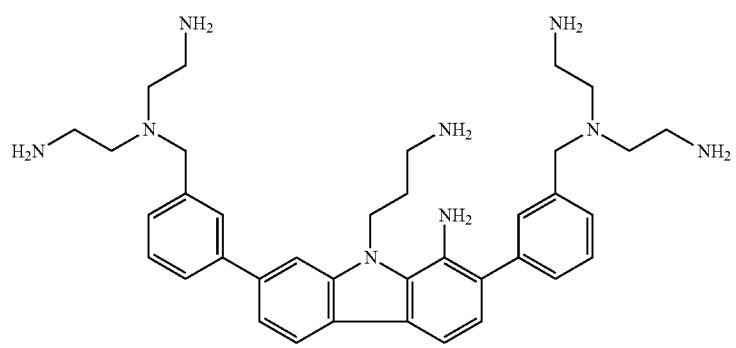
Compound 158
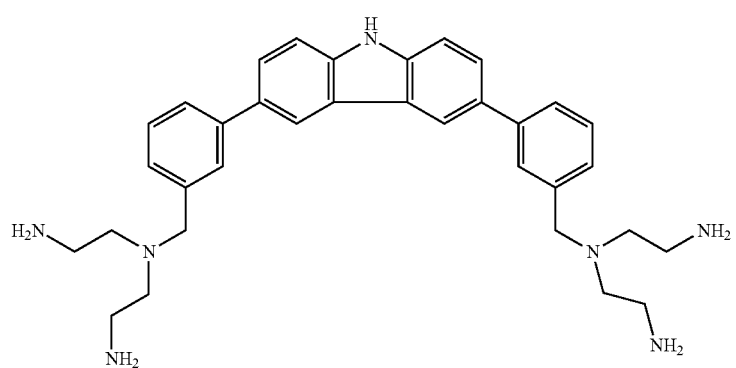

Compound 159
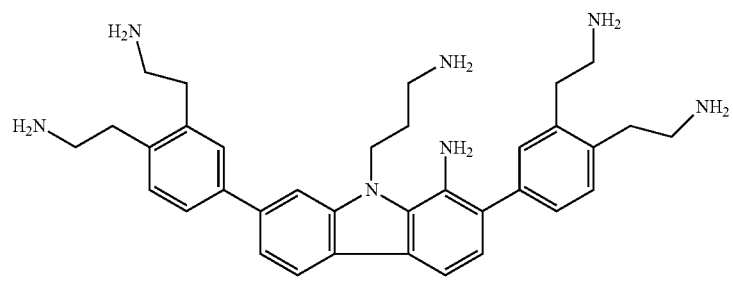
Compound 160
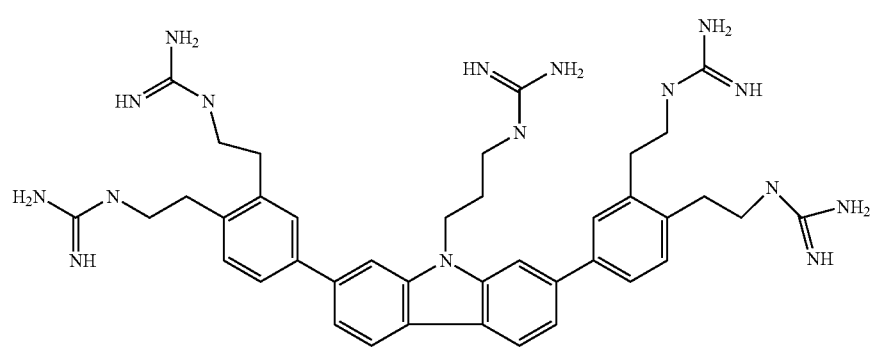
Compound 161
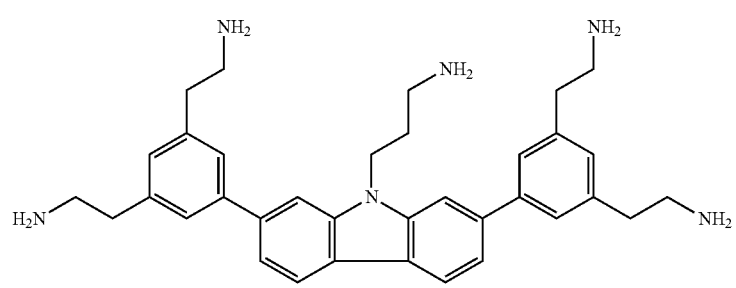
Compound 162
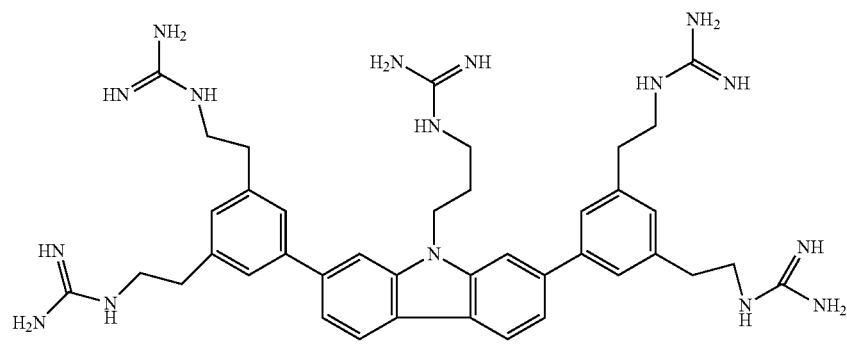

-continued

Compound 163

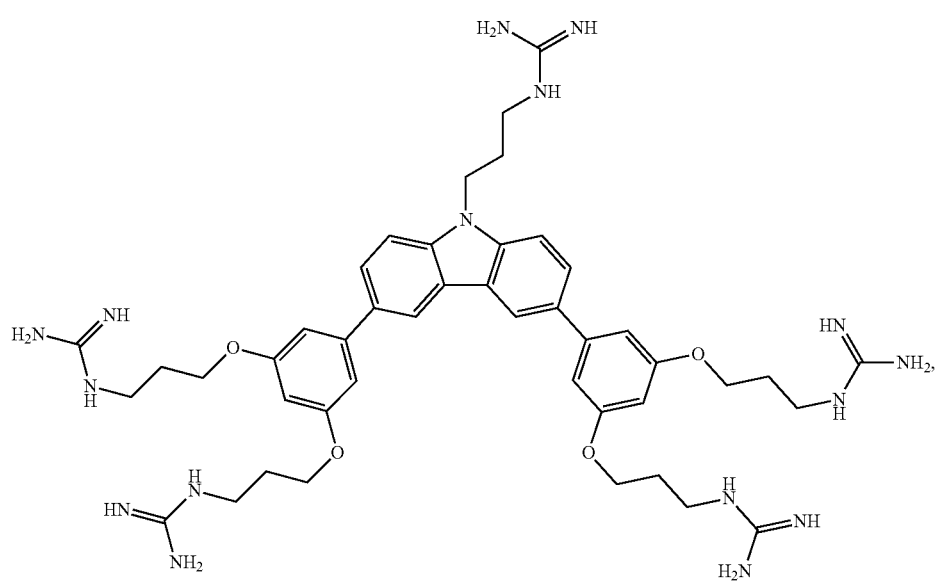

or a pharmaceutically acceptable salt thereof.

The present disclosure also provides compounds of Formula IV

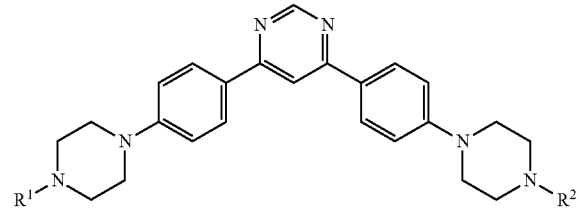
(IV)

wherein:

R[1] and R[2] are, independently, —C(=NH)NH$_2$, —(CH$_2$)$_n$NH$_2$, or —(CH$_2$)$_n$NC(=NH)NH$_2$, where n is 2, 3, or 4;
or a pharmaceutically acceptable salt thereof.

In some embodiments, R[1] and R[2] are, independently, —C(=NH)NH$_2$, —(CH$_2$)$_n$NH$_2$, or —(CH$_2$)$_n$NC(=NH)NH$_2$, where n is 2 or 3.

In some embodiments, R[1] and R[2] are, independently, —C(=NH)NH$_2$ or —(CH$_2$)$_n$NH$_2$, where n is 2 or 3.

In some embodiments, the compound is:

Compound 136

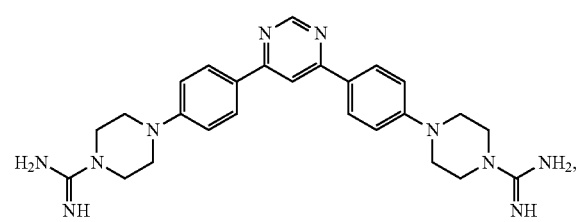

or a pharmaceutically acceptable salt thereof.

In some embodiments, any one or more of the above compounds may be excluded from any of the genus of compounds described above.

The present disclosure also provides compositions comprising one or more of the compounds or salts described above and a pharmaceutically acceptable carrier.

The present disclosure also provides methods of preventing or treating candidiasis (oral and/or disseminated) or an *aspergillus* infection in a mammal comprising administering to the mammal in need thereof an effective amount of a compound of Formula IV:

(IV)

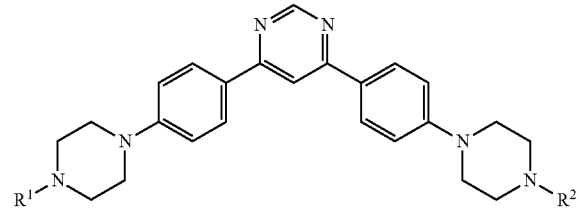

wherein:

R[1] and R[2] are, independently, —C(=NH)NH$_2$, —(CH$_2$)$_n$NH$_2$, or —(CH$_2$)$_n$NC(=NH)NH$_2$, where n is 2, 3, or 4;
or a pharmaceutically acceptable salt thereof.

In some embodiments, R[1] and R[2] are, independently, —C(=NH)NH$_2$, —(CH$_2$)$_n$NH$_2$, or —(CH$_2$)$_n$NC(=NH)NH$_2$, where n is 2 or 3.

In some embodiments, R[1] and R[2] are, independently, —C(=NH)NH$_2$ or —(CH$_2$)$_n$NH$_2$, where n is 2 or 3.

In some embodiments, the compound is:

Compound 136

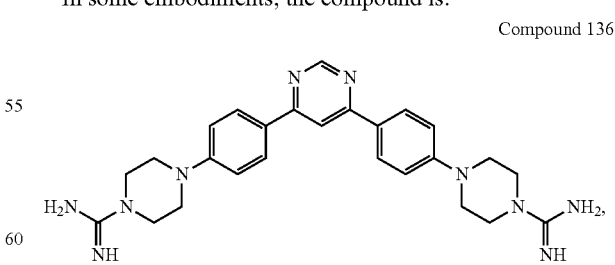

or a pharmaceutically acceptable salt thereof.

The present disclosure also provides methods of killing or inhibiting the growth of a *Candida* or *Aspergillus* species comprising contacting the *Candida* or *Aspergillus* species with an effective amount of a compound of Formula IV:

(IV)

wherein:

R[1] and R[2] are, independently, —C(=NH)NH$_2$, —(CH$_2$)$_n$NH$_2$, or —(CH$_2$)$_n$NC(=NH)NH$_2$, where n is 2, 3, or 4;

or a pharmaceutically acceptable salt thereof.

In some embodiments, R[1] and R[2] are, independently, —C(=NH)NH$_2$, —(CH$_2$)$_n$NH$_2$, or —(CH$_2$)$_n$NC(=NH)NH$_2$, where n is 2 or 3.

In some embodiments, R[1] and R[2] are, independently, —C(=NH)NH$_2$ or —(CH$_2$)$_n$NH$_2$, where n is 2 or 3.

In some embodiments, the compound is:

Compound 136 or a pharmaceutically acceptable salt thereof.

The present disclosure also provides compounds of Formula V:

(V)

wherein:

R[1] is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

R[2] is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

R[3] is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

R[4] is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

R[5] is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

R[6] is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4; and R[7] is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

or a pharmaceutically acceptable salt thereof.

In some embodiments, R[1] is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or R[1] is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or R[1] is —NH(CH$_2$)$_n$NH$_2$, —(CH$_2$)$_n$NH$_2$, or —O—(CH$_2$)$_n$NH$_2$, where n is 2, 3, or 4; or R[1] is —(CH$_2$)$_n$NH$_2$ or —O—(CH$_2$)$_n$NH$_2$, where n is 2, 3, or 4; or R[1] is —O—(CH$_2$)$_n$NH$_2$, where n is 2, 3, or 4.

In any of the above embodiments, R[2] is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or R[2] is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or R[2] is —NH(CH$_2$)$_n$NH$_2$, —(CH$_2$)$_n$NH$_2$, or —O—(CH$_2$)$_n$NH$_2$, where n is 2, 3, or 4; or R[2] is —(CH$_2$)$_n$NH$_2$ or —O—(CH$_2$)$_n$NH$_2$, where n is 2, 3, or 4; or R[2] is —O—(CH$_2$)$_n$NH$_2$, where n is 2, 3, or 4.

In any of the above embodiments, R[3] is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or R[3] is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or R[3] is —NH(CH$_2$)$_n$NH$_2$, —(CH$_2$)$_n$NH$_2$, or —O—(CH$_2$)$_n$NH$_2$, where n is 2, 3, or 4; or R[3] is —(CH$_2$)$_n$NH$_2$ or —O—(CH$_2$)$_n$NH$_2$, where n is 2, 3, or 4; or R[3] is —O—(CH$_2$)$_n$NH$_2$, where n is 2, 3, or 4.

In any of the above embodiments, R[4] is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or R[4] is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or R$^4$ is —NH(CH$_2$)$_n$NH$_2$, —(CH$_2$)$_n$NH$_2$, or —O—(CH$_2$)$_n$NH$_2$, where n is 2, 3, or 4; or R$^4$ is —(CH$_2$)$_n$NH$_2$ or —O—(CH$_2$)$_n$NH$_2$, where n is 2, 3, or 4; or R$^4$ is —O—(CH$_2$)$_n$NH$_2$, where n is 2, 3, or 4.

In any of the above embodiments, R$^5$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or R$^5$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or R$^5$ is —NH(CH$_2$)$_n$NH$_2$, —(CH$_2$)$_n$NH$_2$, or —O—(CH$_2$)$_n$NH$_2$, where n is 2, 3, or 4; or R$^5$ is —(CH$_2$)$_n$NH$_2$ or —O—(CH$_2$)$_n$NH$_2$, where n is 2, 3, or 4; or R$^5$ is —O—(CH$_2$)$_n$NH$_2$, where n is 2, 3, or 4.

In any of the above embodiments, R$^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or R$^6$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or R$^6$ is H, —NH(CH$_2$)$_n$NH$_2$, —(CH$_2$)$_n$NH$_2$, or —O—(CH$_2$)$_n$NH$_2$, where n is 2, 3, or 4; or R$^6$ is H or —(CH$_2$)$_n$NH$_2$, where n is 2, 3, or 4; or R$^6$ is H or —O—(CH$_2$)$_n$NH$_2$, where n is 3 or 4.

In any of the above embodiments, R$^7$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or R$^7$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or R$^7$ is H, —NH(CH$_2$)$_n$NH$_2$, —(CH$_2$)$_n$NH$_2$, or —O—(CH$_2$)$_n$NH$_2$, where n is 2, 3, or 4; or R$^7$ is H or —(CH$_2$)$_n$NH$_2$, where n is 2, 3, or 4; or R$^7$ is H or —O—(CH$_2$)$_n$NH$_2$, where n is 3 or 4.

In some embodiments:
R$^1$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4;
R$^2$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4;
R$^3$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4;
R$^4$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4;
R$^5$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4;
R$^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; and
R$^7$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4.

In some embodiments:
R$^1$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4;
R$^2$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4;
R$^3$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4;
R$^4$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4;
R$^5$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4;
R$^6$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; and
R$^7$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4.

In some embodiments:
R$^1$ is —NH(CH$_2$)$_n$NH$_2$, —(CH$_2$)$_n$NH$_2$, or —O—(CH$_2$)$_n$NH$_2$, where n is 2, 3, or 4;
R$^2$ is —NH(CH$_2$)$_n$NH$_2$, —(CH$_2$)$_n$NH$_2$, or —O—(CH$_2$)$_n$NH$_2$, where n is 2, 3, or 4;
R$^3$ is —NH(CH$_2$)$_n$NH$_2$, —(CH$_2$)$_n$NH$_2$, or —O—(CH$_2$)$_n$NH$_2$, where n is 2, 3, or 4;
R$^4$ is —NH(CH$_2$)$_n$NH$_2$, —(CH$_2$)$_n$NH$_2$, or —O—(CH$_2$)$_n$NH$_2$, where n is 2, 3, or 4;
R$^5$ is —NH(CH$_2$)$_n$NH$_2$, —(CH$_2$)$_n$NH$_2$, or —O—(CH$_2$)$_n$NH$_2$, where n is 2, 3, or 4;
R$^6$ is H, —NH(CH$_2$)$_n$NH$_2$, —(CH$_2$)$_n$NH$_2$, or —O—(CH$_2$)$_n$NH$_2$, where n is 2, 3, or 4; and
R$^7$ is H, —NH(CH$_2$)$_n$NH$_2$, —(CH$_2$)$_n$NH$_2$, or —O—(CH$_2$)$_n$NH$_2$, where n is 2, 3, or 4.

In some embodiments:
R$^1$ is —(CH$_2$)$_n$NH$_2$ or —O—(CH$_2$)$_n$NH$_2$, where n is 2, 3, or 4;
R$^2$ is —(CH$_2$)$_n$NH$_2$ or —O—(CH$_2$)$_n$NH$_2$, where n is 2, 3, or 4;
R$^3$ is —(CH$_2$)$_n$NH$_2$ or —O—(CH$_2$)$_n$NH$_2$, where n is 2, 3, or 4;
R$^4$ is —(CH$_2$)$_n$NH$_2$ or —O—(CH$_2$)$_n$NH$_2$, where n is 2, 3, or 4;
R$^5$ is —(CH$_2$)$_n$NH$_2$ or —O—(CH$_2$)$_n$NH$_2$, where n is 2, 3, or 4;
R$^6$ is H or —(CH$_2$)$_n$NH$_2$, where n is 2, 3, or 4; and
R$^7$ is H or —(CH$_2$)$_n$NH$_2$, where n is 2, 3, or 4.

In some embodiments:
R$^1$ is —O—(CH$_2$)$_n$NH$_2$, where n is 2, 3, or 4;
R$^2$ is —O—(CH$_2$)$_n$NH$_2$, where n is 2, 3, or 4;
R$^3$ is —O—(CH$_2$)$_n$NH$_2$, where n is 2, 3, or 4;
R$^4$ is —O—(CH$_2$)$_n$NH$_2$, where n is 2, 3, or 4;
R$^5$ is —O—(CH$_2$)$_n$NH$_2$, where n is 2, 3, or 4;
R$^6$ is H or —O—(CH$_2$)$_n$NH$_2$, where n is 3 or 4; and
R$^7$ is H or —O—(CH$_2$)$_n$NH$_2$, where n is 3 or 4.

In some embodiments, the compound is

Compound 137

In some embodiments, any one or more of the above compounds may be excluded from any of the genus of compounds described above.

The present disclosure also provides compositions comprising one or more of the compounds or salts described above and a pharmaceutically acceptable carrier.

The present disclosure also provides methods of preventing or treating candidiasis (oral and/or disseminated) or an *aspergillus* infection in a mammal comprising administering to the mammal in need thereof an effective amount of a compound of Formula V:

(V)

[Chemical structure showing a central benzene ring with R2 substituent, connected via two triazole rings to two phenyl rings bearing R1, R6, R4 on one side and R3, R7, R5 on the other]

wherein:

$R^1$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^2$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^3$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4; and $R^7$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

or a pharmaceutically acceptable salt thereof.

In some embodiments, $R^1$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or $R^1$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or $R^1$ is —NH(CH$_2$)$_n$NH$_2$, —(CH$_2$)$_n$NH$_2$, or —O—(CH$_2$)$_n$NH$_2$, where n is 2, 3, or 4; or $R^1$ is —(CH$_2$)$_n$NH$_2$ or —O—(CH$_2$)$_n$NH$_2$, where n is 2, 3, or 4; or $R^1$ is —O—(CH$_2$)$_n$NH$_2$, where n is 2, 3, or 4.

In any of the above embodiments, $R^2$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or $R^2$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or $R^2$ is —NH(CH$_2$)$_n$NH$_2$, —(CH$_2$)$_n$NH$_2$, or —O—(CH$_2$)$_n$NH$_2$, where n is 2, 3, or 4; or $R^2$ is —(CH$_2$)$_n$NH$_2$ or —O—(CH$_2$)$_n$NH$_2$, where n is 2, 3, or 4; or $R^2$ is —O—(CH$_2$)$_n$NH$_2$, where n is 2, 3, or 4.

In any of the above embodiments, $R^3$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or $R^3$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or $R^3$ is —NH(CH$_2$)$_n$NH$_2$, —(CH$_2$)$_n$NH$_2$, or —O—(CH$_2$)$_n$NH$_2$, where n is 2, 3, or 4; or $R^3$ is —(CH$_2$)$_n$NH$_2$ or —O—(CH$_2$)$_n$NH$_2$, where n is 2, 3, or 4; or $R^3$ is —O—(CH$_2$)$_n$NH$_2$, where n is 2, 3, or 4.

In any of the above embodiments, $R^4$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or $R^4$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or $R^4$ is —NH(CH$_2$)$_n$NH$_2$, —(CH$_2$)$_n$NH$_2$, or —O—(CH$_2$)$_n$NH$_2$, where n is 2, 3, or 4; or $R^4$ is —(CH$_2$)$_n$NH$_2$ or —O—(CH$_2$)$_n$NH$_2$, where n is 2, 3, or 4; or $R^4$ is —O—(CH$_2$)$_n$NH$_2$, where n is 2, 3, or 4.

In any of the above embodiments, $R^5$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or $R^5$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or $R^5$ is —NH(CH$_2$)$_n$NH$_2$, —(CH$_2$)$_n$NH$_2$, or —O—(CH$_2$)$_n$NH$_2$, where n is 2, 3, or 4; or $R^5$ is —(CH$_2$)$_n$NH$_2$ or —O—(CH$_2$)$_n$NH$_2$, where n is 2, 3, or 4; or $R^5$ is —O—(CH$_2$)$_n$NH$_2$, where n is 2, 3, or 4.

In any of the above embodiments, $R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or $R^6$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or $R^6$ is H, —NH(CH$_2$)$_n$NH$_2$, —(CH$_2$)$_n$NH$_2$, or —O—(CH$_2$)$_n$NH$_2$, where n is 2, 3, or 4; or $R^6$ is H or —$(CH_2)_nNH_2$, where n is 2, 3, or 4; or $R^6$ is H or —O—$(CH_2)_nNH_2$, where n is 3 or 4.

In any of the above embodiments, $R^7$ is H, —NH$(CH_2)_n$NH$_2$, —NH$(CH_2)_n$NC(=N)NH$_2$, —$(CH_2)_n$NH$_2$, —O—$(CH_2)_n$NH$_2$, —$(CH_2)_n$NC(=N)NH$_2$, or —O—$(CH_2)_n$NC(=N)NH$_2$, where n is 2, 3, or 4; or $R^7$ is H, —NH$(CH_2)_n$NH$_2$, —$(CH_2)_n$NH$_2$, —O—$(CH_2)_n$NH$_2$, or —$(CH_2)_n$NC(=N)NH$_2$, where n is 2, 3, or 4; or $R^7$ is H, —NH$(CH_2)_n$NH$_2$, —$(CH_2)_n$NH$_2$, or —O—$(CH_2)_n$NH$_2$, where n is 2, 3, or 4; or $R^7$ is H or —$(CH_2)_n$NH$_2$, where n is 2, 3, or 4; or $R^7$ is H or —O—$(CH_2)_n$NH$_2$, where n is 3 or 4.

In some embodiments:

$R^1$ is —NH$(CH_2)_n$NH$_2$, —NH$(CH_2)_n$NC(=N)NH$_2$, —$(CH_2)_n$NH$_2$, —$(CH_2)_n$NC(=N)NH$_2$, —O—$(CH_2)_n$NH$_2$, or —O—$(CH_2)_n$NC(=N)NH$_2$, where n is 2, 3, or 4;

$R^2$ is —NH$(CH_2)_n$NH$_2$, —NH$(CH_2)_n$NC(=N)NH$_2$, —$(CH_2)_n$NH$_2$, —$(CH_2)_n$NC(=N)NH$_2$, —O—$(CH_2)_n$NH$_2$, or —O—$(CH_2)_n$NC(=N)NH$_2$, where n is 2, 3, or 4;

$R^3$ is —NH$(CH_2)_n$NH$_2$, —NH$(CH_2)_n$NC(=N)NH$_2$, —$(CH_2)_n$NH$_2$, —$(CH_2)_n$NC(=N)NH$_2$, —O—$(CH_2)_n$NH$_2$, or —O—$(CH_2)_n$NC(=N)NH$_2$, where n is 2, 3, or 4;

$R^4$ is —NH$(CH_2)_n$NH$_2$, —NH$(CH_2)_n$NC(=N)NH$_2$, —$(CH_2)_n$NH$_2$, —$(CH_2)_n$NC(=N)NH$_2$, —O—$(CH_2)_n$NH$_2$, or —O—$(CH_2)_n$NC(=N)NH$_2$, where n is 2, 3, or 4;

$R^5$ is —NH$(CH_2)_n$NH$_2$, —NH$(CH_2)_n$NC(=N)NH$_2$, —$(CH_2)_n$NH$_2$, —$(CH_2)_n$NC(=N)NH$_2$, —O—$(CH_2)_n$NH$_2$, or —O—$(CH_2)_n$NC(=N)NH$_2$, where n is 2, 3, or 4;

$R^6$ is H, —NH$(CH_2)_n$NH$_2$, —NH$(CH_2)_n$NC(=N)NH$_2$, —$(CH_2)_n$NH$_2$, —O—$(CH_2)_n$NH$_2$, —$(CH_2)_n$NC(=N)NH$_2$, or —O—$(CH_2)_n$NC(=N)NH$_2$, where n is 2, 3, or 4; and $R^7$ is H, —NH$(CH_2)_n$NH$_2$, —NH$(CH_2)_n$NC(=N)NH$_2$, —$(CH_2)_n$NH$_2$, —O—$(CH_2)_n$NH$_2$, —$(CH_2)_n$NC(=N)NH$_2$, or —O—$(CH_2)_n$NC(=N)NH$_2$, where n is 2, 3, or 4.

In some embodiments:

$R^1$ is —NH$(CH_2)_n$NH$_2$, —$(CH_2)_n$NH$_2$, —$(CH_2)_n$NC(=N)NH$_2$, or —O—$(CH_2)_n$NH$_2$, where n is 2, 3, or 4;

$R^2$ is —NH$(CH_2)_n$NH$_2$, —$(CH_2)_n$NH$_2$, —$(CH_2)_n$NC(=N)NH$_2$, or —O—$(CH_2)_n$NH$_2$, where n is 2, 3, or 4;

$R^3$ is —NH$(CH_2)_n$NH$_2$, —$(CH_2)_n$NH$_2$, —$(CH_2)_n$NC(=N)NH$_2$, or —O—$(CH_2)_n$NH$_2$, where n is 2, 3, or 4;

$R^4$ is —NH$(CH_2)_n$NH$_2$, —$(CH_2)_n$NH$_2$, —$(CH_2)_n$NC(=N)NH$_2$, or —O—$(CH_2)_n$NH$_2$, where n is 2, 3, or 4;

$R^5$ is —NH$(CH_2)_n$NH$_2$, —$(CH_2)_n$NH$_2$, —$(CH_2)_n$NC(=N)NH$_2$, or —O—$(CH_2)_n$NH$_2$, where n is 2, 3, or 4;

$R^6$ is H, —NH$(CH_2)_n$NH$_2$, —$(CH_2)_n$NH$_2$, —O—$(CH_2)_n$NH$_2$, or —$(CH_2)_n$NC(=N)NH$_2$, where n is 2, 3, or 4; and $R^7$ is H, —NH$(CH_2)_n$NH$_2$, —$(CH_2)_n$NH$_2$, —O—$(CH_2)_n$NH$_2$, or —$(CH_2)_n$NC(=N)NH$_2$, where n is 2, 3, or 4.

In some embodiments:

$R^1$ is —NH$(CH_2)_n$NH$_2$, —$(CH_2)_n$NH$_2$, or —O—$(CH_2)_n$NH$_2$, where n is 2, 3, or 4;

$R^2$ is —NH$(CH_2)_n$NH$_2$, —$(CH_2)_n$NH$_2$, or —O—$(CH_2)_n$NH$_2$, where n is 2, 3, or 4;

$R^3$ is —NH$(CH_2)_n$NH$_2$, —$(CH_2)_n$NH$_2$, or —O—$(CH_2)_n$NH$_2$, where n is 2, 3, or 4;

$R^4$ is —NH$(CH_2)_n$NH$_2$, —$(CH_2)_n$NH$_2$, or —O—$(CH_2)_n$NH$_2$, where n is 2, 3, or 4;

$R^5$ is —NH$(CH_2)_n$NH$_2$, —$(CH_2)_n$NH$_2$, or —O—$(CH_2)_n$NH$_2$, where n is 2, 3, or 4;

$R^6$ is H, —NH$(CH_2)_n$NH$_2$, —$(CH_2)_n$NH$_2$, or —O—$(CH_2)_n$NH$_2$, where n is 2, 3, or 4; and $R^7$ is H, —NH$(CH_2)_n$NH$_2$, —$(CH_2)_n$NH$_2$, or —O—$(CH_2)_n$NH$_2$, where n is 2, 3, or 4.

In some embodiments:

$R^1$ is —$(CH_2)_n$NH$_2$ or —O—$(CH_2)_n$NH$_2$, where n is 2, 3, or 4;

$R^2$ is —$(CH_2)_n$NH$_2$ or —O—$(CH_2)_n$NH$_2$, where n is 2, 3, or 4;

$R^3$ is —$(CH_2)_n$NH$_2$ or —O—$(CH_2)_n$NH$_2$, where n is 2, 3, or 4;

$R^4$ is —$(CH_2)_n$NH$_2$ or —O—$(CH_2)_n$NH$_2$, where n is 2, 3, or 4;

$R^5$ is —$(CH_2)_n$NH$_2$ or —O—$(CH_2)_n$NH$_2$, where n is 2, 3, or 4;

$R^6$ is H or —$(CH_2)_n$NH$_2$, where n is 2, 3, or 4; and $R^7$ is H or —$(CH_2)_n$NH$_2$, where n is 2, 3, or 4.

In some embodiments:

$R^1$ is —O—$(CH_2)_n$NH$_2$, where n is 2, 3, or 4;

$R^2$ is —O—$(CH_2)_n$NH$_2$, where n is 2, 3, or 4;

$R^3$ is —O—$(CH_2)_n$NH$_2$, where n is 2, 3, or 4;

$R^4$ is —O—$(CH_2)_n$NH$_2$, where n is 2, 3, or 4;

$R^5$ is —O—$(CH_2)_n$NH$_2$, where n is 2, 3, or 4;

$R^6$ is H or —O—$(CH_2)_n$NH$_2$, where n is 3 or 4; and $R^7$ is H or —O—$(CH_2)_n$NH$_2$, where n is 3 or 4.

In some embodiments, the compound is

Compound 137

[Chemical structure of Compound 137: a central benzene ring with two triazole-linked aryl ether substituents bearing aminopropoxy groups]

The present disclosure also provides methods of killing or inhibiting the growth of a *Candida* or *Aspergillus* species comprising contacting the *Candida* or *Aspergillus* species with an effective amount of a compound of Formula V:

$$(V)$$

wherein:

$R^1$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^2$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^3$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4; and $R^7$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

or a pharmaceutically acceptable salt thereof.

In some embodiments, $R^1$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or $R^1$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or $R^1$ is —NH(CH$_2$)$_n$NH$_2$, —(CH$_2$)$_n$NH$_2$, or —O—(CH$_2$)$_n$NH$_2$, where n is 2, 3, or 4; or $R^1$ is —(CH$_2$)$_n$NH$_2$ or —O—(CH$_2$)$_n$NH$_2$, where n is 2, 3, or 4; or $R^1$ is —O—(CH$_2$)$_n$NH$_2$, where n is 2, 3, or 4.

In any of the above embodiments, $R^2$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or $R^2$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or $R^2$ is —NH(CH$_2$)$_n$NH$_2$, —(CH$_2$)$_n$NH$_2$, or —O—(CH$_2$)$_n$NH$_2$, where n is 2, 3, or 4; or $R^2$ is —(CH$_2$)$_n$NH$_2$ or —O—(CH$_2$)$_n$NH$_2$, where n is 2, 3, or 4; or $R^2$ is —O—(CH$_2$)$_n$NH$_2$, where n is 2, 3, or 4.

In any of the above embodiments, $R^3$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or $R^3$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or $R^3$ is —NH(CH$_2$)$_n$NH$_2$, —(CH$_2$)$_n$NH$_2$, or —O—(CH$_2$)$_n$NH$_2$, where n is 2, 3, or 4; or $R^3$ is —(CH$_2$)$_n$NH$_2$ or —O—(CH$_2$)$_n$NH$_2$, where n is 2, 3, or 4; or $R^3$ is —O—(CH$_2$)$_n$NH$_2$, where n is 2, 3, or 4.

In any of the above embodiments, $R^4$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or $R^4$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or $R^4$ is —NH(CH$_2$)$_n$NH$_2$, —(CH$_2$)$_n$NH$_2$, or —O—(CH$_2$)$_n$NH$_2$, where n is 2, 3, or 4; or $R^4$ is —(CH$_2$)$_n$NH$_2$ or —O—(CH$_2$)$_n$NH$_2$, where n is 2, 3, or 4; or $R^4$ is —O—(CH$_2$)$_n$NH$_2$, where n is 2, 3, or 4.

In any of the above embodiments, $R^5$ is —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, or —O—(CH$_2$)$_n$NC(=N)NH$_2$, where n is 2, 3, or 4; or $R^5$ is —NH(CH$_2$)$_n$NH$_2$, —(CH$_2$)$_n$NH$_2$, —(CH$_2$)$_n$NC(=N)NH$_2$, or —O—(CH$_2$)$_n$NH$_2$, where n is 2, 3, or 4; or $R^5$ is —NH(CH$_2$)$_n$NH$_2$, —(CH$_2$)$_n$NH$_2$, or —O—(CH$_2$)$_n$NH$_2$, where n is 2, 3, or 4; or $R^5$ is —(CH$_2$)$_n$NH$_2$ or —O—(CH$_2$)$_n$NH$_2$, where n is 2, 3, or 4; or $R^5$ is —O—(CH$_2$)$_n$NH$_2$, where n is 2, 3, or 4.

In any of the above embodiments, $R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or $R^6$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or $R^6$ is H, —NH(CH$_2$)$_n$NH$_2$, —(CH$_2$)$_n$NH$_2$, or —O—(CH$_2$)$_n$NH$_2$, where n is 2, 3, or 4; or $R^6$ is H or —(CH$_2$)$_n$NH$_2$, where n is 2, 3, or 4; or $R^6$ is H or —O—(CH$_2$)$_n$NH$_2$, where n is 3 or 4.

In any of the above embodiments, $R^7$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or $R^7$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or $R^7$ is H, —NH(CH$_2$)$_n$NH$_2$, —(CH$_2$)$_n$NH$_2$, or —O—(CH$_2$)$_n$NH$_2$, where n is 2, 3, or 4; or $R^7$ is H or —$(CH_2)_nNH_2$, where n is 2, 3, or 4; or $R^7$ is H or —O—$(CH_2)_nNH_2$, where n is 3 or 4.

In some embodiments:
$R^1$ is —NH$(CH_2)_nNH_2$, —NH$(CH_2)_nNC(=N)NH_2$, —$(CH_2)_nNH_2$, —$(CH_2)_nNC(=N)NH_2$, —O—$(CH_2)_nNH_2$, or —O—$(CH_2)_nNC(=N)NH_2$, where n is 2, 3, or 4;
$R^2$ is —NH$(CH_2)_nNH_2$, —NH$(CH_2)_nNC(=N)NH_2$, —$(CH_2)_nNH_2$, —$(CH_2)_nNC(=N)NH_2$, —O—$(CH_2)_nNH_2$, or —O—$(CH_2)_nNC(=N)NH_2$, where n is 2, 3, or 4;
$R^3$ is —NH$(CH_2)_nNH_2$, —NH$(CH_2)_nNC(=N)NH_2$, —$(CH_2)_nNH_2$, —$(CH_2)_nNC(=N)NH_2$, —O—$(CH_2)_nNH_2$, or —O—$(CH_2)_nNC(=N)NH_2$, where n is 2, 3, or 4;
$R^4$ is —NH$(CH_2)_nNH_2$, —NH$(CH_2)_nNC(=N)NH_2$, —$(CH_2)_nNH_2$, —$(CH_2)_nNC(=N)NH_2$, —O—$(CH_2)_nNH_2$, or —O—$(CH_2)_nNC(=N)NH_2$, where n is 2, 3, or 4;
$R^5$ is —NH$(CH_2)_nNH_2$, —NH$(CH_2)_nNC(=N)NH_2$, —$(CH_2)_nNH_2$, —$(CH_2)_nNC(=N)NH_2$, —O—$(CH_2)_nNH_2$, or —O—$(CH_2)_nNC(=N)NH_2$, where n is 2, 3, or 4;
$R^6$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4; and
$R^7$ is H, —NH$(CH_2)_nNH_2$, —NH$(CH_2)_nNC(=N)NH_2$, —$(CH_2)_nNH_2$, —O—$(CH_2)_nNH_2$, —$(CH_2)_nNC(=N)NH_2$, or —O—$(CH_2)_nNC(=N)NH_2$, where n is 2, 3, or 4.

In some embodiments:
$R^1$ is —NH$(CH_2)_nNH_2$, —$(CH_2)_nNH_2$, —$(CH_2)_nNC(=N)NH_2$, or —O—$(CH_2)_nNH_2$, where n is 2, 3, or 4;
$R^2$ is —NH$(CH_2)_nNH_2$, —$(CH_2)_nNH_2$, —$(CH_2)_nNC(=N)NH_2$, or —O—$(CH_2)_nNH_2$, where n is 2, 3, or 4;
$R^3$ is —NH$(CH_2)_nNH_2$, —$(CH_2)_nNH_2$, —$(CH_2)_nNC(=N)NH_2$, or —O—$(CH_2)_nNH_2$, where n is 2, 3, or 4;
$R^4$ is —NH$(CH_2)_nNH_2$, —$(CH_2)_nNH_2$, —$(CH_2)_nNC(=N)NH_2$, or —O—$(CH_2)_nNH_2$, where n is 2, 3, or 4;
$R^5$ is —NH$(CH_2)_nNH_2$, —$(CH_2)_nNH_2$, —$(CH_2)_nNC(=N)NH_2$, or —O—$(CH_2)_nNH_2$, where n is 2, 3, or 4;
$R^6$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4; and
$R^7$ is H, —NH$(CH_2)_nNH_2$, —$(CH_2)_nNH_2$, —O—$(CH_2)_nNH_2$, or —$(CH_2)_nNC(=N)NH_2$, where n is 2, 3, or 4.

In some embodiments:
$R^1$ is —NH$(CH_2)_nNH_2$, —$(CH_2)_nNH_2$, or —O—$(CH_2)_nNH_2$, where n is 2, 3, or 4;
$R^2$ is —NH$(CH_2)_nNH_2$, —$(CH_2)_nNH_2$, or —O—$(CH_2)_nNH_2$, where n is 2, 3, or 4;
$R^3$ is —NH$(CH_2)_nNH_2$, —$(CH_2)_nNH_2$, or —O—$(CH_2)_nNH_2$, where n is 2, 3, or 4;
$R^4$ is —NH$(CH_2)_nNH_2$, —$(CH_2)_nNH_2$, or —O—$(CH_2)_nNH_2$, where n is 2, 3, or 4;
$R^5$ is —NH$(CH_2)_nNH_2$, —$(CH_2)_nNH_2$, or —O—$(CH_2)_nNH_2$, where n is 2, 3, or 4;
$R^6$ is H, —NH$(CH_2)_nNH_2$, —$(CH_2)_nNH_2$, or —O—$(CH_2)_n NH_2$, where n is 2, 3, or 4; and
$R^7$ is H, —NH$(CH_2)_nNH_2$, —$(CH_2)_nNH_2$, or —O—$(CH_2)_n NH_2$, where n is 2, 3, or 4.

In some embodiments:
$R^1$ is —$(CH_2)_nNH_2$ or —O—$(CH_2)_nNH_2$, where n is 2, 3, or 4;
$R^2$ is —$(CH_2)_nNH_2$ or —O—$(CH_2)_nNH_2$, where n is 2, 3, or 4;
$R^3$ is —$(CH_2)_nNH_2$ or —O—$(CH_2)_nNH_2$, where n is 2, 3, or 4;
$R^4$ is —$(CH_2)_nNH_2$ or —O—$(CH_2)_nNH_2$, where n is 2, 3, or 4;
$R^5$ is —$(CH_2)_nNH_2$ or —O—$(CH_2)_nNH_2$, where n is 2, 3, or 4;
$R^6$ is H or —$(CH_2)_nNH_2$, where n is 2, 3, or 4; and
$R^7$ is H or —$(CH_2)_nNH_2$, where n is 2, 3, or 4.

In some embodiments:
$R^1$ is —O—$(CH_2)_nNH_2$, where n is 2, 3, or 4;
$R^2$ is —O—$(CH_2)_nNH_2$, where n is 2, 3, or 4;
$R^3$ is —O—$(CH_2)_nNH_2$, where n is 2, 3, or 4;
$R^4$ is —O—$(CH_2)_nNH_2$, where n is 2, 3, or 4;
$R^5$ is —O—$(CH_2)_nNH_2$, where n is 2, 3, or 4;
$R^6$ is H or —O—$(CH_2)_nNH_2$, where n is 3 or 4; and
$R^7$ is H or —O—$(CH_2)_nNH_2$, where n is 3 or 4.

In some embodiments, the compound is

Compound 137

[Chemical structure]

The present disclosure also provides compounds of Formula VI:

(VI)

[Chemical structure]

wherein:

$R^1$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^2$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^3$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4; and $R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

or a pharmaceutically acceptable salt thereof.

In some embodiments, $R^2$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or $R^2$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or $R^2$ is H, —(CH$_2$)$_n$NH$_2$, or —O—(CH$_2$)$_n$NH$_2$, where n is 2, 3, or 4; or $R^2$ is H or —(CH$_2$)$_n$NH$_2$, where n is 2, 3, or 4; or $R^2$ is H.

In any of the above embodiments, $R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or $R^4$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or $R^4$ is H, —(CH$_2$)$_n$NH$_2$, or —O—(CH$_2$)$_n$NH$_2$, where n is 2, 3, or 4; or $R^4$ is H or —(CH$_2$)$_n$NH$_2$, where n is 2, 3, or 4; or $R^4$ is H.

In any of the above embodiments, $R^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or $R^5$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or $R^5$ is H, —(CH$_2$)$_n$NH$_2$, or —O—(CH$_2$)$_n$NH$_2$, where n is 2, 3, or 4; or $R^5$ is H or —(CH$_2$)$_n$NH$_2$, where n is 2, 3, or 4; or $R^5$ is H.

In any of the above embodiments, $R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or $R^6$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or $R^6$ is H, —(CH$_2$)$_n$NH$_2$, or —O—(CH$_2$)$_n$NH$_2$, where n is 2, 3, or 4; or $R^6$ is H or —(CH$_2$)$_n$NH$_2$, where n is 2, 3, or 4; or $R^6$ is H.

In any of the above embodiments, $R^1$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or $R^1$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or $R^1$ is —NH(CH$_2$)$_n$NH$_2$, —(CH$_2$)$_n$NH$_2$, or —O—(CH$_2$)$_n$NH$_2$, where n is 2, 3, or 4; or $R^1$ is —(CH$_2$)$_n$NH$_2$ or —O—(CH$_2$)$_n$NH$_2$, where n is 2, 3, or 4; or $R^1$ is —O—(CH$_2$)$_n$NH$_2$, where n is 2, 3, or 4.

In any of the above embodiments, $R^3$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or $R^3$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or $R^3$ is —NH(CH$_2$)$_n$NH$_2$, —(CH$_2$)$_n$NH$_2$, or —O—(CH$_2$)$_n$NH$_2$, where n is 2, 3, or 4; or $R^3$ is —(CH$_2$)$_n$NH$_2$ or —O—(CH$_2$)$_n$NH$_2$, where n is 2, 3, or 4; or $R^3$ is —O—(CH$_2$)$_n$NH$_2$, where n is 2, 3, or 4.

In some embodiments:

$R^2$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;

$R^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;

$R^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;

$R^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;

$R^1$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; and $R^3$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4.

In some embodiments:

$R^2$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4;

$R^4$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4;

$R^5$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4;

$R^6$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4;

$R^1$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; and $R^3$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4;

In some embodiments:
R² is H, —(CH₂)ₙNH₂, or —O—(CH₂)ₙNH₂, where n is 2, 3, or 4;
R⁴ is H, —(CH₂)ₙNH₂, or —O—(CH₂)ₙNH₂, where n is 2, 3, or 4;
R⁵ is H, —(CH₂)ₙNH₂, or —O—(CH₂)ₙNH₂, where n is 2, 3, or 4;
R⁶ is H, —(CH₂)ₙNH₂, or —O—(CH₂)ₙNH₂, where n is 2, 3, or 4;
R¹ is —NH(CH₂)ₙNH₂, —(CH₂)ₙNH₂, or —O—(CH₂)ₙNH₂, where n is 2, 3, or 4; and
R³ is —NH(CH₂)ₙNH₂, —(CH₂)ₙNH₂, or —O—(CH₂)ₙNH₂, where n is 2, 3, or 4.

In some embodiments:
R² is H or —(CH₂)ₙNH₂, where n is 2, 3, or 4;
R⁴ is H or —(CH₂)ₙNH₂, where n is 2, 3, or 4;
R⁵ is H or —(CH₂)ₙNH₂, where n is 2, 3, or 4;
R⁶ is H or —(CH₂)ₙNH₂, where n is 2, 3, or 4;
R¹ is —(CH₂)ₙNH₂ or —O—(CH₂)ₙNH₂, where n is 2, 3, or 4; and
R³ is —(CH₂)ₙNH₂ or —O—(CH₂)ₙNH₂, where n is 2, 3, or 4.

In some embodiments:
R², R⁴, R⁵, and R⁶ are H;
R¹ is —O—(CH₂)ₙNH₂, where n is 2, 3, or 4; and
R³ is —O—(CH₂)ₙNH₂, where n is 2, 3, or 4.
In some embodiments, the compound is Compound 138

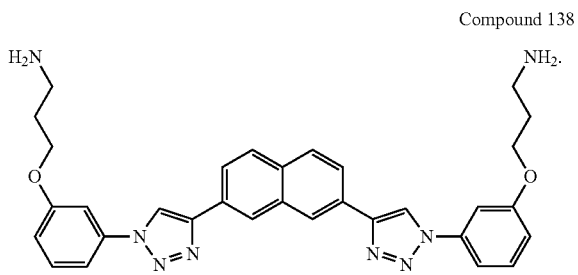 [SMILES: NCCCOc1cccc(-n2cc(-c3ccc4ccc(-c5cn(-c6cccc(OCCCN)c6)nn5)cc4c3)nn2)c1]

In some embodiments, any one or more of the above compounds may be excluded from any of the genus of compounds described above.

The present disclosure also provides compositions comprising one or more of the compounds or salts described above and a pharmaceutically acceptable carrier.

The present disclosure also provides methods of preventing or treating candidiasis (oral and/or disseminated) or an *aspergillus* infection in a mammal comprising administering to the mammal in need thereof an effective amount of a compound of Formula VI:

(VI)

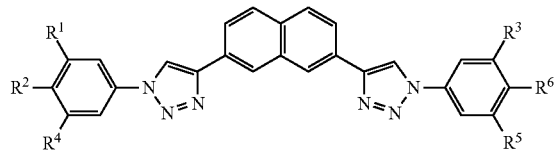

wherein:
R¹ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4;

R² is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4;

R³ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4;

R⁴ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4;

R⁵ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4; and R⁶ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, —O—(CH₂)ₙNC(=N)NH₂, —CH=CH—CH₂NH₂, —CH=CH—CH₂NC(=N)NH₂, —CH=CH—(CH₂)₂NH₂, —CH=CH—(CH₂)₂NC(=N)NH₂, —C≡C—CH₂NH₂, —C≡C—(CH₂)₂NH₂, —C≡C—CH₂NC(=N)NH₂, or —C≡C—(CH₂)₂—NC(=N)NH₂, where n is 2, 3, or 4;

or a pharmaceutically acceptable salt thereof.

In some embodiments, R² is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, or —O—(CH₂)ₙNC(=N)NH₂, where n is 2, 3, or 4; or R² is H, —NH(CH₂)ₙNH₂, —(CH₂)ₙNH₂, —O—(CH₂)ₙNH₂, or —(CH₂)ₙNC(=N)NH₂, where n is 2, 3, or 4; or R² is H, —(CH₂)ₙNH₂, or —O—(CH₂)ₙNH₂, where n is 2, 3, or 4; or R² is H or —(CH₂)ₙNH₂, where n is 2, 3, or 4; or R² is H.

In any of the above embodiments, R⁴ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, or —O—(CH₂)ₙNC(=N)NH₂, where n is 2, 3, or 4; or R⁴ is H, —NH(CH₂)ₙNH₂, —(CH₂)ₙNH₂, —O—(CH₂)ₙNH₂, or —(CH₂)ₙNC(=N)NH₂, where n is 2, 3, or 4; or R⁴ is H, —(CH₂)ₙNH₂, or —O—(CH₂)ₙNH₂, where n is 2, 3, or 4; or R⁴ is H or —(CH₂)ₙNH₂, where n is 2, 3, or 4; or R⁴ is H.

In any of the above embodiments, R⁵ is H, —NH(CH₂)ₙNH₂, —NH(CH₂)ₙNC(=N)NH₂, —(CH₂)ₙNH₂, —O—(CH₂)ₙNH₂, —(CH₂)ₙNC(=N)NH₂, or —O—(CH₂)ₙNC(=N)NH₂, where n is 2, 3, or 4; or R⁵ is H, —NH(CH₂)ₙNH₂, —(CH₂)ₙNH₂, —O—(CH₂)ₙNH₂, or —(CH₂)ₙNC(=N)NH₂, where n is 2, 3, or 4; or R⁵ is H, —(CH₂)ₙNH₂, or —O—(CH$_2$)$_n$NH$_2$, where n is 2, 3, or 4; or R$^5$ is H or —(CH$_2$)$_n$ NH$_2$, where n is 2, 3, or 4; or R$^5$ is H.

In any of the above embodiments, R$^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or R$^6$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or R$^6$ is H, —(CH$_2$)$_n$NH$_2$, or —O—(CH$_2$)$_n$NH$_2$, where n is 2, 3, or 4; or R$^6$ is H or —(CH$_2$)$_n$ NH$_2$, where n is 2, 3, or 4; or R$^6$ is H.

In any of the above embodiments, R$^1$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or R$^1$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or R$^1$ is —NH(CH$_2$)$_n$NH$_2$, —(CH$_2$)$_n$ NH$_2$, or —O—(CH$_2$)$_n$NH$_2$, where n is 2, 3, or 4; or R$^1$ is —(CH$_2$)$_n$NH$_2$ or —O—(CH$_2$)$_n$NH$_2$, where n is 2, 3, or 4; or R$^1$ is —O—(CH$_2$)$_n$NH$_2$, where n is 2, 3, or 4.

In any of the above embodiments, R$^3$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; or R$^3$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; or R$^3$ is —NH(CH$_2$)$_n$NH$_2$, —(CH$_2$)$_n$ NH$_2$, or —O—(CH$_2$)$_n$NH$_2$, where n is 2, 3, or 4; or R$^3$ is —(CH$_2$)$_n$NH$_2$ or —O—(CH$_2$)$_n$NH$_2$, where n is 2, 3, or 4; or R$^3$ is —O—(CH$_2$)$_n$NH$_2$, where n is 2, 3, or 4.

In some embodiments:
R$^2$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;
R$^4$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;
R$^5$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;
R$^6$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4;
R$^1$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4; and
R$^3$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, or —O—(CH$_2$)$_n$NC(=N)NH$_2$, where n is 2, 3, or 4.

In some embodiments:
R$^2$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4;
R$^4$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4;
R$^5$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4;
R$^6$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4;
R$^1$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4; and
R$^3$ is H, —NH(CH$_2$)$_n$NH$_2$, —(CH$_2$)$_n$NH$_2$, —O—(CH$_2$)$_n$NH$_2$, or —(CH$_2$)$_n$NC(=N)NH$_2$, where n is 2, 3, or 4.

In some embodiments:
R$^2$ is H, —(CH$_2$)$_n$NH$_2$, or —O—(CH$_2$)$_n$NH$_2$, where n is 2, 3, or 4;
R$^4$ is H, —(CH$_2$)$_n$NH$_2$, or —O—(CH$_2$)$_n$NH$_2$, where n is 2, 3, or 4;
R$^5$ is H, —(CH$_2$)$_n$NH$_2$, or —O—(CH$_2$)$_n$NH$_2$, where n is 2, 3, or 4;
R$^6$ is H, —(CH$_2$)$_n$NH$_2$, or —O—(CH$_2$)$_n$NH$_2$, where n is 2, 3, or 4;
R$^1$ is —NH(CH$_2$)$_n$NH$_2$, —(CH$_2$)$_n$NH$_2$, or —O—(CH$_2$)$_n$NH$_2$, where n is 2, 3, or 4; and
R$^3$ is —NH(CH$_2$)$_n$NH$_2$, —(CH$_2$)$_n$NH$_2$, or —O—(CH$_2$)$_n$NH$_2$, where n is 2, 3, or 4.

In some embodiments:
R$^2$ is H or —(CH$_2$)$_n$NH$_2$, where n is 2, 3, or 4;
R$^4$ is H or —(CH$_2$)$_n$NH$_2$, where n is 2, 3, or 4;
R$^5$ is H or —(CH$_2$)$_n$NH$_2$, where n is 2, 3, or 4;
R$^6$ is H or —(CH$_2$)$_n$NH$_2$, where n is 2, 3, or 4;
R$^1$ is —(CH$_2$)$_n$NH$_2$ or —O—(CH$_2$)$_n$NH$_2$, where n is 2, 3, or 4; and
R$^3$ is —(CH$_2$)$_n$NH$_2$ or —O—(CH$_2$)$_n$NH$_2$, where n is 2, 3, or 4.

In some embodiments:
R$^2$, R$^4$, R$^5$, and R$^6$ is H;
R$^1$ is —O—(CH$_2$)$_n$NH$_2$, where n is 2, 3, or 4; and
R$^3$ is —O—(CH$_2$)$_n$NH$_2$, where n is 2, 3, or 4.

In some embodiments, the compound is

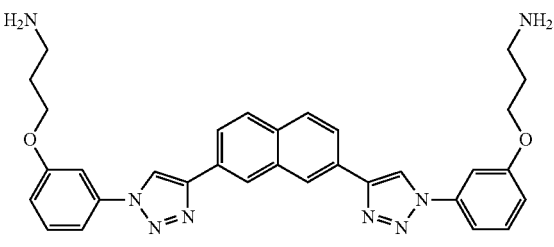

Compound 138

The present disclosure also provides methods of killing or inhibiting the growth of a *Candida* or *Aspergillus* species comprising contacting the *Candida* or *Aspergillus* species with an effective amount of a compound of Formula VI:

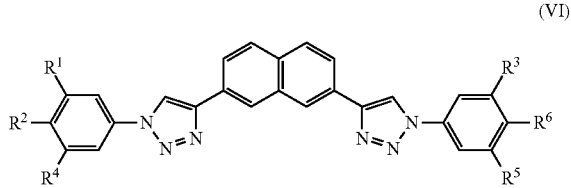

(VI)

wherein:
R$^1$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;
R$^2$ is H, —NH(CH$_2$)$_n$NH$_2$, —NH(CH$_2$)$_n$NC(=N)NH$_2$, —(CH$_2$)$_n$NH$_2$, —O—(CH$_2$)$_n$NH$_2$, —(CH$_2$)$_n$NC(=N)NH$_2$, —O—(CH$_2$)$_n$NC(=N)NH$_2$, —CH=CH—CH$_2$NH$_2$, —CH=CH—CH$_2$NC(=N)NH$_2$, —CH=CH—(CH$_2$)$_2$NH$_2$, —CH=CH—(CH$_2$)$_2$NC(=N)NH$_2$, —C≡C—CH$_2$NH$_2$, —C≡C—(CH$_2$)$_2$NH$_2$, —C≡C—CH$_2$NC(=N)NH$_2$, or —C≡C—(CH$_2$)$_2$—NC(=N)NH$_2$, where n is 2, 3, or 4;

$R^3$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, $-O-(CH_2)_nNC(=N)NH_2$, $-CH=CH-CH_2NH_2$, $-CH=CH-CH_2NC(=N)NH_2$, $-CH=CH-(CH_2)_2NH_2$, $-CH=CH-(CH_2)_2NC(=N)NH_2$, $-C\equiv C-CH_2NH_2$, $-C\equiv C-(CH_2)_2NH_2$, $-C\equiv C-CH_2NC(=N)NH_2$, or $-C\equiv C-(CH_2)_2-NC(=N)NH_2$, where n is 2, 3, or 4;

$R^4$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, $-O-(CH_2)_nNC(=N)NH_2$, $-CH=CH-CH_2NH_2$, $-CH=CH-CH_2NC(=N)NH_2$, $-CH=CH-(CH_2)_2NH_2$, $-CH=CH-(CH_2)_2NC(=N)NH_2$, $-C\equiv C-CH_2NH_2$, $-C\equiv C-(CH_2)_2NH_2$, $-C\equiv C-CH_2NC(=N)NH_2$, or $-C\equiv C-(CH_2)_2-NC(=N)NH_2$, where n is 2, 3, or 4;

$R^5$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, $-O-(CH_2)_nNC(=N)NH_2$, $-CH=CH-CH_2NH_2$, $-CH=CH-CH_2NC(=N)NH_2$, $-CH=CH-(CH_2)_2NH_2$, $-CH=CH-(CH_2)_2NC(=N)NH_2$, $-C\equiv C-CH_2NH_2$, $-C\equiv C-(CH_2)_2NH_2$, $-C\equiv C-CH_2NC(=N)NH_2$, or $-C\equiv C-(CH_2)_2-NC(=N)NH_2$, where n is 2, 3, or 4; and $R^6$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, $-O-(CH_2)_nNC(=N)NH_2$, $-CH=CH-CH_2NH_2$, $-CH=CH-CH_2NC(=N)NH_2$, $-CH=CH-(CH_2)_2NH_2$, $-CH=CH-(CH_2)_2NC(=N)NH_2$, $-C\equiv C-CH_2NH_2$, $-C\equiv C-(CH_2)_2NH_2$, $-C\equiv C-CH_2NC(=N)NH_2$, or $-C\equiv C-(CH_2)_2-NC(=N)NH_2$, where n is 2, 3, or 4;

or a pharmaceutically acceptable salt thereof.

In some embodiments, $R^2$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4; or $R^2$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4; or $R^2$ is H, $-(CH_2)_nNH_2$, or $-O-(CH_2)_nNH_2$, where n is 2, 3, or 4; or $R^2$ is H or $-(CH_2)_nNH_2$, where n is 2, 3, or 4; or $R^2$ is H.

In any of the above embodiments, $R^4$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4; or $R^4$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4; or $R^4$ is H, $-(CH_2)_nNH_2$, or $-O-(CH_2)_nNH_2$, where n is 2, 3, or 4; or $R^4$ is H or $-(CH_2)_nNH_2$, where n is 2, 3, or 4; or $R^4$ is H.

In any of the above embodiments, $R^5$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4; or $R^5$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4; or $R^5$ is H, $-(CH_2)_nNH_2$, or $-O-(CH_2)_nNH_2$, where n is 2, 3, or 4; or $R^5$ is H or $-(CH_2)_nNH_2$, where n is 2, 3, or 4; or $R^5$ is H.

In any of the above embodiments, $R^6$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4; or $R^6$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4; or $R^6$ is H, $-(CH_2)_nNH_2$, or $-O-(CH_2)_nNH_2$, where n is 2, 3, or 4; or $R^6$ is H or $-(CH_2)_nNH_2$, where n is 2, 3, or 4; or $R^6$ is H.

In any of the above embodiments, $R^1$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4; or $R^1$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4; or $R^1$ is $-NH(CH_2)_nNH_2$, $-(CH_2)_nNH_2$, or $-O-(CH_2)_nNH_2$, where n is 2, 3, or 4; or $R^1$ is $-(CH_2)_nNH_2$ or $-O-(CH_2)_nNH_2$, where n is 2, 3, or 4; or $R^1$ is $-O-(CH_2)_nNH_2$, where n is 2, 3, or 4.

In any of the above embodiments, $R^3$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4; or $R^3$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4; or $R^3$ is $-NH(CH_2)_nNH_2$, $-(CH_2)_nNH_2$, or $-O-(CH_2)_nNH_2$, where n is 2, 3, or 4; or $R^3$ is $-(CH_2)_nNH_2$ or $-O-(CH_2)_nNH_2$, where n is 2, 3, or 4; or $R^3$ is $-O-(CH_2)_nNH_2$, where n is 2, 3, or 4.

In some embodiments:

$R^2$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4;

$R^4$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4;

$R^5$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4;

$R^6$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4;

$R^1$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4; and $R^3$ is H, $-NH(CH_2)_nNH_2$, $-NH(CH_2)_nNC(=N)NH_2$, $-(CH_2)_nNH_2$, $-O-(CH_2)_nNH_2$, $-(CH_2)_nNC(=N)NH_2$, or $-O-(CH_2)_nNC(=N)NH_2$, where n is 2, 3, or 4.

In some embodiments:

$R^2$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4;

$R^4$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4;

$R^5$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4;

$R^6$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4;

$R^1$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4; and $R^3$ is H, $-NH(CH_2)_nNH_2$, $-(CH_2)_nNH_2$, $-O-(CH_2)_nNH_2$, or $-(CH_2)_nNC(=N)NH_2$, where n is 2, 3, or 4;

In some embodiments:

$R^2$ is H, $-(CH_2)_nNH_2$, or $-O-(CH_2)_nNH_2$, where n is 2, 3, or 4;

$R^4$ is H, $-(CH_2)_nNH_2$, or $-O-(CH_2)_nNH_2$, where n is 2, 3, or 4;

$R^5$ is H, $-(CH_2)_nNH_2$, or $-O-(CH_2)_nNH_2$, where n is 2, 3, or 4;

$R^6$ is H, $-(CH_2)_nNH_2$, or $-O-(CH_2)_nNH_2$, where n is 2, 3, or 4;

$R^1$ is $-NH(CH_2)_nNH_2$, $-(CH_2)_nNH_2$, or $-O-(CH_2)_nNH_2$, where n is 2, 3, or 4; and $R^3$ is $-NH(CH_2)_nNH_2$, $-(CH_2)_nNH_2$, or $-O-(CH_2)_nNH_2$, where n is 2, 3, or 4.

In some embodiments:

$R^2$ is H or $-(CH_2)_nNH_2$, where n is 2, 3, or 4;

$R^4$ is H or $-(CH_2)_nNH_2$, where n is 2, 3, or 4;

$R^5$ is H or $-(CH_2)_nNH_2$, where n is 2, 3, or 4;

$R^6$ is H or $-(CH_2)_nNH_2$, where n is 2, 3, or 4;

R¹ is —(CH₂)ₙNH₂ or —O—(CH₂)ₙNH₂, where n is 2, 3, or 4; and
R³ is —(CH₂)ₙNH₂ or —O—(CH₂)ₙNH₂, where n is 2, 3, or 4.

In some embodiments:
R², R⁴, R⁵, and R⁶ is H;
R¹ is —O—(CH₂)ₙNH₂, where n is 2, 3, or 4; and
R³ is —O—(CH₂)ₙNH₂, where n is 2, 3, or 4.

In some embodiments, the compound is

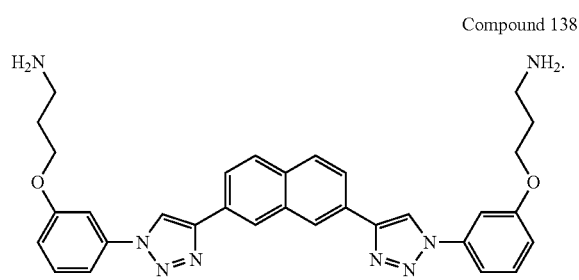 [SMILES: NCCCOc1cccc(-n2cc(-c3ccc4ccc(-c5cn(-c6cccc(OCCCN)c6)nn5)cc4c3)nn2)c1]

Compound 138

The present disclosure also provides compounds of Formula VII:

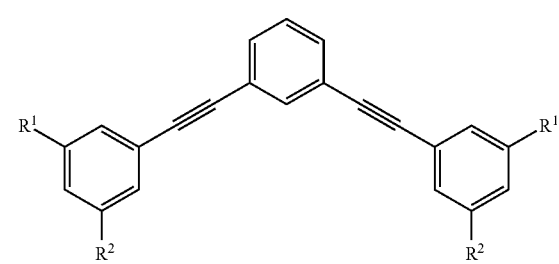

(VII)

wherein:
each R¹ is, independently, H, —C₁-C₈alkyl, —C₁-C₈alkoxy, halo, —OH, —CF₃, or —CN;
each R² is, independently, —(CH₂)ₙ—NH₂ or —(CH₂)ₙ—NH—C(=NH)NH₂, where each n is, independently, 1 to 4;
or a pharmaceutically acceptable salt thereof.

In some embodiments, each R¹ is, independently, —C₁-C₈alkyl, halo, —OH, —CF₃, or —CN. In some embodiments, each R¹ is, independently, —C₁-C₃alkyl, halo, —CF₃, or —CN. In some embodiments, each R¹ is methyl or halo. In some embodiments, each R¹ is Br, F, or Cl.

In any of the above embodiments, each R² is, independently, —(CH₂)ₙ—NH—C(=NH)NH₂, where each n is, independently, 1 to 4. In some embodiments, each R² is —(CH₂)ₙ—NH—C(=NH)NH₂, where each n is 1 to 4. In some embodiments, each R² is —(CH₂)ₙ—NH—C(=NH)NH₂, where each n is 1 or 2.

In some embodiments, each R¹ is, independently, —C₁-C₈alkyl, halo, —OH, —CF₃, or —CN; and each R² is, independently, —(CH₂)ₙ—NH—C(=NH)NH₂, where each n is, independently, 1 to 4.

In some embodiments, each R¹ is, independently, —C₁-C₃alkyl, halo, —CF₃, or —CN; and each R² is —(CH₂)ₙ—NH—C(=NH)NH₂, where each n is 1 to 4.

In some embodiments, each R¹ is methyl or halo; and each R² is —(CH₂)ₙ—NH—C(=NH)NH₂, where each n is 1 or 2.

In some embodiments, the compound is:

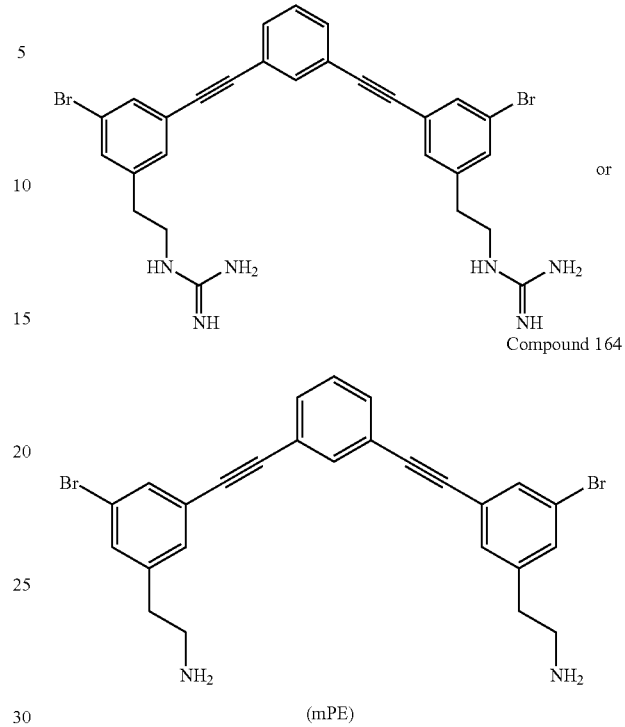

Compound 166 or

Compound 164

(mPE)

or a pharmaceutically acceptable salt thereof.

In some embodiments, any one or more of the above compounds may be excluded from any of the genus of compounds described above.

The present disclosure also provides compositions comprising one or more of the compounds or salts described above and a pharmaceutically acceptable carrier.

The present disclosure also provides methods of preventing or treating candidiasis (oral and/or disseminated) or an *aspergillus* infection in a mammal comprising administering to the mammal in need thereof an effective amount of a compound of Formula VII:

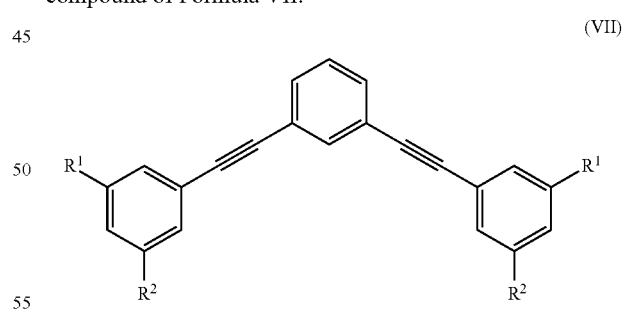

(VII)

wherein:
each R¹ is, independently, H, —C₁-C₈alkyl, —C₁-C₈alkoxy, halo, —OH, —CF₃, or —CN;
each R² is, independently, —(CH₂)ₙ—NH₂ or —(CH₂)ₙ—NH—C(=NH)NH₂, where each n is, independently, 1 to 4;
or a pharmaceutically acceptable salt thereof.

In some embodiments, each R¹ is, independently, —C₁-C₈alkyl, halo, —OH, —CF₃, or —CN. In some embodiments, each R¹ is, independently, —C₁-C₃alkyl, halo, —CF₃, or —CN. In some embodiments, each R¹ is methyl or halo. In some embodiments, each R¹ is Br, F, or Cl.

In any of the above embodiments, each $R^2$ is, independently, —$(CH_2)_n$—NH—C(=NH)$NH_2$, where each n is, independently, 1 to 4. In some embodiments, each $R^2$ is —$(CH_2)_n$—NH—C(=NH)$NH_2$, where each n is 1 to 4. In some embodiments, each $R^2$ is —$(CH_2)_n$—NH—C(=NH)$NH_2$, where each n is 1 or 2.

In some embodiments, each $R^1$ is, independently, —$C_1$-$C_8$alkyl, halo, —OH, —$CF_3$, or —CN; and each $R^2$ is, independently, —$(CH_2)_n$—NH—C(=NH)$NH_2$, where each n is, independently, 1 to 4.

In some embodiments, each $R^1$ is, independently, —$C_1$-$C_3$alkyl, halo, —$CF_3$, or —CN; and each $R^2$ is —$(CH_2)_n$—NH—C(=NH)$NH_2$, where each n is 1 to 4.

In some embodiments, each $R^1$ is methyl or halo; and each $R^2$ is —$(CH_2)_n$—NH—C(=NH)$NH_2$, where each n is 1 or 2.

In some embodiments, the compound is:

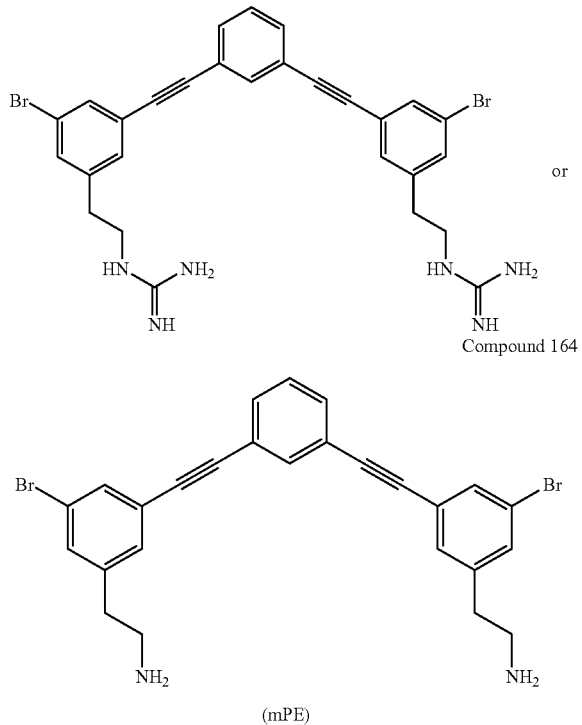

Compound 164

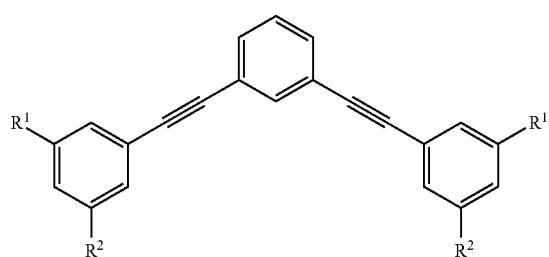

(mPE)

or a pharmaceutically acceptable salt thereof.

The present disclosure also provides methods of killing or inhibiting the growth of a *Candida* or *Aspergillus* species comprising contacting the *Candida* or *Aspergillus* species with an effective amount of a compound of Formula VII:

(VII)

wherein:
each $R^1$ is, independently, H, —$C_1$-$C_8$alkyl, —$C_1$-$C_8$alkoxy, halo, —OH, —$CF_3$, or —CN;

each $R^2$ is, independently, —$(CH_2)_n$—$NH_2$ or —$(CH_2)_n$—NH—C(=NH)$NH_2$, where each n is, independently, 1 to 4; or a pharmaceutically acceptable salt thereof.

In some embodiments, each $R^1$ is, independently, —$C_1$-$C_8$alkyl, halo, —OH, —$CF_3$, or —CN. In some embodiments, each $R^1$ is, independently, —$C_1$-$C_3$alkyl, halo, —$CF_3$, or —CN. In some embodiments, each $R^1$ is methyl or halo. In some embodiments, each $R^1$ is Br, F, or Cl.

In any of the above embodiments, each $R^2$ is, independently, —$(CH_2)_n$—NH—C(=NH)$NH_2$, where each n is, independently, 1 to 4. In some embodiments, each $R^2$ is —$(CH_2)_n$—NH—C(=NH)$NH_2$, where each n is 1 to 4. In some embodiments, each $R^2$ is —$(CH_2)_n$—NH—C(=NH)$NH_2$, where each n is 1 or 2.

In some embodiments, each $R^1$ is, independently, —$C_1$-$C_8$alkyl, halo, —OH, —$CF_3$, or —CN; and each $R^2$ is, independently, —$(CH_2)_n$—NH—C(=NH)$NH_2$, where each n is, independently, 1 to 4.

In some embodiments, each $R^1$ is, independently, —$C_1$-$C_3$alkyl, halo, —$CF_3$, or —CN; and each $R^2$ is —$(CH_2)_n$—NH—C(=NH)$NH_2$, where each n is 1 to 4.

In some embodiments, each $R^1$ is methyl or halo; and each $R^2$ is —$(CH_2)_n$—NH—C(=NH)$NH_2$, where each n is 1 or 2.

In some embodiments, the compound is:

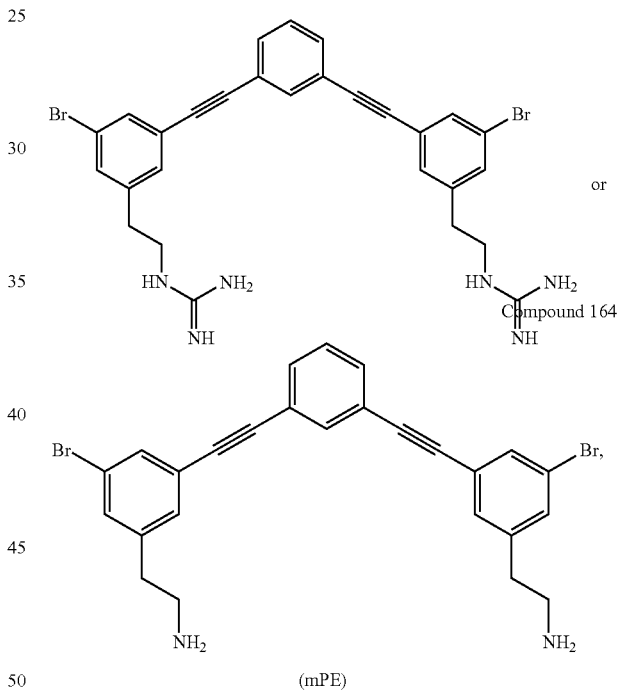

Compound 164

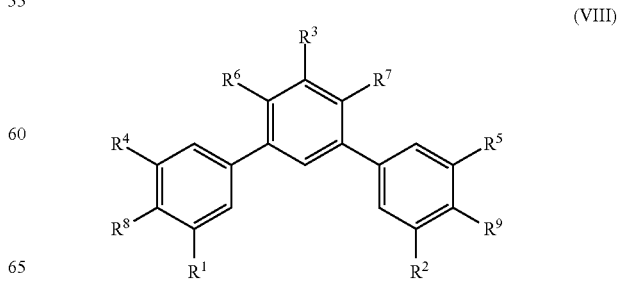

(mPE)

or a pharmaceutically acceptable salt thereof.

The present disclosure also provides compounds of Formula VIII:

(VIII)

wherein:

$R^1$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$(CH_2)_2NH_2$, —CH=CH—$CH_2NH_2$, —CH=CH—$CH_2NC(=N)NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—NC(=N)$NH_2$, where n is 2, 3, or 4;

$R^2$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—NC(=N)$NH_2$, where n is 2, 3, or 4;

$R^3$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—NC(=N)$NH_2$, where n is 2, 3, or 4;

$R^4$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—NC(=N)$NH_2$, where n is 2, 3, or 4;

$R^5$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—NC(=N)$NH_2$, where n is 2, 3, or 4;

$R^6$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—NC(=N)$NH_2$, where n is 2, 3, or 4;

$R^7$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—NC(=N)$NH_2$, where n is 2, 3, or 4;

$R^8$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—NC(=N)$NH_2$, where n is 2, 3, or 4; and $R^9$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_n$NC(=N)$NH_2$, —O—$(CH_2)_nNH_2$, —O—$(CH_2)_n$NC(=N)$NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—NC(=N)$NH_2$, where n is 2, 3, or 4; or a pharmaceutically acceptable salt thereof.

In some embodiments, $R^1$ is halo, —$CF_3$, —$(CH_2)_nNH_2$, —O—$(CH_2)_nNH_2$, —C≡C—$CH_2NH_2$, —$(CH_2)_n$NC(=N)$NH_2$, —CH=CH—$CH_2NC(=N)NH_2$, —CH=CH—$CH_2NH_2$, or —C≡C—$CH_2NC(=N)NH_2$. In some embodiments, $R^1$ is halo, —$CF_3$, —$(CH_2)_2NH_2$, —$(CH_2)_3NH_2$, —O—$(CH_2)_3NH_2$, —$(CH_2)_3$NC(=N)$NH_2$, —$(CH_2)_2$NC(=N)$NH_2$, —CH=CH—$CH_2NC(=N)NH_2$, —CH=CH—$CH_2NH_2$, —C≡C—$CH_2NH_2$, or —C≡C—$CH_2NC(=N)NH_2$.

In any of the above embodiments, $R^2$ is halo, —$CF_3$, —$(CH_2)_nNH_2$, —O—$(CH_2)_nNH_2$, —$(CH_2)_n$NC(=N)$NH_2$, —CH=CH—$CH_2NC(=N)NH_2$, —CH=CH—$CH_2NH_2$, —C≡C—$CH_2NH_2$, or —C≡C—$CH_2NC(=N)NH_2$. In some embodiments, $R^2$ is halo, —$CF_3$, —$(CH_2)_2NH_2$, —$(CH_2)_3NH_2$, —O—$(CH_2)_3NH_2$, —$(CH_2)_3$NC(=N)$NH_2$, —$(CH_2)_2$NC(=N)$NH_2$, —CH=CH—$CH_2NH_2$, —C≡C—$CH_2NH_2$, —CH=CH—$CH_2NC(=N)NH_2$, or —C≡C—$CH_2NC(=N)NH_2$.

In any of the above embodiments, $R^3$ is H, —$CF_3$, —O—$(CH_2)_nNH_2$, or —O—$(CH_2)_n$NC(=N)$NH_2$. In some embodiments, $R^3$ is H, —$CF_3$, —O—$(CH_2)_3NH_2$, or —O—$(CH_2)_3$NC(=N)$NH_2$.

In any of the above embodiments, $R^4$ is H, halo, —O—$(CH_2)_nNH_2$, —$(CH_2)_nNH_2$, —$(CH_2)_n$NC(=N)$NH_2$, —C≡C—$CH_2NH_2$, —CH=CH—$CH_2NC(=N)NH_2$, —CH=CH—$CH_2NH_2$, —C≡C—$(CH_2)_nNH_2$, or —C≡C—$(CH_2)_n$NC(=N)$NH_2$. In some embodiments, $R^4$ is H, halo, —O—$(CH_2)_3NH_2$, —$(CH_2)_2NH_2$, —$(CH_2)_2$NC(=N)$NH_2$, —C≡C—$CH_2NH_2$, —CH=CH—$CH_2NH_2$, —CH=CH—$CH_2NC(=N)NH_2$, —C≡C—$(CH_2)_2NH_2$, —C≡C—$CH_2NC(=N)NH_2$, or —C≡C—$(CH_2)_2$NC(=N)$NH_2$.

In any of the above embodiments, $R^5$ is H, halo, —O—$(CH_2)_nNH_2$, —$(CH_2)_nNH_2$, —$(CH_2)_n$NC(=N)$NH_2$, —CH=CH—$CH_2NC(=N)NH_2$, —CH=CH—$CH_2NH_2$, —C≡C—$(CH_2)_nNH_2$, or —C≡C—$(CH_2)_n$NC(=N)$NH_2$. In some embodiments, $R^5$ is H, halo, —O—$(CH_2)_3NH_2$, —$(CH_2)_2NH_2$, —$(CH_2)_2$NC(=N)$NH_2$, —C≡C—$CH_2NH_2$, —CH=CH—$CH_2NC(=N)NH_2$, —CH=CH—$CH_2NH_2$, —C≡C—$(CH_2)_2NH_2$, —C≡C—$CH_2NC(=N)NH_2$, or —C≡C—$(CH_2)_2$NC(=N)$NH_2$.

In any of the above embodiments, $R^6$ is H, —$(CH_2)_nNH_2$, or —O—$(CH_2)_n$NC(=N)$NH_2$. In some embodiments, $R^6$ is H, —$(CH_2)_3NH_2$, or —O—$(CH_2)_3$NC(=N)$NH_2$.

In any of the above embodiments, $R^7$ is H, —$(CH_2)_nNH_2$, or —O—$(CH_2)_n$NC(=N)$NH_2$. In some embodiments, $R^7$ is H, —$(CH_2)_3NH_2$, or —O—$(CH_2)_3$NC(=N)$NH_2$.

In any of the above embodiments, $R^8$ is H or halo.

In any of the above embodiments, $R^9$ is H or halo.

In some embodiments, $R^1$ is halo, —$CF_3$, —$(CH_2)_2NH_2$, —$(CH_2)_3NH_2$, —O—$(CH_2)_3NH_2$, —$(CH_2)_3$NC(=N)$NH_2$, —$(CH_2)_2$NC(=N)$NH_2$, —CH=CH—$CH_2NC(=N)NH_2$, —CH=CH—$CH_2NH_2$, —C≡C—$CH_2NH_2$, or —C≡C—$CH_2NC(=N)NH_2$; $R^2$ is halo, —$CF_3$, —$(CH_2)_2NH_2$, —$(CH_2)_3NH_2$, —O—$(CH_2)_3NH_2$, —$(CH_2)_3$NC(=N)$NH_2$, —$(CH_2)_2$NC(=N)$NH_2$, —CH=CH—$CH_2NC(=N)NH_2$, —CH=CH—$CH_2NH_2$, —C≡C—$CH_2NH_2$, or —C≡C—$CH_2NC(=N)NH_2$; $R^3$ is H, —$CF_3$, —O—$(CH_2)_3NH_2$, or —O—$(CH_2)_3$NC(=N)$NH_2$; $R^4$ is H, halo, —O—$(CH_2)_3NH_2$, —$(CH_2)_2NH_2$, —$(CH_2)_2$NC(=N)$NH_2$, —C≡C—

141

$CH_2NH_2$, $-CH=CH-CH_2NC(=N)NH_2$, $-CH=CH-CH_2NH_2$, $-C\equiv C-(CH_2)_2NH_2$, $-C\equiv C-CH_2NC(=N)NH_2$, or $-C\equiv C-(CH_2)_2NC(=N)NH_2$; $R^5$ is H, halo, $-O-(CH_2)_3NH_2$, $-(CH_2)_2NH_2$, $-(CH_2)_2NC(=N)NH_2$, $-C\equiv C-CH_2NH_2$, $-CH=CH-CH_2NH_2$, $-CH=CH-CH_2NC(=N)NH_2$, $-C\equiv C-(CH_2)_2NH_2$, $-C\equiv C-$

142

$CH_2NC(=N)NH_2$, or $-C\equiv C-(CH_2)_2NC(=N)NH_2$; $R^6$ is H, $-(CH_2)_3NH_2$ or $-O-(CH_2)_3NC(=N)NH_2$; $R^7$ is H, $-(CH_2)_3NH_2$ or $-O-(CH_2)_3NC(=N)NH_2$; $R^8$ is H or halo; and $R^9$ is H or halo.

In some embodiments, the compound is chosen from

Compound 167

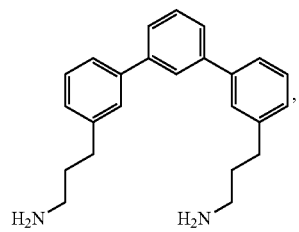

Compound 168

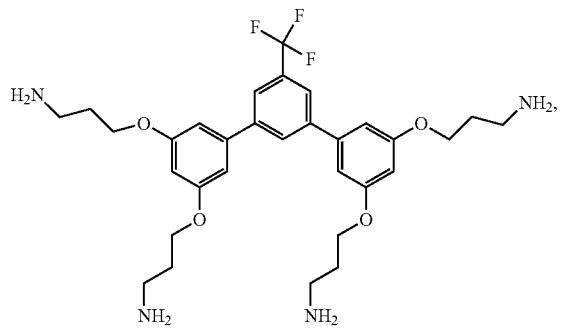

Compound 169

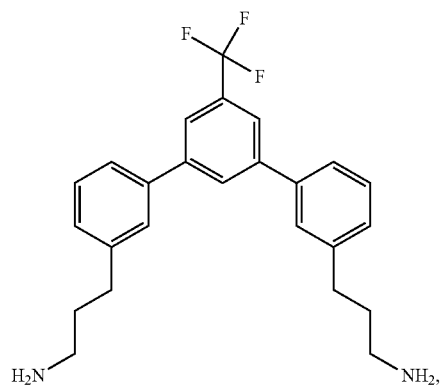

Compound 170

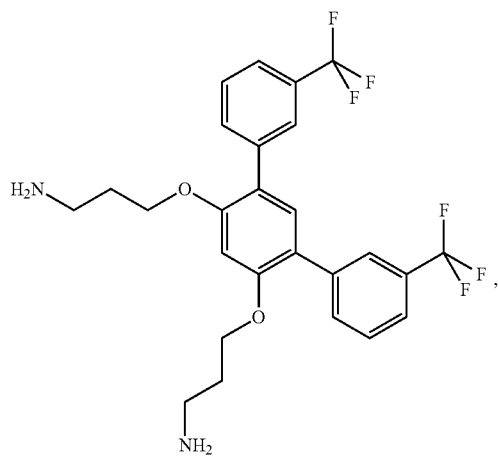

Compound 171

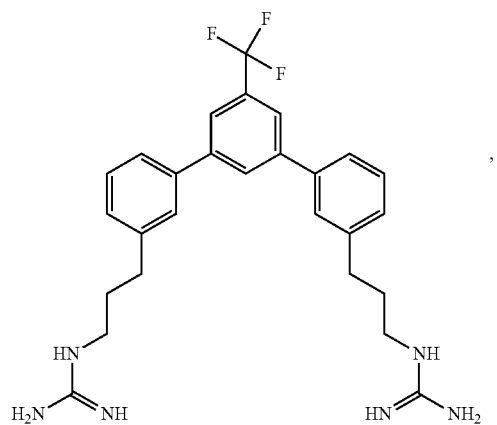

Compound 172

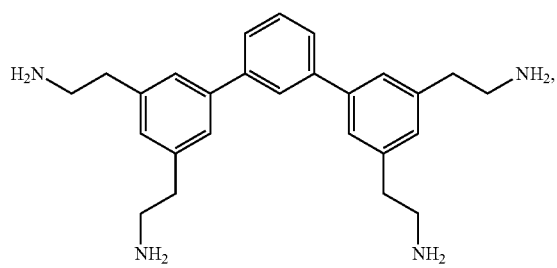

-continued
Compound 173
Compound 174
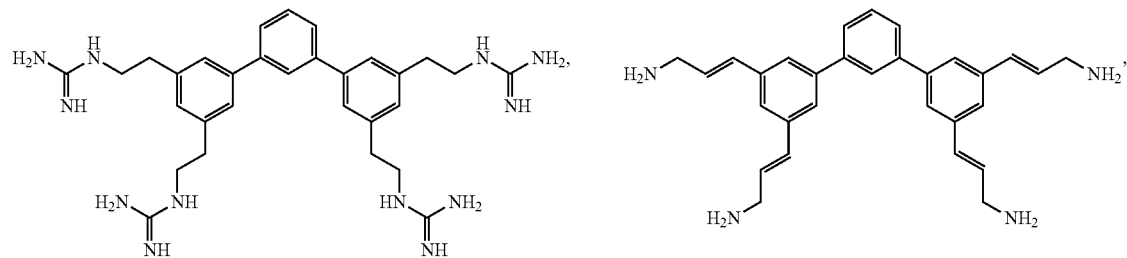
Compound 175
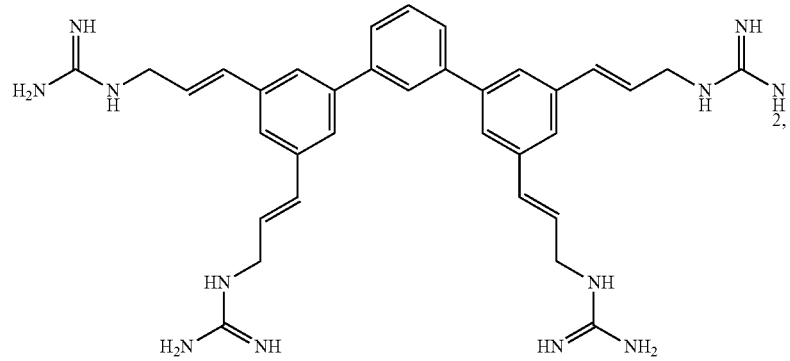
Compound 176
Compound 177
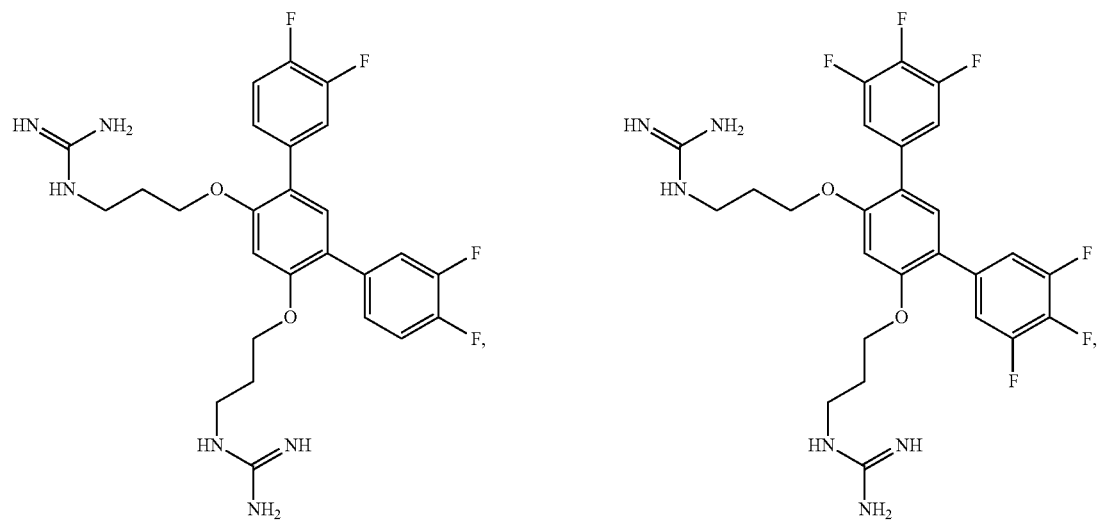

-continued
Compound 178
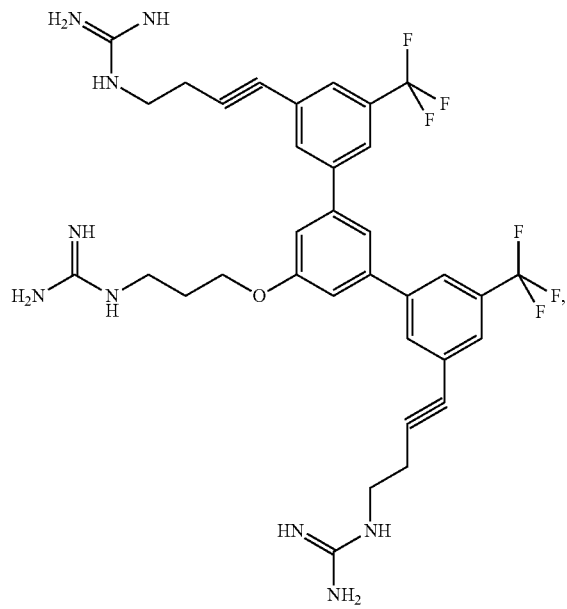
Compound 179
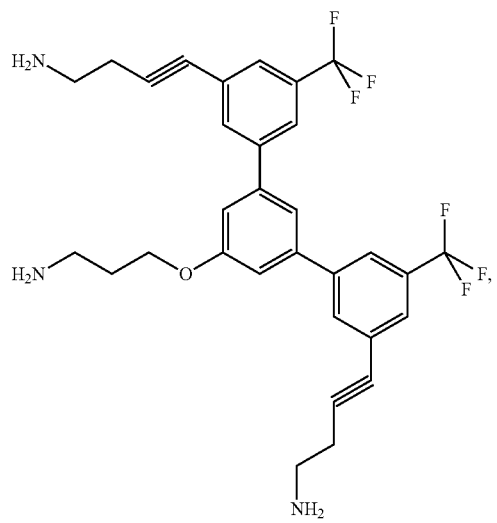
Compound 165
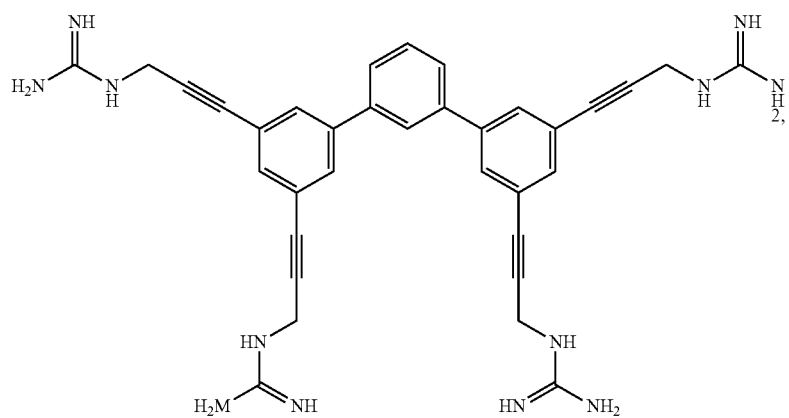
Compound 180
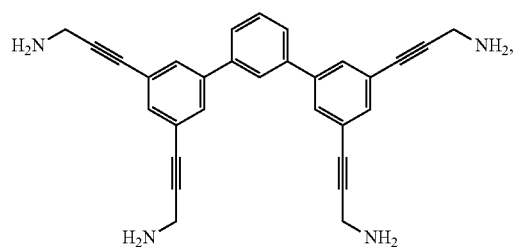
Compound 181
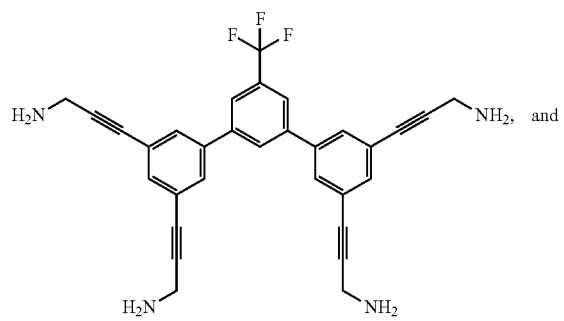
and Compound 182

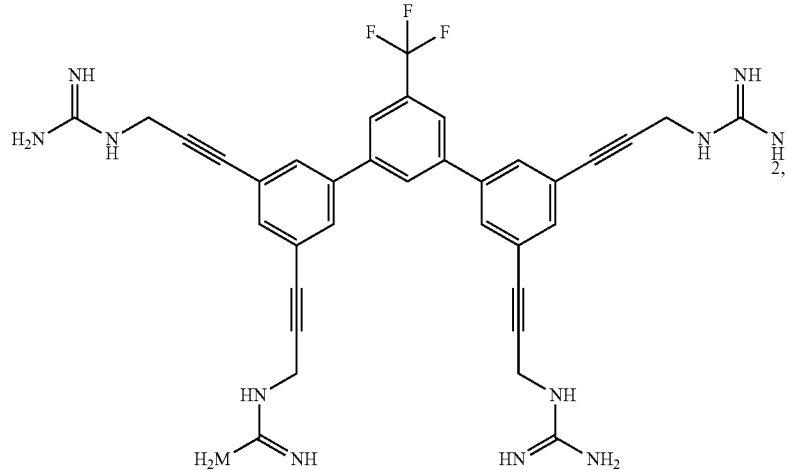

or a pharmaceutically acceptable salt thereof.

In some embodiments, any one or more of the above compounds may be excluded from any of the genus of compounds described above.

The present disclosure also provides compositions comprising one or more of the compounds or salts described above and a pharmaceutically acceptable carrier.

The present disclosure also provides methods of preventing or treating candidiasis (oral and/or disseminated) or an *aspergillus* infection in a mammal comprising administering to the mammal in need thereof an effective amount of a compound of Formula VIII:

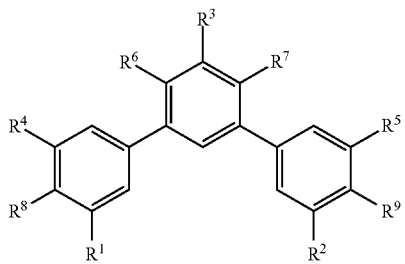

(VIII)

wherein:

$R^1$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—(CH$_2$)$_2$NH$_2$, —CH=CH—CH$_2$NH$_2$, —CH=CH—CH$_2$NC(=N)NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4;

$R^2$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4;

$R^3$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4;

$R^4$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4;

$R^5$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4;

$R^6$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4;

$R^7$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4;

$R^8$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC (=N)NH$_2$, —C≡C—CH$_2$NC(=N)NH$_2$, or —C≡C—(CH$_2$)$_2$—NC(=N)NH$_2$, where n is 2, 3, or 4; and R$^9$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4; or a pharmaceutically acceptable salt thereof.

In some embodiments, R$^1$ is halo, —CF$_3$, —(CH$_2$)$_n$NH$_2$, —O—(CH$_2$)$_n$NH$_2$, —C≡C—CH$_2$NH$_2$, —(CH$_2$)$_n$NC(=N)NH$_2$, —CH=CH—CH$_2$NC(=N)NH$_2$, —CH=CH—CH$_2$NH$_2$, or —C≡C—CH$_2$NC(=N)NH$_2$. In some embodiments, R$^1$ is halo, —CF$_3$, —(CH$_2$)$_2$NH$_2$, —(CH$_2$)$_3$NH$_2$, —O—(CH$_2$)$_3$NH$_2$, —(CH$_2$)$_3$NC(=N)NH$_2$, —(CH$_2$)$_2$NC(=N)NH$_2$, —CH=CH—CH$_2$NC(=N)NH$_2$, —CH=CH—CH$_2$NH$_2$, —C≡C—CH$_2$NH$_2$, or —C≡C—CH$_2$NC(=N)NH$_2$.

In any of the above embodiments, R$^2$ is halo, —CF$_3$, —(CH$_2$)$_n$NH$_2$, —O—(CH$_2$)$_n$NH$_2$, —(CH$_2$)$_n$NC(=N)NH$_2$, —CH=CH—CH$_2$NC(=N)NH$_2$, —CH=CH—CH$_2$NH$_2$, —C≡C—CH$_2$NH$_2$, or —C≡C—CH$_2$NC(=N)NH$_2$. In some embodiments, R$^2$ is halo, —CF$_3$, —(CH$_2$)$_2$NH$_2$, —(CH$_2$)$_3$NH$_2$, —O—(CH$_2$)$_3$NH$_2$, —(CH$_2$)$_3$NC(=N)NH$_2$, —(CH$_2$)$_2$NC(=N)NH$_2$, —CH=CH—CH$_2$NH$_2$, —C≡C—CH$_2$NH$_2$, —CH=CH—CH$_2$NC(=N)NH$_2$, or —C≡C—CH$_2$NC(=N)NH$_2$.

In any of the above embodiments, R$^3$ is H, —CF$_3$, —O—(CH$_2$)$_n$NH$_2$, or —O—(CH$_2$)$_n$NC(=N)NH$_2$. In some embodiments, R$^3$ is H, —CF$_3$, —O—(CH$_2$)$_3$NH$_2$, or —O—(CH$_2$)$_3$NC(=N)NH$_2$.

In any of the above embodiments, R$^4$ is H, halo, —O—(CH$_2$)$_n$NH$_2$, —(CH$_2$)$_n$NH$_2$, —(CH$_2$)$_n$NC(=N)NH$_2$, —C≡C—CH$_2$NH$_2$, —CH=CH—CH$_2$NC(=N)NH$_2$, —CH=CH—CH$_2$NH$_2$, —C≡C—(CH$_2$)$_n$NH$_2$, or —C≡C—(CH$_2$)$_n$NC(=N)NH$_2$. In some embodiments, R$^4$ is H, halo, —O—(CH$_2$)$_3$NH$_2$, —(CH$_2$)$_2$NH$_2$, —(CH$_2$)$_2$NC(=N)NH$_2$, —C≡C—CH$_2$NH$_2$, —CH=CH—CH$_2$NH$_2$, —CH=CH—CH$_2$NC(=N)NH$_2$, —C≡C—(CH$_2$)$_2$NH$_2$, —C≡C—CH$_2$NC(=N)NH$_2$, or —C≡C—(CH$_2$)$_2$NC(=N)NH$_2$.

In any of the above embodiments, R$^5$ is H, halo, —O—(CH$_2$)$_n$NH$_2$, —(CH$_2$)$_n$NH$_2$, —(CH$_2$)$_n$NC(=N)NH$_2$, —CH=CH—CH$_2$NC(=N)NH$_2$, —CH=CH—CH$_2$NH$_2$, —C≡C—(CH$_2$)$_n$NH$_2$, or —C≡C—(CH$_2$)$_n$NC(=N)NH$_2$. In some embodiments, R$^5$ is H, halo, —O—(CH$_2$)$_3$NH$_2$, —(CH$_2$)$_2$NH$_2$, —(CH$_2$)$_2$NC(=N)NH$_2$, —C≡C—CH$_2$NH$_2$, —CH=CH—CH$_2$NC(=N)NH$_2$, —CH=CH—CH$_2$NH$_2$, —C≡C—(CH$_2$)$_2$NH$_2$, —C≡C—CH$_2$NC(=N)NH$_2$, or —C≡C—(CH$_2$)$_2$NC(=N)NH$_2$.

In any of the above embodiments, R$^6$ is H, —(CH$_2$)$_n$NH$_2$, or —O—(CH$_2$)$_n$NC(=N)NH$_2$. In some embodiments, R$^6$ is H, —(CH$_2$)$_3$NH$_2$, or —O—(CH$_2$)$_3$NC(=N)NH$_2$.

In any of the above embodiments, R$^7$ is H, —(CH$_2$)$_n$NH$_2$, or —O—(CH$_2$)$_n$NC(=N)NH$_2$. In some embodiments, R$^7$ is H, —(CH$_2$)$_3$NH$_2$, or —O—(CH$_2$)$_3$NC(=N)NH$_2$.

In any of the above embodiments, R$^8$ is H or halo.

In any of the above embodiments, R$^9$ is H or halo.

In some embodiments, R$^1$ is halo, —CF$_3$, —(CH$_2$)$_2$NH$_2$, —(CH$_2$)$_3$NH$_2$, —O—(CH$_2$)$_3$NH$_2$, —(CH$_2$)$_3$NC(=N)NH$_2$, —(CH$_2$)$_2$NC(=N)NH$_2$, —CH=CH—CH$_2$NC(=N)NH$_2$, —CH=CH—CH$_2$NH$_2$, —C≡C—CH$_2$NH$_2$, or —C≡C—CH$_2$NC(=N)NH$_2$; R$^2$ is halo, —CF$_3$, —(CH$_2$)$_2$NH$_2$, —(CH$_2$)$_3$NH$_2$, —O—(CH$_2$)$_3$NH$_2$, —(CH$_2$)$_3$NC(=N)NH$_2$, —(CH$_2$)$_2$NC(=N)NH$_2$, —CH=CH—CH$_2$NC(=N)NH$_2$, —CH=CH—CH$_2$NH$_2$, —C≡C—CH$_2$NH$_2$, or —C≡C—CH$_2$NC(=N)NH$_2$; R$^3$ is H, —CF$_3$, —O—(CH$_2$)$_3$NH$_2$, or —O—(CH$_2$)$_3$NC(=N)NH$_2$; R$^4$ is H, halo, —O—(CH$_2$)$_3$NH$_2$, —(CH$_2$)$_2$NH$_2$, —(CH$_2$)$_2$NC(=N)NH$_2$, —C≡C—CH$_2$NH$_2$, —CH=CH—CH$_2$NC(=N)NH$_2$, —CH=CH—CH$_2$NH$_2$, —C≡C—(CH$_2$)$_2$NH$_2$, —C≡C—CH$_2$NC(=N)NH$_2$, or —C≡C—(CH$_2$)$_2$NC(=N)NH$_2$; R$^5$ is H, halo, —O—(CH$_2$)$_3$NH$_2$, —(CH$_2$)$_2$NH$_2$, —(CH$_2$)$_2$NC(=N)NH$_2$, —C≡C—CH$_2$NH$_2$, —CH=CH—CH$_2$NH$_2$, —CH=CH—CH$_2$NC(=N)NH$_2$, —C≡C—(CH$_2$)$_2$NH$_2$, —C≡C—CH$_2$NC(=N)NH$_2$, or —C≡C—(CH$_2$)$_2$NC(=N)NH$_2$; R$^6$ is H, —(CH$_2$)$_3$NH$_2$ or —O—(CH$_2$)$_3$NC(=N)NH$_2$; R$^7$ is H, —(CH$_2$)$_3$NH$_2$ or —O—(CH$_2$)$_3$NC(=N)NH$_2$; R$^8$ is H or halo; and R$^9$ is H or halo.

In some embodiments, the compound is chosen from

Compound 167

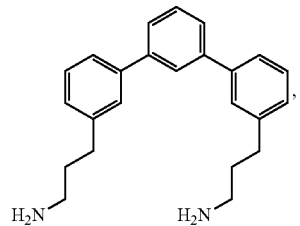

Compound 168

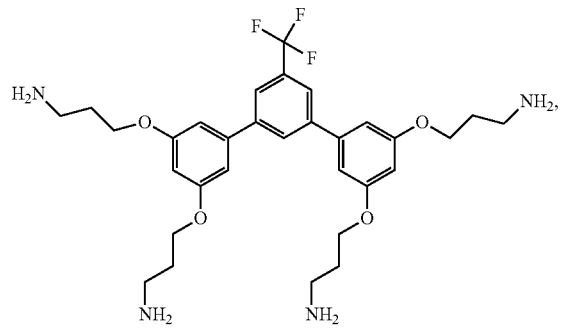

-continued
Compound 169
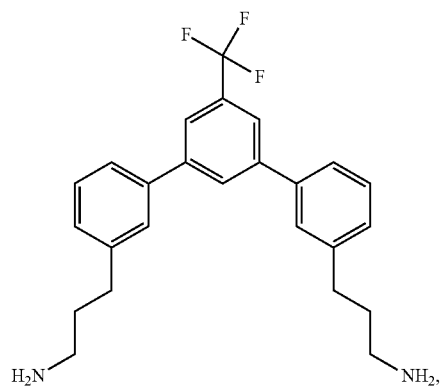
Compound 170
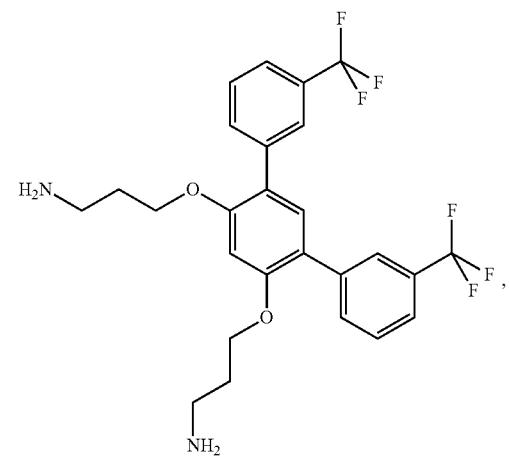
Compound 171
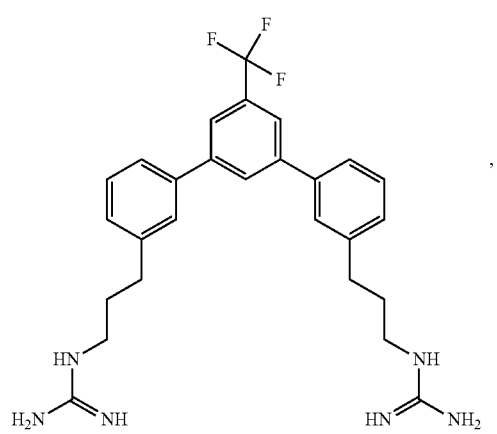
Compound 172
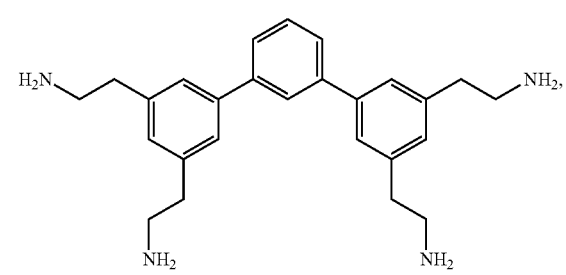
Compound 173
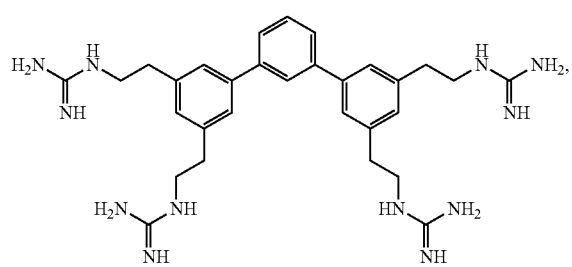
Compound 174
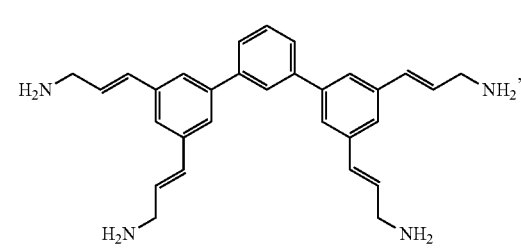
Compound 175
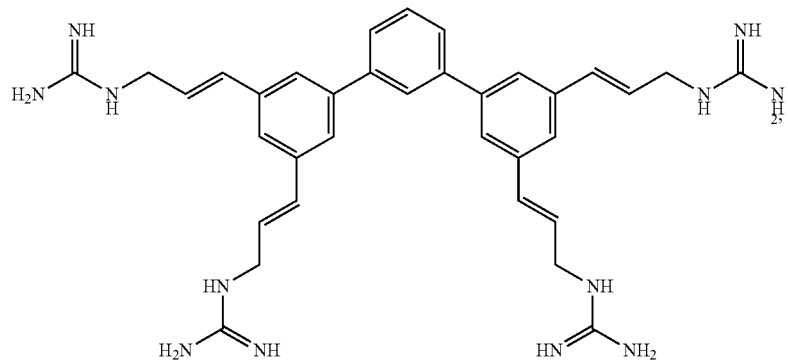

-continued
Compound 176
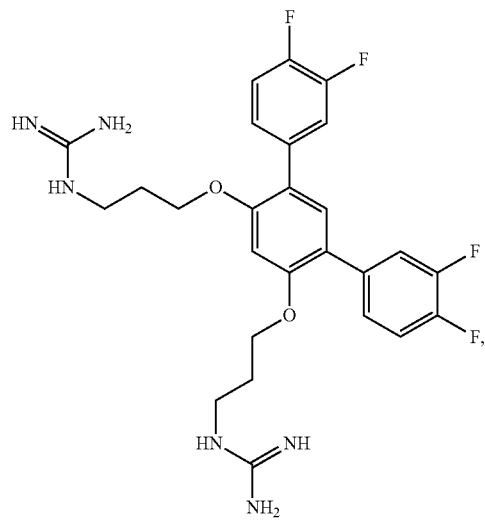
Compound 177
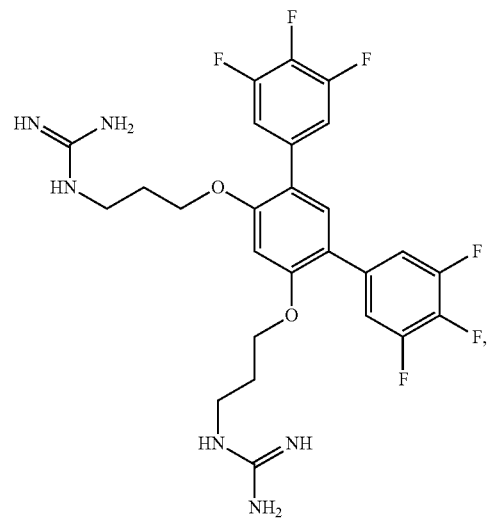
Compound 178
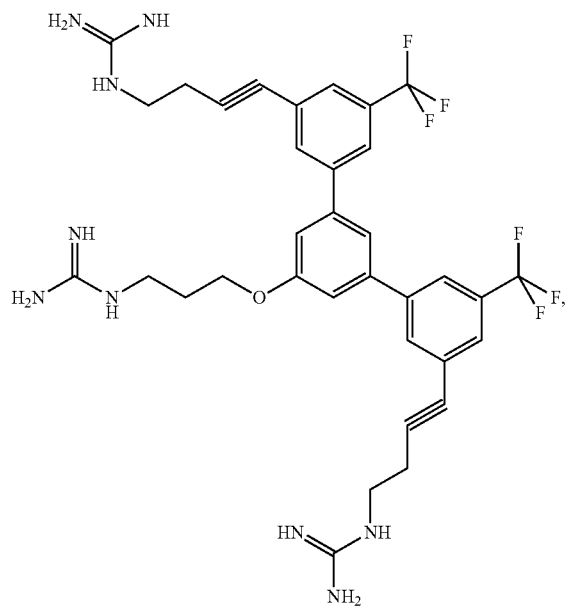
Compound 179
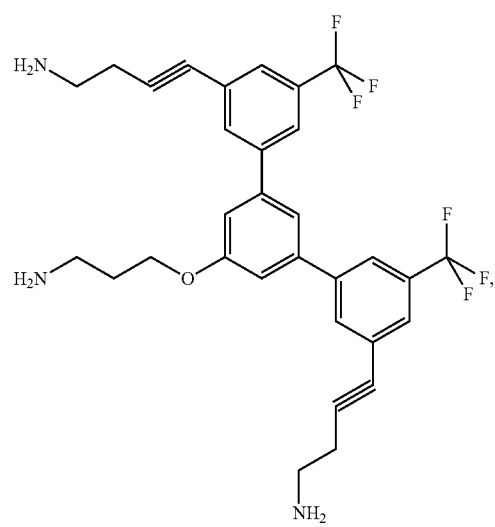
Compound 165
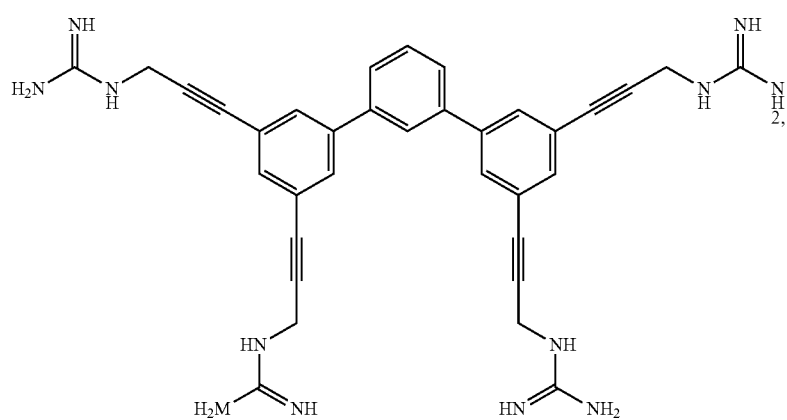

-continued

Compound 180

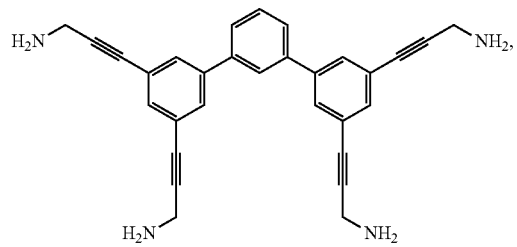

Compound 181

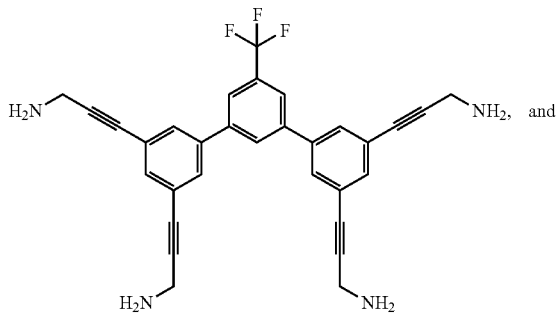

Compound 182

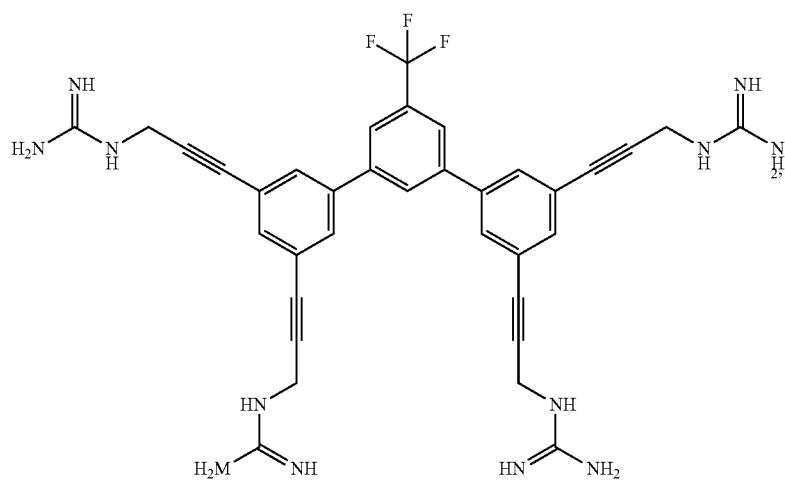

or a pharmaceutically acceptable salt thereof.

The present disclosure also provides methods of killing or inhibiting the growth of a *Candida* or *Aspergillus* species comprising contacting the *Candida* or *Aspergillus* species with an effective amount of a compound of Formula VIII:

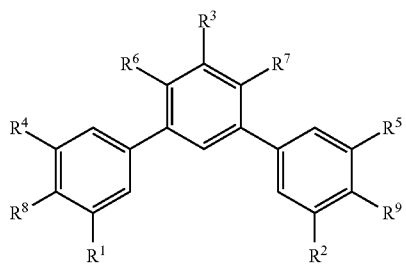

(VIII)

wherein:

$R^1$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$(CH_2)_2NH_2$, —CH=CH—$CH_2NH_2$, —CH=CH—$CH_2NC(=N)NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—$NC(=N)NH_2$, where n is 2, 3, or 4;

$R^2$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—$NC(=N)NH_2$, where n is 2, 3, or 4;

$R^3$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—$NC(=N)NH_2$, where n is 2, 3, or 4;

$R^4$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—$NC(=N)NH_2$, where n is 2, 3, or 4;

$R^5$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_nNC(=N)NH_2$, —O—$(CH_2)_nNH_2$, —O—$(CH_2)_nNC(=N)NH_2$, —C≡C—$CH_2NH_2$, —CH=CH—$CH_2NH_2$, —CH=CH—$CH_2NC(=N)NH_2$, —CH=CH—$(CH_2)_2NH_2$, —C≡C—$(CH_2)_2NH_2$, —CH=CH—$(CH_2)_2NC(=N)NH_2$, —C≡C—$CH_2NC(=N)NH_2$, or —C≡C—$(CH_2)_2$—$NC(=N)NH_2$, where n is 2, 3, or 4;

$R^6$ is H, halo, haloalkyl, —$NH_2$, —$C_{1-3}$alkyl, —$NH(CH_2)_n$$NH_2$, —$NH(CH_2)_nNC(=N)NH_2$, —$(CH_2)_nNH_2$, —$(CH_2)_n$ NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4;

R$^7$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4;

R$^8$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4; and R$^9$ is H, halo, haloalkyl, —NH$_2$, —C$_{1-3}$alkyl, —NH(CH$_2$)$_n$NH$_2$, —NH(CH$_2$)$_n$NC(=N)NH$_2$, —(CH$_2$)$_n$NH$_2$, —(CH$_2$)$_n$NC(=N)NH$_2$, —O—(CH$_2$)$_n$NH$_2$, —O—(CH$_2$)$_n$NC(=N)NH$_2$, —C≡C—CH$_2$NH$_2$, —CH=CH—CH$_2$NH$_2$, —CH=CH—CH$_2$NC(=N)NH$_2$, —CH=CH—(CH$_2$)$_2$NH$_2$, —C≡C—(CH$_2$)$_2$NH$_2$, —CH=CH—(CH$_2$)$_2$NC(=N)NH$_2$, —C≡C—CH$_2$NC(=N)NH$_2$, or —C≡C—(CH$_2$)$_2$—NC(=N)NH$_2$, where n is 2, 3, or 4; or a pharmaceutically acceptable salt thereof.

In some embodiments, R$^1$ is halo, —CF$_3$, —(CH$_2$)$_n$NH$_2$, —O—(CH$_2$)$_n$NH$_2$, —C≡C—CH$_2$NH$_2$, —(CH$_2$)$_n$NC(=N)NH$_2$, —CH=CH—CH$_2$NC(=N)NH$_2$, —CH=CH—CH$_2$NH$_2$, or —C≡C—CH$_2$NC(=N)NH$_2$. In some embodiments, R$^1$ is halo, —CF$_3$, —(CH$_2$)$_2$NH$_2$, —(CH$_2$)$_3$NH$_2$, —O—(CH$_2$)$_3$NH$_2$, —(CH$_2$)$_3$NC(=N)NH$_2$, —(CH$_2$)$_2$NC(=N)NH$_2$, —CH=CH—CH$_2$NC(=N)NH$_2$, —CH=CH—CH$_2$NH$_2$, —C≡C—CH$_2$NH$_2$, or —C≡C—CH$_2$NC(=N)NH$_2$.

In any of the above embodiments, R$^2$ is halo, —CF$_3$, —(CH$_2$)$_n$NH$_2$, —O—(CH$_2$)$_n$NH$_2$, —(CH$_2$)$_n$NC(=N)NH$_2$, —CH=CH—CH$_2$NC(=N)NH$_2$, —CH=CH—CH$_2$NH$_2$, —C≡C—CH$_2$NH$_2$, or —C≡C—CH$_2$NC(=N)NH$_2$. In some embodiments, R$^2$ is halo, —CF$_3$, —(CH$_2$)$_2$NH$_2$, —(CH$_2$)$_3$NH$_2$, —O—(CH$_2$)$_3$NH$_2$, —(CH$_2$)$_3$NC(=N)NH$_2$, —(CH$_2$)$_2$NC(=N)NH$_2$, —CH=CH—CH$_2$NH$_2$, —C≡C—CH$_2$NH$_2$, —CH=CH—CH$_2$NC(=N)NH$_2$, or —C≡C—CH$_2$NC(=N)NH$_2$.

In any of the above embodiments, R$^3$ is H, —CF$_3$, —O—(CH$_2$)$_n$NH$_2$, or —O—(CH$_2$)$_n$NC(=N)NH$_2$. In some embodiments, R$^3$ is H, —CF$_3$, —O—(CH$_2$)$_3$NH$_2$, or —O—(CH$_2$)$_3$NC(=N)NH$_2$.

In any of the above embodiments, R$^4$ is H, halo, —O—(CH$_2$)$_n$NH$_2$, —(CH$_2$)$_n$NH$_2$, —(CH$_2$)$_n$NC(=N)NH$_2$, —C≡C—CH$_2$NH$_2$, —CH=CH—CH$_2$NC(=N)NH$_2$, —CH=CH—CH$_2$NH$_2$, —C≡C—(CH$_2$)$_n$NH$_2$, or —C≡C—(CH$_2$)$_n$NC(=N)NH$_2$. In some embodiments, R$^4$ is H, halo, —O—(CH$_2$)$_3$NH$_2$, —(CH$_2$)$_2$NH$_2$, —(CH$_2$)$_2$NC(=N)NH$_2$, —C≡C—CH$_2$NH$_2$, —CH=CH—CH$_2$NH$_2$, —CH=CH—CH$_2$NC(=N)NH$_2$, —C≡C—(CH$_2$)$_2$NH$_2$, —C≡C—CH$_2$NC(=N)NH$_2$, or —C≡C—(CH$_2$)$_2$NC(=N)NH$_2$.

In any of the above embodiments, R$^5$ is H, halo, —O—(CH$_2$)$_n$NH$_2$, —(CH$_2$)$_n$NH$_2$, —(CH$_2$)$_n$NC(=N)NH$_2$, —CH=CH—CH$_2$NC(=N)NH$_2$, —CH=CH—CH$_2$NH$_2$, —C≡C—(CH$_2$)$_n$NH$_2$, or —C≡C—(CH$_2$)$_n$NC(=N)NH$_2$. In some embodiments, R$^5$ is H, halo, —O—(CH$_2$)$_3$NH$_2$, —(CH$_2$)$_2$NH$_2$, —(CH$_2$)$_2$NC(=N)NH$_2$, —C≡C—CH$_2$NH$_2$, —CH=CH—CH$_2$NC(=N)NH$_2$, —CH=CH—CH$_2$NH$_2$, —C≡C—(CH$_2$)$_2$NH$_2$, —C≡C—CH$_2$NC(=N)NH$_2$, or —C≡C—(CH$_2$)$_2$NC(=N)NH$_2$.

In any of the above embodiments, R$^6$ is H, —(CH$_2$)$_n$NH$_2$, or —O—(CH$_2$)$_n$NC(=N)NH$_2$. In some embodiments, R$^6$ is H, —(CH$_2$)$_3$NH$_2$, or —O—(CH$_2$)$_3$NC(=N)NH$_2$.

In any of the above embodiments, R$^7$ is H, —(CH$_2$)$_n$NH$_2$, or —O—(CH$_2$)$_n$NC(=N)NH$_2$. In some embodiments, R$^7$ is H, —(CH$_2$)$_3$NH$_2$, or —O—(CH$_2$)$_3$NC(=N)NH$_2$.

In any of the above embodiments, R$^8$ is H or halo.

In any of the above embodiments, R$^9$ is H or halo.

In some embodiments, R$^1$ is halo, —CF$_3$, —(CH$_2$)$_2$NH$_2$, —(CH$_2$)$_3$NH$_2$, —O—(CH$_2$)$_3$NH$_2$, —(CH$_2$)$_3$NC(=N)NH$_2$, —(CH$_2$)$_2$NC(=N)NH$_2$, —CH=CH—CH$_2$NC(=N)NH$_2$, —CH=CH—CH$_2$NH$_2$, —C≡C—CH$_2$NH$_2$, or —C≡C—CH$_2$NC(=N)NH$_2$; R$^2$ is halo, —CF$_3$, —(CH$_2$)$_2$NH$_2$, —(CH$_2$)$_3$NH$_2$, —O—(CH$_2$)$_3$NH$_2$, —(CH$_2$)$_3$NC(=N)NH$_2$, —(CH$_2$)$_2$NC(=N)NH$_2$, —CH=CH—CH$_2$NC(=N)NH$_2$, —CH=CH—CH$_2$NH$_2$, —C≡C—CH$_2$NH$_2$, or —C≡C—CH$_2$NC(=N)NH$_2$; R$^3$ is H, —CF$_3$, —O—(CH$_2$)$_3$NH$_2$, or —O—(CH$_2$)$_3$NC(=N)NH$_2$; R$^4$ is H, halo, —O—(CH$_2$)$_3$NH$_2$, —(CH$_2$)$_2$NH$_2$, —(CH$_2$)$_2$NC(=N)NH$_2$, —C≡C—CH$_2$NH$_2$, —CH=CH—CH$_2$NC(=N)NH$_2$, —CH=CH—CH$_2$NH$_2$, —C≡C—(CH$_2$)$_2$NH$_2$, —C≡C—CH$_2$NC(=N)NH$_2$, or —C≡C—(CH$_2$)$_2$NC(=N)NH$_2$; R$^5$ is H, halo, —O—(CH$_2$)$_3$NH$_2$, —(CH$_2$)$_2$NH$_2$, —(CH$_2$)$_2$NC(=N)NH$_2$, —C≡C—CH$_2$NH$_2$, —CH=CH—CH$_2$NH$_2$, —CH=CH—CH$_2$NC(=N)NH$_2$, —C≡C—(CH$_2$)$_2$NH$_2$, —C≡C—CH$_2$NC(=N)NH$_2$, or —C≡C—(CH$_2$)$_2$NC(=N)NH$_2$; R$^6$ is H, —(CH$_2$)$_3$NH$_2$ or —O—(CH$_2$)$_3$NC(=N)NH$_2$; R$^7$ is H, —(CH$_2$)$_3$NH$_2$ or —O—(CH$_2$)$_3$NC(=N)NH$_2$; R$^8$ is H or halo; and R$^9$ is H or halo.

In some embodiments, the compound is chosen from

Compound 167

Compound 168

-continued
Compound 169
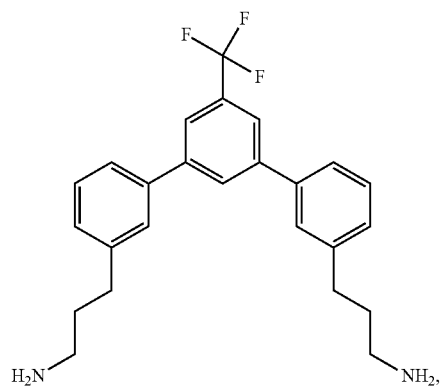
Compound 170
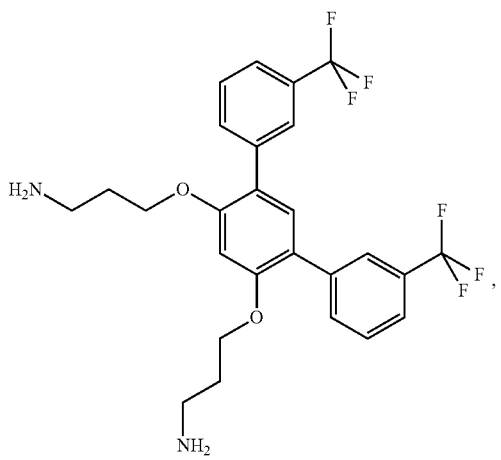
Compound 171
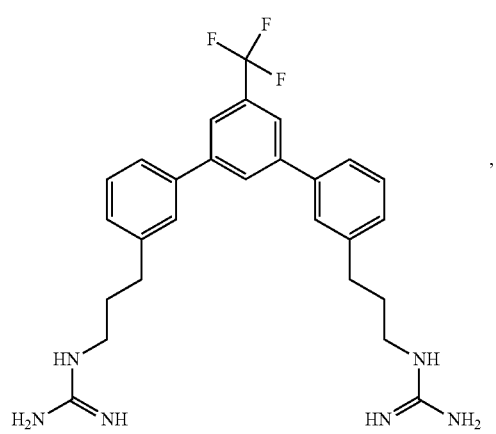
Compound 172
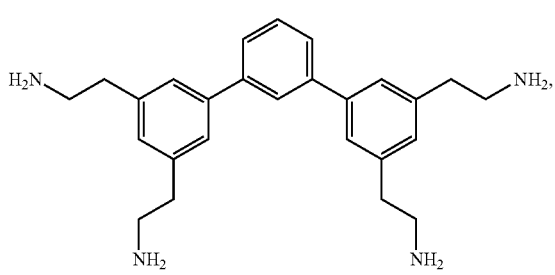
Compound 173
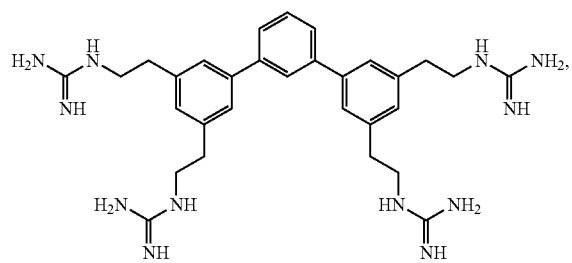
Compound 174
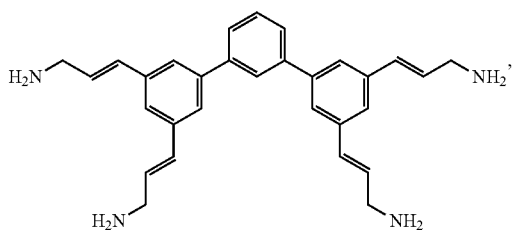
Compound 175
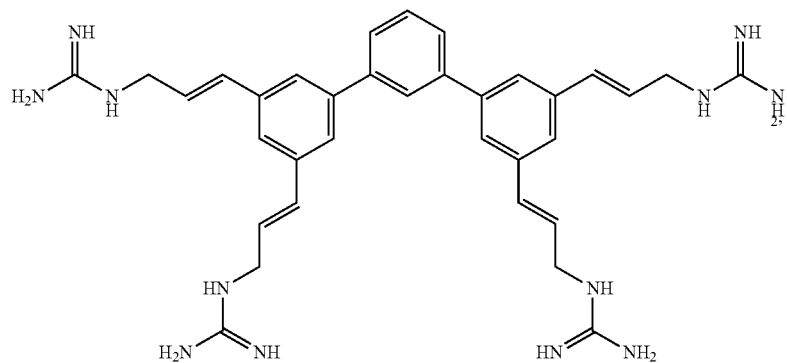

Compound 176
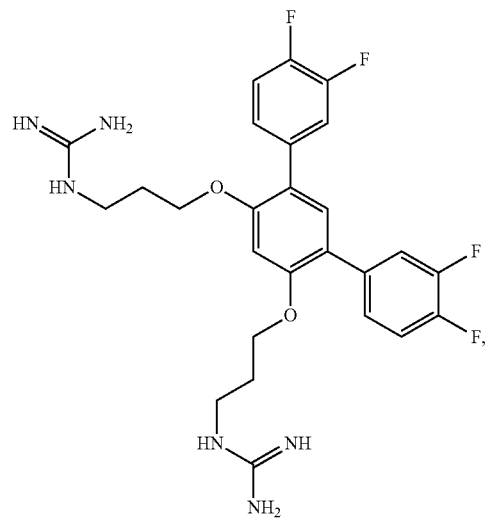
Compound 177
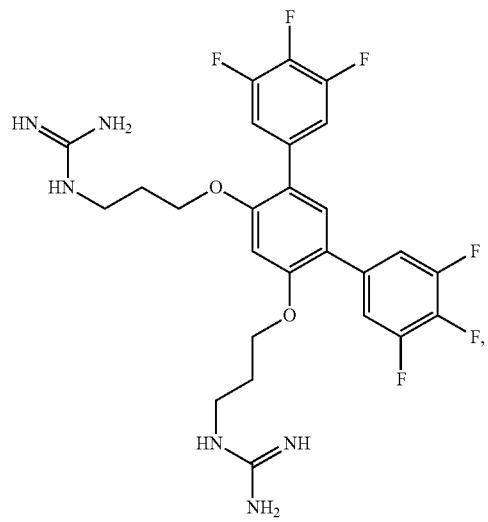
Compound 178
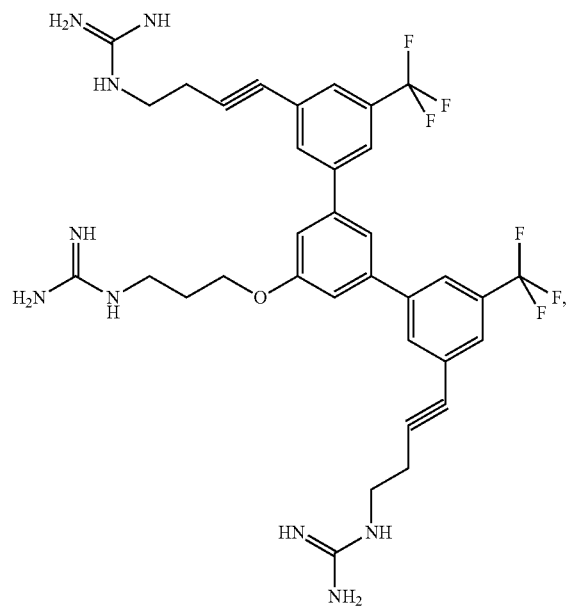
Compound 179
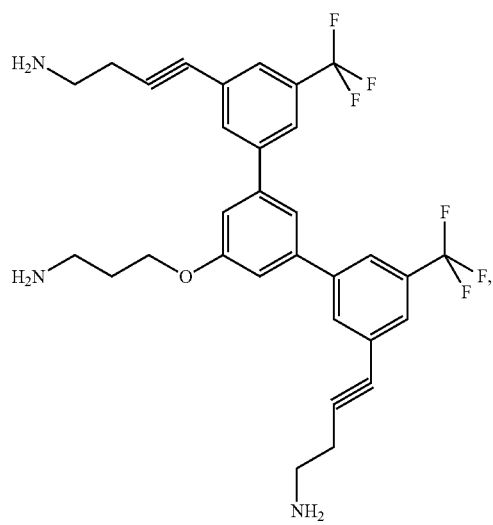
Compound 165
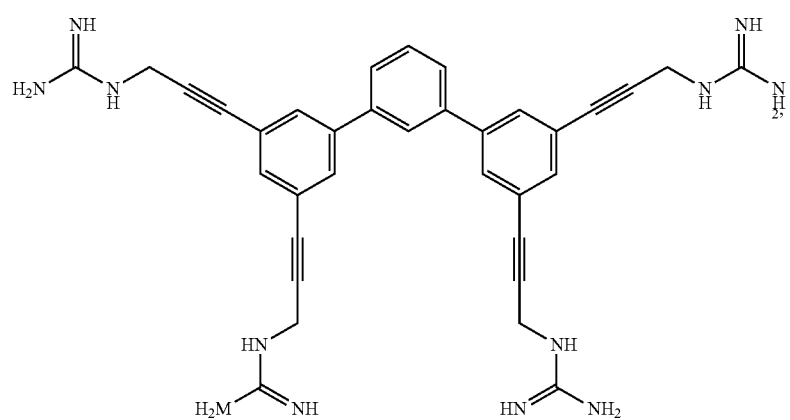

-continued

Compound 180

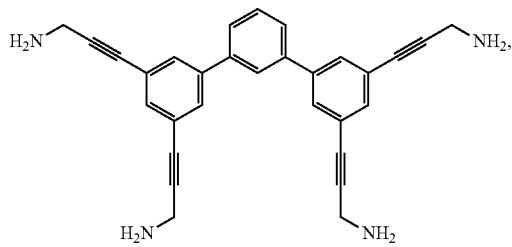

Compound 181

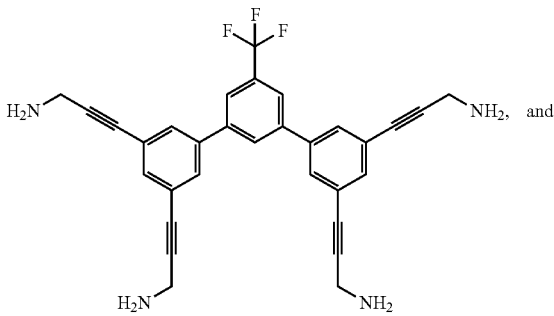, and

Compound 182

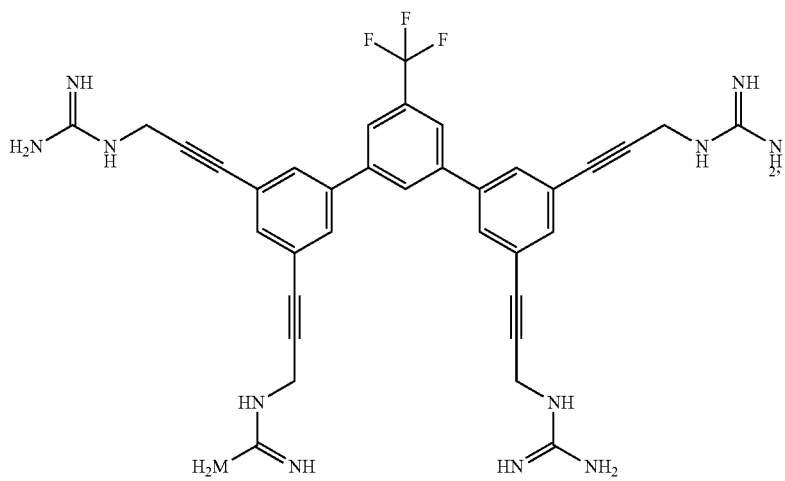

or a pharmaceutically acceptable salt thereof.

The present disclosure also provides compounds of Formula IX:

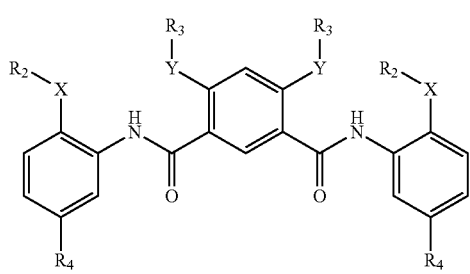

(IX)

wherein:
each X is, independently, O or S;
each Y is, independently, O or S;
each $R_2$ is, independently, —$C_1$-$C_9$ straight or branched alkyl optionally substituted with one or more —$NH_2$, —$N(CH_3)_2$ or —NH—C(=NH)$NH_2$;
each $R_3$ is, independently, —$C_1$-$C_9$ straight or branched alkyl optionally substituted with one or more —$NH_2$, —$N(CH_3)_2$ or —NH—C(=NH)$NH_2$; and
each $R_4$ is, independently, —$(CH_2)_n$—$NH_2$ or —$(CH_2)_n$—NH—C(=NH)$NH_2$, where n is an integer from 1 to 4;
or a pharmaceutically acceptable salt thereof.

In some embodiments, each X is O.
In any of the above embodiments, each Y is O.

In any of the above embodiments, each $R_2$ is, independently, —$C_1$-$C_6$ straight or branched alkyl optionally substituted with one or more —$NH_2$, —$N(CH_3)_2$ or —NH—C(=NH)$NH_2$; or each $R_2$ is, independently, —$C_1$-$C_6$ straight or branched alkyl; or each $R_2$ is, independently, —$C_1$-$C_4$ straight alkyl; or each $R_2$ is methyl.

In any of the above embodiments, each $R_3$ is, independently, —$C_1$-$C_6$ straight or branched alkyl optionally substituted with one or more —$NH_2$, —$N(CH_3)_2$ or —NH—C(=NH)$NH_2$; or each $R_3$ is, independently, —$C_1$-$C_6$ straight or branched alkyl; or each $R_3$ is, independently, —$C_3$-$C_5$ straight or branched alkyl; or each $R_3$ is —$(CH_2)_2$—CH($CH_3)_2$.

In any of the above embodiments, each $R_4$ is, independently, —$(CH_2)_n$—$NH_2$ or —$(CH_2)_n$—NH—C(=NH)$NH_2$, where n is an integer from 1 or 2; or each $R_4$ is, independently, —$(CH_2)_n$—NH—C(=NH)$NH_2$, where n is an integer from 1 or 2; or each $R_4$ is —$(CH_2)$—NH—C(=NH)$NH_2$.

In some embodiments,
each X and Y are O;
each $R_2$ is, independently, —$C_1$-$C_6$ straight or branched alkyl optionally substituted with one or more —$NH_2$, —$N(CH_3)_2$ or —NH—C(=NH)$NH_2$;
each $R_3$ is, independently, —$C_1$-$C_6$ straight or branched alkyl optionally substituted with one or more —$NH_2$, —$N(CH_3)_2$ or —NH—C(=NH)$NH_2$; and
each $R_4$ is, independently, —$(CH_2)_n$—$NH_2$ or —$(CH_2)_n$—NH—C(=NH)$NH_2$, where n is an integer from 1 or 2.

In some embodiments,
each X and Y are O;
each $R_2$ is, independently, —$C_1$-$C_6$ straight or branched alkyl;

each $R_3$ is, independently, —$C_1$-$C_6$ straight or branched alkyl; and each $R_4$ is, independently, —$(CH_2)_n$—NH—C(=NH)$NH_2$, where n is an integer from 1 or 2.

In some embodiments, each $R_2$ is, independently, —$C_1$-$C_4$ straight alkyl;

each $R_3$ is, independently, —$C_3$-$C_5$ straight or branched alkyl; and each $R_4$ is —$(CH_2)$—NH—C(=NH)$NH_2$.

In some embodiments, each X and Y are O;

each $R_2$ is methyl;

each $R_3$ is —$(CH_2)_2$—CH$(CH_3)_2$; and each $R_4$ is —$(CH_2)$—NH—C(=NH)$NH_2$.

In some embodiments, the compound is

Compound 184

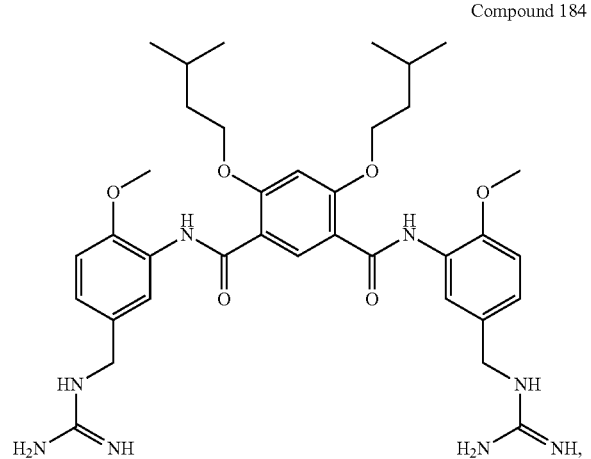 [SMILES: COc1ccc(CNC(=N)N)cc1NC(=O)c1cc(C(=O)Nc2cc(CNC(=N)N)ccc2OC)c(OCCC(C)C)cc1OCCC(C)C]

or a pharmaceutically acceptable salt thereof.

The present disclosure also provides methods of preventing or treating candidiasis (oral and/or disseminated) or an *aspergillus* infection in a mammal comprising administering to the mammal in need thereof an effective amount of a compound of Formula IX:

(IX)

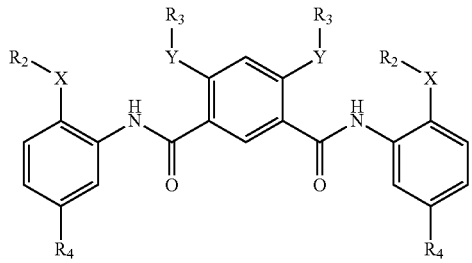

wherein:

each X is, independently, O or S;

each Y is, independently, O or S;

each $R_2$ is, independently, —$C_1$-$C_9$ straight or branched alkyl optionally substituted with one or more —$NH_2$, —$N(CH_3)_2$ or —NH—C(=NH)$NH_2$;

each $R_3$ is, independently, —$C_1$-$C_9$ straight or branched alkyl optionally substituted with one or more —$NH_2$, —$N(CH_3)_2$ or —NH—C(=NH)$NH_2$; and each $R_4$ is, independently, —$(CH_2)_n$—$NH_2$ or —$(CH_2)_n$—NH—C(=NH)$NH_2$, where n is an integer from 1 to 4;

or a pharmaceutically acceptable salt thereof.

In some embodiments, each X is O.

In any of the above embodiments, each Y is O.

In any of the above embodiments, each $R_2$ is, independently, —$C_1$-$C_6$ straight or branched alkyl optionally substituted with one or more —$NH_2$, —$N(CH_3)_2$ or —NH—C(=NH)$NH_2$; or each $R_2$ is, independently, —$C_1$-$C_6$ straight or branched alkyl; or each $R_2$ is, independently, —$C_1$-$C_4$ straight alkyl; or each $R_2$ is methyl.

In any of the above embodiments, each $R_3$ is, independently, —$C_1$-$C_6$ straight or branched alkyl optionally substituted with one or more —$NH_2$, —$N(CH_3)_2$ or —NH—C(=NH)$NH_2$; or each $R_3$ is, independently, —$C_1$-$C_6$ straight or branched alkyl; or each $R_3$ is, independently, —$C_3$-$C_5$ straight or branched alkyl; or each $R_3$ is —$(CH_2)_2$—CH$(CH_3)_2$.

In any of the above embodiments, each $R_4$ is, independently, —$(CH_2)_n$—$NH_2$ or —$(CH_2)_n$—NH—C(=NH)$NH_2$, where n is an integer from 1 or 2; or each $R_4$ is, independently, —$(CH_2)_n$—NH—C(=NH)$NH_2$, where n is an integer from 1 or 2; or each $R_4$ is —$(CH_2)$—NH—C(=NH)$NH_2$.

In some embodiments, each X and Y are O;

each $R_2$ is, independently, —$C_1$-$C_6$ straight or branched alkyl optionally substituted with one or more —$NH_2$, —$N(CH_3)_2$ or —NH—C(=NH)$NH_2$;

each $R_3$ is, independently, —$C_1$-$C_6$ straight or branched alkyl optionally substituted with one or more —$NH_2$, —$N(CH_3)_2$ or —NH—C(=NH)$NH_2$; and each $R_4$ is, independently, —$(CH_2)_n$—$NH_2$ or —$(CH_2)_n$—NH—C(=NH)$NH_2$, where n is an integer from 1 or 2.

In some embodiments, each X and Y are O;

each $R_2$ is, independently, —$C_1$-$C_6$ straight or branched alkyl;

each $R_3$ is, independently, —$C_1$-$C_6$ straight or branched alkyl; and each $R_4$ is, independently, —$(CH_2)_n$—NH—C(=NH)$NH_2$, where n is an integer from 1 or 2.

In some embodiments, each $R_2$ is, independently, —$C_1$-$C_4$ straight alkyl;

each $R_3$ is, independently, —$C_3$-$C_5$ straight or branched alkyl; and each $R_4$ is —$(CH_2)$—NH—C(=NH)$NH_2$.

In some embodiments, each X and Y are O;

each $R_2$ is methyl;

each $R_3$ is —$(CH_2)_2$—CH$(CH_3)_2$; and each $R_4$ is —$(CH_2)$—NH—C(=NH)$NH_2$.

In some embodiments, the compound is

Compound 184

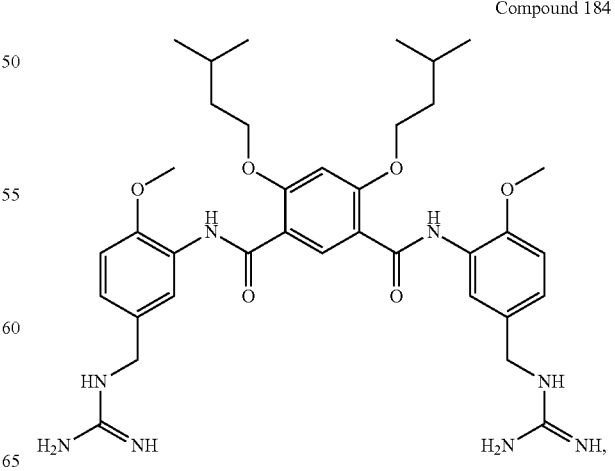

or a pharmaceutically acceptable salt thereof.

The present disclosure also provides methods of killing or inhibiting the growth of a *Candida* or *Aspergillus* species comprising contacting the *Candida* or *Aspergillus* species with an effective amount of a compound of Formula IX:

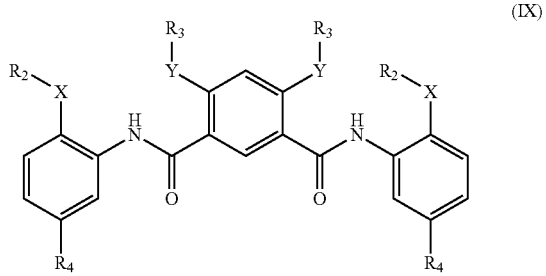

wherein:
each X is, independently, O or S;
each Y is, independently, O or S;
each $R_2$ is, independently, —$C_1$-$C_9$ straight or branched alkyl optionally substituted with one or more —$NH_2$, —$N(CH_3)_2$ or —NH—C(=NH)$NH_2$;
each $R_3$ is, independently, —$C_1$-$C_9$ straight or branched alkyl optionally substituted with one or more —$NH_2$, —$N(CH_3)_2$ or —NH—C(=NH)$NH_2$; and
each $R_4$ is, independently, —$(CH_2)_n$—$NH_2$ or —$(CH_2)_n$—NH—C(=NH)$NH_2$, where n is an integer from 1 to 4;
or a pharmaceutically acceptable salt thereof.

In some embodiments, each X is O.
In any of the above embodiments, each Y is O.
In any of the above embodiments, each $R_2$ is, independently, —$C_1$-$C_6$ straight or branched alkyl optionally substituted with one or more —$NH_2$, —$N(CH_3)_2$ or —NH—C(=NH)$NH_2$; or each $R_2$ is, independently, —$C_1$-$C_6$ straight or branched alkyl; or each $R_2$ is, independently, —$C_1$-$C_4$ straight alkyl; or each $R_2$ is methyl.

In any of the above embodiments, each $R_3$ is, independently, —$C_1$-$C_6$ straight or branched alkyl optionally substituted with one or more —$NH_2$, —$N(CH_3)_2$ or —NH—C(=NH)$NH_2$; or each $R_3$ is, independently, —$C_1$-$C_6$ straight or branched alkyl; or each $R_3$ is, independently, —$C_3$-$C_5$ straight or branched alkyl; or each $R_3$ is —$(CH_2)_2$—CH$(CH_3)_2$.

In any of the above embodiments, each $R_4$ is, independently, —$(CH_2)_n$—$NH_2$ or —$(CH_2)_n$—NH—C(=NH)$NH_2$, where n is an integer from 1 or 2; or each $R_4$ is, independently, —$(CH_2)_n$—NH—C(=NH)$NH_2$, where n is an integer from 1 or 2; or each $R_4$ is —$(CH_2)$—NH—C(=NH)$NH_2$.

In some embodiments,
each X and Y are O;
each $R_2$ is, independently, —$C_1$-$C_6$ straight or branched alkyl optionally substituted with one or more —$NH_2$, —$N(CH_3)_2$ or —NH—C(=NH)$NH_2$;
each $R_3$ is, independently, —$C_1$-$C_6$ straight or branched alkyl optionally substituted with one or more —$NH_2$, —$N(CH_3)_2$ or —NH—C(=NH)$NH_2$; and
each $R_4$ is, independently, —$(CH_2)_n$—$NH_2$ or —$(CH_2)_n$—NH—C(=NH)$NH_2$, where n is an integer from 1 or 2.

In some embodiments,
each X and Y are O;
each $R_2$ is, independently, —$C_1$-$C_6$ straight or branched alkyl;
each $R_3$ is, independently, —$C_1$-$C_6$ straight or branched alkyl; and each $R_4$ is, independently, —$(CH_2)_n$—NH—C(=NH)$NH_2$, where n is an integer from 1 or 2.

In some embodiments,
each $R_2$ is, independently, —$C_1$-$C_4$ straight alkyl;
each $R_3$ is, independently, —$C_3$-$C_5$ straight or branched alkyl; and
each $R_4$ is —$(CH_2)$—NH—C(=NH)$NH_2$.

In some embodiments,
each X and Y are O;
each $R_2$ is methyl;
each $R_3$ is —$(CH_2)_2$—CH$(CH_3)_2$; and
each $R_4$ is —$(CH_2)$—NH—C(=NH)$NH_2$.

In some embodiments, the compound is

Compound 184

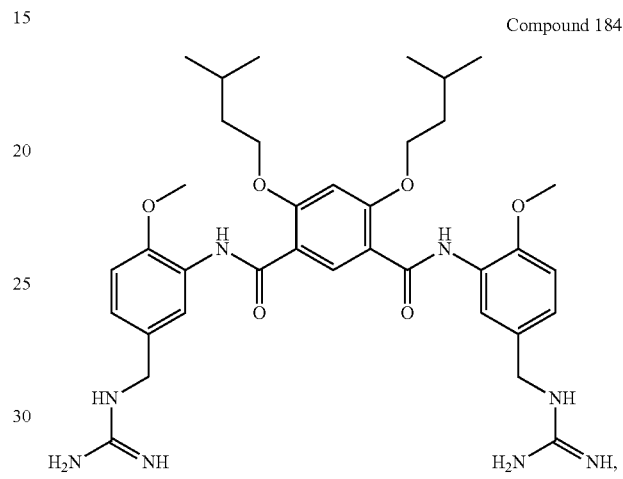

or a pharmaceutically acceptable salt thereof.

The present disclosure also provides compounds of Formula X:

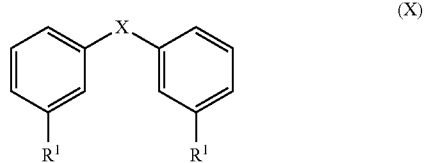

wherein:
X is

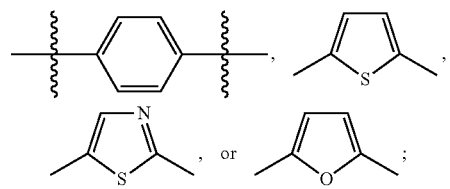

and
each $R^1$ is, independently, —$(CH_2)_n$—$NH_2$ or —$(CH_2)_n$—NH—C(=NH)$NH_2$, where n is an integer from 1 to 4;
or a pharmaceutically acceptable salt thereof.

In some embodiments, each $R^1$ is, independently, —$(CH_2)_n$—$NH_2$ or —$(CH_2)_n$—NH—C(=NH)$NH_2$, where n is 1 or 2; or each $R^1$ is, independently —$(CH_2)_n$—NH—C(=NH)$NH_2$, where n is 1 or 2; or each $R^1$ is —$(CH_2)_2$—NHC(=NH)$NH_2$.

In some embodiments, the compound is

Compound 185

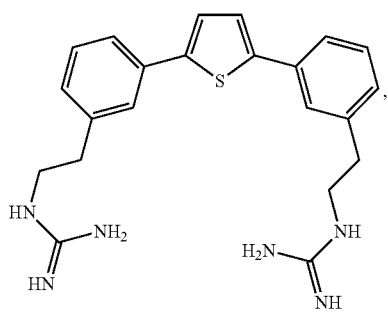

Compound 186

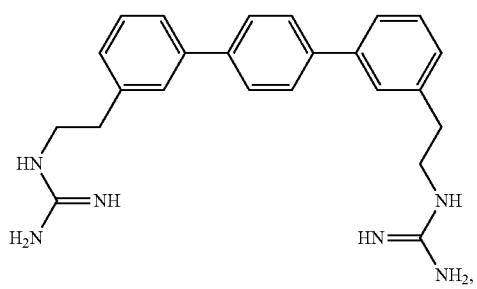

Compound 187

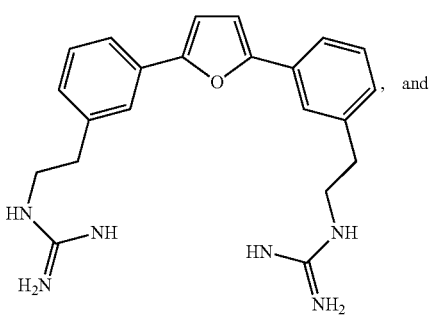

Compound 188

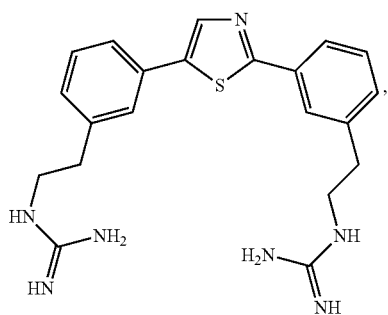

or a pharmaceutically acceptable salt thereof.

The present disclosure also provides methods of preventing or treating candidiasis (oral and/or disseminated) or an *aspergillus* infection in a mammal comprising administering to the mammal in need thereof an effective amount of a compound of Formula X:

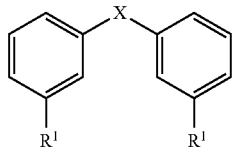

(X)

wherein:

X is

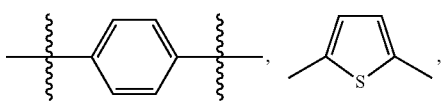

and each $R^1$ is, independently, —$(CH_2)_n$—$NH_2$ or —$(CH_2)_n$—NH—C(=NH)$NH_2$, where n is an integer from 1 to 4;

or a pharmaceutically acceptable salt thereof.

In some embodiments, each $R^1$ is, independently, —$(CH_2)_n$—$NH_2$ or —$(CH_2)_n$—NH—C(=NH)$NH_2$, where n is 1 or 2; or each $R^1$ is, independently —$(CH_2)_n$—NH—C(=NH)$NH_2$, where n is 1 or 2; or each $R^1$ is —$(CH_2)_2$—NHC(=NH)$NH_2$.

In some embodiments, the compound is

Compound 185

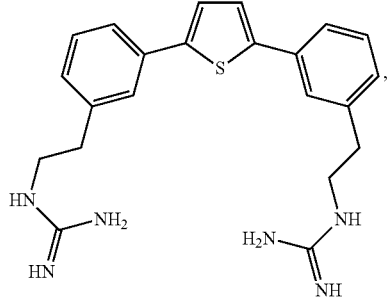

Compound 186

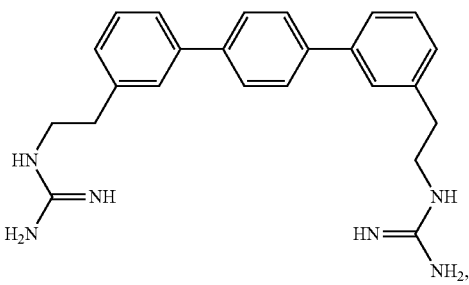

Compound 187

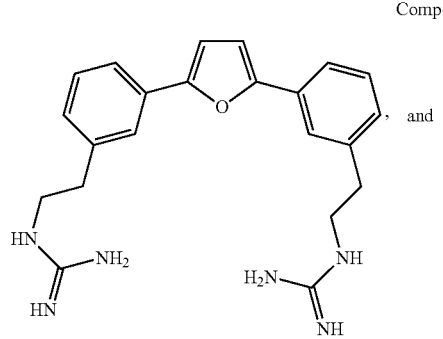, and

Compound 185

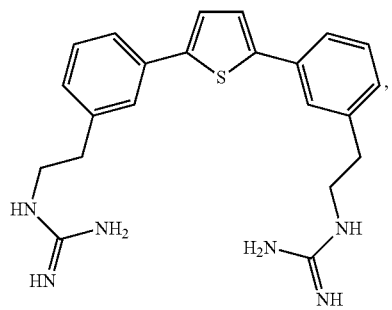,

Compound 188

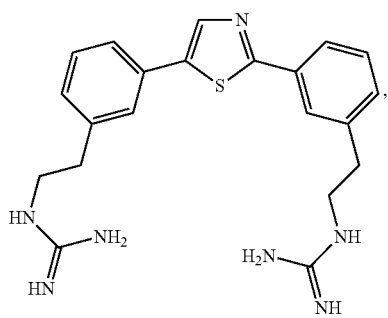,

Compound 186

, or a pharmaceutically acceptable salt thereof.

The present disclosure also provides methods of killing or inhibiting the growth of a *Candida* or *Aspergillus* species comprising contacting the *Candida* or *Aspergillus* species with an effective amount of a compound of Formula X:

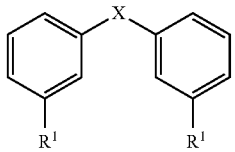 (X)

wherein:
X is

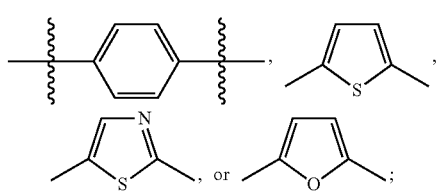

and
each $R^1$ is, independently, —$(CH_2)_n$—$NH_2$ or —$(CH_2)_n$—NH—C(=NH)$NH_2$, where n is an integer from 1 to 4;
or a pharmaceutically acceptable salt thereof.

In some embodiments, each $R^1$ is, independently, —$(CH_2)_n$—$NH_2$ or —$(CH_2)_n$—NH—C(=NH)$NH_2$, where n is 1 or 2; or each $R^1$ is, independently —$(CH_2)_n$—NH—C(=NH)$NH_2$, where n is 1 or 2; or each $R^1$ is —$(CH_2)_2$—NHC(=NH)$NH_2$.

In some embodiments, the compound is

Compound 187

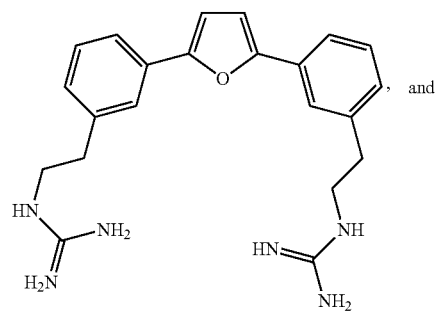, and

Compound 188

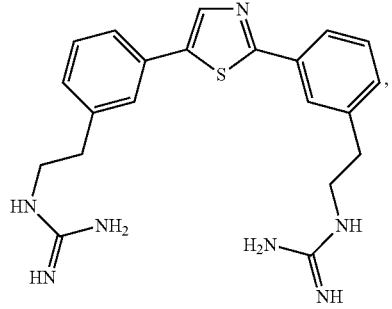, or a pharmaceutically acceptable salt thereof.

In any of the above embodiments, one or more of the compounds recited herein may be more effective (better $IC_{50}$ or $EC_{50}$ value) against a *Candida* species (such a *C. albicans*) than any one or more of *E. coli* 25922, *S. aureus* 27660, *E. faecalis* 29212, *P. aeruginosa* 10145, and *K. pneumoniae* 13883. Thus, one or more of the compounds recited herein may be more selective for a *Candida* species (such a *C. albicans*) than any one or more of *E. coli* 25922, *S. aureus* 27660, *E. faecalis* 29212, *P. aeruginosa* 10145, and *K. pneumoniae* 13883. Some of the active compounds described herein are, thus, highly selective for *C. albicans* over Gram-positive and Gram-negative bacteria. This may be advantageous in situations where one skilled in the art does not desire to disrupt normal flora within an individual. Thus, when administered to a mammal, any one or more of the compounds recited herein may kill or inhibit the growth of *Candida* (such a *C. albicans*) or *Aspergillus* species without significantly disturbing the normal flora of the individual.

Polyamides and polyesters that are useful in the present disclosure can be prepared by typical condensation polymerization and addition polymerization processes (see, for example, G. Odian, Principles of Polymerization, John Wiley & Sons, Third Edition (1991), and M. Steven, Polymer Chemistry, Oxford University Press (1999)). Most commonly, the polyamides are prepared by a) thermal dehydration of amine salts of carboxylic acids, b) reaction of acid chlorides with amines, and c) aminolysis of esters. Methods a) and c) are of limited use in polymerizations of aniline derivatives which are generally prepared utilizing acid chlorides. The skilled chemist, however, will recognize that there are many alternative active acylating agents, for example phosphoryl anhydrides, active esters or azides, which may replace an acid chloride and which, depending of the particular polymer being prepared, may be superior to an acid chloride. The acid chloride route is probably the most versatile and has been used extensively for the synthesis of aromatic polyamides.

Homopolymers derived from substituted aminobenzoic acid derivatives can also prepared in a stepwise fashion. A stepwise process comprises coupling an N-protected amino acid to an amine (or hydroxy group) and subsequently removing the amine-protecting group and repeating the process. These techniques have been highly refined for synthesis of specific peptides, allow for the synthesis of specific sequences, and both solid-phase and solution techniques for peptide synthesis are directly applicable to the present disclosure. An alternative embodiment is the corresponding polysulfonamides that can be prepared in analogous fashion by substituting sulfonyl chlorides for carboxylic acid chlorides.

The most common method for the preparation of polyureas is the reaction of diamines with diisocyanates (see, Yamaguchi et al., Polym. Bull., 2000, 44, 247). This exothermic reaction can be carried out by solution techniques or by interfacial techniques. One skilled in organic and polymer chemistry will appreciate that the diisocyanate can be replaced with a variety of other bis-acylating agents, such as phosgene or N,N'-(diimidazolyl)carbonyl, with similar results. Polyurethanes are prepared by comparable techniques using a diisocyanate and a dialcohol or by reaction of a diamine with a bis-chloroformate.

The syntheses of compounds described herein can be carried out by routine and/or known methods such as those disclosed in, for example, U.S. Patent Application Publication Nos. 2005-0287108, 2006-0041023, U.S. Pat. No. 7,173, 102, International Publication Nos. WO 2005/123660, WO 2004/082643, and WO 2006/093813, and U.S. Application Publication No. 2010-0081665, each of which is incorporated herein by reference in its entirety. Numerous pathways are available to incorporate polar and nonpolar side chains. Phenolic groups on the monomer can be alkylated. Alkylation of the commercially available phenol will be accomplished with standard Williamson ether synthesis for the non-polar side chain with ethyl bromide as the alkylating agent. Polar sidechains can be introduced with bifunctional alkylating agents such as BOC—NH(CH$_2$)$_2$Br. Alternately, the phenol group can be alkylated to install the desired polar side chain function by employing the Mitsonobu reaction with BOC—NH(CH$_2$)$_2$—OH, triphenyl phosphine, and diethyl acetylenedicarboxylate. Standard conditions for reduction of the nitro groups and hydrolysis of the ester afford the amino acid. With the aniline and benzoic acid in hand, coupling can be effected under a variety of conditions. Alternatively, the hydroxy group of the (di)nitrophenol can be converted to a leaving group and a functionality introduced under nucleophilic aromatic substitution conditions. Other potential scaffolds that can be prepared with similar sequences are methyl 2-nitro-4-hydroxybenzoate and methyl 2-hydroxy-4-nitrobenzoate.

Compounds described herein can also be synthesized by solid-phase synthetic procedures well know to those of skill in the art (see, Tew et al., Proc. Natl. Acad. Sci. USA, 2002, 99, 5110-5114; Barany et al., Int. J. Pept. Prot. Res., 1987, 30, 705-739; Solid-phase Synthesis: A Practical Guide, Kates, S. A., and Albericio, F., eds., Marcel Dekker, New York (2000); and Dörwald, F. Z., Organic Synthesis on Solid Phase: Supports, Linkers, Reactions, 2nd Ed., Wiley-VCH, Weinheim (2002)).

The compounds described herein can also be designed using computer-aided computational techniques, such as de novo design techniques, to embody the amphiphilic properties. In general, de novo design of compounds is performed by defining a three-dimensional framework of the backbone assembled from a repeating sequence of monomers using molecular dynamics and quantum force field calculations. Next, side groups are computationally grafted onto the backbone to maximize diversity and maintain drug-like properties. The best combinations of functional groups are then computationally selected to produce a cationic, amphiphilic structures. Representative compounds can be synthesized from this selected library to verify structures and test their biological activity. Novel molecular dynamic and coarse grain modeling programs have also been developed for this approach because existing force fields developed for biological molecules, such as peptides, were unreliable in these oligomer applications (see, Car et al., Phys. Rev. Lett., 1985, 55, 2471-2474; Siepmann et al., Mol. Phys., 1992, 75, 59-70; Martin et al., J. Phys. Chem., 1999, 103, 4508-4517; and Brooks et al., J. Comp. Chem., 1983, 4, 187-217). Several chemical structural series of compounds have been prepared. See, for example, International Publication No. WO 2002/100295, which is incorporated herein by reference in its entirety. The compounds described herein can be prepared in a similar manner. Molecular dynamic and coarse grain modeling programs can be used for a design approach. See, for example, U.S. Application Publication No. 2004-0107056, and U.S. Application Publication No. 2004-0102941, each of which is incorporated herein by reference in its entirety.

After verifying the suitability of the force field by comparing computed predictions of the structure and thermodynamic properties to molecules that have similar torsional patterns and for which experimental data are available, the fitted torsions can then be combined with bond stretching, bending, one-four, van der Waals, and electrostatic potentials borrowed from the CHARMM (see, Brooks et al., J. Comp. Chem., 1983, 4,187-217) and TraPPE (Martin et al., J. Phys. Chem., 1999, 103, 4508-4517; and Wick et al., J. Phys. Chem., 2000, 104, 3093-3104) molecular dynamics force fields. To identify conformations that can adopt periodic folding patterns with polar groups and apolar groups lined up on the opposite sides, initial structures can be obtained with the Gaussian package (see, Frisch et al., Gaussian 98 (revision A.7) Gaussian Inc., Pittsburgh, Pa. 1998). Then, the parallelized plane-wave Car-Parrinello CP-MD (see, Car et al., Phys. Rev. Lett., 1985, 55, 2471-2474) program, (see, Röthlisberger et al., J. Chem. Phys., 1996, 3692-3700) can be used to obtain energies at the minimum and constrained geometries. The conformations of the compounds without side-chains can be investigated in the gas phase. Both MD and MC methods can be used to sample the conformations. The former is useful for global motions of the compound. With biasing techniques (see, Siepmann et al., Mol. Phys., 1992, 75, 59-70; Martin et al., J. Phys. Chem., 1999, 103, 4508-4517; and Vlugt et al., Mol. Phys., 1998, 94, 727-733), the latter allows efficient sampling for compounds with multiple local minimum configurations that are separated by relatively large barriers.

The potential conformations are examined for positions to attach pendant groups that will impart amphiphilic character to the secondary structure. Compounds selected from the gas phase studies with suitable backbone conformations and with side-chains at the optimal positions to introduce amphiphilicity can be further evaluated in a model interfacial system. n-hexane/water can be chosen because it is simple and cheap for calculations while it mimics well the lipid/water bilayer environment. Compound secondary structures that require inter-compound interactions can be identified by repeating the above-mentioned calculations using a periodically repeated series of unit cells of various symmetries (so called variable cell molecular dynamics or Monte Carlo technique) with or without solvent. The results of these calculations can guide the selection of candidates for synthesis.

The compounds described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, sublingual, or ocular routes, or intravaginally, by inhalation, by depot injections, or by implants. The mode of administration can depend on the pathogen or microbe to be targeted. The selection of the specific route of administration can be selected or adjusted by the clinician according to methods known to the clinician to obtain the desired clinical response.

In some embodiments, it may be desirable to administer one or more compounds, or a pharmaceutically acceptable salt thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as sialastic membranes, or fibers.

The compounds described herein can be administered either alone or in combination (concurrently or serially) with other pharmaceuticals. The compounds can be administered in combination with anti-cancer or anti-neoplastic agents, or in combination with other cancer therapies other than chemotherapy, such as, for example, surgery or radiotherapy. In some embodiments, the compounds described herein can also be administered in combination with (i.e., as a combined formulation or as separate formulations) with antibiotics (in particular, anti-yeast compounds), such as, for example: 1) protein synthesis inhibitors including, but not limited to, amikacin, anisomycin, apramycin, azithromycin, blasticidine S, brefeldin A, butirosin, chloramphenicol, chlortetracycline, clindamycin, clotrimazole, cycloheximide, demeclocycline, dibekacin, dihydrostreptomycin, doxycycline, duramycin, emetine, erythromycin, fusidic acid, G 418, gentamicin, helvolic acid, hygromycin B, josamycin, kanamycin, kirromycin, lincomycin, meclocycline, mepartricin, midecamycin, minocycline, neomycin, netilmicin, nitrofurantoin, nourseothricin, oleandomycin, oxytetracycline, paromomycin, puromycin, rapamycin, ribostamycin, rifampicin, rifamycin, rosamicin, sisomicin, spectinomycin, spiramycin, streptomycin, tetracycline, thiamphenicol, thiostrepton, tobramycin, tunicamycin, tylosin, viomycin, and virginiamycin; 2) DNA synthesis interfering agents including, but not limited to, camptothecin, 10-deacetylbaccatin III, azacytidine, 7-aminoactinomycin D, 8-quinolinol, 9-dihydro-13-acetylbaccatin III, aclarubicin, actinomycin D, actinomycin I, actinomycin V, bafilomycin A1, bleomycin, capreomycin, chromomycin, cinoxacin, ciprofloxacin, cis-diammineplatinum(II) dichloride, coumermycin A1, L(+)-lactic acid, cytochalasin B, cytochalasin D, dacarbazine, daunorubicin, distamycin A, doxorubicin, echinomycin, enrofloxacin, etoposide, flumequine, formycin, fumagillin, ganciclovir, gliotoxin, lomefloxacin, metronidazole, mithramycin A, mitomycin C, nalidixic acid, netropsin, nitrofurantoin, nogalamycin, nonactin, novobiocin, ofloxacin, oxolinic acid, paclitaxel, phenazine, phleomycin, pipemidic acid, rebeccamycin, sinefungin, streptonigrin, streptozocin, succinylsulfathiazole, sulfadiazine, sulfadimethoxine, sulfaguanidine purum, sulfamethazine, sulfamonomethoxine, sulfanilamide, sulfaquinoxaline, sulfasalazine, sulfathiazole, trimethoprim, tubercidin, 5-azacytidine, cordycepin, and formycin A; 3) cell wall synthesis interfering agents including, but not limited to, (+)-6-aminopenicillanic acid, 7-Aminodesacetoxycephalosporanic acid, amoxicillin, ampicillin, azlocillin, bacitracin, carbenicillin, cefaclor, cefamandole, cefazolin, cefmetazole, cefoperazone, cefotaxime, cefsulodin, ceftriaxone, cephalexin, cephalosporin C, cephalothin, cephradine, cloxacillin, D-cycloserine, dicloxacillin, D-penicillamine, econazole, ethambutol, lysostaphin, moxalactam, nafcillin, nikkomycin Z, nitrofurantoin, oxacillin, penicillic, penicillin G, phenethicillin, phenoxymethylpenicillinic acid, phosphomycin, pipemidic acid, piperacillin, ristomycin, and vancomycin; 4) cell membrane permeability interfering agents (ionophores) including, but not limited to, 2-mercaptopyridine, 4-bromocalcimycin A23187, alamethicin, amphotericin B, calcimycin A23187, chlorhexidine, clotrimazole, colistin, econazole, hydrocortisone, filipin, gliotoxin, gramicidin A, gramicidin C, ionomycin, lasalocid A, lonomycin A, monensin, N-(6-aminohexyl)-5-chloro-1-naphthalenesulfonamide, narasin, nigericin, nisin, nonactin, nystatin, phenazine, pimaricin, polymyxin B, DL-penicillamine, polymyxin B, praziquantel, salinomycin, surfactin, and valinomycin; 5) enzyme inhibitors including, but not limited to, (+)-usnic acid, (±)-miconazole, (S)-(+)-camptothecin, 1-deoxymannojirimycin, 2-heptyl-hydroxyquinoline N-oxide, cordycepin, 1,10-phenanthroline, 6-diazo-5-oxo-L-norleucine, 8-quinolinol, antimycin, antipain, ascomycin, azaserine, bafilomycin, cerulenin, chloroquine, cinoxacin, ciprofloxacin, mevastatin, concanamycin A, concanamycin C, coumermycin A1, L(+)-lactic acid, cyclosporin A, econazole, enrofloxacin, etoposide, flumequine, formycin A, furazolidone, fusaric acid, geldanamycin, gliotoxin, gramicidin A, gramicidin C, herbimycin A, indomethacin, irgasan, lomefloxacin, mycophenolic acid, myxothiazol, N-(6-aminohexyl)-5-chloro-1-naphthalenesulfonamide, nalidixic acid, netropsin, niclosamide, nikkomycin, N-methyl-1-deoxynojirimycin, nogalamycin, nonactin, novobiocin, ofloxacin, oleandomycin, oligomycin, oxolinic acid, piericidin A, pipemidic acid, radicicol, rapamycin, rebeccamycin, sinefungin, staurosporine, stigmatellin, succinylsulfathiazole, succinylsulfathiazole, sulfadiazine, sulfadimethoxine, sulfaguanidine, sulfamethazine, sulfamonomethoxine, sulfanilamide, sulfaquinoxaline, sulfasalazine, sulfathiazole, triacsin C, trimethoprim, and vineomycin A1; and 6) membrane modifiers including, but not limited to, paracelsin. In some embodiments, one or more compounds described herein can be administered in combination with one or more anti-fungal drugs, such as nystatin, miconazole, Gentian violet, or amphotericin B.

The means and methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The standard dosing for protamine can be used and adjusted (i.e., increased or decreased) depending upon the factors described above. The selection of the specific dose regimen can be selected or adjusted or titrated by the clinician according to methods known to the clinician to obtain the desired clinical response.

The amount of a compound described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

In some embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. Suitable dosage ranges for other modes of administration can be calculated based on the forgoing dosages as known by those skilled in the art. For example, recommended dosages for intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The compounds described herein can be formulated for parenteral administration by injection, such as by bolus injection or continuous infusion. The compounds can be administered by continuous infusion subcutaneously over a period of about 15 minutes to about 24 hours. Formulations for injection can be presented in unit dosage form, such as in ampoules or in multi-dose containers, with an added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds described herein can be formulated by combining the compounds with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compounds described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds can be applied to a plaster, or can be applied by transdermal, therapeutic systems that are consequently supplied to the organism. In some embodiments, the compounds are present in creams, solutions, powders, fluid emulsions, fluid suspensions, semi-solids, ointments, pastes, gels, jellies, and foams, or in patches containing any of the same.

The compounds described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In yet another embodiment, the compounds can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

It is also known in the art that the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

In some embodiments, the compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Suitable compositions include, but are not limited to, oral non-absorbed compositions. Suitable compositions also include, but are not limited to saline, water, cyclodextrin solutions, and buffered solutions of pH 3-9.

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the excipient is a multi-component system chosen from 20% w/v propylene glycol in saline, 30% w/v propylene glycol in saline, 40% w/v propylene glycol in saline, 50% w/v propylene glycol in saline, 15% w/v propylene glycol in purified water, 30% w/v propylene glycol in purified water, 50% w/v propylene glycol in purified water, 30% w/v propylene glycol and 5 w/v ethanol in purified water, 15% w/v glycerin in purified water, 30% w/v glycerin in purified water, 50% w/v glycerin in purified water, 20% w/v Kleptose in purified water, 40% w/v Kleptose in purified water, and 25% w/v Captisol in purified water. In some embodiments, the excipient is chosen from 50% w/v propylene glycol in purified water, 15% w/v glycerin in purified water, 20% w/v Kleptose in purified water, 40% w/v Kleptose in purified water, and 25% w/v Captisol in purified water. In some embodiments, the excipient is chosen from 20% w/v Kleptose in purified water, 20% w/v propylene glycol in purified water, and 15% w/v glycerin in purified water.

In some embodiments, the composition comprises 50 mg/mL of compound in 20% w/v Kleptose in purified water.

In some embodiments, the formulation can be lyophilized to a solid and reconstituted with, for example, water prior to use.

When administered to a mammal (e.g., to an animal for veterinary use or to a human for clinical use) the compounds can be administered in isolated form.

When administered to a human, the compounds can be sterile. Water may be a suitable carrier when a compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A.R. Gennaro (Editor) Mack Publishing Co.

In one embodiment, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition of the present disclosure is in the form of a liquid wherein the active agent is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In some embodiments, the compounds are solubilized at least in part by a solubilizing agent. Certain acceptable nonionic surfactants, for example polysorbate 80, can be useful as solubilizing agents, as can ophthalmically acceptable glycols, polyglycols, e.g., polyethylene glycol 400 (PEG-400), and glycol ethers.

Suitable solubilizing agents for solution and solution/suspension compositions are cyclodextrins. Suitable cyclodextrins can be chosen from $\alpha$-cyclodextrin, $\beta$-cyclodextrin, $\gamma$-cyclodextrin, alkylcyclodextrins (e.g., methyl-$\beta$-cyclodextrin, dimethyl-$\beta$-cyclodextrin, diethyl-$\beta$-cyclodextrin), hydroxyalkylcyclodextrins (e.g., hydroxyethyl-$\beta$-cyclodextrin, hydroxypropyl-$\beta$-cyclodextrin), carboxy-alkylcyclodextrins (e.g., carboxymethyl-$\beta$-cyclodextrin), sulfoalkylether cyclodextrins (e.g., sulfobutylether-$\beta$-cyclodextrin), and the like. Ophthalmic applications of cyclodextrins have been reviewed in Rajewski et al., Journal of Pharmaceutical Sciences, 1996, 85, 1155-1159. A cyclodextrin can optionally be present in an ophthalmic composition at a concentration from about 1 to about 200 mg/ml, from about 5 to about 100 mg/ml, or from about 10 to about 50 mg/ml.

In some embodiments, the composition optionally contains a suspending agent. For example, in those embodiments in which the composition is an aqueous suspension or solution/suspension, the composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

One or more acceptable salts can be included in the compositions described herein in an amount required to bring osmolality of the composition into an acceptable range. Such salts include, but are not limited to, those having sodium, potassium or ammonium cations and chloride, citrate, ascorbate, borate, phosphate, bicarbonate, sulfate, thiosulfate or bisulfite anions. In some embodiments, salts include sodium chloride, potassium chloride, sodium thiosulfate, sodium bisulfite and ammonium sulfate. In some embodiments, the salt is sodium chloride.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

One or more lubricating agents can also be included optionally in the compositions. Such agents include, but are not limited to, polyvinyl alcohol, methylcellulose, hydroxypropyl methylcellulose, polyvinylpyrrolidone, and the like.

Compositions of the present disclosure typically include a combination of one or more of the optional excipients listed above. For example, in some embodiments, the ophthalmic composition can optionally further comprise glycerin in an amount from about 0.5% to about 5%, from about 1% to about 2.5%, or from about 1.5% to about 2% by weight. Glycerin can be useful to increase viscosity of the composition and for adjustment of osmolality. Independently of the presence of glycerin, the composition can also further comprise a cyclodextrin, such as hydroxypropyl-β-cyclodextrin, in an amount from about 0.5% to about 25% by weight, as a solubilizing agent, and an antimicrobially effective amount of a preservative, e.g., imidazolidinyl urea in an amount from about 0.03% to about 0.5%; methylparaben in an amount from about 0.015% to about 0.25%; propylparaben in an amount from about 0.005% to about 0.01%; phenoxyethanol in an amount from about 0.25% to about 1%; disodium EDTA in an amount from about 0.05% to about 0.2%; thimerosal in an amount from 0.001% to about 0.15%; chlorobutanol in an amount from about 0.1% to about 0.5%; and/or sorbic acid in an amount from about 0.05% to about 0.2%; all by weight.

The compounds described herein can also be incorporated into compositions such as, for example, polishes, paints, sprays, or detergents formulated for application to a surface to inhibit the growth of a *Candida* or *Aspergillus* species thereon. These surfaces include, but are not limited to, countertops, desks, chairs, laboratory benches, tables, floors, bed stands, tools, equipment, doorknobs, windows, and the like. The compounds described herein can also be incorporated into soaps and hand lotions. The present compositions, including the cleansers, polishes, paints, sprays, soaps, and detergents, can contain one or more of the compounds described herein. In addition, the compositions can optionally contain one or more of each of the following: solvents, carriers, thickeners, pigments, fragrances, deodorizers, emulsifiers, surfactants, wetting agents, waxes, and/or oils. For example, in some embodiments, the compounds can be incorporated into a formulation for external use as a pharmaceutically acceptable skin cleanser, particularly for the surfaces of human hands. Cleansers, polishes, paints, sprays, soaps, hand lotions, and detergents and the like containing the compounds described herein can be useful in homes and institutions, particularly but not exclusively, in hospital settings for the prevention of nosocomial infections.

The present disclosure also provides pharmaceutical packs or kits comprising one or more containers filled with one or more compounds described herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single injectable dosage form, such as a single dose within an injectable device such as a syringe with a needle.

The present disclosure also provides methods of inhibiting the growth of a *Candida* or *Aspergillus* species comprising contacting the *Candida* or *Aspergillus* species with one or more compounds described above, or a pharmaceutically acceptable salt thereof. In some embodiments, the compound can act as an antiseptic agent for cleansing surfaces, such as in, for example, kitchens and bathrooms. In these embodiments, the compound can be formulated for such uses by procedures well known to the skilled artisan.

The present disclosure also provides methods of treating a mammal having oral candidiasis comprising administering to the mammal in need thereof an effective amount of one or more compounds described above, or a pharmaceutically acceptable salt thereof. In some embodiments, the mammal can be pre-diagnosed with oral candidiasis prior to treatment. In some embodiments, no formal diagnosis may have been made; in such embodiments, the mammal may be suspected of having oral candidiasis for which treatment is recognized as being desirable.

In some embodiments, the yeast is, or the oral or disseminated candidiasis infection is due to, *Candida albicans, Candida glabrata, Candida tropicalis*, or *Candida krusei*.

The present disclosure also provides one or more compounds described above, or a pharmaceutically acceptable salt thereof, or a pharmaceutical composition comprising one or more compounds described above, for treating candidiasis (oral and/or disseminated) or an *Aspergillus* infection.

The present disclosure also provides one or more compounds described above, or a pharmaceutically acceptable salt thereof, or a pharmaceutical composition comprising one or more compounds described above, for use in the manufacture of a medicament for treating candidiasis (oral and/or disseminated) or an *Aspergillus* infection.

The present disclosure also provides the use of one or more compounds described above, or a pharmaceutically acceptable salt thereof, or a pharmaceutical composition comprising one or more compounds described above, in the inhibition of growth of a *Candida* or *Aspergillus* species.

The present disclosure also provides the use of one or more compounds described above, or a pharmaceutically acceptable salt thereof, or a pharmaceutical composition comprising one or more compounds described above, for treating candidiasis (oral and/or disseminated) or an *Aspergillus* infection in a mammal.

In some embodiments, the compositions are administered with an anti-microbial agent, such as, e.g., an anti-bacterial, anti-fungal, anti-mold, or anti-viral agent. For example, the anti-microbial agent can be a second compound disclosed herein, or the anti-microbial agent can be another anti-microbial agent such as, for example, an antibiotic selected from the group consisting of aminoglycosides, cephalosporins, diaminopyridines, fluoroquinolones, sulfonamides and tetracyclines. Examples of useful antibiotics which can serve as additional anti-microbials include, but are not limited to, amikacin, azithromycin, cefixime, cefoperazone, cefotaxime, ceftazidime, ceftizoxime, ceftriaxone, chloramphenicol, ciprofloxacin, clindamycin, colistin, domeclocycline, doxycycline, erythromycin, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin, and trimethoprim.

In those embodiments in which the composition is administered with an anti-microbial agent, the present disclosure provides administration at the same time or sequentially, of a composition comprising one or more of the compounds disclosed herein, and a separate composition of the anti-microbial agent, in a treatment regimen intended to provide a beneficial effect from co-action of the two types of anti-microbial agents. "Co-formulation" herein means that the compound and the additional anti-microbial agent are administered as components of a single composition.

Any medicament having utility in treating oral candidiasis can be used in co-therapy, co-administration, or co-formulation with a composition described above. Such additional medicaments include, but are not limited to, anti-inflammatory agents (e.g., steroidal anti-inflammatory agents, non-steroidal anti-inflammatory agents (NSAIDs), and selective cyclooxygenase-2 inhibitors); topical and/or regional anesthetic agents; anti-allergic agents (e.g., anti-histamines); demulcents; acetylcholine blocking agents; adrenergic agonists, beta-adrenergic blocking agents and other anti-glaucoma agents; anti-hypertensives; anti-cataract agents; anti-microbial agents, and anti-allergic agents.

Examples of suitable non-steroidal anti-inflammatory agents include, but are not limited to, prostaglandin H synthetase inhibitors (Cos I or Cox II), also referred to as cyclooxygenase type I and type II inhibitors, such as diclofenac, flurbiprofen, ketorolac, suprofen, nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, tenoxicam and carprofen; cyclooxygenase type II selective inhibitors, such as vioxx, celecoxib, etodolac; PAF antagonists, such as apafant, bepafant, minopafant, nupafant and modipafant; PDE IV inhibitors, such as ariflo, torbafylline, rolipram, filaminast, piclamilast, cipamfylline, and roflumilast; inhibitors of cytokine production, such as inhibitors of the NFkB transcription factor; or other anti-inflammatory agents know to those skilled in the art.

Examples of suitable topical or regional anesthetic agents include, but are not limited to, benzocaine.

Examples of suitable anti-allergic agents include, but are not limited to, pemirolast, olopatadine, and the corticosteroids (prednisolone, fluorometholone, loteprenol and dexamthasone).

Frequency of administration is typically such that the dosing interval, for example, the period of time between one dose and the next, during waking hours is from about 2 to about 12 hours, from about 3 to about 8 hours, or from about 4 to about 6 hours. It will be understood by those of skill in the art that an appropriate dosing interval is dependent to some degree on the length of time for which the selected composition is capable of maintaining a concentration of the compound(s) in the lacrimal fluid and/or in the target tissue (e.g., the conjunctiva) above the $MIC_{90}$ (the minimum concentration of the oligomer or polymer which inhibits microbial growth by 90%). Ideally the concentration remains above the $MIC_{90}$ for at least 100% of the dosing interval. Where this is not achievable it is desired that the concentration should remain above the $MIC_{90}$ for at least about 60% of the dosing interval, or should remain above the $MIC_{90}$ for at least about 40% of the dosing interval.

The activity of anti-microbials is generally expressed as the minimum concentration of a compound (active agent) required to inhibit the growth of a specified pathogen. This concentration is also referred to as the "minimum inhibitory concentration" or "MIC." The term "$MIC_{90}$" refers to the minimum concentration of an antimicrobial active agent required to inhibit the growth of ninety percent (90%) of the tested isolates for one particular organism. The concentration of a compound required to totally kill a specified bacterial species is referred to as the "minimum bactericidal concentration" or "MBC."

In some embodiments, an effective concentration of the compound in the composition will generally be from about 0.01% to about 20% by weight (wt %) of the composition, from about 0.05% to about 10% by weight, from about 0.1% to about 8.0% by weight, from about 0.5% to about 5.0% by weight, from about 1.0% to about 5.0% by weight, or from about 2.0% to about 4.0% of the composition.

In some embodiments, the animal being treated, such as a human, is "in need thereof." That is, the animal is in need of treatment. Thus, in some embodiments, the animal is treated for the purpose of preventing or treating the *Candida* or *Aspergillus* infection. In some embodiments, the animal has been diagnosed with a *Candida* or *Aspergillus* infection or is suspected of having a *Candida* or *Aspergillus* infection. In some embodiments, the animal, or human, is in a population at risk of having a *Candida* or *Aspergillus* infection, such as in a prison or hospital.

In order that the present disclosure may be more efficiently understood, examples are provided below. It should be understood that these examples are for illustrative purposes only and are not to be construed as limiting the disclosure in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Screen for Anti-Candida Activity

Over 800 compounds were screened at a single concentration of 10 M against a clinical isolate of *C. albicans* GDH2346 (see, triangles in FIG. 1 below), and an additional 400 compounds were screened with 11 concentrations to give an $IC_{50}$ (see, green squares in FIG. 1 below). The activity was determined at 24 and 48 hours by $OD_{600}$ and fluorescence.

106 compounds showed greater than 90% inhibition, giving a hit rate of 12%. These compounds are all cidal. 109 compounds showed an $IC_{50}$<5 μg/mL and an additional 90 had an $IC_{50}$<10 μg/mL.

Example 2

Activity Against Hyphae

Figure 2:
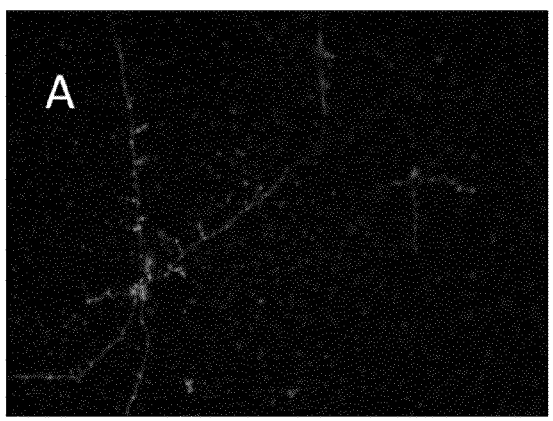
FIG. 2 shows results of fluorescence microscopy of *C. albicans* (GDH2346) hyphae treated with Compound 100 (8 μg/mL) for 0 minutes (FIG. 2A), 15 minutes (FIG. 2B), 30 minutes (FIG. 2C), or 60 minutes (FIG. 2D).
Figure 2:
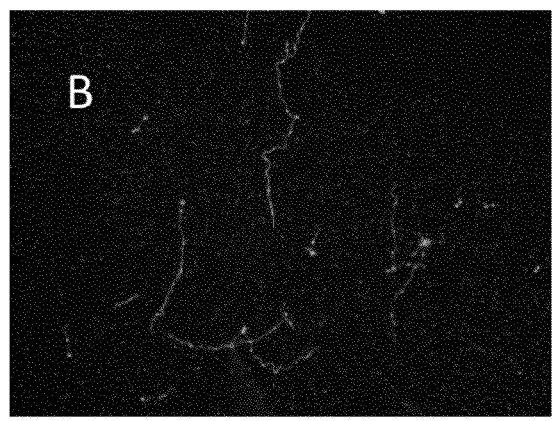
Figure 2:
Figure 2:

*C. albicans* (GDH2346) was grown in 10% FCS for 3 days to achieve hyphae. Hyphae were treated with Compound 100 (8 μg/mL) for 0 minutes (see, FIG. 2A), 15 minutes (see, FIG. 2B), 30 minutes (see, FIG. 2C), or 60 minutes (see, FIG. 2D). Cultures were stained with FungaLight Live-Dead stain (Invitrogen) and observed under fluorescence microscopy (100× magnification).

Compound 100 rapidly caused death of hyphal cultures at low concentrations.

Example 3

Permeabilization (A) *C. albicans* GDH2346 was treated with Compound 100 at the concentrations indicated (g/mL) for 30 minutes, followed by staining with PI and quantification by flow cytometry. Ethanol treatment was used to establish 100% uptake.

(B) Cells were treated with Compound 100 at 32 μg/mL for the times indicated.

Figure 3:
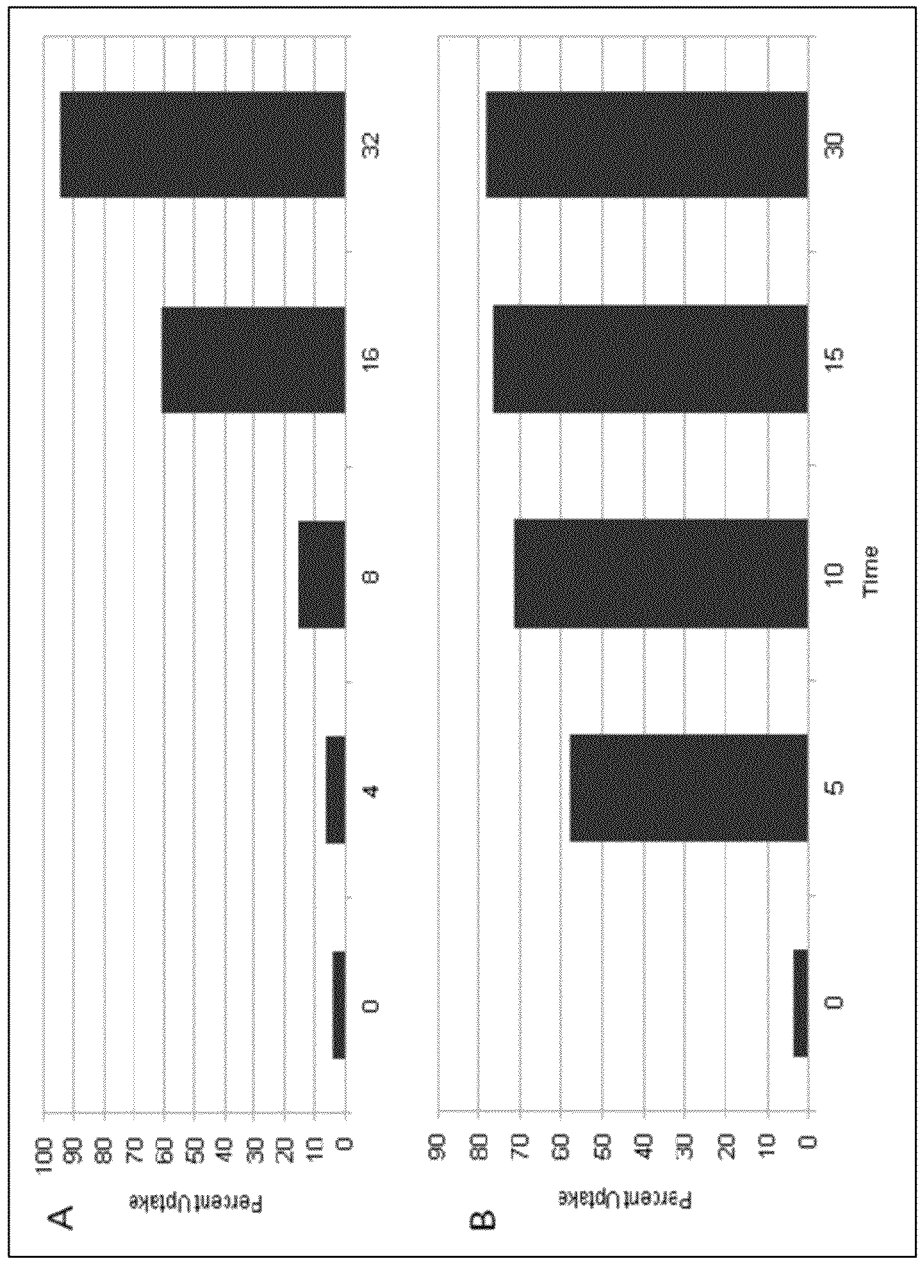
FIG. 3 shows results of dose-dependent membrane permeabilization of *Candida*, resulting in cellular accumulation of PI evident within 30 minutes at 8 to 32 μg/mL Compound 100 concentrations (FIG. 3A) and permeabilized after a 5-minute treatment with Compound 100 at 32 μg/mL (FIG. 3B).

To determine whether the compounds act at the membrane, like many host defense proteins, or intracellularly like histatins, the ability of Compound 100 to cause membrane permeability was assessed. Dose-dependent membrane permeabilization of *Candida*, as shown by cellular accumulation of PI, was evident within 30 minutes at 8 to 32 μg/mL Compound 100 concentrations (see FIG. 3A). Influx was rapid, where >75% of cells were permeabilized after a 5-minute treatment with Compound 100 at 32 μg/mL (see FIG. 3B).

Example 4

Cellular Efflux—ATP Release (A) *C. albicans* GDH2346 was treated with either Compound 100 or histatin 5 for 30 minutes, followed by the separation of the extracellular medium and the cells. Intracellular and extracellular ATP levels were quantified by luciferase assay and measurement in a luminometer, relative to a standard control. Treatment 1=no treatment; Treatment 2=16 μg/mL Compound 100; Treatment 3=32 μg/mL Compound 100; and Treatment 4=Histatin 5 (1 mg/mL).

(B) Time dependent release of ATP of cells treated with Compound 100 at 32 μg/mL.

Figure 4A:
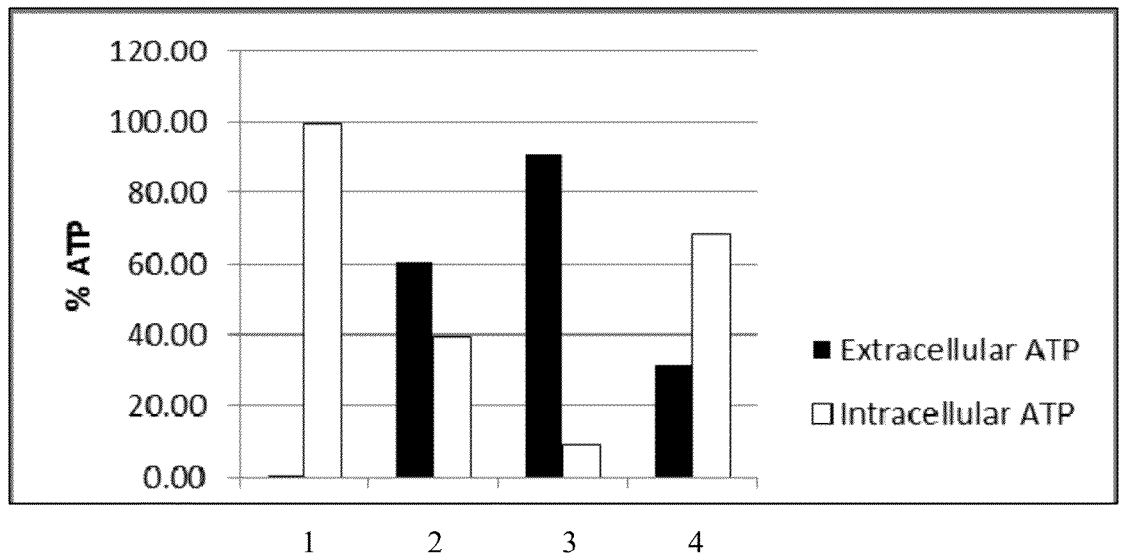
FIG. 4 shows results of cells treated with either Compound 100 or Histatin 5; levels of intracellular and extracellular ATP in cells (FIG. 4A); time-frame of ATP efflux following treatment (FIG. 4B); and dose-dependent efflux over 30 minutes of exposure time (FIG. 4C).
Figure 4B:
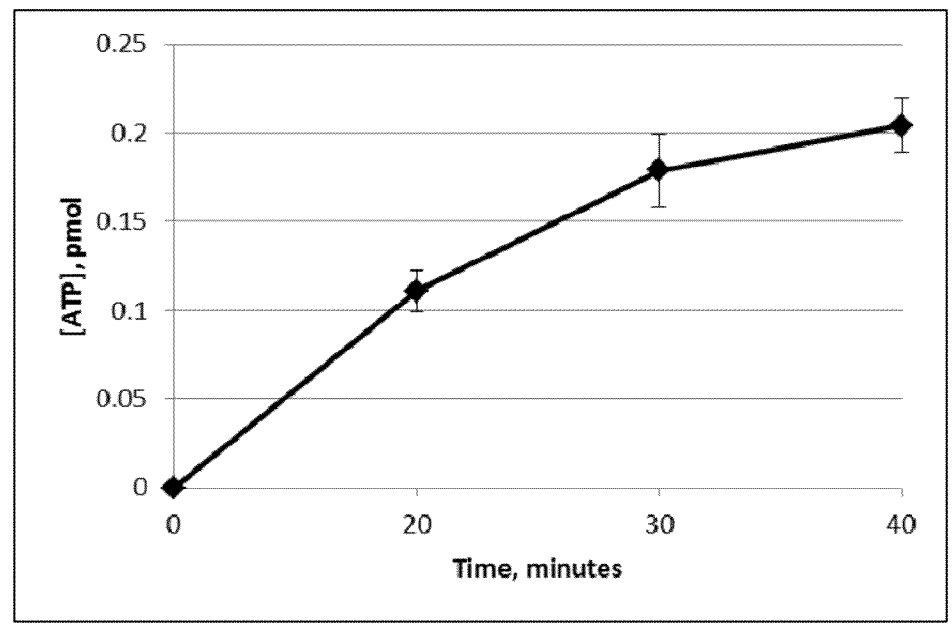
Figure 4C:
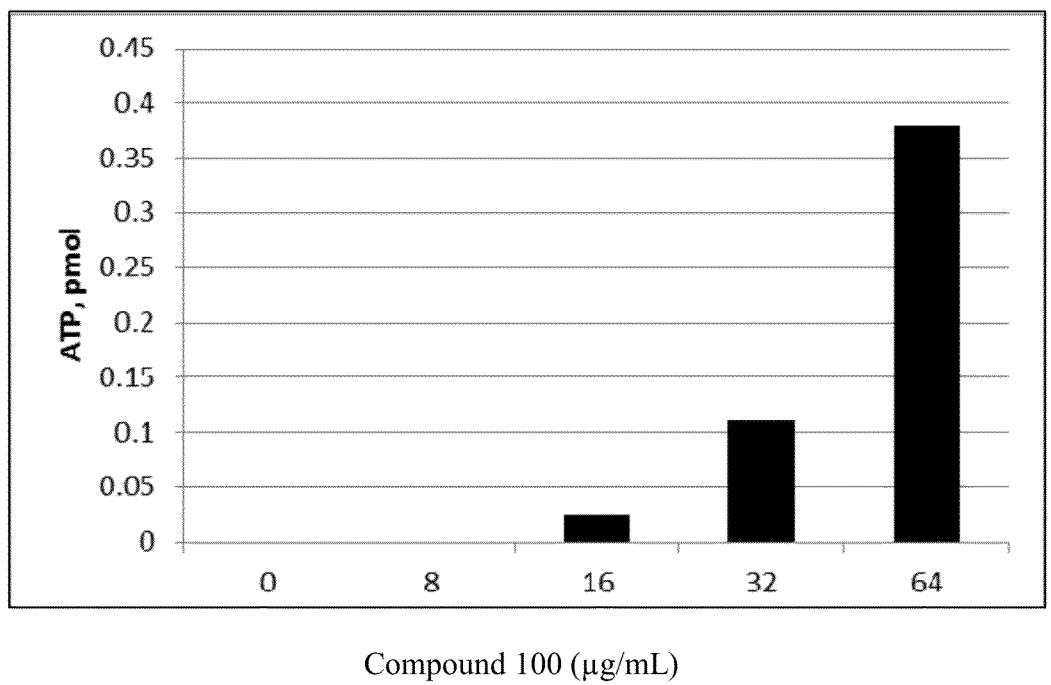

Efflux was also dose-dependent over 30 minutes of exposure time, with detectable ATP levels evident at 16 μg/mL (see, FIG. 4C).

Example 5

IC$_{50}$ Profiles

*Candida* IC$_{50}$s were determined by OD$_{600}$ and fluorescence from vegetative cells and by MTS viability assay in the hyphal state. MICs were determined using a broth microdilution assay under standard CLSI conditions Bacteria strains: *E. coli* 25922 (EC), *S. aureus* 27660 (SA), *E. faecalis* 29212 (EF), *P. aeruginosa* 10145 (PA), and *K. pneumoniae* 13883 (KP). Cytotoxicity (EC$_{50}$) was determined against mouse 3T3 fibroblasts, human transformed liver HepG2 cells, and human oral keratinocyte cell line, OKF6/TERT using an MTS viability assay. *Candida* IC$_{50}$s<10 μg/mL, MICs<5 μg/mL and cytotoxicity EC$_{50}$s>100 μM are indicated in green. MICs>5 μg/mL and cytotoxicity EC$_{50}$s<100 μM are indicated in red. Results are shown in Table 1 below.

TABLE 1

| Activity | Compound | | | | | | |
|---|---|---|---|---|---|---|---|
| | 100 | 114 | 136 | 138 | 135 | 137 | 115 |
| IC50 *Candida*, Vegetative | 4.93 | 7.57 | 4.24 | 4.10 | 1.44 | 1.89 | 4.74 |
| IC50 *Candida*, Hyphal (μg/ml) | 4.90 | 3.17 | 0.71 | 7.50 | 2.68 | 2.29 | 4.07 |
| EC50 EC (μg/ml) | 1.56 | >50 | >50 | >50 | 6.25 | 50 | >50 |
| EC50 SA | 0.78 | 50 | 0.39 | >50 | 12.5 | 25 | >50 |
| EC50 EF (μg/ml) | 0.78 | 25 | 0.098 | >50 | 12.5 | 25 | >50 |
| EC50 PA | 3.13 | >50 | 50 | >50 | >50 | 50 | >50 |
| EC50 KP | 1.56 | >50 | 50 | >50 | 12.5 | >50 | >50 |
| IC50 NIH3T3 (μM) | 439 | 543 | 311 | 406 | 436 | 83 | 358 |
| IC50 HepG2 | >1000 | 255 | 453 | 502 | 885 | 182 | >1000 |
| IC50 OKF6/TERT (μM) | >1000 | 172 | 466 | 491 | 766 | 42 | 309 |

(C) Dose response of cells treated for 30 minutes, followed by quantification of extracellular ATP.

To demonstrate efflux, effects of Compound 100 on ATP release were examined. Cells were treated with either Compound 100 or Histatin 5, and levels of intracellular and extracellular ATP were measured after 30 minutes. At 32 μg/mL Compound 100, almost all of the ATP from the cell was extracellular, which exceeded efflux with 1 mg/mL of histatin 5 (see, FIG. 4A).

At 32 μg/mL, ATP efflux was rapid with significant extracellular accumulation occurring by 20 minutes following treatment (see, FIG. 4B).

Example 6

IC$_{50}$ Profiles

*Candida* IC$_{50}$s (CA) were determined by OD$_{600}$ and fluorescence from vegetative cells. MICs were determined using a broth microdilution assay under standard CLSI conditions Bacteria strains: *E. coli* 25922 (EC), *S. aureus* 27660 (SA), *E. faecalis* 29212 (EF), *P. aeruginosa* 10145 (PA), and *K. pneumoniae* 13883 (KP). Cytotoxicity (EC$_{50}$) was determined against mouse 3T3 fibroblasts and human transformed liver HepG2 cells using an MTS viability assay. Results are shown in Table 2 below.

TABLE 2

| Compound | CA μg/mL | 3T3 μM | HepG2 μM | EC μg/mL | SA μg/mL | EF μg/mL | PA μg/mL | KP μg/mL |
|---|---|---|---|---|---|---|---|---|
| 139 | >100 | | | | | | | |
| 117 | 3.10 | | | | | | | |
| 118 | 3.64 | 40 | 90 | | | | | |
| 119 | 6.17 | | | | | | | |
| 140 | 3.58 | 159 | 99 | 0.78 | 0.195 | 3.13 | 3.13 | 3.13 |
| 141 | | 107 | 62 | 12.5 | 12.5 | | 100 | 25 |
| 142 | 1.65 | 131 | 100 | 3.13 | 1.56 | 6.25 | 25 | 3.13 |
| 143 | 6.48 | 222 | 140 | 3.13 | 0.39 | 1.56 | 50 | 6.25 |

TABLE 2-continued

| Compound | CA μg/mL | 3T3 μM | HepG2 μM | EC μg/mL | SA μg/mL | EF μg/mL | PA μg/mL | KP μg/mL |
|---|---|---|---|---|---|---|---|---|
| 144 | 3.95 | 80 | 188 | 3.13 | 0.098 | 0.195 | 3.13 | 6.25 |
| 145 | 23.94 | >1000 | 790 | >50 | 25 | 3.13 | 50 | >50 |
| 146 | 44.59 | 307 | 341 | 50 | 0.39 | 0.39 | 12.5 | >50 |
| 147 |  |  |  | 1.56 | 0.098 | 0.39 | 6.25 | 1.56 |
| 148 | 8.74 | 450 | 312 | 25 | 3.13 | >50 | >50 | >50 |
| 149 | >100 | 29 | 20 | 3.13 | 0.049 | 1.56 | >100 | 3.13 |
| 150 | 3.34 | 54 | 58 | 0.78 | 0.049 | 1.56 | 3.13 | 3.13 |
| 151 | 3.85 | 56 | 78 | 3.13 | 0.195 | 6.25 | 6.25 | 12.5 |
| 152 | 3.77 | 34 | 12 | 1.56 | 0.39 | 1.56 | 3.13 | 1.56 |
| 153 |  | 46 | 65 | 12.5 | 1.56 | 12.5 | 100 | 12.5 |
| 154 | 1.88 | 451 | 853 | 1.56 | 0.39 | 6.25 | 12.5 | 6.25 |
| 155 | 2.63 |  |  | 12.5 | 0.39 | >50 | 12.5 | >50 |
| 156 | 1.94 | 487 | >1000 | 1.56 | 1.56 | >50 | 12.5 | >50 |
| 157 | 6.21 |  | 228 | 3.13 | 0.39 | 12.5 | 12.5 | 12.5 |
| 158 | 17.47 | 179 | 615 | 1.56 | 1.56 | >50 | 25 | >50 |
| 159 | 2.11 | 61 | 64 | 0.78 | 0.78 | 3.13 | 6.25 | 3.13 |
| 160 | 1.48 | 28 | 28 | 1.56 | 1.95 | 3.13 | 6.25 | 3.13 |
| 161 | 11.8 | 356 | 466 | 1.56 | 6.25 | >50 | 50 | 6.25 |
| 162 | 3.12 | 49 | 273 | 1.56 | 0.39 | 12.5 | 3.13 | 3.13 |
| 163 | 1.79 | 31 | 113 | 3.13 | 3.13 | 3.13 | 50 | 25 |

Example 7

Efficacy in a Mouse Model of Oral Candidiasis 8-week old male mBD-1(−/−) mice on a C57B1/6 background were pre-treated for 5 days with 2.5 mg/mL oral tetracycline to reduce normal oral flora (n=5 per group; n=4 for nystatin group). Day 0: infection initiated by oral inoculation of a 50 μL suspension of C. albicans (clinical isolate GDH2346 at 5×10$^7$ cfu/mL) onto a cotton ball after lightly scoring the tongues. Day 3: Single topical administration of test agent (10 mg/mL) applied in 0.05 mL hydrogel. Tissue was harvested 24 hours post-treatment, homogenized, and quantitated by serial dilution and plating.

Figure 5A:
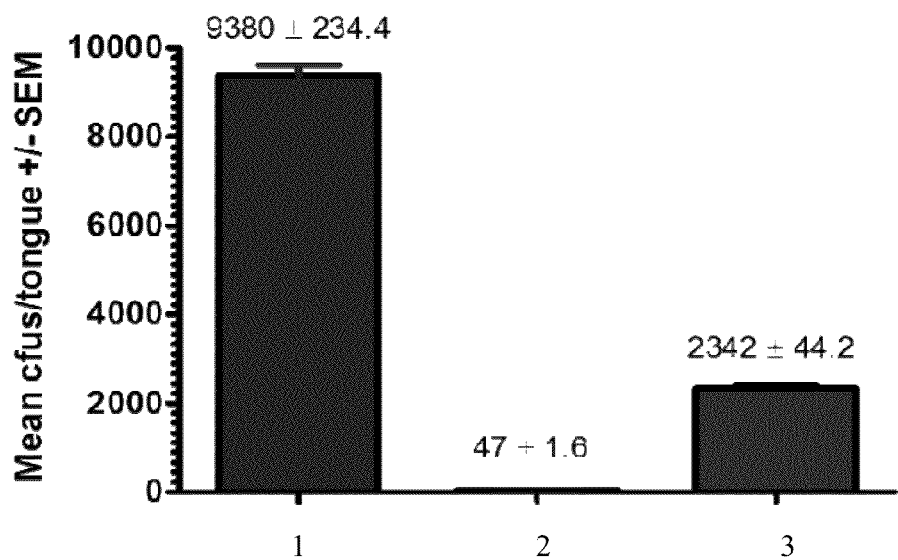
FIG. 5 shows results of sterilization of infected tongue following a single topical dose of Compound 100 or Nystatin (FIG. 5A); and a photomicrograph of a 10 μm section of a tongue from an infected mouse on day 4, stained with PAS (FIG. 5B).
Figure 5B:
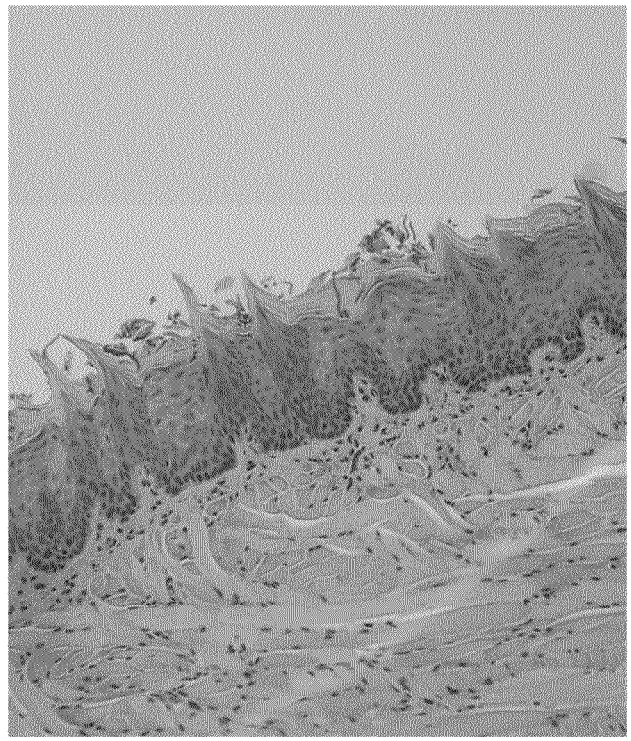

Compound 100 nearly sterilized the infected tongue following a single topical dose and was 50-fold more efficacious than Nystatin. Results are shown in FIG. 5A. (Treatment 1=Control; Treatment 2=Compound 100 at 10 mg/mL; and Treatment 3=Nyststin at 10 mg/mL). FIG. 5B is a photomicrograph of a 10 μm section of a tongue from an infected mouse on day 4, stained with PAS (Magnification=100×). Arrows show hyphae and hyphal insertion into tissue.

Example 8

Anti-Candida Activity; In Vitro Profiles

Candida MIC assays were determined in accordance with CLSI guidelines M27-A3 using a clinically isolated C. albicans strain, GDH2346. 50% human serum was added to determine activity in the presence of serum.

For determination of anti-Candida IC$_{50}$s, the method was modified by using RPMI/MOPS buffer pH 6.3 and by addition of FDGlu, a substrate for the yeast enzyme exoglucanase which is secreted during cell growth. This provides a fluorescent readout for cell growth which was used in addition to the traditional optical density measure of growth. OD$_{600}$ and fluorescence were determined at 24 and 48 hours and the average of all 4 reads was used for the final IC$_{50}$ determination.

To form the biofilm, yeast were grown in RPMI/MOPS, 0.4% sucrose pH7.4 media supplemented with 10% FBS in tissue culture-treated flat bottom 96 well plates for 48 hours. The filamentous yeast cultures were then vigorously washed to remove any non-filamentous, non-attached yeast. The remaining attached filamentous biofilm yeast were incubated in saline containing serially diluted compounds for 24 hours. The cultures were aspirated to remove compound, rinsed and overlayed with RPMI/MOPS, 0.4% sucrose pH7.4 media. Biofilm viability was measured using a cell proliferation assay (CellTiter96 Aqueous Kit from Promega) and IC$_{50}$s were determined using Prism GraphPad software (nonlinear fit, Table 3).

Time kills were performed in the same manner as IC$_{50}$s. At each time point yeast were removed, diluted as necessary and plated on YPD agar to determine viable CFUs.

Bacterial MICs were determined using a broth microdilution assay under standard

CLSI conditions Bacteria strains: clinical isolates; yeast strains: C. dubliniensis (NCPF3949), C. glabrata (ATCC 90030), C. krusei (ATCC 6258), C. parapsilosis (ATCC 22019), and C. tropicalis (ATCC 750). Cytotoxicity (EC$_{50}$) was determined against mouse 3T3 fibroblasts, human transformed liver HepG2 cells, and human oral keratinocyte cell line, OKF6/TERT using an MTS viability assay.

Table 3 shows potent activity of several compounds against vegetative and 2-day hyphal biofilm cultures.

TABLE 3

| | Anti-C. albicans GDH2346 (μg/ml) | |
|---|---|---|
| Compound | Vegetative | Hyphal |
| 164 | 4.88 | 11.04 |
| 100 | 4.93 | 4.90 |
| 136 | 4.24 | 0.71 |
| 135 | 1.44 | 2.68 |
| 185 | 1.09 | 1.00 |
| 186 | 1.03 | 1.40 |
| 187 | 2.20 | ND |
| 188 | 2.08 | 2.22 |

Figure 6A:
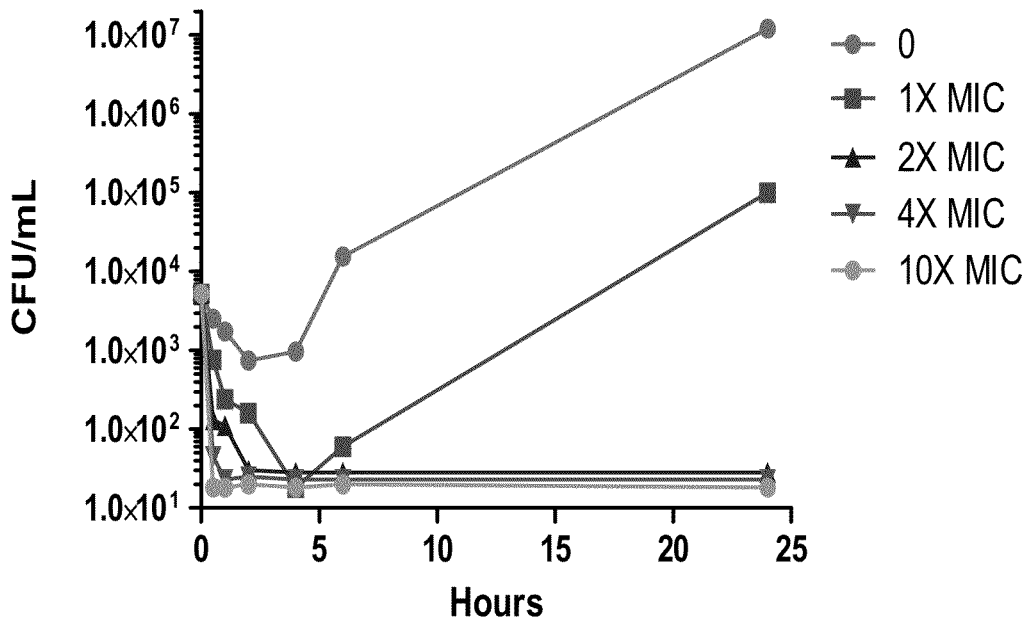
FIG. 6 shows cidal activity with rapid killing kinetics of Compound 100 (FIG. 6A) and Compound 135 (FIG. 6B).
Figure 6B:
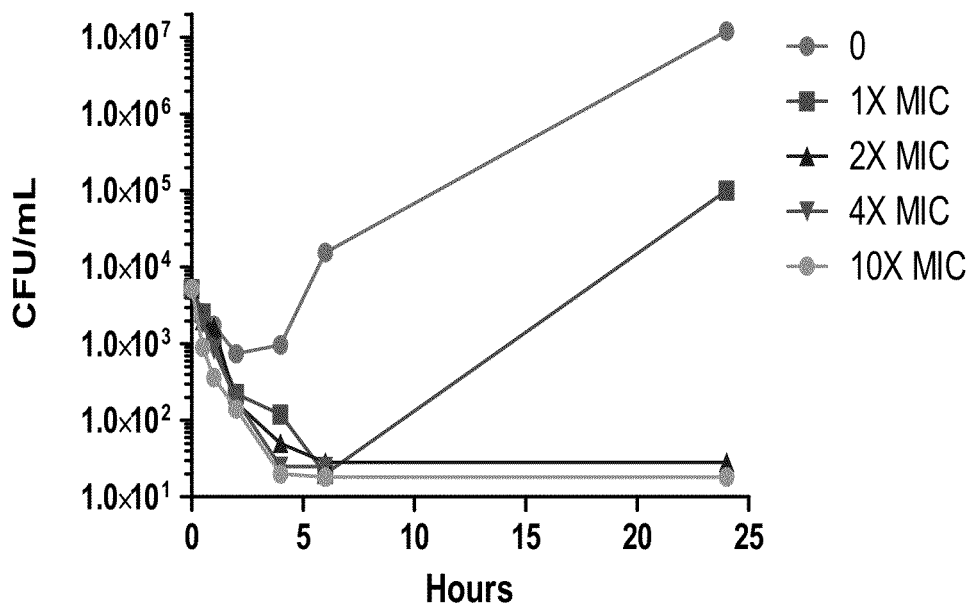

FIGS. 6A and 6B show cidal activity with rapid killing kinetics of Compound 100 and Compound 135, respectively.

Table 4 shows a subset of compounds active in serum.

TABLE 4

| | MIC (µg/ml) | | | |
|---|---|---|---|---|
| Compound | Cmpd 136 | Cmpd 136 + 50% HS | Cmpd 135 | Cmpd 135 + 50% HS |
| C. albicans GDH2346 | 4 | 2 | 4 | 2 |
| C. dubliniensis | 8 | 2 | 4 | 1 |
| C. glabrata | 4 | 1 | 2 | 2 |

HS = human serum

Example 9

Activity Against Commensal Bacteria in Oral Activity and Yeast

Table 5 shows the activity of several compounds against commensal bacteria and different yeast.

TABLE 5

| | Commensal Bacteria MIC (µg/ml) | | Other Yeast Species MIC (µg/ml) | | | | | |
|---|---|---|---|---|---|---|---|---|
| Cmpd | S. salivarius | A. viscosis | C. tropicalis | C. parapsilosis | C. dubliniensis | C. glabrata | C. krusei | C. albicans |
| 100 | >64 | >64 | 4 | 8 | 8 | 16 | 8 | 4-8 |
| 136 | 16 | 4 | 4-8 | 4-8 | 8 | 4 | 32 | 4 |
| 135 | >64 | >64 | 2-4 | 2 | 4 | 2 | 16 | 4 |
| 137 | >64 | >64 | 4 | 4-8 | 8-16 | 8 | 8 | 8 |
| 185 | 8 | 4 | 0.5 | 2 | 2 | 2 | 2 | 2 |
| 186 | 8 | 4 | 0.5 | 2 | 2 | 2 | 2 | 2 |
| 187 | 32 | 8 | 0.5 | 4 | 4 | 4 | 4 | 2 |
| 188 | 64 | 16 | 0.5 | 4 | 4 | 4 | 4 | 2 |

Example 10

Anti-Fungal Activity; Efficacy in Mouse *Candida* Sepsis Model

Mice were made neutropenic with i.p. injections of cyclophosphamide (150 mg/kg in 10 mL/kg) at 4 and 1 day before inoculation. Each animal was then inoculated by injecting 0.1 mL of inoculum of *C. albicans* in a tail vein. The standard was administered orally and the test compounds by IV 1 hour after infection.

The kidneys were collected from four mice in Group 1 at 1 hour after infection and from the remaining mice in the study at 24 hours after infection. Kidneys were combined in a sterile tube. An aliquot of sterile PBS were added to each tube and the contents homogenized with a tissue homogenizer. Serial dilutions of the tissue homogenates were conducted, 0.1 mL aliquots were spread on SDA plates and the plates incubated at 35° C. overnight. The CFU/kidneys were determined from colony counts. One-way ANOVA with Bonferroni Multiple Comparisons Test was performed using GraphPad InStat version 3.00 for Windows 95, GraphPad Software, San Diego Calif. USA.

Figure 7:
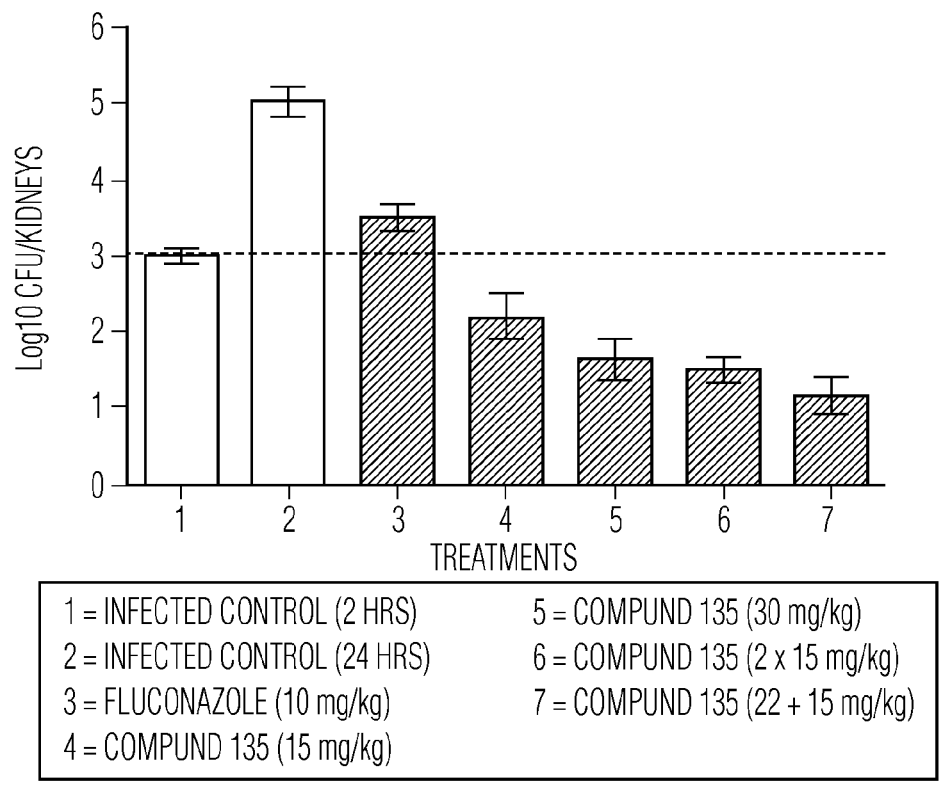
FIG. 7 shows results of cidal activity of Compound 135 with ≥1.5 $\log_{10}$ reductions in tissue burden from treatment onset.
Figure 8:
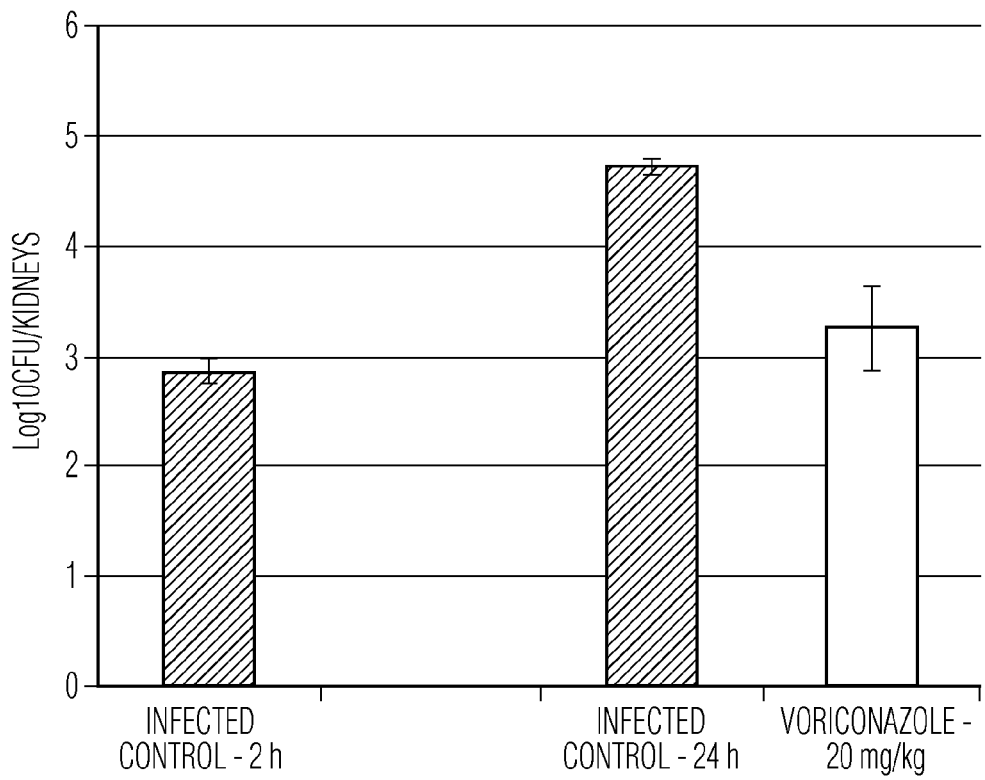
FIG. 8 shows results of static activity with current triazole and anti-fungals in a model.

FIG. 7 shows Compound 135 has cidal activity with ≥1.5 $\log_{10}$ reductions in tissue burden from treatment onset. In contrast, FIG. 8 shows that current triazole and anti-fungals have a static effect in the model.

Example 11

Disseminated Candidiasis Model; Survival Study

Mice were made neutropenic with i.p. injections of cyclophosphamide (150 mg/kg in 10 mL/kg) at 4 and 1 day before inoculation. Each animal was then inoculated by injecting 0.1 mL of inoculum of *C. albicans* in a tail vein. At 2 hours post-infection, the standard was administered orally and the test compound by IV. Compounds were dosed once daily for 4 days.

The kidneys were collected from four mice in Group 1 at 2 hours after infection, from four mice in Groups 2-5 at five days after infection, and from all surviving mice in the infected treatment groups. An aliquot of sterile PBS were added to each tube and the contents homogenized with a tissue homogenizer. Serial dilutions of the tissue homogenates were conducted, 0.1 mL aliquots were spread on SDA plates and the plates incubated at 35° C. overnight. The CFU/kidneys were determined from colony counts.

Survival data was analyzed using the log-rank (Mantel-Cox) test and one-way ANOVA with Tukey's Multiple Comparisons Test was performed on the yeast density and change in body weight data (GraphPad InStat version 5.04).

Figure 9:
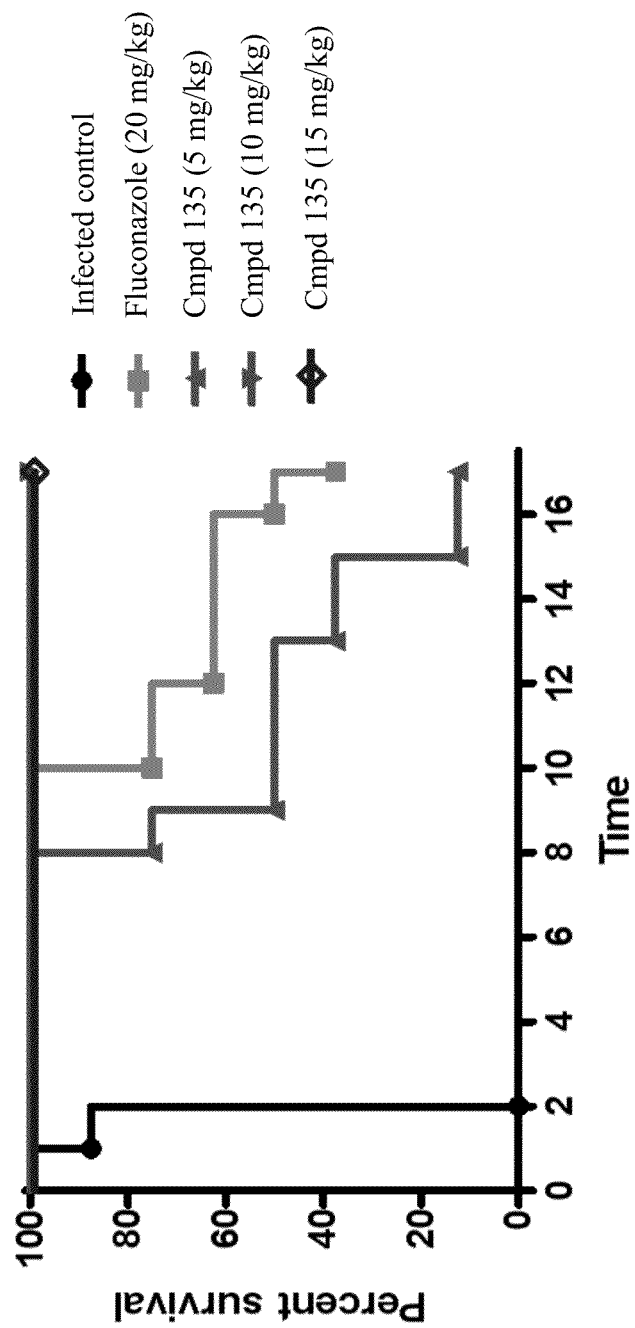
FIG. 9 shows survival of mice over a 14-day period in a disseminated Candidiasis survival study model in which neutropenic mice inoculated with *C. albicans* in a tail vein.

FIG. 9 shows survival of mice over a 14-day period. $p<0.01$ between Fluconazole and Compound 135 (10 mg/kg) and $p<0.01$ between Fluconazole and Compound 135 (15 mg/kg).

Example 12

Anti-Aspergillus Activity

The in vitro efficacy of a library of compounds was assessed for antifungal activity against *A. niger* (AN1), *A. fumigatus* (A1163) and *A. flavus* (NRRL3357) and compared to that of Itraconazole. For a subset of compounds selected based upon efficacy in the screening study a full MIC profile was conducted.

Efficacy of test articles was determined in RPMI 1640 broth with MOPS buffered to pH7.2 in accordance with CLSI guidelines M38-A for Antifungal Susceptibility Testing of Filamentous Fungi. The method was modified by using flat well plates to allow microscopic identification of growth. The final screening concentration of each test article was 10 µM. Assay plates were incubated aerobically at 37° C. for 24-48 hours. Following incubation, plates were assessed visually (by eye and microscopically) for inhibition of growth. Inhibition was recorded at 50%, 80% and 100% inhibition compared to the positive control. A hit was described as a well demonstrating 100% inhibition.

MICs were determined in RPMI 1640 broth plus MOPS buffered to pH7.2 in accordance with CLSI guidelines M38-A for Antifungal Susceptibility Testing of Filamentous Fungi. The method was modified by using flat well plates to allow microscopic identification of growth. The final MIC range was 64-0.125 g/mL.

Table 6 shows several compounds have broad anti-fungal activity with low mammalian cell cytotoxicity.

TABLE 6

| Compound | % Inhibition | | | IC$_{50}$ (μg/ml) | Cytotoxicity EC$_{50}$ (μM) | |
| --- | --- | --- | --- | --- | --- | --- |
| | A. fumigatus | A. niger | A. flavus | C. albicans | Mouse 3T3 | Human HepG2 |
| Cmpd 184 | 100 | 100 | 100 | 3.1 | 1000 | 155 |
| Cmpd 183 | 100 | 100 | 100 | 2.0 | 478 | 1000 |
| Cmpd 136 | 100 | 100 | 100 | 1.4 | 311 | 453 |
| Cmpd 165 | 80 | 100 | 100 | 1.1 | 115 | 138 |

Various modifications of the disclosure, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of killing or inhibiting the growth of a *Candida* or *Aspergillus* species or preventing or treating a mammal having oral or disseminated *candidiasis* or an *aspergillus* infection comprising contacting the *Candida* or *Aspergillus* species with or administering to the mammal in need thereof an effective amount of a compound of Formula IV:

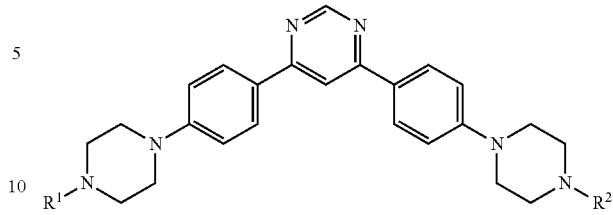

(IV)

wherein:
R$^1$ and R$^2$ are, independently, —C(=NH)NH$_2$, —(CH$_2$)$_n$NH$_2$, or —(CH$_2$)$_n$NC(=NH)NH$_2$, where n is 2, 3, or 4;
or a pharmaceutically acceptable salt thereof.

2. The method of claim 1 wherein R$^1$ and R$^2$ are, independently, —C(=NH)NH$_2$, —(CH$_2$)$_n$NH$_2$, or —(CH$_2$)$_n$NC(=NH)NH$_2$, where n is 2 or 3.

3. The method of claim 1 wherein R$^1$ and R$^2$ are, independently, —C(=NH)NH$_2$ or —(CH$_2$)$_n$NH$_2$, where n is 2 or 3.

4. The method of claim 1 wherein the compound is:

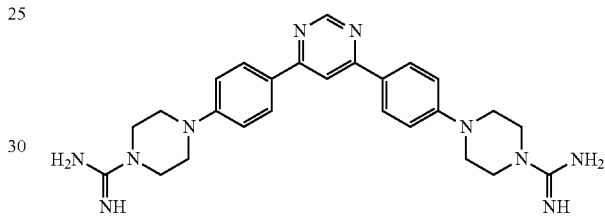

or a pharmaceutically acceptable salt thereof.

* * * * *